United States Patent
Erdman et al.

(10) Patent No.: US 12,419,962 B2
(45) Date of Patent: *Sep. 23, 2025

(54) QUINAZOLINES, PHARMACEUTICAL COMPOSITIONS, AND THERAPEUTIC APPLICATIONS

(71) Applicant: BioTheryX, Inc., San Diego, CA (US)

(72) Inventors: Paul E. Erdman, San Diego, CA (US); Leah M. Fung, San Diego, CA (US); Patrick Papa, Carlsbad, CA (US); Brandon W. Whitefield, San Diego, CA (US)

(73) Assignee: BioTheryX, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/184,077

(22) Filed: Mar. 15, 2023

(65) Prior Publication Data
US 2023/0293702 A1   Sep. 21, 2023

Related U.S. Application Data

(60) Provisional application No. 63/269,462, filed on Mar. 16, 2022.

(51) Int. Cl.
| | | |
|---|---|---|
| *A61K 47/55* | (2017.01) |
| *A61K 47/54* | (2017.01) |
| *A61P 1/00* | (2006.01) |
| *A61P 35/00* | (2006.01) |
| *C07D 401/12* | (2006.01) |
| *C07D 401/14* | (2006.01) |
| *C07D 417/14* | (2006.01) |
| *C07D 471/04* | (2006.01) |

(52) U.S. Cl.
CPC ............ *A61K 47/55* (2017.08); *A61K 47/545* (2017.08); *A61P 1/00* (2018.01); *A61P 35/00* (2018.01); *C07D 401/12* (2013.01); *C07D 401/14* (2013.01); *C07D 417/14* (2013.01); *C07D 471/04* (2013.01)

(58) Field of Classification Search
CPC .. C07D 401/12; C07D 401/14; C07D 417/14; C07D 471/04
See application file for complete search history.

(56) References Cited

U.S. PATENT DOCUMENTS

| | | |
|---|---|---|
| 9,938,302 B2 | 4/2018 | Chan et al. |
| 10,336,771 B2 | 7/2019 | Chan et al. |
| 10,406,165 B2 | 9/2019 | Chan et al. |
| 10,513,515 B2 | 12/2019 | Chan et al. |
| 2019/0194192 A1 | 6/2019 | Ramharter et al. |
| 2019/0322682 A1 | 10/2019 | Chan et al. |
| 2019/0358230 A1 | 11/2019 | Gmachl et al. |
| 2020/0000814 A1 | 1/2020 | Chan et al. |
| 2020/0148663 A1 | 5/2020 | Chan et al. |
| 2020/0199073 A1 | 6/2020 | Ammirante et al. |
| 2020/0369679 A1 | 11/2020 | Chan et al. |

FOREIGN PATENT DOCUMENTS

| | | | |
|---|---|---|---|
| WO | 2016172134 A2 | 10/2016 | |
| WO | 2017201069 A1 | 11/2017 | |
| WO | 2018115380 A1 | 6/2018 | |
| WO | 2019140380 A1 | 7/2019 | |
| WO | 2019173224 A1 | 9/2019 | |
| WO | 2020180770 A1 | 9/2020 | |
| WO | 2021023233 A1 | 2/2021 | |
| WO | 2021051034 A1 | 3/2021 | |
| WO | WO-2022061348 A1 * | 3/2022 | ............. A61P 35/00 |
| WO | 2022197862 A1 | 9/2022 | |
| WO | 2022266248 A1 | 12/2022 | |
| WO | 2023178130 A1 | 9/2023 | |

OTHER PUBLICATIONS

Kazantsev et al., "Ligands for cereblon: 2017-2021 patent overview", 2021, Expert Opinion on Therapeutic Patents, 32, pp. 171-190 (Year: 2021).*
Berge et al., "Pharmaceutical salts," J. Pharm. Sci. 1977, 66, 1-19.
Bos et al., "GEFs and GAPs: critical elements in the control of small G proteins," Cell 2007, 129, 865-77.
Cancer Facts & Figures 2022.
Cox et al., "Drugging the undruggable RAS: Mission possible?" Nat. Rev. Drug. Discov. 2014, 13, 828-51.
Hillig et al., "Discovery of potent SOS1 inhibitors that block RAS activation via disruption of the RAS-SOS1 interaction," Proc. Natl. Acad. Sci. USA 2019, 116, 2551-60.
Milburn et al., "Molecular switch for signal transduction: structural differences between active and inactive forms of protooncogenic ras proteins," Science 1990, 247, 939-45.

(Continued)

*Primary Examiner* — Jeffrey H Murray
*Assistant Examiner* — Madeline E Braun
(74) *Attorney, Agent, or Firm* — Juniv LLP; Lin Yu

(57) ABSTRACT

Provided herein are quinazolines, e.g., a compound of Formula (I), and pharmaceutical compositions thereof. Also provided herein are methods of their use for treating, preventing, or ameliorating one or more symptoms of an SOS1-mediated disorder, disease, or condition.

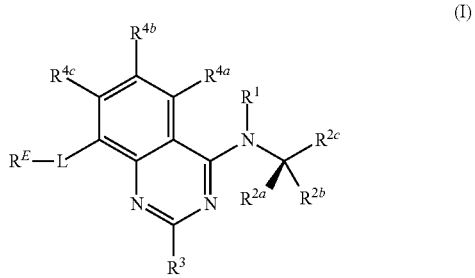

23 Claims, No Drawings

(56) References Cited

OTHER PUBLICATIONS

Papke and Der, "Drugging RAS: Know the enemy," Science 2017, 355, 1158-63.
Rebocho and Marais, "New insight puts CRAF in sight as a therapeutic target," Cancer Discov. 2011, 1, 98-9.
Schapira et al., "Targeted protein degradation: expanding the toolbox," Nat. Rev. Drug. Discov. 2019, 18, 949-63.
Simanshu et al., "RAS Proteins and Their Regulators in Human Disease," Cell 2017, 170, 17-33.
Steinebach et al., "Systematic exploration of different E3 ubiquitin ligases: an approach towards potent and selective CDK6 degraders," Chem. Sci. 2020, 11, 3474-86.
Uras et al., "Targeting KRAS Mutant Non-Small-Cell Lung Cancer: Past, Present and Future," Int. J. Mol. Sci. 2020, 21, 4325.
Wang et al., "Ras inhibition via direct Ras binding—is there a path forward?" Bioorg. Med. Chem. Lett. 2012, 22, 5766-76.

\* cited by examiner

QUINAZOLINES, PHARMACEUTICAL COMPOSITIONS, AND THERAPEUTIC APPLICATIONS

CROSS REFERENCE TO RELATED APPLICATION

This application claims the benefit of the priority of U.S. Provisional Application No. 63/269,462, filed Mar. 16, 2022; the disclosure of which is incorporated herein by reference in its entirety.

FIELD

Provided herein are quinazolines and pharmaceutical compositions thereof. Also provided herein are methods of their use for treating, preventing, or ameliorating one or more symptoms of an SOS1-mediated disorder, disease, or condition.

BACKGROUND

The three RAS oncogenes, KRAS, HRAS, and NRAS, are from the most frequently mutated oncogene family in cancer. Milburn et al., *Science* 1990, 247, 939-45; Cox et al., *Nat. Rev. Drug Discov.* 2014, 13, 828-51; Papke and Der, *Science* 2017, 355, 1158-63. RAS mutations have been detected in up to 30% of all human cancer. Cox et al., *Nat. Rev. Drug Discov.* 2014, 13, 828-51. RAS mutations are found in about 95% of pancreatic ductal adenocarcinomas (PDACs), about 50% of colorectal adenocarcinomas (CRCs), and about 30% of lung adenocarcinomas (CACs). Papke and Der, *Science* 2017, 355, 1158-63. Among the three, KRAS mutations are the most common and alone account for about a million death per year worldwide. Cox et al., *Nat. Rev. Drug Discov.* 2014, 13, 828-51; Simanshu et al., *Cell* 2017, 170, 17-33.

A RAS protein is a small GTPase encoded by a RAS oncogene. Papke and Der, *Science* 2017, 355, 1158-63. The RAS protein functions as a molecular switch cycling between the active guanosine triphosphate (GTP)-bound and inactive guanosine diphosphate (GDP)-bound states. Milburn et al., *Science* 1990, 247, 939-45. The GTP-bound active RAS activates downstream effector pathways, including rat fibrosarcoma/mitogen-activated protein kinase kinase/extracellular regulated kinase (RAF/MEK/ERK) and phosphoinositide 3-kinase/protein kinase B/mechanistic target of rapamycin kinase (PI3K/AKT/mTOR). Rebocho and Marais, *Cancer Discov.* 2011, 1, 98-9. Oncogenic mutations in RAS proteins impair their ability for GTP hydrolysis, resulting in the accumulation of GTP-bound active RAS and hyperactivation of downstream signaling cascades that lead to uncontrolled cell proliferation and survival. Uras et al., *Int. J. Mol. Sci.* 2020, 21, 4325.

The RAS signaling is tightly regulated by guanine nucleotide exchange factor (GEF) proteins, which catalyze the exchange of GDP for GTP, and GTPase-activating proteins (GAPs), which increase the rate of GTP hydrolysis to GDP. Simanshu et al., *Cell* 2017, 170, 17-33. In other words, the RAS GTP/GDP cycle is regulated negatively by GAPs and positively by GEFs. Bos, *Cell* 2007, 129, 865-77. The son of sevenless homolog 1 (SOS1) is a GEF that binds to RAS to promote nucleotide exchange and formation of GTP-bound active RAS. Wang et al., *Bioorg. Med. Chem. Lett.* 2012, 22, 5766-76. Small molecule SOS1 inhibitors have been shown to be effective in downregulating active RAS in tumor cells with wild-type KRAS as well as tumor cells bearing a KRAS mutation. Hillig et al., *Proc. Nat. Acad. Sci.* 2019, 114, 2551-60. By preventing formation of the KRAS-SOS1 complex, the SOS1 inhibitors block reloading of KRAS with GTP, leading to antiproliferative activity. Id.

Despite the advances in cancer treatment, cancer remains a major worldwide public health problem. It was estimated that there will be 1,918,030 new cancer cases diagnosed and 609,360 cancer deaths in the US alone in 2022. *Cancer Facts & Figures* 2022. Therefore, there is a need for an effective therapy for cancer treatment.

SUMMARY OF THE DISCLOSURE

Provided herein is a compound of Formula (I):

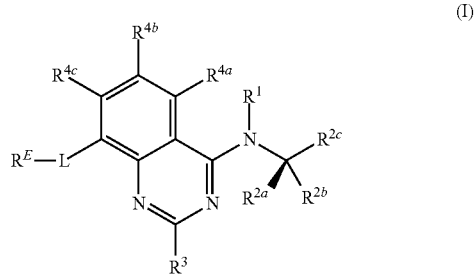

(I)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^3$, $R^{4a}$, $R^{4b}$, and $R^{4c}$ are each independently (i) hydrogen, deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, —C(O)O$R^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^c$, or —S(O)$_2$NR$^{1b}$R$^{1c}$;

$R^{2a}$ and $R^{2b}$ are each independently hydrogen, deuterium, halo, $C_{1-6}$ alkyl, $C_{2-6}$ alkenyl, $C_{2-6}$ alkynyl, $C_{3-10}$ cycloalkyl, $C_{6-14}$ aryl, heteroaryl, or heterocyclyl;

$R^{2c}$ is $C_{3-10}$ cycloalkyl, $C_{6-14}$ aryl, heteroaryl, or heterocyclyl;

$R^E$ is an E3 ubiquitin ligase binding moiety;

L is a linker; and each $R^{1a}$, $R^{1b}$, $R^{1c}$, and $R^{1d}$ is independently hydrogen, deuterium, $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

wherein each alkyl, heteroalkyl, alkenyl, alkynyl, cycloalkyl, aryl, aralkyl, heteroaryl, and heterocyclyl is optionally substituted with one or more, in one embodiment, one, two, three, or four, substituents Q, wherein each Q is independently selected from: (a) deuterium, cyano, halo, imino, nitro, and oxo; (b) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(N$R^a$)N$R^bR^c$, —OC(S)$R^a$, —OC(S)O$R^a$, —OC(S)N$R^bR^c$, —OP(O)(O$R^b$)O$R^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, cyano, halo, nitro, imino, and oxo; (b) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(N$R^e$)N$R^fR^g$, —OC(S)$R^e$, —OC(S)O$R^e$, —OC(S)N$R^fR^g$, —OP(O)(O$R^f$)O$R^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —NRC(N$R^h$)N$R^fR^g$, —N$R^e$C(S)$R^h$, —N$R^e$C(S)O$R^f$, —N$R^e$C(S)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Also provided herein is a pharmaceutical composition comprising a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

Additionally provided herein is a method of treating, preventing, or ameliorating one or more symptoms of a disorder, disease, or condition mediated by a son of sevenless homolog 1 (SOS1) in a subject, comprising administering the subject in need thereof a therapeutically effective amount of a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

Furthermore, provided herein is a method of treating, preventing, or ameliorating one or more symptoms of a disorder, disease, or condition mediated by a RAS in a subject, comprising administering to the subject in need thereof a therapeutically effective amount of a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of treating, preventing, or ameliorating one or more symptoms of a proliferative disease in a subject, comprising administering to the subject in need thereof a therapeutically effective amount of a compound of Formula (I), or an enantiomer, a mixture of enantiomers, a diastereomer, a mixture of two or more diastereomers, a tautomer, a mixture of two or more tautomers, or an isotopic variant thereof, or a pharmaceutically acceptable salt, solvate, hydrate, or prodrug thereof.

Provided herein is a method of inhibiting the growth of a cell, comprising contacting the cell with a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

Provided herein is a method of inducing degradation of an SOS1, comprising contacting the SOS1 with a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and a biological molecule (e.g., a protein, enzyme, RNA, or DNA), cell, or tissue such that a physiological and/or chemical effect takes place as a result of such contact. Contacting can take place in vitro, ex vivo, or in vivo. In one embodiment, a therapeutic agent is contacted with a biological molecule in vitro to determine the effect of the therapeutic agent on the biological molecule. In another embodiment, a therapeutic agent is contacted with a cell in cell culture (in vitro) to determine the effect of the therapeutic agent on the cell. In yet another embodiment, the contacting of a therapeutic agent with a biological molecule, cell, or tissue includes the administration of a therapeutic agent to a subject having the biological molecule, cell, or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "$IC_{50}$" or "$EC_{50}$" refers to an amount, concentration, or dosage of a compound that is required for 50% inhibition of a maximal response in an assay that measures such a response.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human) without excessive toxicity, irritation, allergic response, immunogenicity, or other problems or complications, and commensurate with a reasonable benefit/risk ratio. See, e.g., *Remington: The Science and Practice of Pharmacy*, 23rd ed.; Adejare Ed.; Academic Press, 2020; *Handbook of Pharmaceutical Excipients*, 9th ed.; Sheskey et al., Eds.; Pharmaceutical Press, 2020; *Handbook of Pharmaceutical Additives*, 3rd ed.; Ash and Ash Eds.; Synapse Information Resources, 2007; *Pharmaceutical Preformulation and Formulation*, 1st ed.; Gibson Ed.; CRC Press, 2015.

The term "about" or "approximately" means an acceptable error for a particular value as determined by one of ordinary skill in the art, which depends in part on how the value is measured or determined. In certain embodiments, the term "about" or "approximately" means within 1, 2, or 3 standard deviations. In certain embodiments, the term "about" or "approximately" means within 25%, 20%, 15%, 10%, 9%, 8%, 7%, 6%, 5%, 4%, 3%, 2%, 1%, 0.5%, or 0.05% of a given value or range.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and isopropyl), butyl (including all isomeric forms, e.g., n-butyl, isobutyl, sec-butyl, and t-butyl), pentyl (including all isomeric forms, e.g., n-pentyl, isopentyl, sec-pentyl, neopentyl, and tert-pentyl), and hexyl (including all isomeric forms, e.g., n-hexyl, isohexyl, and sec-hexyl).

The terms "alkylene" and "alkanediyl" are used interchangeably herein in reference to a linear or branched saturated divalent hydrocarbon radical, wherein the alkanediyl is optionally be substituted with one or more substituents Q as described herein. For example, $C_{1-6}$ alkanediyl refers to a linear saturated divalent hydrocarbon radical of 1 to 6 carbon atoms or a branched saturated divalent hydrocarbon radical of 3 to 6 carbon atoms. In certain embodiments, the alkanediyl is a linear saturated divalent hydrocarbon radical that has 1 to 30 ($C_{1-30}$), 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 30 ($C_{3-30}$), 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkanediyl groups are also referred as "lower alkanediyl." Examples of alkanediyl groups include, but are not limited to, methanediyl, ethanediyl (including all isomeric forms, e.g., ethane-1,1-diyl and ethane-1,2-diyl), propanediyl (including all isomeric forms, e.g., propane-1,1-diyl, propane-1,2-diyl, and propane-1,3-diyl), butanediyl (including all isomeric forms, e.g., butane-1,1-diyl, butane-1,2-diyl, butane-1,3-diyl, and butane-1,4-diyl), pentanediyl (including all isomeric forms, e.g., pentane-1,1-diyl, pentane-1,2-diyl, pentane-1,3-diyl, and pentane-1,5-diyl), and hexanediyl (including all isomeric forms, e.g., hexane-1,1-diyl, hexane-1,2-diyl, hexane-1,3-diyl, and hexane-1,6-diyl). Examples of substituted alkanediyl groups include, but are not limited to, $-C(O)CH_2-$, $-C(O)(CH_2)_2-$, $-C(O)(CH_2)_3-$, $-C(O)(CH_2)_4-$, $-C(O)(CH_2)_5-$, $-C(O)(CH_2)_6-$, $-C(O)(CH_2)_7-$, $-C(O)(CH_2)_8-$, $-C(O)(CH_2)_9-$, $-C(O)(CH_2)_{10}-$, $-C(O)CH_2C(O)-$, $-C(O)(CH_2)_2C(O)-$, $-C(O)(CH_2)_3C(O)-$, $-C(O)(CH_2)_4C(O)-$, or $-C(O)(CH_2)_5C(O)-$.

The term "heteroalkyl" refers to a linear or branched saturated monovalent hydrocarbon radical that contains one or more heteroatoms on its main chain, each independently selected from O, S, and N. The heteroalkyl is optionally substituted with one or more substituents Q as described herein. For example, $C_{1-6}$ heteroalkyl refers to a linear saturated monovalent hydrocarbon radical of 1 to 6 carbon atoms or a branched saturated monovalent hydrocarbon radical of 3 to 6 carbon atoms. In certain embodiments, the heteroalkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkyl groups are also referred as "lower heteroalkyl." Examples of heteroalkyl groups include, but are not limited to, —$OCH_3$, —$OCH_2CH_3$, —$CH_2OCH_3$, —$NHCH_3$, —$ONHCH_3$, —$NHOCH_3$, —$SCH_3$, —$CH_2NHCH_2CH_3$, and —$NHCH_2CH_2CH_3$. Examples of substituted heteroalkyl groups include, but are not limited to, —$CH_2NHC(O)CH_3$ and —$NHC(O)CH_2CH_3$.

The terms "heteroalkylene" and "heteroalkanediyl" are used interchangeably herein in reference to a linear or branched saturated divalent hydrocarbon radical that contains one or more heteroatoms in its main chain, each independently selected from O, S, and N. The heteroalkylene is optionally substituted with one or more substituents Q as described herein. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —$CH_2O$—, —$(CH_2)_2O$—, —$(CH_2)_3O$—, —$(CH_2)_4O$—, —$(CH_2)_5O$—, —$(CH_2)_6O$—, —$(CH_2)_7O$—, —$(CH_2)_8O$—, —$(CH_2)_9O$—, —$(CH_2)_{10}O$—, —$CH_2OCH_2$—, —$CH_2CH_2O$—, —$(CH_2CH_2O)_2$—, —$(CH_2CH_2O)_3$—, —$(CH_2CH_2O)_4$—, —$(CH_2CH_2O)_5$—, —$CH_2NH$—, —$CH_2NHCH_2$—, —$CH_2CH_2NH$—, —$CH_2S$—, —$CH_2SCH_2$—, and —$CH_2CH_2S$—. Examples of substituted heteroalkylene groups include, but are not limited to, —$C(O)CH_2O$—, —$C(O)(CH_2)_2O$—, —$C(O)(CH_2)_3O$—, —$C(O)(CH_2)_4O$—, —$C(O)(CH_2)_5O$—, —$C(O)(CH_2)_6O$—, —$C(O)(CH_2)_7O$—, —$C(O)(CH_2)_8O$—, —$C(O)(CH_2)_9O$—, —$C(O)(CH_2)_{10}O$—, —$C(O)CH_2OCH_2CH_2O$—, —$C(O)CH_2O(CH_2CH_2O)_2$—, —$C(O)CH_2O(CH_2CH_2O)_3$—, —$C(O)CH_2O(CH_2CH_2O)_4$—, —$C(O)CH_2O(CH_2CH_2O)_5$—, —$CH_2NHC(O)CH_2$—, or —$CH_2CH_2C(O)NH$—.

The term "alkenyl" refers to a linear or branched monovalent hydrocarbon radical, which contains one or more, in one embodiment, one, two, three, or four, in another embodiment, one, carbon-carbon double bond(s). The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propenyl (including all isomeric forms, e.g., propen-1-yl, propen-2-yl, and allyl), and butenyl (including all isomeric forms, e.g., buten-1-yl, buten-2-yl, buten-3-yl, and 2-buten-1-yl).

The terms "alkenylene" and "alkenediyl" are used interchangeably herein in reference to a linear or branched divalent hydrocarbon radical, which contains one or more, in one embodiment, one, two, three, or four, in another embodiment, one, carbon-carbon double bond(s). The alkenediyl is optionally substituted with one or more substituents Q as described herein. The term "alkenediyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenediyl refers to a linear unsaturated divalent hydrocarbon radical of 2 to 6 carbon atoms or a branched unsaturated divalent hydrocarbon radical of 3 to 6 carbon atoms. In certain embodiments, the alkenediyl is a linear divalent hydrocarbon radical of 2 to 30 ($C_{2-30}$), 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 30 ($C_{3-30}$), 3 to 20 ($C_{3-20}$), 3 to 15 ($C_{3-15}$), 3 to 10 ($C_{3-10}$), or 3 to 6 ($C_{3-6}$) carbon atoms. Examples of alkenediyl groups include, but are not limited to, ethenediyl (including all isomeric forms, e.g., ethene-1,1-diyl and ethene-1,2-diyl), propanediyl (including all isomeric forms, e.g., 1-propene-1,1-diyl, 1-propene-1,2-diyl, and 1-propene-1,3-diyl), butenediyl (including all isomeric forms, e.g., 1-butene-1,1-diyl, 1-butene-1,2-diyl, and 1-butene-1,4-diyl), pentanediyl (including all isomeric forms, e.g., 1-pentene-1,1-diyl, 1-pentene-1,2-diyl, and 1-pentene-1,5-diyl), and hexanediyl (including all isomeric forms, e.g., 1-hexene-1,1-diyl, 1-hexene-1,2-diyl, 1-hexene-1,3-diyl, 1-hexene-1,4-diyl, 1-hexene-1,5-diyl, and 1-hexene-1,6-diyl).

The terms "heteroalkenylene" and "heteroalkenediyl" are used interchangeably herein in reference to a linear or branched divalent hydrocarbon radical, which contains one or more, in one embodiment, one, two, three, or four, in another embodiment, one, carbon-carbon double bond(s), and which contains one or more heteroatoms each independently selected from O, S, and N in the hydrocarbon chain. The heteroalkenylene is optionally substituted with one or more substituents Q as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, —CH=CHO—, —CH=CHOCH$_2$—, —CH=CHCH$_2$O—, —CH=CHS—, —CH=CHSCH$_2$—, —CH=CHCH$_2$S—, or —CH=CHCH$_2$NH—.

The term "alkynyl" refers to a linear or branched monovalent hydrocarbon radical, which contains one or more, in one embodiment, one, two, three, or four, in another embodiment, one, carbon-carbon triple bond(s). An alkynyl group does not contain a carbon-carbon double bond. The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$)

carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl and 2-hexyn-1-yl).

The terms "alkynylene" and "alkynediyl" are used interchangeably herein in reference to a linear or branched divalent hydrocarbon radical, which contains one or more, in one embodiment, one, two, three, or four, in another embodiment, one, carbon-carbon triple bond(s). An alkynylene group does not contain a carbon-carbon double bond. The alkynediyl is optionally substituted with one or more substituents Q as described herein. For example, $C_{2-6}$ alkynediyl refers to a linear unsaturated divalent hydrocarbon radical of 2 to 6 carbon atoms or a branched unsaturated divalent hydrocarbon radical of 4 to 6 carbon atoms. In certain embodiments, the alkynediyl is a linear divalent hydrocarbon radical of 2 to 30 ($C_{2-30}$), 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 4 to 30 ($C_{4-30}$), 4 to 20 ($C_{4-20}$), 4 to 15 ($C_{4-15}$), 4 to 10 ($C_{4-10}$), or 4 to 6 ($C_{4-6}$) carbon atoms. Examples of alkynediyl groups include, but are not limited to, ethynediyl, propynediyl (including all isomeric forms, e.g., 1-propyne-1,3-diyl and 1-propyne-3,3-diyl), butynediyl (including all isomeric forms, e.g., 1-butyne-1,3-diyl, 1-butyne-1,4-diyl, and 2-butyne-1,1-diyl), pentynediyl (including all isomeric forms, e.g., 1-pentyne-1,3-diyl, 1-pentyne-1,4-diyl, and 2-pentyne-1,1-diyl), and hexynediyl (including all isomeric forms, e.g., 1-hexyne-1,3-diyl, 1-hexyne-1,4-diyl, and 2-hexyne-1,1-diyl).

The terms "heteroalkynylene" and "heteroalkynediyl" are used interchangeably herein in reference to a linear or branched divalent hydrocarbon radical, which contains one or more, in one embodiment, one, two, three, or four, in another embodiment, one, carbon-carbon triple bond(s), and which contains one or more heteroatoms in its main chain, each independently selected from O, S, and N. A heteroalkynylene group does not contain a carbon-carbon double bond. The heteroalkynylene is optionally substituted with one or more substituents Q as described herein. For example, $C_{2-6}$ heteroalkynylene refers to a linear unsaturated divalent hydrocarbon radical of 2 to 6 carbon atoms or a branched unsaturated divalent hydrocarbon radical of 4 to 6 carbon atoms. In certain embodiments, the heteroalkynylene is a linear divalent hydrocarbon radical of 2 to 30 ($C_{2-30}$), 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 4 to 30 ($C_{4-30}$), 4 to 20 ($C_{4-20}$), 4 to 15 ($C_{4-15}$), 4 to 10 ($C_{4-10}$), or 4 to 6 ($C_{4-6}$) carbon atoms. Examples of heteroalkynylene groups include, but are not limited to, —C≡CCH$_2$O—, —C≡CCH$_2$S—, or —C≡CCH$_2$NH—.

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged or non-bridged, and/or fused bicyclic group. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. In one embodiment, the cycloalkyl is monocyclic. In another embodiment, the cycloalkyl is bicyclic. In yet another embodiment, the cycloalkyl is tricyclic. In still another embodiment, the cycloalkyl is polycyclic. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[1.1.1]pentyl, bicyclo[2.1.1]hexyl, bicyclo[2.2.1]heptyl, bicyclo[2.2.2]octyl, decalinyl, and adamantyl.

The terms "cycloalkylene" and "cycloalkanediyl" are used interchangeably herein in reference to a cyclic divalent hydrocarbon radical, which may be optionally substituted with one or more substituents Q as described herein. In one embodiment, cycloalkanediyl groups may be saturated or unsaturated but non-aromatic, and/or bridged, and/or non-bridged, and/or fused bicyclic groups. In certain embodiments, the cycloalkanediyl has from 3 to 30 ($C_{3-30}$), 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkanediyl groups include, but are not limited to, cyclopropanediyl (including all isomeric forms, e.g., cyclopropane-1,1-diyl and cyclopropane-1,2-diyl), cyclobutanediyl (including all isomeric forms, e.g., cyclobutane-1,1-diyl, cyclobutane-1,2-diyl, and cyclobutane-1,3-diyl), cyclopentanediyl (including all isomeric forms, e.g., cyclopentane-1,1-diyl, cyclopentane-1,2-diyl, and cyclopentane-1,3-diyl), cyclohexanediyl (including all isomeric forms, e.g., cyclohexane-1,1-diyl, cyclohexane-1,2-diyl, cyclohexane-1,3-diyl, and cyclohex-1,4-diyl), cycloheptanediyl (including all isomeric forms, e.g., cycloheptane-1,1-diyl, cycloheptane-1,2-diyl, cycloheptane-1,3-diyl, and cycloheptane-1,4-diyl), decalinediyl (including all isomeric forms, e.g., decaline-1,1-diyl, decaline-1,2-diyl, and decaline-1,8-diyl), and adamantdiyl (including all isomeric forms, e.g., adamant-1,2-diyl, adamant-1,3-diyl, and adamant-1,8-diyl).

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 15 ($C_{6-15}$), or from 6 to 10 ($C_{6-10}$) ring carbon atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is bicyclic. In yet another embodiment, the aryl is tricyclic. In still another embodiment, the aryl is polycyclic. In certain embodiments, the aryl is optionally substituted with one or more substituents Q as described herein.

The terms "arylene" and "arenediyl" are used interchangeably herein in reference to a divalent monocyclic aromatic hydrocarbon radical or divalent polycyclic aromatic hydrocarbon radical that contains at least one aromatic hydrocarbon ring. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene (including all isomeric forms, e.g., phen-1,2-diyl, phen-1,3-diyl, and phen-1,4-diyl), naphthylene (including all isomeric forms, e.g., naphth-1,2-diyl, naphth-1,3-diyl, and naphth-1,8-diyl), fluorenylene (including all isomeric forms, e.g., fluoren-1,2-diyl, fluoren-1,3-diyl, and fluoren-1,8-diyl), azulenylene (including all isomeric forms, e.g., azulen-1,2-diyl, azulen-1,3-diyl, and azulen-1,8-diyl), anthrylene (including all isomeric forms, e.g., anthr-1,2-diyl, anthr-1,3-diyl, and anthr-1,8-diyl), phenanthrylene (including all isomeric forms, e.g., phenanthr-1,2-diyl, phenanthr-1,3-diyl, and phenanthr-1,8-diyl), pyrenylene (including all isomeric forms, e.g., pyren-1,2-diyl, pyren-1,3-diyl, and pyren-1,8-diyl), biphenylene (including all isomeric forms, e.g., biphen-2,3-diyl, biphen-3,4'-diyl, and biphen-4,4'-diyl), and terphenylene (including all isomeric forms, e.g., terphen-2,3-diyl, terphen-3,4'-diyl, and terphen-4,4'-diyl). Arylene also refers to bicyclic or tricyclic carbon rings, where one of the rings is aromatic and the others of which may be saturated, partially unsaturated, or aromatic, for example, dihydronaphthylene (including all isomeric forms, e.g., dihydronaphth-1,2-diyl and dihydronaphth-1,8-diyl), indenylene (including all isomeric forms, e.g., inden-1,2-diyl, inden-1,5-diyl, and inden-1,7-diyl), indanylene (including all isomeric forms, e.g., indan-1,2-diyl, indan-1,5-diyl, and indan-1,7-diyl), or tetrahydronaphthylene (tetralinylene) (including all isomeric forms, e.g., tetrahydronaphth-1,2-diyl, tetrahydronaphth-1,5-diyl, and tetrahydronaphth-1,8-diyl). In certain embodiments, arylene is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, phenylethyl (including all isomeric forms, e.g., 1-phenylethyl and 2-phenylethyl), and phenylpropyl (including all isomeric forms, e.g., 1-phenylpropyl, 2-phenylpropyl, and 3-phenylpropyl). In certain embodiments, the aralkyl is optionally substituted with one or more substituents Q as described herein.

The term "aralkylene" or "arylalkylene" refers to a divalent alkyl group substituted with one or more aryl groups. In certain embodiments, the aralkylene has from 7 to 30 ($C_{7-30}$), from 7 to 20 ($C_{7-20}$), or from 7 to 16 ($C_{7-16}$) carbon atoms. Examples of aralkylene groups include, but are not limited to, benzylene (including all isomeric forms, e.g., phenylmethdiyl), phenylethylene (including all isomeric forms, e.g., 2-phenyl-ethan-1,1-diyl and 2-phenyl-ethan-1,2-diyl), and phenylpropylene (including all isomeric forms, e.g., 3-phenyl-propan-1,1-diyl, 3-phenyl-propan-1,2-diyl, and 3-phenyl-propan-1,3-diyl). In certain embodiments, the aralkylene is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each independently selected from O, S, and N, in the ring. For a heteroaryl group containing a heteroaromatic ring and a nonaromatic heterocyclic ring, the heteroaryl group is not bonded to the rest of a molecule through its nonaromatic heterocyclic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In another embodiment, the heteroaryl is bicyclic. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, fluoropyridyl (including all isomeric forms, e.g., furo[2,3-b]pyridinyl, furo[2,3-c]pyridinyl, furo[3,2-b]pyridinyl, furo[3,2-c]pyridinyl, furo[3,4-b]pyridinyl, and furo[3,4-c]pyridinyl), imidazopyridinyl (including all isomeric forms, e.g., imidazo[1,2-a]pyridinyl, imidazo[4,5-b]pyridinyl, and imidazo[4,5-c]pyridinyl), imidazothiazolyl (including all isomeric forms, e.g., imidazo[2,1-b]thiazolyl and imidazo[4,5-d]thiazolyl), indazolyl, indolizinyl, indolyl, isobenzofuranyl, isobenzothienyl (i.e., benzo[c]thienyl), isoindolyl, isoquinolinyl, naphthyridinyl (including all isomeric forms, e.g., 1,5-naphthyridinyl, 1,6-naphthyridinyl, 1,7-naphthyridinyl, and 1,8-naphthyridinyl), oxazolopyridinyl (including all isomeric forms, e.g., oxazolo[4,5-b]pyridinyl, oxazolo[4,5-c]pyridinyl, oxazolo[5,4-b]pyridinyl, and oxazolo[5,4-c]pyridinyl), phthalazinyl, pteridinyl, purinyl, pyrrolopyridyl (including all isomeric forms, e.g., pyrrolo[2,3-b]pyridinyl, pyrrolo[2,3-c]pyridinyl, pyrrolo[3,2-b]pyridinyl, and pyrrolo[3,2-c]pyridinyl), quinolinyl, quinoxalinyl, quinazolinyl, thiadiazolopyrimidyl (including all isomeric forms, e.g., [1,2,5]thiadiazolo[3,4-d]pyrimidinyl and [1,2,3]thiadiazolo[4,5-d]pyrimidinyl), and thienopyridyl (including all isomeric forms, e.g., thieno[2,3-b]pyridinyl, thieno[2,3-c]pyridinyl, thieno[3,2-b]pyridinyl, and thieno[3,2-c]pyridinyl). In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl (including all isomeric forms, e.g., 1,5-phenanthrolinyl, 1,6-phenanthrolinyl, 1,7-phenanthrolinyl, 1,9-phenanthrolinyl, and 2,10-phenanthrolinyl), phenarsazinyl, phenazinyl, phenothiazinyl, phenoxazinyl, and xanthenyl. In certain embodiments, the heteroaryl is optionally substituted with one or more substituents Q as described herein.

The terms "heteroarylene" and "heteroarenediyl" are used interchangeably herein in reference to a divalent monocyclic aromatic group or divalent polycyclic aromatic group that contains at least one aromatic ring, wherein at least one aromatic ring contains one or more heteroatoms in the ring, each of which is independently selected from O, S, and N. For a heteroarylene group containing a heteroaromatic ring and a nonaromatic heterocyclic ring, the heteroarylene group is not bonded to the rest of a molecule via its nonaromatic heterocyclic ring. Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furandiyl, imidazoldiyl, isothiazoldiyl, isoxazoldiyl, oxadiazoldiyl, oxazoldiyl, pyrazindiyl, pyrazoldiyl, pyridazindiyl, pyridindiyl, pyrimidindiyl, pyrroldiyl, thiadiazoldiyl, thiazoldiyl, thiendiyl, tetrazoldiyl, triazinediyl, and triazoldiyl. Examples of bicyclic heteroarylene groups include, but are not limited to, benzofurandiyl, benzimidazoldiyl, benzoisoxazoldiyl, benzopyrandiyl, benzothiadiazoldiyl, benzothiazoldiyl, benzothiendiyl, benzotriazoldiyl, benzoxazoldiyl, furopyridindiyl (including all isomeric forms, e.g., furo[2,3-b]pyridindiyl, furo[2,3-c]pyridindiyl, furo[3,2-b]pyridindiyl, furo[3,2-c]pyridindiyl, furo[3,4-b]pyridindiyl, and furo[3,4-c]pyridindiyl), imidazopyridindiyl (including all isomeric forms, e.g., imidazo[1,2-a]pyridindiyl, imidazo[4,5-b]pyridindiyl, and imidazo[4,5-c]-pyridindiyl), imidazothiazoldiyl (including all isomeric forms, e.g., imidazo[2,1-b]thiazoldiyl and imidazo[4,5-d]thiazoldiyl), indazoldiyl, indolizindiyl, indoldiyl, isobenzofurandiyl, isobenzothiendiyl (i.e., benzo[c]thiendiyl), isoindoldiyl, isoquinolindiyl, naphthyridindiyl (including all isomeric forms, e.g., 1,5-naphthyridindiyl, 1,6-naphthyridindiyl, 1,7-naphthyridindiyl, and 1,8-naphthyridindiyl), oxazolopyridindiyl (including all isomeric forms, e.g., oxazolo[4,5-b]pyridindiyl, oxazolo[4,5-c]pyridindiyl, oxazolo[5,4-b]pyridindiyl, and oxazolo[5,4-c]pyridindiyl), phthalazindiyl, pteridindiyl, purindiyl, pyrrolopyridindiyl (including all isomeric forms, e.g., pyrrolo[2,3-b]pyridindiyl, pyrrolo[2,3-c]pyridindiyl, pyrrolo[3,2-b]pyridindiyl, and pyrrolo[3,2-c]pyridindiyl), quinolindiyl, quinoxalindiyl, quinazolindiyl, thiadiazolopyrimidindiyl (including all isomeric forms, e.g., [1,2,5]thiadiazolo[3,4-d]-pyrimidindiyl and [1,2,3]thiadiazolo[4,5-d]pyrimidindiyl), and thienopyridindiyl (including all isomeric forms, e.g., thieno[2,3-b]pyridindiyl, thieno[2,3-c]pyridindiyl, thieno[3,2-b]pyridindiyl, and thieno[3,2-c]pyridindiyl). Examples of tricyclic heteroarylene groups include, but are not limited to, acridindiyl, benzindoldiyl, carbazoldiyl, dibenzofurandiyl, perimidindiyl, phenanthrolindiyl (including all isomeric forms, e.g., 1,5-phenanthrolindiyl, 1,6-phenanthrolindiyl, 1,7-phenanthrolindiyl, 1,9-phenanthrolindiyl, and 2,10-phenanthrolindiyl), phenanthridindiyl, phenarsazindiyl, phenazindiyl, phenothiazindiyl, phenoxazindiyl, and xanthendiyl. In certain embodiments, heteroarylene is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each independently selected from O, S, and N; and the remaining ring atoms are carbon atoms. For a heterocyclyl group containing a heteroaromatic ring and a nonaromatic heterocyclic ring, the heterocyclyl group is not bonded to the rest of a molecule through the heteroaromatic ring. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclyls and heterocyclic groups include, but are not limited to, azepinyl, benzodioxanyl, benzodioxolyl, benzofuranonyl, chromanyl, decahydroisoquinolinyl, dihydrobenzofuranyl, dihydrobenzisothiazolyl, dihydrobenzisoxazinyl (including all isomeric forms, e.g., 1,4-dihydrobenzo[d][1,3]oxazinyl, 3,4-dihydrobenzo[c][1,2]-oxazinyl, and 3,4-dihydrobenzo[d][1,2]oxazinyl), dihydrobenzothienyl, dihydroisobenzofuranyl, dihydrobenzo[c]thienyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isochromanyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, thiochromanyl, tetrahydroquinolinyl, and 1,3,5-trithianyl. In certain embodiments, the heterocyclyl is optionally substituted with one or more substituents Q as described herein.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. For a heterocyclylene group containing a heteroaromatic ring and a nonaromatic heterocyclic ring, the heterocyclylene group has at least one bond to the rest of a molecule via its nonaromatic heterocyclic ring. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclylene groups include, but are not limited to, azepindiyl, benzodioxandiyl, benzodioxoldiyl, benzofuranondiyl, chromandiyl, decahydroisoquinolindiyl, dihydrobenzofurandiyl, dihydrobenzisothiazoldiyl, dihydrobenzisoxazindiyl (including all isomeric forms, e.g., 1,4-dihydrobenzo[d][1,3]oxazindiyl, 3,4-dihydrobenzo[c][1,2]oxazindiyl, and 3,4-dihydrobenzo[d][1,2]oxazindiyl), dihydrobenzothiendiyl, dihydroisobenzofurandiyl, dihydrobenzo[c]thiendiyl, dihydrofurdiyl, dihydroisoindoldiyl, dihydropyrandiyl, dihydropyrazoldiyl, dihydropyrazindiyl, dihydropyridindiyl, dihydropyrimidindiyl, dihydropyrroldiyl, dioxolandiyl, 1,4-dithiandiyl, furanondiyl, imidazolidindiyl, imidazolindiyl, indolindiyl, isochromandiyl, isoindolindiyl, isothiazolidindiyl, isoxazolidindiyl, morpholindiyl, octahydroindoldiyl, octahydroisoindoldiyl, oxazolidinondiyl, oxazolidindiyl, oxirandiyl, piperazindiyl, piperidindiyl, 4-piperidondiyl, pyrazolidindiyl, pyrazolindiyl, pyrrolidindiyl, pyrrolindiyl, quinuclidindiyl, tetrahydrofurdiyl, tetrahydroisoquinolindiyl, tetrahydropyrandiyl, tetrahydrothiendiyl, thiamorpholindiyl, thiazolidindiyl, thiochromandiyl, tetrahydroquinolindiyl, and 1,3,5-trithiandiyl. In certain embodiments, the heterocyclylene is optionally substituted with one or more substituents Q as described herein.

The term "halogen," "halide," or "halo" refers to fluoro, chloro, bromo, and/or iodo.

The term "optionally substituted" is intended to mean that a group or substituent, such as an alkyl, alkylene, heteroalkyl, heteroalkylene, alkenyl, alkenylene, heteroalkenylene, alkynyl, alkynylene, heteroalkynylene, cycloalkyl, cycloalkylene, aryl, arylene, aralkyl, aralkylene, heteroaryl, heteroarylene, heterocyclyl, or heterocyclylene group, may be substituted with one or more, in one embodiment, one, two, three, or four, substituents Q, each of which is independently selected from, e.g., (a) deuterium (-D), cyano (—CN), halo, imino (=NH), nitro (—NO$_2$), and oxo (=O); (b) C$_{1-6}$ alkyl, C$_{1-6}$ heteroalkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(NR$^a$)NR$^b$R$^c$, —OC(S)R$^a$, —OC(S)OR$^a$, —OC(S)NR$^b$R$^c$, —OP(O)(OR$^b$)OR, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) C$_{1-6}$ alkyl, C$_{1-6}$ heteroalkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is optionally substituted with one or more, in one embodiment, one, two, three, or four, substituents Q$^a$; or (iii) R$^b$ and R$^c$ together with the N atom to which they are attached form heterocyclyl optionally substituted with one or more, in one embodiment, one, two, three, or four, substituents Q$^a$. As used herein, all groups that can be substituted are "optionally substituted."

In one embodiment, each Q$^a$ is independently selected from: (a) deuterium, cyano, halo, imino, nitro, and oxo; (b) C$_{1-6}$ alkyl, C$_{1-6}$ heteroalkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(NR$^e$)NR$^f$R$^g$, —OC(S)R$^e$, —OC(S)OR$^e$, —OC(S)NR$^f$R$^g$, —OP(O)(OR$^f$)OR$^g$, —OS(O)R$^e$, —OS(O)$_2$R$^e$, —OS(O)NR$^f$R$^g$, —OS(O)$_2$NR$^f$R$^g$, —NR$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In certain embodiments, "optically active" and "enantiomerically active" refer to a collection of molecules, which has an enantiomeric excess of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question. In certain embodiments, an optically active compound comprises about 98% or more of one enantiomer and about 2% or less of the other enantiomer based on the total weight of the enantiomeric mixture in question. In certain embodiments, an optically active compound comprises about 99% or more of one enantiomer and about 1% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen ($^1$H), deuterium ($^2$H), carbon-12 ($^{12}$C), carbon-13 ($^{13}$C), nitrogen-14 (14N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium (3H), carbon-11 ($^{11}$C), carbon-14 (14C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I, iodine-125 ($^{125}$I), iodine-129 ($^{129}$I), and iodine-131 ($^{131}$I). It will be understood that, in a compound as provided herein, any hydrogen can be $^2$H, as example, or any carbon can be $^{13}$C, as example, or any nitrogen can be $^{15}$N, as example, or any oxygen can be $^{18}$O, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^1$H for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium (1H), deuterium (2H or D), and tritium ($^3$H), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}C$) and carbon-13 ($^{13}C$) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}C$ enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean, when referred to a substance, sufficiently homogeneous to appear free of readily detectable impurities as determined by a standard analytical method used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 95%, at least about 96%, at least about 97%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which are present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

For a divalent group described herein, no orientation is implied by the direction in which the divalent group is presented. For example, unless a particular orientation is specified, the formula —C(O)NH— represents both —C(O)NH— and —NHC(O)—.

The phrase "an enantiomer, a mixture of enantiomers, a diastereomer, a mixture of two or more diastereomers, a tautomer, a mixture of two or more tautomers, or an isotopic variant thereof, or a pharmaceutically acceptable salt, solvate, hydrate, or prodrug thereof" has the same meaning as the phrase "(i) an enantiomer, a mixture of enantiomers, a diastereomer, a mixture of two or more diastereomers, a tautomer, a mixture of two or more tautomers, or an isotopic variant of the compound referenced therein; (ii) a pharmaceutically acceptable salt, solvate, hydrate, or prodrug of the compound referenced therein; or (iii) a pharmaceutically acceptable salt, solvate, hydrate, or prodrug of an enantiomer, a mixture of enantiomers, a diastereomer, a mixture of two or more diastereomers, a tautomer, a mixture of two or more tautomers, or an isotopic variant of the compound referenced therein."

Compounds

In one embodiment, provided herein is a compound of Formula (I):

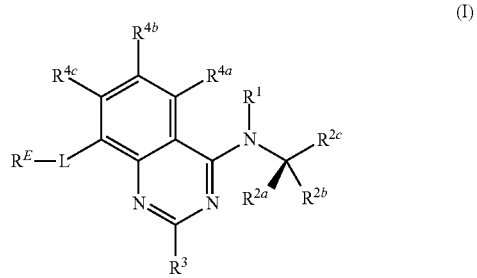

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^3$, $R^{4a}$, $R^{4b}$, and $R^{4c}$ are each independently (i) hydrogen, deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, —C(O)O$R^{1a}$, —C(O)N$R^{1b}R^{1c}$, —C(O)S$R^{1a}$, —C(NR$^{1a}$)NR$^{1b}R^{1c}$, —C(S)$R^{1a}$, —C(S)O$R^{1a}$, —C(S)NR$^{1b}R^{1c}$, —O$R^{1a}$, —OC(O)$R^{1a}$, —OC(O)O$R^{1a}$, —OC(O)NR$^{1b}R^{1c}$, —OC(O)S$R^{1a}$, —OC(NR$^{1a}$)NR$^{1b}R^{1c}$, —OC(S)$R^{1a}$, —OC(S)O$R^{1a}$, —OC(S)NR$^{1b}R^{1c}$, —OS(O)$R^{1a}$, —OS(O)$_2R^{1a}$, —OS(O)NR$^{1b}R^{1c}$, —OS(O)$_2$NR$^{1b}R^{1c}$, —NR$^{1b}R^{1c}$, —NR$^{1a}$C(O)$R^{1d}$, —NR$^{1a}$C(O)O$R^{1d}$, —NR$^{1a}$C(O)NR$^{1b}R^{1c}$, —NR$^{1a}$C(O)S$R^{1d}$, —NR$^{1a}$C(NR$^{1d}$)NR$^{1b}R^{1c}$, —NR$^{1a}$C(S)$R^{1d}$, —NR$^{1a}$C(S)O$R^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{2a}$ and R$^{2b}$ are each independently hydrogen, deuterium, halo, C$_{1-6}$ alkyl, C$_{2-6}$ alkenyl, C$_{2-6}$ alkynyl, C$_{3-10}$ cycloalkyl, C$_{6-14}$ aryl, heteroaryl, or heterocyclyl;

R$^{2c}$ is C$_{3-10}$ cycloalkyl, C$_{6-14}$ aryl, heteroaryl, or heterocyclyl;

R$^E$ is an E3 ubiquitin ligase binding moiety;

L is a linker; and each R$^{1a}$, R$^{1b}$, R$^{1c}$, and R$^{1d}$ is independently hydrogen, deuterium, C$_{1-6}$ alkyl, C$_{1-6}$ heteroalkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl;

wherein each alkyl, heteroalkyl, alkenyl, alkynyl, cycloalkyl, aryl, aralkyl, heteroaryl, and heterocyclyl is optionally substituted with one or more, in one embodiment, one, two, three, or four, substituents Q, wherein each Q is independently selected from: (a) deuterium, cyano, halo, imino, nitro, and oxo; (b) C$_{1-6}$ alkyl, C$_{1-6}$ heteroalkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(NR$^a$)NR$^b$R$^c$, —OC(S)R$^a$, —OC(S)OR$^a$, —OC(S)NR$^b$R$^c$, —OP(O)(OR$^b$)OR$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) C$_{1-6}$ alkyl, C$_{1-6}$ heteroalkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$;

wherein each Q$^a$ is independently selected from: (a) deuterium, cyano, halo, nitro, imino, and oxo; (b) C$_{1-6}$ alkyl, C$_{1-6}$ heteroalkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(NR)NR$^f$R$^g$, —OC(S)R$^e$, —OC(S)OR$^e$, —OC(S)NR$^f$R$^g$, —OP(O)(OR$^f$)OR$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR, —NR$^e$C(O)NR$^f$R$^g$, —NR$^e$C(O)SR$^f$, —NRC(NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In certain embodiments, the compound provided herein is not 3-(4-(1-(7-(4-(((R)-1-(3-bromophenyl)ethyl)amino)-6,7-dimethoxy-2-methylquinazolin-8-yl)heptyl)piperidin-4-yl)-6-fluoro-1-oxoisoindolin-2-yl)piperidine-2,6-dione. In certain embodiments, the compound provided herein is not 3-(4-(1-(7-(6,7-dimethoxy-2-methyl-4-(((R)-1-(4-(2-((methylamino)-methyl)phenyl)thiophen-2-yl)ethyl)amino) quinazolin-8-yl)heptyl)piperidin-4-yl)-6-fluoro-1-oxoisoindolin-2-yl)piperidine-2,6-dione. In certain embodiments, the compound provided herein is not 3-(4-(1-(7-(6,7-dimethoxy-2-methyl-4-(((S)-1-(4-(2-((methylamino)methyl)-phenyl)-thiophen-2-yl)ethyl)amino)quinazolin-8-yl)heptyl)piperidin-4-yl)-6-fluoro-1-oxoisoindolin-2-yl)piperidine-2,6-dione.

In certain embodiments, in Formula (I), R$^{2c}$ is C$_{3-10}$ cycloalkyl, optionally substituted with one or more substituents Q. In certain embodiments, in Formula (I), R$^{2c}$ is C$_{6-14}$ aryl, optionally substituted with one or more substituents Q. In certain embodiments, in Formula (I), R$^{2c}$ is heteroaryl, optionally substituted with one or more substituents Q. In certain embodiments, in Formula (I), R$^{2c}$ is heterocyclyl, optionally substituted with one or more substituents Q.

In certain embodiments, in Formula (I), R$^{2c}$ is C$_{6-14}$ aryl or heteroaryl, each optionally substituted with one, two, or three substituents Q. In certain embodiments, in Formula (I), R$^{2c}$ is C$_{6-14}$ aryl, optionally substituted with one, two, or three substituents Q. In certain embodiments, in Formula (I), R$^{2c}$ is C$_{6-14}$ aryl, substituted with one, two, or three substituents Q. In certain embodiments, in Formula (I), R$^{2c}$ is C$_{6-14}$ aryl, substituted with one substituent Q. In certain embodiments, in Formula (I), R$^{2c}$ is C$_{6-14}$ aryl, substituted with two substituents Q. In certain embodiments, in Formula (I), R$^{2c}$ is C$_{6-14}$ aryl, substituted with three substituents Q.

In certain embodiments, in Formula (I), R$^{2c}$ is C$_{6-14}$ aryl, substituted with one, two, or three substituents, wherein each substituent is independently (i) cyano or halo; (ii) C$_{1-6}$ alkyl or C$_{6-14}$ aryl, each optionally substituted with one or more substituents Q; or (iii) —OR$^{1a}$, —NR$^{1b}$R$^{1c}$, or —S(O)$_2$R$^{1a}$, wherein each R$^{1a}$, R$^{1b}$, and R$^{1c}$ is as defined herein. In certain embodiments, in Formula (I), R$^{2c}$ is C$_{6-14}$ aryl, substituted with one, two, or three substituents, wherein each substituent is independently cyano, fluoro, chloro, bromo, methyl, ethyl, fluoromethyl, difluoromethyl, trifluoromethyl, 1-cyano-1,1-difluoromethyl, 1,1-difluoro-2-hydroxy-ethyl, 1,1-difluoro-2-hydroxy-2-methylpropyl, methylaminomethyl, 2-aminomethylphenyl, 2-(2-aminoethyl)phenyl, 2-methylaminomethylphenyl, 2-dimethylaminomethylphenyl, hydroxyl, methoxy, amino, or methylsulfonyl. In certain embodiments, in Formula (I), R$^{2c}$ is C$_{6-14}$ aryl, substituted with one, two, or three substituents, wherein each substituent is independently fluoro, methyl, difluoromethyl, trifluoromethyl, 1,1-difluoro-2-hydroxyethyl, or amino.

In certain embodiments, in Formula (I), R$^{2c}$ is phenyl, optionally substituted with one, two, or three substituents Q. In certain embodiments, in Formula (I), R$^{2c}$ is phenyl, substituted with one, two, or three substituents Q. In certain embodiments, in Formula (I), R$^{2c}$ is phenyl, substituted with one substituent Q. In certain embodiments, in Formula (I), R$^{2c}$ is phenyl, substituted with two substituents Q. In certain embodiments, in Formula (I), R$^{2c}$ is phenyl, substituted with three substituents Q.

In certain embodiments, in Formula (I), R$^{2c}$ is phenyl, substituted with one, two, or three substituents, wherein each substituent is independently (i) cyano or halo; (ii) $C_{1-6}$ alkyl or $C_{6-14}$ aryl, each optionally substituted with one or more substituents Q; or (iii) —$OR^{1a}$, —$NR^{1b}R^{1c}$, or —$S(O)_2R^{1a}$, wherein each $R^{1a}$, $R^{1b}$, and $R^{1c}$ is as defined herein. In certain embodiments, in Formula (I), $R^{2c}$ is phenyl, substituted with one, two, or three substituents, wherein each substituent is independently cyano, fluoro, chloro, bromo, methyl, ethyl, fluoromethyl, difluoromethyl, trifluoromethyl, 1-cyano-1,1-difluoromethyl, 1,1-difluoro-2-hydroxy-ethyl, 1,1-difluoro-2-hydroxy-2-methylpropyl, methylaminomethyl, 2-aminomethylphenyl, 2-(2-aminoethyl)phenyl, 2-methylaminomethylphenyl, 2-dimethylaminomethylphenyl, hydroxyl, methoxy, amino, or methylsulfonyl. In certain embodiments, in Formula (I), $R^{2c}$ is phenyl, substituted with one, two, or three substituents, wherein each substituent is independently fluoro, methyl, difluoromethyl, trifluoromethyl, 1,1-difluoro-2-hydroxyethyl, or amino.

In certain embodiments, in Formula (I), $R^{2c}$ is 3-cyanophenyl, 3-bromophenyl, 3-methylphenyl, 3-difluoromethylphenyl, 3-trifluoromethylphenyl, 3-(1-cyano-1,1-difluoromethyl)phenyl, 3-(1,1-difluoro-2-hydroxyethyl)phenyl, 3-(2-aminomethylphenyl)phenyl, 3-cyano-5-fluorophenyl, 3-cyano-2-methylphenyl, 3-cyano-5-methylphenyl, 3-cyano-2-trifluoromethylphenyl, 3-cyano-5-hydroxyphenyl, 3-cyano-2-methoxyphenyl, 2,3-difluorophenyl, 2,4-difluorophenyl, 2-chloro-3-fluorophenyl, 2-chloro-4-fluorophenyl, 2-chloro-3-difluoromethylphenyl, 2-chloro-3-methylphenyl, 3-chloro-2-methylphenyl, 3-difluoromethyl-2-fluorophenyl, 3-difluoromethyl-2-methylphenyl, 2-fluoro-3-(1,1-difluoro-2-hydroxy-2-methylpropyl)phenyl, 2-fluoro-3-methylphenyl, 3-fluoro-2-methylphenyl, 3-fluoro-4-methylphenyl, 4-fluoro-2-methylphenyl, 2-fluoro-3-difluoromethylphenyl, 2-fluoro-3-trifluoromethylphenyl, 3-fluoro-5-trifluoromethylphenyl, 2-fluoromethyl-3-difluoromethylphenyl, 2,3-di(difluoromethyl)phenyl, 2-methyl-3-trifluoromethylphenyl, 2-ethyl-3-difluoromethylphenyl, 2-methyl-3-methylaminomethylphenyl, 2-methyl-3-methylsulfonylphenyl, 3-methyl-5-trifluoromethylphenyl, 3-hydroxy-5-trifluoromethylphenyl, 3-amino-5-trifluoromethylphenyl, 3-amino-4-fluoro-5-trifluoromethylphenyl, 5-amino-2-fluoro-3-trifluoromethylphenyl, 5-amino-2-methyl-3-trifluoromethylphenyl, 3-cyano-2,5-difluorophenyl, 3-cyano-5-fluoro-2-methylphenyl, or 5-fluoro-2-methyl-3-trifluoromethylphenyl.

In certain embodiments, in Formula (I), $R^{2c}$ is bicyclic $C_{8-14}$ aryl, optionally substituted with one, two, or three substituents Q. In certain embodiments, in Formula (I), $R^{2c}$ is bicyclic $C_{8-14}$ aryl, substituted with one, two, or three substituents Q. In certain embodiments, in Formula (I), $R^{2c}$ is bicyclic $C_{8-14}$ aryl, substituted with one substituent Q. In certain embodiments, in Formula (I), $R^{2c}$ is bicyclic $C_{8-14}$ aryl, substituted with two substituents Q. In certain embodiments, in Formula (I), $R^{2c}$ is bicyclic $C_{8-14}$ aryl, substituted with three substituents Q.

In certain embodiments, in Formula (I), $R^{2c}$ is 5,6- or 6,6-fused $C_{9-14}$ aryl, each optionally substituted with one, two, or three substituents Q. In certain embodiments, in Formula (I), $R^{2c}$ is 2,3-dihydroindenyl or naphthyl, each optionally substituted with one, two, or three substituents Q. In certain embodiments, in Formula (I), $R^{2c}$ is 2,3-dihydroindenyl or naphthyl, each optionally substituted with one, two, or three substituents, wherein each substituent is independently (i) cyano or halo; (ii) $C_{1-6}$ alkyl or $C_{6-14}$ aryl, each optionally substituted with one or more substituents Q; or (iii) —$OR^{1a}$, —$NR^{1b}R^{1c}$, or —$S(O)_2R^{1a}$, wherein each $R^{1a}$, $R^{1b}$, and $R^{1c}$ is as defined herein. In certain embodiments, in Formula (I), $R^{2c}$ is 2,3-dihydroinden-4-yl, 2,3-dihydroinden-5-yl, naphth-1-yl, or naphth-2-yl, each optionally substituted with one, two, or three substituents, wherein each substituent is independently cyano, fluoro, chloro, bromo, methyl, ethyl, fluoromethyl, difluoromethyl, trifluoromethyl, 1-cyano-1,1-difluoromethyl, 1,1-difluoro-2-hydroxyethyl, 1,1-difluoro-2-hydroxy-2-methylpropyl, methylaminomethyl, 2-aminomethylphenyl, 2-(2-aminoethyl)phenyl, 2-methylaminomethylphenyl, 2-dimethylaminomethylphenyl, hydroxyl, methoxy, amino, or methylsulfonyl. In certain embodiments, in Formula (I), $R^{2c}$ is 1,1-difluoro-2,3-dihydroinden-4-yl or naphth-1-yl.

In certain embodiments, in Formula (I), $R^{2c}$ is heteroaryl, optionally substituted with one, two, or three substituents Q. In certain embodiments, in Formula (I), $R^{2c}$ is monocyclic heteroaryl, optionally substituted with one, two, or three substituents Q. In certain embodiments, in Formula (I), $R^{2c}$ is 5- or 6-membered heteroaryl, each optionally substituted with one, two, or three substituents Q. In certain embodiments, in Formula (I), $R^{2c}$ is thienyl or pyridinyl, each optionally substituted with one, two, or three substituents Q. In certain embodiments, in Formula (I), $R^{2c}$ is thien-2-yl or thien-3-yl, each independently substituted with $C_{6-14}$ aryl or heteroaryl, where the aryl and heteroaryl are each optionally further substituted with one, two, or three substituents $Q^a$. In certain embodiments, in Formula (I), $R^{2c}$ is thienyl or pyridinyl, each optionally substituted with one, two, or three substituents, wherein each substituent is independently (i) cyano or halo; (ii) $C_{1-6}$ alkyl or $C_{6-14}$ aryl, each optionally substituted with one or more substituents Q; or (iii) —$OR^{1a}$, —$NR^{1b}R^{1c}$, or —$S(O)_2R^{1a}$, wherein each $R^{1a}$, $R^{1b}$, and $R^{1c}$ is as defined herein. In certain embodiments, in Formula (I), $R^{2c}$ is thien-2-yl, thien-3-yl, pyridin-2-yl, pyridin-3-yl, or pyridin-4-yl, each optionally substituted with one, two, or three substituents, wherein each substituent is independently cyano, fluoro, chloro, bromo, methyl, ethyl, fluoromethyl, difluoromethyl, trifluoromethyl, 1-cyano-1,1-difluoromethyl, 1,1-difluoro-2-hydroxyethyl, 1,1-difluoro-2-hydroxy-2-methylpropyl, methylaminomethyl, 2-aminomethylphenyl, 2-(2-aminoethyl)phenyl, 2-methylaminomethylphenyl, 2-dimethylaminomethylphenyl, hydroxyl, methoxy, amino, or methylsulfonyl. In certain embodiments, in Formula (I), $R^{2c}$ is 1,1-difluoro-2,3-dihydroinden-4-yl or naphth-1-yl. In certain embodiments, in Formula (I), $R^{2c}$ is thien-2-yl, 5-(2-hydroxymethylphenyl)thien-2-yl, 5-(2-aminomethylphenyl)thien-2-yl, 4-(2-methylamino-methylphenyl)thien-2-yl, or 5-(2-(2-aminoethyl)phenyl)thien-2-yl. In certain embodiments, in Formula (I), $R^{2c}$ is bicyclic heteroaryl, optionally substituted with one, two, or three substituents Q. In certain embodiments, in Formula (I), $R^{2c}$ is 5,5-, 5,6-, or 6,6-fused heteroaryl, each optionally substituted with one, two, or three substituents Q. In certain embodiments, in Formula (I), $R^{2c}$ is 5,5-fused heteroaryl, optionally substituted with one, two, or three substituents Q. In certain embodiments, in Formula (I), $R^{2c}$ is 5,6-fused heteroaryl, optionally substituted with one, two, or three substituents Q. In certain embodiments, in Formula (I), $R^{2c}$ is 6,6-fused heteroaryl, optionally substituted with one, two, or three substituents Q. In certain embodiments, in Formula (I), $R^{2c}$ is thien-2-yl, 5-(2-hydroxymethylphenyl)thien-2-yl, 5-(2-aminomethylphenyl)thien-2-yl, 4-(2-methylaminomethylphenyl)thien-2-yl, 5-(2-(2-amino-ethyl)phenyl)thien-2-yl, or 5-(6,7-dihydropyrrolo[1,2-a]imidazol-3-yl)thien-2-yl.

In certain embodiments, in Formula (I), $R^{2c}$ is heterocyclyl, optionally substituted with one, two, or three substituents Q. In certain embodiments, in Formula (I), $R^{2c}$ is monocyclic heterocyclyl, optionally substituted with one, two, or three substituents Q. In certain embodiments, in Formula (I), $R^{2c}$ is 3-, 4-, 5-, 6-, or 7-membered heterocyclyl, each optionally substituted with one, two, or three substituents Q. In certain embodiments, in Formula (I), $R^{2c}$ is bicyclic heterocyclyl, optionally substituted with one, two, or three substituents Q. In certain embodiments, in Formula (I), $R^{2c}$ is 5,5-, 5,6-, or 6,6-fused heterocyclyl, each optionally substituted with one, two, or three substituents Q.

In certain embodiments, in Formula (I), $R^{2c}$ is 3-cyanophenyl, 3-bromophenyl, 3-methylphenyl, 3-difluoromethylphenyl, 3-trifluoromethylphenyl, 3-(1,1-difluoroethyl)phenyl, 3-(1-cyano-1-fluoromethyl)phenyl, 3-(1-cyano-1,1-difluoromethyl)phenyl, 3-(1,1-difluoro-2-hydroxyethyl)phenyl, 3-(2-aminomethylphenyl)phenyl, 3-cyano-5-fluorophenyl, 3-cyano-2-methylphenyl, 3-cyano-5-methylphenyl, 3-cyano-2-trifluoromethylphenyl, 3-cyano-5-hydroxyphenyl, 3-cyano-2-methoxyphenyl, 2,3-difluorophenyl, 2,4-difluorophenyl, 2-chloro-3-fluorophenyl, 2-chloro-4-fluorophenyl, 2-chloro-3-difluoromethylphenyl, 2-chloro-3-methylphenyl, 3-chloro-2-methylphenyl, 3-difluoromethyl-2-fluorophenyl, 3-difluoromethyl-2-methylphenyl, 2-fluoro-3-(1,1-difluoro-2-hydroxy-2-methylpropyl)phenyl, 2-fluoro-3-methylphenyl, 3-fluoro-2-methylphenyl, 3-fluoro-4-methylphenyl, 4-fluoro-2-methylphenyl, 2-fluoro-3-difluoromethylphenyl, 2-fluoro-3-trifluoromethylphenyl, 3-fluoro-5-trifluoromethylphenyl, 2-fluoromethyl-3-difluoromethylphenyl, 2,3-di(difluoromethyl)phenyl, 2-methyl-3-trifluoromethylphenyl, 2-ethyl-3-difluoromethylphenyl, 2-methyl-3-methylaminomethylphenyl, 2-methyl-3-methylsulfonylphenyl, 3-methyl-5-trifluoromethylphenyl, 3-hydroxy-5-trifluoromethylphenyl, 3-amino-5-trifluoromethylphenyl, 3-amino-4-fluoro-5-trifluoromethylphenyl, 5-amino-2-fluoro-3-trifluoromethylphenyl, 5-amino-2-methyl-3-trifluoromethylphenyl, 3-cyano-2,5-difluorophenyl, 3-cyano-5-fluoro-2-methylphenyl, 5-fluoro-2-methyl-3-trifluoromethylphenyl, 1,1-difluoro-2,3-dihydro-inden-4-yl, naphth-1-yl, 5-(2-aminomethylphenyl)thien-2-yl, 5-(2-(2-aminoethyl)phenyl)thien-2-yl, 4-(2-methylaminomethylphenyl)thien-2-yl, 4-(2-dimethylaminomethylphenyl)thien-2-yl, 5-(2-methylaminomethylphenyl)thien-2-yl, 5-(3-fluoro-2-methylaminomethylphenyl)thien-2-yl, 5-(2-dimethylaminomethylphenyl)thien-2-yl, 2-methyl-pyridin-3-yl, 4-amino-6-difluoromethyl-pyridin-2-yl, 4-amino-6-trifluoromethylpyridin-2-yl, or 3,3-difluoro-2,3-dihydrobenzofuran-7-yl. In certain embodiments, in Formula (I), $R^2$, is 2-fluoro-3-difluoromethylphenyl, 2-methyl-3-trifluoromethylphenyl, 3-amino-5-trifluoromethylphenyl, or 3-(1,1-difluoro-2-hydroxyethyl)-phenyl.

In certain embodiments, in Formula (I), $R^{2c}$ is 3-bromophenyl. In certain embodiments, in Formula (I), $R^{2c}$ is 4-(2-methylaminomethylphenyl)thien-2-yl.

In another embodiment, provided herein is a compound of Formula (II):

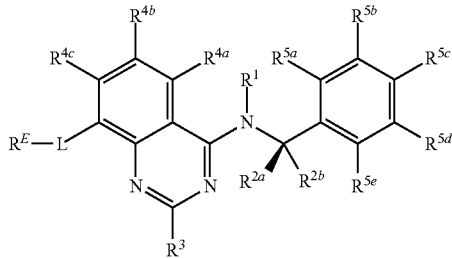

(II)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein:

$R^{5a}$, $R^{5b}$, $R^{5c}$, $R^{5d}$, and $R^{5e}$ are each independently (i) hydrogen, deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, or three, substituents Q; or (iii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^d$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; or $R^{5a}$ and $R^{5b}$ or $R^{5b}$ and $R^{5c}$ together with the carbon atoms to which they are attached form $C_{5-10}$ cycloalkyl, $C_{6-14}$ aryl, heteroaryl, or heterocyclyl, each of which is optionally substituted with one or more, in one embodiment, one, two, or three, substituents Q; and $R^1$, $R^3$, $R^{1a}$, $R^{1b}$, $R^{1c}$, $R^{1d}$, $R^{2a}$, $R^{2b}$, $R^{4a}$, $R^{4b}$, $R^{4c}$, $R^E$, and L are each as defined herein.

In certain embodiments, in any one of the formulae provided herein, $R^{5a}$ is hydrogen. In certain embodiments, in any one of the formulae provided herein, $R^{5a}$ is deuterium. In certain embodiments, in any one of the formulae provided herein, $R^{5a}$ is cyano. In certain embodiments, in any one of the formulae provided herein, $R^{5a}$ is halo. In certain embodiments, in any one of the formulae provided herein, $R^{5a}$ is fluoro or chloro. In certain embodiments, in any one of the formulae provided herein, $R^{5a}$ is fluoro. In certain embodiments, in any one of the formulae provided herein, $R^{5a}$ is nitro.

In certain embodiments, in any one of the formulae provided herein, $R^{5a}$ is $C_{1-6}$ alkyl, optionally substituted with one or more substituents Q. In certain embodiments, in any one of the formulae provided herein, $R^{5a}$ is methyl, optionally substituted with one or more substituents Q. In certain embodiments, in any one of the formulae provided herein, $R^{5a}$ is methyl. In certain embodiments, in any one of the formulae provided herein, $R^{5a}$ is $C_{1-6}$ heteroalkyl, optionally substituted with one or more substituents Q. In certain embodiments, in any one of the formulae provided herein, $R^{5a}$ is $C_{2-6}$ alkenyl, optionally substituted with one or more substituents Q. In certain embodiments, in any one of the formulae provided herein, $R^{5a}$ is $C_{2-6}$ alkynyl, optionally substituted with one or more substituents Q. In certain embodiments, in any one of the formulae provided herein, $R^{5a}$ is $C_{3-10}$ cycloalkyl, optionally substituted with one or more substituents Q. In certain embodiments, in any one of the formulae provided herein, $R^{5a}$ is $C_{6-14}$ aryl, optionally substituted with one or more substituents Q. In certain embodiments, in any one of the formulae provided herein, $R^{5a}$ is $C_{7-15}$ aralkyl, optionally substituted with one or more substituents Q. In certain embodiments, in any one of the formulae provided herein, $R^{5a}$ is heteroaryl, optionally substituted with one or more substituents Q. In certain embodiments, in any one of the formulae provided herein, $R^{5a}$ is heterocyclyl, optionally substituted with one or more substituents Q.

In certain embodiments, in any one of the formulae provided herein, $R^{5a}$ is —C(O)$R^{1a}$, wherein $R^{1a}$ is as defined herein. In certain embodiments, in any one of the formulae provided herein, $R^{5a}$ is —C(O)O$R^{1a}$, wherein $R^{1a}$ is as defined herein. In certain embodiments, in any one of the formulae provided herein, $R^{5a}$ is —C(O)N$R^{1b}R^{1c}$, wherein $R^{1b}$ and $R^{1c}$ are each as defined herein. In certain embodiments, in any one of the formulae provided herein, $R^{5a}$ is —C(O)S$R^{1a}$, wherein $R^{1a}$ is as defined herein. In certain embodiments, in any one of the formulae provided herein, $R^{5a}$ is —C(N$R^{1a}$)N$R^{1b}R^{1c}$, wherein $R^{1a}$, $R^{1b}$, and $R^{1c}$ are each as defined herein. In certain embodiments, in any one of the formulae provided herein, $R^{5a}$ is —C(S)$R^{1a}$, wherein $R^{1a}$ is as defined herein. In certain embodiments, in any one of the formulae provided herein, $R^{5a}$ is —C(S)O$R^{1a}$, wherein $R^{1a}$ is as defined herein. In certain embodiments, in any one of the formulae provided herein, $R^{5a}$ is —C(S)N$R^{1b}R^{1c}$, wherein $R^{1b}$ and $R^{1c}$ are each as defined herein. In certain embodiments, in any one of the formulae provided herein, $R^{5a}$ is —O$R^{1a}$, wherein $R^{1a}$ is as defined herein. In certain embodiments, in any one of the formulae provided herein, $R^{5a}$ is —OC(O)$R^{1a}$, wherein $R^{1a}$ is as defined herein. In certain embodiments, in any one of the formulae provided herein, $R^{5a}$ is —OC(O)O$R^{1a}$, wherein $R^{1a}$ is as defined herein. In certain embodiments, in any one of the formulae provided herein, $R^{5a}$ is —OC(O)N$R^{1b}R^{1c}$, wherein $R^{1b}$ and $R^{1c}$ are each as defined herein. In certain embodiments, in any one of the formulae provided herein, $R^{5a}$ is —OC(O)S$R^{1a}$, wherein $R^{1a}$ is as defined herein. In certain embodiments, in any one of the formulae provided herein, $R^{5a}$ is —OC(N$R^{1a}$)N$R^{1b}R^{1c}$, wherein $R^{1a}$, $R^{1b}$, and $R^{1c}$ are each as defined herein. In certain embodiments, in any one of the formulae provided herein, $R^{5a}$ is —OC(S)$R^{1a}$, wherein $R^{1a}$ is as defined herein. In certain embodiments, in any one of the formulae provided herein, $R^{5a}$ is —OC(S)O$R^{1a}$, wherein $R^{1a}$ is as defined herein. In certain embodiments, in any one of the formulae provided herein, $R^{5a}$ is —OC(S)N$R^{1b}R^{1c}$, wherein $R^{1b}$ and $R^{1c}$ are each as defined herein. In certain embodiments, in any one of the formulae provided herein, $R^{5a}$ is —OS(O)$R^{1a}$, wherein $R^{1a}$ is as defined herein. In certain embodiments, in any one of the formulae provided herein, $R^{5a}$ is —OS(O)$_2R^{1a}$, wherein $R^{1a}$ is as defined herein. In certain embodiments, in any one of the formulae provided herein, $R^{5a}$ is —OS(O)N$R^{1b}R^{1c}$, wherein $R^{1b}$ and $R^{1c}$ are each as defined herein. In certain embodiments, in any one of the formulae provided herein, $R^{5a}$ is —OS(O)$_2$N$R^{1b}R^{1c}$, wherein $R^{1b}$ and $R^{1c}$ are each as defined herein. In certain embodiments, in any one of the formulae provided herein, $R^{5a}$ is —N$R^{1b}R^{1c}$ wherein $R^{1b}$ and $R^{1c}$ are each as defined herein. In certain embodiments, in any one of the formulae provided herein, $R^{5a}$ is —N$R^{1a}$C(O)$R^{1d}$, wherein $R^{1a}$ and $R^{1d}$ are each as defined herein. In certain embodiments, in any one of the formulae provided herein, $R^{5a}$ is —N$R^{1a}$C(O)O$R^{1d}$, wherein $R^{1a}$ and $R^{1d}$ are each as defined herein. In certain embodiments, in any one of the formulae provided herein, $R^{5a}$ is —N$R^{1a}$C(O)N$R^{1b}R^{1c}$, wherein $R^{1b}$ and $R^{1c}$ are each as defined herein. In certain embodiments, in any one of the formulae provided herein, $R^{5a}$ is —N$R^{1a}$C(O)S$R^{1d}$, wherein $R^{1a}$ and $R^{1d}$ are each as defined herein. In certain embodiments, in any one of the formulae provided herein, $R^{5a}$ is —N$R^{1a}$C(N$R^{1d}$)N$R^{1b}R^{1c}$, wherein $R^{1a}$, $R^{1b}$, $R^{1c}$, and $R^{1d}$ are each as defined herein. In certain embodiments, in any one of the formulae provided herein, $R^{5a}$ is —N$R^{1a}$C(S)$R^{1d}$, wherein $R^{1a}$ and $R^{1d}$ are each as defined herein. In certain embodiments, in any one of the formulae provided herein, $R^{5a}$ is —N$R^{1a}$C(S)O$R^{1d}$, wherein $R^{1a}$ and $R^{1d}$ are each as defined herein. In certain embodiments, in any one of the formulae provided herein, $R^{5a}$ is —N$R^{1a}$C(S)N$R^{1b}R^{1c}$, wherein $R^{1a}$, $R^{1b}$, and $R^{1c}$ are each as defined herein. In certain embodiments, in any one of the formulae provided herein, $R^{5a}$ is —N$R^{1a}$S(O)$R^{1d}$, wherein $R^{1a}$ and $R^{1d}$ are each as defined herein. In certain embodiments, in any one of the formulae provided herein, $R^{5a}$ is —N$R^{1a}$S(O)$_2R^{1d}$, wherein $R^{1a}$ and $R^{1d}$ are each as defined herein. In certain embodiments, in any one of the formulae provided herein, $R^{5a}$ is —N$R^{1a}$S(O)N$R^{1b}R^{1c}$, wherein $R^{1a}$, $R^{1b}$, and $R^{1c}$ are each as defined herein. In certain embodiments, in any one of the formulae provided herein, $R^{5a}$ is —N$R^{1a}$S(O)$_2$N$R^{1b}R^{1c}$, wherein $R^{1a}$, $R^{1b}$, and $R^{1c}$ are each as defined herein. In certain embodiments, in any one of the formulae provided herein, $R^{5a}$ is —S$R^{1a}$, wherein $R^{1a}$ is as defined herein. In certain embodiments, in any one of the formulae provided herein, $R^{5a}$ is —S(O)$R^{1a}$, wherein $R^{1a}$ is as defined herein. In certain embodiments, in any one of the formulae provided herein, $R^{5a}$ is —S(O)$_2R^{1a}$, wherein $R^{1a}$ is as defined herein. In certain embodiments, in any one of the formulae provided herein, $R^{5a}$ is —S(O)N$R^{1b}R^{1c}$, wherein $R^{1b}$ and $R^{1c}$ are each as defined herein. In certain embodiments, in any one of the formulae provided herein, $R^{5a}$ is —S(O)$_2$N$R^{1b}R^{1c}$, wherein $R^{1b}$ and $R^{1c}$ are each as defined herein.

In certain embodiments, in any one of the formulae provided herein, $R^{5a}$ is (i) hydrogen, cyano, or halo; (ii) $C_{1-6}$ alkyl or $C_{6-14}$ aryl, each optionally substituted with one or more substituents Q; or (iii) —O$R^{1a}$, —N$R^{1b}R^{1c}$, or —S(O)$_2R^{1a}$, wherein each $R^{1a}$, $R^{1b}$, and $R^{1c}$ is as defined herein. In certain embodiments, in any one of the formulae provided herein, $R^{5a}$ is hydrogen, cyano, fluoro, chloro, methyl, ethyl, fluoromethyl, difluoromethyl, trifluoromethyl, 1-cyano-1,1-difluoromethyl, 1,1-difluoro-2-hydroxyethyl, 1,1-difluoro-2-hydroxy-2-methylpropyl, methylaminomethyl, 2-aminomethylphenyl, 2-(2-aminoethyl)phenyl, 2-methylaminomethylphenyl, 2-dimethylaminomethylphenyl, hydroxyl, methoxy, amino, or methylsulfonyl. In certain embodiments, in any one of the formulae provided herein, $R^{5a}$ is hydrogen, fluoro, chloro, methyl, ethyl, fluoromethyl, difluoromethyl, trifluoromethyl, or methoxy. In certain embodiments, in any one of the formulae provided herein, $R^{5a}$ is hydrogen, fluoro, or methyl. In certain embodiments, in any one of the formulae provided herein, $R^{5a}$ is hydrogen. In certain embodiments, in any one of the formulae provided herein, $R^{5a}$ is fluoro. In certain embodiments, in any one of the formulae provided herein, $R^{5a}$ is methyl.

In certain embodiments, in any one of the formulae provided herein, $R^{5b}$ is hydrogen. In certain embodiments, in any one of the formulae provided herein, $R^{5b}$ is deuterium. In certain embodiments, in any one of the formulae provided herein, $R^{5b}$ is cyano. In certain embodiments, in any one of the formulae provided herein, $R^{5b}$ is halo. In certain embodiments, in any one of the formulae provided herein, $R^{5b}$ is fluoro or chloro. In certain embodiments, in any one of the formulae provided herein, $R^{5b}$ is fluoro. In certain embodiments, in any one of the formulae provided herein, $R^{5b}$ is nitro.

In certain embodiments, in any one of the formulae provided herein, $R^{5b}$ is $C_{1-6}$ alkyl, optionally substituted with one or more substituents Q. In certain embodiments, in any one of the formulae provided herein, $R^{5b}$ is methyl or ethyl, each optionally substituted with one or more substituents Q. In certain embodiments, in any one of the formulae provided herein, $R^{5b}$ is difluoromethyl, trifluoromethyl, or 1,1-difluoro-2-hydroxyethyl. In certain embodiments, in any one of the formulae provided herein, $R^{5b}$ is $C_{1-6}$ heteroalkyl, optionally substituted with one or more substituents Q. In certain embodiments, in any one of the formulae provided herein, $R^{5b}$ is $C_{2-6}$ alkenyl, optionally substituted with one or more substituents Q. In certain embodiments, in any one of the formulae provided herein, $R^{5b}$ is $C_{2-6}$ alkynyl, optionally substituted with one or more substituents Q. In certain embodiments, in any one of the formulae provided herein, $R^{5b}$ is $C_{3-10}$ cycloalkyl, optionally substituted with one or more substituents Q. In certain embodiments, in any one of the formulae provided herein, $R^{5b}$ is $C_{6-14}$ aryl, optionally substituted with one or more substituents Q. In certain embodiments, in any one of the formulae provided herein, $R^{5b}$ is $C_{7-15}$ aralkyl, optionally substituted with one or more substituents Q. In certain embodiments, in any one of the formulae provided herein, $R^{5b}$ is heteroaryl, optionally substituted with one or more substituents Q. In certain embodiments, in any one of the formulae provided herein, $R^{5b}$ is heterocyclyl, optionally substituted with one or more substituents Q.

In certain embodiments, in any one of the formulae provided herein, $R^{5b}$ is —C(O)$R^{1a}$, wherein $R^{1a}$ is as defined herein. In certain embodiments, in any one of the formulae provided herein, $R^{5b}$ is —C(O)O$R^{1a}$, wherein $R^{1a}$ is as defined herein. In certain embodiments, in any one of the formulae provided herein, $R^{5b}$ is —C(O)N$R^{1b}R^{1c}$, wherein $R^{1b}$ and $R^{1c}$ are each as defined herein. In certain embodiments, in any one of the formulae provided herein, $R^{5b}$ is —C(O)S$R^{1a}$, wherein $R^{1a}$ is as defined herein. In certain embodiments, in any one of the formulae provided herein, $R^{5b}$ is —C(N$R^{1a}$)N$R^{1b}R^{1c}$, wherein $R^{1a}$, $R^{1b}$, and $R^{1c}$ are each as defined herein. In certain embodiments, in any one of the formulae provided herein, $R^{5b}$ is —C(S)$R^{1a}$, wherein $R^{1a}$ is as defined herein. In certain embodiments, in any one of the formulae provided herein, $R^{5b}$ is —C(S)O$R^{1a}$, wherein $R^{1a}$ is as defined herein. In certain embodiments, in any one of the formulae provided herein, $R^{5b}$ is —C(S)N$R^{1b}R^{1c}$, wherein $R^{1b}$ and $R^{1c}$ are each as defined herein. In certain embodiments, in any one of the formulae provided herein, $R^{5b}$ is —O$R^{1a}$, wherein $R^{1a}$ is as defined herein. In certain embodiments, in any one of the formulae provided herein, $R^{5b}$ is —OC(O)$R^{1a}$, wherein $R^{1a}$ is as defined herein. In certain embodiments, in any one of the formulae provided herein, $R^{5b}$ is —OC(O)O$R^{1a}$, wherein $R^{1a}$ is as defined herein. In certain embodiments, in any one of the formulae provided herein, $R^{5b}$ is —OC(O)N$R^{1b}R^{1c}$, wherein $R^{1b}$ and $R^{1c}$ are each as defined herein. In certain embodiments, in any one of the formulae provided herein, $R^{5b}$ is —OC(O)S$R^{1a}$, wherein $R^{1a}$ is as defined herein. In certain embodiments, in any one of the formulae provided herein, $R^{5b}$ is —OC(N$R^{1a}$)N$R^{1b}R^{1c}$, wherein $R^{1a}$, $R^{1b}$, and $R^{1c}$ are each as defined herein. In certain embodiments, in any one of the formulae provided herein, $R^{5b}$ is —OC(S)$R^{1a}$, wherein $R^{1a}$ is as defined herein. In certain embodiments, in any one of the formulae provided herein, $R^{5b}$ is —OC(S)O$R^{1a}$, wherein $R^{1a}$ is as defined herein. In certain embodiments, in any one of the formulae provided herein, $R^{5b}$ is —OC(S)N$R^{1b}R^{1c}$, wherein $R^{1b}$ and $R^{1c}$ are each as defined herein. In certain embodiments, in any one of the formulae provided herein, $R^{5b}$ is —OS(O)$R^{1a}$, wherein $R^{1a}$ is as defined herein. In certain embodiments, in any one of the formulae provided herein, $R^{5b}$ is —OS(O)$_2R^{1a}$, wherein $R^{1a}$ is as defined herein. In certain embodiments, in any one of the formulae provided herein, $R^{5b}$ is —OS(O)N$R^{1b}R^{1c}$, wherein $R^{1b}$ and $R^{1c}$ are each as defined herein. In certain embodiments, in any one of the formulae provided herein, $R^{5b}$ is —OS(O)$_2$N$R^{1b}R^{1c}$, wherein $R^{1b}$ and $R^{1c}$ are each as defined herein. In certain embodiments, in any one of the formulae provided herein, $R^{5b}$ is —N$R^{1b}R^{1c}$ wherein $R^{1b}$ and $R^{1c}$ are each as defined herein. In certain embodiments, in any one of the formulae provided herein, $R^{5b}$ is amino. In certain embodiments, in any one of the formulae provided herein, $R^{5b}$ is —N$R^{1a}$C(O)$R^{1d}$, wherein $R^{1a}$ and $R^{1d}$ are each as defined herein. In certain embodiments, in any one of the formulae provided herein, $R^{5b}$ is —N$R^{1a}$C(O)O$R^{1d}$, wherein $R^{1a}$ and $R^{1d}$ are each as defined herein. In certain embodiments, in any one of the formulae provided herein, $R^{5b}$ is —N$R^{1a}$C(O)N$R^{1b}R^{1c}$, wherein $R^{1b}$ and $R^{1c}$ are each as defined herein. In certain embodiments, in any one of the formulae provided herein, $R^{5b}$ is —N$R^{1a}$C(O)S$R^{1d}$, wherein $R^{1a}$ and $R^{1d}$ are each as defined herein. In certain embodiments, in any one of the formulae provided herein, $R^{5b}$ is —N$R^{1a}$C(N$R^{1d}$)N$R^{1b}R^{1c}$, wherein $R^{1a}$, $R^{1b}$, $R^{1c}$, and $R^{1d}$ are each as defined herein. In certain embodiments, in any one of the formulae provided herein, $R^{5b}$ is —N$R^{1a}$C(S)$R^{1d}$, wherein $R^{1a}$ and $R^{1d}$ are each as defined herein. In certain embodiments, in any one of the formulae provided herein, $R^{5b}$ is —N$R^{1a}$C(S)O$R^{1d}$, wherein $R^{1a}$ and $R^{1d}$ are each as defined herein. In certain embodiments, in any one of the formulae provided herein, $R^{5b}$ is —N$R^{1a}$C(S)N$R^{1b}R^{1c}$, wherein $R^{1a}$, $R^{1b}$, and $R^{1c}$ are each as defined herein. In certain embodiments, in any one of the formulae provided herein, $R^{5b}$ is —N$R^{1a}$S(O)$R^{1d}$, wherein $R^{1a}$ and $R^{1d}$ are each as defined herein. In certain embodiments, in any one of the formulae provided herein, $R^{5b}$ is —N$R^{1a}$S(O)$_2R^{1d}$, wherein $R^{1a}$ and $R^{1d}$ are each as defined herein. In certain embodiments, in any one of the formulae provided herein, $R^{5b}$ is —N$R^{1a}$S(O)N$R^{1b}R^{1c}$, wherein $R^{1a}$, $R^{1b}$, and $R^{1c}$ are each as defined herein. In certain embodiments, in any one of the formulae provided herein, $R^{5b}$ is —N$R^{1a}$S(O)$_2$N$R^{1b}R^{1c}$, wherein $R^{1a}$, $R^{1b}$, and $R^{1c}$ are each as defined herein. In certain embodiments, in any one of the formulae provided herein, $R^{5b}$ is —S$R^{1a}$, wherein $R^{1a}$ is as defined herein. In certain embodiments, in any one of the formulae provided herein, $R^{5b}$ is —S(O)$R^{1a}$, wherein $R^{1a}$ is as defined herein. In certain embodiments, in any one of the formulae provided herein, $R^{5b}$ is —S(O)$_2R^{1a}$, wherein $R^{1a}$ is as defined herein. In certain embodiments, in any one of the formulae provided herein, $R^{5b}$ is —S(O)N$R^{1b}R^{1c}$, wherein $R^{1b}$ and $R^{1c}$ are each as defined herein. In certain embodiments, in any one of the formulae provided herein, $R^{5b}$ is —S(O)$_2$N$R^{1b}R^{1c}$, wherein $R^{1b}$ and $R^{1c}$ are each as defined herein.

In certain embodiments, in any one of the formulae provided herein, $R^{1b}$ is (i) hydrogen, cyano, or halo; (ii) $C_{1-6}$ alkyl or $C_{6-14}$ aryl, each optionally substituted with one or more substituents Q; or (iii) —O$R^{1a}$, —N$R^{1b}R^c$, or —S(O)$_2R^{1a}$, wherein each $R^{1a}$, $R^{1b}$, and $R^{1c}$ is as defined herein. In certain embodiments, in any one of the formulae provided herein, $R^{5b}$ is hydrogen, cyano, fluoro, chloro, bromo, methyl, ethyl, fluoromethyl, difluoromethyl, trifluoromethyl, 1-cyano-1,1-difluoromethyl, 1,1-difluoro-2-hydroxyethyl, 1,1-difluoro-2-hydroxy-2-methylpropyl, methylaminomethyl, 2-aminomethylphenyl, 2-(2-aminoethyl)phenyl, 2-methylaminomethylphenyl, 2-dimethylaminomethylphenyl, hydroxyl, methoxy, amino, or methylsulfonyl. In certain embodiments, in any one of the formulae provided herein, $R^{5b}$ is hydrogen, cyano, fluoro, chloro, methyl, difluoromethyl, trifluoromethyl, 1-cyano-1, 1-difluoromethyl, 1,1-difluoro-2-hydroxyethyl, 1,1-difluoro-2-hydroxy-2-methylpropyl, methylaminomethyl, hydroxyl, amino, or methylsulfonyl. In certain embodiments, in any one of the formulae provided herein, $R^{1b}$ is difluoromethyl, trifluoromethyl, 1,1-difluoro-2-hydroxy-2- methylpropyl, or amino. In certain embodiments, in any one of the formulae provided herein, $R^{5b}$ is difluoromethyl. In certain embodiments, in any one of the formulae provided herein, $R^{5b}$ is trifluoromethyl. In certain embodiments, in any one of the formulae provided herein, $R^{5b}$ is 1,1-difluoro-2-hydroxy-2-methylpropyl. In certain embodiments, in any one of the formulae provided herein, $R^{5b}$ is amino. In certain embodiments, in any one of the formulae provided herein, $R^{5b}$ is not bromo.

In certain embodiments, in any one of the formulae provided herein, $R^{5c}$ is hydrogen. In certain embodiments, in any one of the formulae provided herein, $R^{5c}$ is deuterium. In certain embodiments, in any one of the formulae provided herein, $R^{5c}$ is cyano. In certain embodiments, in any one of the formulae provided herein, $R^{5c}$ is halo. In certain embodiments, in any one of the formulae provided herein, $R^{5c}$ is fluoro or chloro. In certain embodiments, in any one of the formulae provided herein, $R^{5c}$ is fluoro. In certain embodiments, in any one of the formulae provided herein, $R^{5c}$ is nitro.

In certain embodiments, in any one of the formulae provided herein, $R^{5c}$ is $C_{1-6}$ alkyl, optionally substituted with one or more substituents Q. In certain embodiments, in any one of the formulae provided herein, $R^{5c}$ is $C_{1-6}$ heteroalkyl, optionally substituted with one or more substituents Q. In certain embodiments, in any one of the formulae provided herein, $R^{5c}$ is $C_{2-6}$ alkenyl, optionally substituted with one or more substituents Q. In certain embodiments, in any one of the formulae provided herein, $R^{5c}$ is $C_{2-6}$ alkynyl, optionally substituted with one or more substituents Q. In certain embodiments, in any one of the formulae provided herein, $R^{5c}$ is $C_{3-10}$ cycloalkyl, optionally substituted with one or more substituents Q. In certain embodiments, in any one of the formulae provided herein, $R^{5c}$ is $C_{6-14}$ aryl, optionally substituted with one or more substituents Q. In certain embodiments, in any one of the formulae provided herein, $R^{5c}$ is $C_{7-15}$ aralkyl, optionally substituted with one or more substituents Q. In certain embodiments, in any one of the formulae provided herein, $R^{5c}$ is heteroaryl, optionally substituted with one or more substituents Q. In certain embodiments, in any one of the formulae provided herein, $R^{5c}$ is heterocyclyl, optionally substituted with one or more substituents Q.

In certain embodiments, in any one of the formulae provided herein, $R^{5c}$ is —C(O)$R^{1a}$, wherein $R^{1a}$ is as defined herein. In certain embodiments, in any one of the formulae provided herein, $R^{5c}$ is —C(O)O$R^{1a}$, wherein $R^{1a}$ is as defined herein. In certain embodiments, in any one of the formulae provided herein, $R^{5c}$ is —C(O)N$R^{1b}R^{1c}$, wherein $R^{1b}$ and $R^{1c}$ are each as defined herein. In certain embodiments, in any one of the formulae provided herein, $R^{5c}$ is —C(O)S$R^{1a}$, wherein $R^{1a}$ is as defined herein. In certain embodiments, in any one of the formulae provided herein, $R^{5c}$ is —C(N$R^{1a}$)N$R^{1b}R^{1c}$, wherein $R^{1a}$, $R^{1b}$, and $R^{1c}$ are each as defined herein. In certain embodiments, in any one of the formulae provided herein, $R^{5c}$ is —C(S)$R^{1a}$, wherein $R^{1a}$ is as defined herein. In certain embodiments, in any one of the formulae provided herein, $R^{5c}$ is —C(S)O$R^{1a}$, wherein $R^{1a}$ is as defined herein. In certain embodiments, in any one of the formulae provided herein, $R^{5c}$ is —C(S)N$R^{1b}R^{1c}$, wherein $R^{1b}$ and $R^{1c}$ are each as defined herein. In certain embodiments, in any one of the formulae provided herein, $R^{5c}$ is —O$R^{1a}$, wherein $R^{1a}$ is as defined herein. In certain embodiments, in any one of the formulae provided herein, $R^{5c}$ is —OC(O)$R^{1a}$, wherein $R^{1a}$ is as defined herein. In certain embodiments, in any one of the formulae provided herein, $R^{5c}$ is —OC(O)O$R^{1a}$, wherein $R^{1a}$ is as defined herein. In certain embodiments, in any one of the formulae provided herein, $R^{5c}$ is —OC(O)N$R^{1b}R^{1c}$, wherein $R^{1b}$ and $R^{1c}$ are each as defined herein. In certain embodiments, in any one of the formulae provided herein, $R^{5c}$ is —OC(O)S$R^{1a}$, wherein $R^{1a}$ is as defined herein. In certain embodiments, in any one of the formulae provided herein, $R^{5c}$ is —OC(N$R^{1a}$)N$R^{1b}R^{1c}$, wherein $R^{1a}$, $R^{1b}$, and $R^{1c}$ are each as defined herein. In certain embodiments, in any one of the formulae provided herein, $R^{5c}$ is —OC(S)$R^{1a}$, wherein $R^{1a}$ is as defined herein. In certain embodiments, in any one of the formulae provided herein, $R^{5c}$ is —OC(S)O$R^{1a}$, wherein $R^{1a}$ is as defined herein. In certain embodiments, in any one of the formulae provided herein, $R^{5c}$ is —OC(S)N$R^{1b}R^{1c}$, wherein $R^{1b}$ and $R^{1c}$ are each as defined herein. In certain embodiments, in any one of the formulae provided herein, $R^{5c}$ is —OS(O)$R^{1a}$, wherein $R^{1a}$ is as defined herein. In certain embodiments, in any one of the formulae provided herein, $R^{5c}$ is —OS(O)$_2R^{1a}$, wherein $R^{1a}$ is as defined herein. In certain embodiments, in any one of the formulae provided herein, $R^{5c}$ is —OS(O)N$R^{1b}R^{1c}$, wherein $R^{1b}$ and $R^{1c}$ are each as defined herein. In certain embodiments, in any one of the formulae provided herein, $R^{5c}$ is —OS(O)$_2$N$R^{1b}R^{1c}$, wherein $R^{1b}$ and $R^{1c}$ are each as defined herein. In certain embodiments, in any one of the formulae provided herein, $R^{5c}$ is —N$R^{1b}R^{1c}$ wherein $R^{1b}$ and $R^{1c}$ are each as defined herein. In certain embodiments, in any one of the formulae provided herein, $R^{5c}$ is —N$R^{1a}$C(O)$R^{1d}$, wherein $R^{1a}$ and $R^{1d}$ are each as defined herein. In certain embodiments, in any one of the formulae provided herein, $R^{5c}$ is —N$R^{1a}$C(O)O$R^{1d}$, wherein $R^{1a}$ and $R^{1d}$ are each as defined herein. In certain embodiments, in any one of the formulae provided herein, $R^{5c}$ is —N$R^{1a}$C(O)N$R^{1b}R^{1c}$, wherein $R^{1b}$ and $R^{1c}$ are each as defined herein. In certain embodiments, in any one of the formulae provided herein, $R^{5c}$ is —N$R^{1a}$C(O)S$R^{1d}$, wherein $R^{1a}$ and $R^{1d}$ are each as defined herein. In certain embodiments, in any one of the formulae provided herein, $R^{5c}$ is —N$R^{1a}$C(N$R^{1d}$)N$R^{1b}R^{1c}$, wherein $R^{1a}$, $R^{1b}$, $R^{1c}$, and $R^{1d}$ are each as defined herein. In certain embodiments, in any one of the formulae provided herein, $R^{5c}$ is —N$R^{1a}$C(S)$R^{1d}$, wherein $R^{1a}$ and $R^{1d}$ are each as defined herein. In certain embodiments, in any one of the formulae provided herein, $R^{5c}$ is —N$R^{1a}$C(S)O$R^{1d}$, wherein $R^{1a}$ and $R^{1d}$ are each as defined herein. In certain embodiments, in any one of the formulae provided herein, $R^{5c}$ is —N$R^{1a}$C(S)N$R^{1b}R^{1c}$, wherein $R^{1a}$, $R^{1b}$, and $R^{1c}$ are each as defined herein. In certain embodiments, in any one of the formulae provided herein, $R^{5c}$ is —N$R^{1a}$S(O)$R^{1d}$, wherein $R^{1a}$ and $R^{1d}$ are each as defined herein. In certain embodiments, in any one of the formulae provided herein, $R^{5c}$ is —N$R^{1a}$S(O)$_2R^{1d}$, wherein $R^{1a}$ and $R^{1d}$ are each as defined herein. In certain embodiments, in any one of the formulae provided herein, $R^{5c}$ is —N$R^{1a}$S(O)N$R^{1b}R^{1c}$, wherein $R^{1a}$, $R^{1b}$, and $R^{1c}$ are each as defined herein. In certain embodiments, in any one of the formulae provided herein, $R^{5c}$ is —N$R^{1a}$S(O)$_2$N$R^{1b}R^{1c}$, wherein $R^{1a}$, $R^{1b}$, and $R^{1c}$ are each as defined herein. In certain embodiments, in any one of the formulae provided herein, $R^{5c}$ is —S$R^{1a}$, wherein $R^{1a}$ is as defined herein. In certain embodiments, in any one of the formulae provided herein, $R^{5c}$ is —S(O)$R^{1a}$, wherein $R^{1a}$ is as defined herein. In certain embodiments, in any one of the formulae provided herein, $R^{5c}$ is —S(O)$_2R^{1a}$, wherein $R^{1a}$ is as defined herein. In certain embodiments, in any one of the formulae provided herein, $R^{5c}$ is —S(O)N$R^{1b}R^{1c}$, wherein $R^{1b}$ and $R^{1c}$ are each as defined herein. In certain embodiments, in any one of the formulae provided herein, $R^{5c}$ is —S(O)$_2$N$R^{1b}R^{1c}$, wherein $R^{1b}$ and $R^{1c}$ are each as defined herein.

In certain embodiments, in any one of the formulae provided herein, $R^{5c}$ is (i) hydrogen, cyano, or halo; (ii) $C_{1-6}$ alkyl or $C_{6-14}$ aryl, each optionally substituted with one or more substituents Q; or (iii) —$OR^{1a}$, —$NR^{1b}R^{1c}$, or —$S(O)_2R^{1a}$, wherein each $R^{1a}$, $R^{1b}$, and $R^{1c}$ is as defined herein. In certain embodiments, in any one of the formulae provided herein, $R^{5c}$ is hydrogen, cyano, fluoro, chloro, bromo, methyl, ethyl, fluoromethyl, difluoromethyl, trifluoromethyl, 1-cyano-1,1-difluoromethyl, 1,1-difluoro-2-hydroxyethyl, 1,1-difluoro-2-hydroxy-2-methylpropyl, methylaminomethyl, 2-aminomethylphenyl, 2-(2-aminoethyl)phenyl, 2-methyl-aminomethylphenyl, 2-dimethylaminomethylphenyl, hydroxyl, methoxy, amino, or methylsulfonyl. In certain embodiments, in any one of the formulae provided herein, $R^{5c}$ is hydrogen, fluoro, or methyl. In certain embodiments, in any one of the formulae provided herein, $R^{5c}$ is hydrogen.

In certain embodiments, in any one of the formulae provided herein, $R^{5d}$ is hydrogen. In certain embodiments, in any one of the formulae provided herein, $R^{5d}$ is deuterium. In certain embodiments, in any one of the formulae provided herein, $R^{5d}$ is cyano. In certain embodiments, in any one of the formulae provided herein, $R^{5d}$ is halo. In certain embodiments, in any one of the formulae provided herein, $R^{5d}$ is fluoro, chloro, or bromo. In certain embodiments, in any one of the formulae provided herein, $R^{5d}$ is fluoro. In certain embodiments, in any one of the formulae provided herein, $R^{5d}$ is nitro.

In certain embodiments, in any one of the formulae provided herein, $R^{5d}$ is $C_{1-6}$ alkyl, optionally substituted with one or more substituents Q. In certain embodiments, in any one of the formulae provided herein, $R^{5b}$ is methyl, optionally substituted with one or more substituents Q. In certain embodiments, in any one of the formulae provided herein, $R^{5b}$ is trifluoromethyl. In certain embodiments, in any one of the formulae provided herein, $R^{5d}$ is $C_{1-6}$ heteroalkyl, optionally substituted with one or more substituents Q. In certain embodiments, in any one of the formulae provided herein, $R^{5d}$ is $C_{2-6}$ alkenyl, optionally substituted with one or more substituents Q. In certain embodiments, in any one of the formulae provided herein, $R^{5d}$ is $C_{2-6}$ alkynyl, optionally substituted with one or more substituents Q. In certain embodiments, in any one of the formulae provided herein, $R^{5d}$ is $C_{3-10}$ cycloalkyl, optionally substituted with one or more substituents Q. In certain embodiments, in any one of the formulae provided herein, $R^{5d}$ is $C_{6-14}$ aryl optionally substituted with one or more substituents Q. In certain embodiments, in any one of the formulae provided herein, $R^{5d}$ is $C_{7-15}$ aralkyl, optionally substituted with one or more substituents Q. In certain embodiments, in any one of the formulae provided herein, $R^{5d}$ is heteroaryl, optionally substituted with one or more substituents Q. In certain embodiments, in any one of the formulae provided herein, $R^{5d}$ is heterocyclyl, optionally substituted with one or more substituents Q.

In certain embodiments, in any one of the formulae provided herein, $R^{5d}$ is —$C(O)R^{1a}$, wherein $R^{1a}$ is as defined herein. In certain embodiments, in any one of the formulae provided herein, $R^{5d}$ is —$C(O)OR^{1a}$, wherein $R^{1a}$ is as defined herein. In certain embodiments, in any one of the formulae provided herein, $R^{5d}$ is —$C(O)NR^{1b}R^{1c}$, wherein $R^{1b}$ and $R^{1c}$ are each as defined herein. In certain embodiments, in any one of the formulae provided herein, $R^{5d}$ is —$C(O)SR^{1a}$, wherein $R^{1a}$ is as defined herein. In certain embodiments, in any one of the formulae provided herein, $R^{5d}$ is —$C(NR^{1a})NR^{1b}R^{1c}$, wherein $R^{1a}$, $R^{1b}$, and $R^{1c}$ are each as defined herein. In certain embodiments, in any one of the formulae provided herein, $R^{5d}$ is —$C(S)R^{1a}$, wherein $R^{1a}$ is as defined herein. In certain embodiments, in any one of the formulae provided herein, $R^{5d}$ is —$C(S)OR^{1a}$, wherein $R^{1a}$ is as defined herein. In certain embodiments, in any one of the formulae provided herein, $R^{5d}$ is —$C(S)NR^{1b}R^{1c}$, wherein $R^{1b}$ and $R^{1c}$ are each as defined herein. In certain embodiments, in any one of the formulae provided herein, $R^{5d}$ is —$OR^{1a}$, wherein $R^{1a}$ is as defined herein. In certain embodiments, in any one of the formulae provided herein, $R^{5d}$ is —$OC(O)R^{1a}$, wherein $R^{1a}$ is as defined herein. In certain embodiments, in any one of the formulae provided herein, $R^{5d}$ is —$OC(O)OR^{1a}$, wherein $R^{1a}$ is as defined herein. In certain embodiments, in any one of the formulae provided herein, $R^{5d}$ is —$OC(O)NR^{1b}R^{1c}$, wherein $R^{1b}$ and $R^{1c}$ are each as defined herein. In certain embodiments, in any one of the formulae provided herein, $R^{5d}$ is —$OC(O)SR^{1a}$, wherein $R^{1a}$ is as defined herein. In certain embodiments, in any one of the formulae provided herein, $R^{5d}$ is —$OC(NR^{1a})NR^{1b}R^{1c}$, wherein $R^{1a}$, $R^{1b}$, and $R^{1c}$ are each as defined herein. In certain embodiments, in any one of the formulae provided herein, $R^{5d}$ is —$OC(S)R^{1a}$, wherein $R^{1a}$ is as defined herein. In certain embodiments, in any one of the formulae provided herein, $R^{5d}$ is —$OC(S)OR^{1a}$, wherein $R^{1a}$ is as defined herein. In certain embodiments, in any one of the formulae provided herein, $R^{5d}$ is —$OC(S)NR^{1b}R^{1c}$, wherein $R^{1b}$ and $R^{1c}$ are each as defined herein. In certain embodiments, in any one of the formulae provided herein, $R^{5d}$ is —$OS(O)R^{1a}$, wherein $R^{1a}$ is as defined herein. In certain embodiments, in any one of the formulae provided herein, $R^{5d}$ is —$OS(O)_2R^{1a}$, wherein $R^{1a}$ is as defined herein. In certain embodiments, in any one of the formulae provided herein, $R^{5d}$ is —$OS(O)NR^{1b}R^{1c}$, wherein $R^{1b}$ and $R^{1c}$ are each as defined herein. In certain embodiments, in any one of the formulae provided herein, $R^{5d}$ is —$OS(O)_2NR^{1b}R^{1c}$, wherein $R^{1b}$ and $R^{1c}$ are each as defined herein. In certain embodiments, in any one of the formulae provided herein, $R^{5d}$ is —$NR^{1b}R^{1c}$ wherein $R^{1b}$ and $R^{1c}$ are each as defined herein. In certain embodiments, in any one of the formulae provided herein, $R^{5d}$ is —$NR^{1a}C(O)R^{1d}$, wherein $R^{1a}$ and $R^{1d}$ are each as defined herein. In certain embodiments, in any one of the formulae provided herein, $R^{5d}$ is —$NR^{1a}C(O)OR^{1d}$, wherein $R^{1a}$ and $R^{1d}$ are each as defined herein. In certain embodiments, in any one of the formulae provided herein, $R^{5d}$ is —$NR^{1a}C(O)NR^{1b}R^{1c}$, wherein $R^{1b}$ and $R^{1c}$ are each as defined herein. In certain embodiments, in any one of the formulae provided herein, $R^{5d}$ is —$NR^{1a}C(O)SR^{1d}$, wherein $R^{1a}$ and $R^{1d}$ are each as defined herein. In certain embodiments, in any one of the formulae provided herein, $R^{5d}$ is —$NR^{1a}C(NR^{1d})NR^{1b}R^{1c}$, wherein $R^{1a}$, $R^{1b}$, $R^{1c}$, and $R^{1d}$ are each as defined herein. In certain embodiments, in any one of the formulae provided herein, $R^{5d}$ is —$NR^{1a}C(S)R^{1d}$, wherein $R^{1a}$ and $R^{1d}$ are each as defined herein. In certain embodiments, in any one of the formulae provided herein, $R^{5d}$ is —$NR^{1a}C(S)OR^{1d}$, wherein $R^{1a}$ and $R^{1d}$ are each as defined herein. In certain embodiments, in any one of the formulae provided herein, $R^{5d}$ is —$NR^{1a}C(S)NR^{1b}R^{1c}$, wherein $R^{1a}$, $R^{1b}$, and $R^{1c}$ are each as defined herein. In certain embodiments, in any one of the formulae provided herein, $R^{5d}$ is —$NR^{1a}S(O)R^{1d}$, wherein $R^{1a}$ and $R^{1d}$ are each as defined herein. In certain embodiments, in any one of the formulae provided herein, $R^{5d}$ is —$NR^{1a}S(O)_2R^{1d}$, wherein $R^{1a}$ and $R^{1d}$ are each as defined herein. In certain embodiments, in any one of the formulae provided herein, $R^{5d}$ is —$NR^{1a}S(O)NR^{1b}R^{1c}$, wherein $R^{1a}$, $R^{1b}$, and $R^{1c}$ are each as defined herein. In certain embodiments, in any one of the formulae provided herein, $R^{5d}$ is —$NR^{1a}S(O)_2NR^{1b}R^{1c}$, wherein $R^{1a}$, $R^{1b}$, and $R^{1c}$ are each as defined herein. In certain embodiments, in any one of the formulae provided herein, $R^{5d}$ is —$SR^{1a}$, wherein $R^{1a}$ is as defined herein. In certain embodiments, in any one of the formulae provided herein, $R^{5d}$ is —$S(O)R^{1a}$, wherein $R^{1a}$ is as defined herein. In certain embodiments, in any one of the formulae provided herein, $R^{5d}$ is —$S(O)_2R^{1a}$, wherein $R^{1a}$ is as defined herein. In certain embodiments, in any one of the formulae provided herein, $R^{5d}$ is —$S(O)NR^{1b}R^{1c}$, wherein $R^{1b}$ and $R^{1c}$ are each as defined herein. In certain embodiments, in any one of the formulae provided herein, $R^{5d}$ is —$S(O)_2NR^{1b}R^{1c}$, wherein $R^{1b}$ and $R^{1c}$ are each as defined herein.

In certain embodiments, in any one of the formulae provided herein, $R^{5d}$ is (i) hydrogen, cyano, or halo; (ii) $C_{1-6}$ alkyl or $C_{6-14}$ aryl, each optionally substituted with one or more substituents Q; or (iii) —$OR^{1a}$, —$NR^{1b}R^c$, or —$S(O)_2R^{1a}$, wherein each $R^{1a}$, $R^{1b}$, and $R^{1c}$ is as defined herein. In certain embodiments, in any one of the formulae provided herein, $R^{5d}$ is hydrogen, cyano, fluoro, chloro, bromo, methyl, ethyl, fluoromethyl, difluoromethyl, trifluoromethyl, 1-cyano-1,1-difluoromethyl, 1,1-difluoro-2-hydroxyethyl, 1,1-difluoro-2-hydroxy-2-methylpropyl, methylaminomethyl, 2-aminomethylphenyl, 2-(2-aminoethyl)phenyl, 2-methyl-aminomethylphenyl, 2-dimethylaminomethylphenyl, hydroxyl, methoxy, amino, or methylsulfonyl. In certain embodiments, in any one of the formulae provided herein, $R^{5d}$ is hydrogen, fluoro, methyl, trifluoromethyl, hydroxyl, or amino. In certain embodiments, in any one of the formulae provided herein, $R^{5d}$ is hydrogen. In certain embodiments, in any one of the formulae provided herein, $R^{5d}$ is trifluoromethyl. In certain embodiments, in any one of the formulae provided herein, $R^{5d}$ is not bromo.

In certain embodiments, in any one of the formulae provided herein, $R^{5e}$ is hydrogen. In certain embodiments, in any one of the formulae provided herein, $R^{5e}$ is deuterium. In certain embodiments, in any one of the formulae provided herein, $R^{5e}$ is cyano. In certain embodiments, in any one of the formulae provided herein, $R^{5e}$ is halo. In certain embodiments, in any one of the formulae provided herein, $R^{5e}$ is fluoro or chloro. In certain embodiments, in any one of the formulae provided herein, $R^{5e}$ is fluoro. In certain embodiments, in any one of the formulae provided herein, $R^{5e}$ is nitro.

In certain embodiments, in any one of the formulae provided herein, $R^{5e}$ is $C_{1-6}$ alkyl, optionally substituted with one or more substituents Q. In certain embodiments, in any one of the formulae provided herein, $R^{5e}$ is $C_{1-6}$ heteroalkyl, optionally substituted with one or more substituents Q. In certain embodiments, in any one of the formulae provided herein, $R^{5e}$ is $C_{2-6}$ alkenyl, optionally substituted with one or more substituents Q. In certain embodiments, in any one of the formulae provided herein, $R^{5e}$ is $C_{2-6}$ alkynyl, optionally substituted with one or more substituents Q. In certain embodiments, in any one of the formulae provided herein, $R^{5e}$ is $C_{3-10}$ cycloalkyl, optionally substituted with one or more substituents Q. In certain embodiments, in any one of the formulae provided herein, $R^{5e}$ is $C_{6-14}$ aryl, optionally substituted with one or more substituents Q. In certain embodiments, in any one of the formulae provided herein, $R^{5e}$ is $C_{7-15}$ aralkyl, optionally substituted with one or more substituents Q. In certain embodiments, in any one of the formulae provided herein, $R^{5e}$ is heteroaryl, optionally substituted with one or more substituents Q. In certain embodiments, in any one of the formulae provided herein, $R^{5e}$ is heterocyclyl, optionally substituted with one or more substituents Q.

In certain embodiments, in one of the formulae provided herein, $R^{5e}$ is —$C(O)R^{1a}$, wherein $R^{1a}$ is as defined herein. In certain embodiments, in any one of the formulae provided herein, $R^{5e}$ is —$C(O)OR^{1a}$, wherein $R^{1a}$ is as defined herein. In certain embodiments, in any one of the formulae provided herein, $R^{5e}$ is —$C(O)NR^{1b}R^{1c}$, wherein $R^{1b}$ and $R^{1c}$ are each as defined herein. In certain embodiments, in any one of the formulae provided herein, $R^{5e}$ is —$C(O)SR^{1a}$, wherein $R^{1a}$ is as defined herein. In certain embodiments, in any one of the formulae provided herein, $R^{5e}$ is —$C(NR^{1a})NR^{1b}R^{1c}$, wherein $R^{1a}$, $R^{1b}$, and $R^{1c}$ are each as defined herein. In certain embodiments, in any one of the formulae provided herein, $R^{5e}$ is —$C(S)R^{1a}$, wherein $R^{1a}$ is as defined herein. In certain embodiments, in any one of the formulae provided herein, $R^{5e}$ is —$C(S)OR^{1a}$, wherein $R^{1a}$ is as defined herein. In certain embodiments, in any one of the formulae provided herein, $R^{5e}$ is —$C(S)NR^{1b}R^{1c}$, wherein $R^{1b}$ and $R^{1c}$ are each as defined herein. In certain embodiments, in any one of the formulae provided herein, $R^{5e}$ is —$OR^{1a}$, wherein $R^{1a}$ is as defined herein. In certain embodiments, in any one of the formulae provided herein, $R^{5e}$ is —$OC(O)R^{1a}$, wherein $R^{1a}$ is as defined herein. In certain embodiments, in any one of the formulae provided herein, $R^{5e}$ is —$OC(O)OR^{1a}$, wherein $R^{1a}$ is as defined herein. In certain embodiments, in any one of the formulae provided herein, $R^{5e}$ is —$OC(O)NR^{1b}R^{1c}$, wherein $R^{1b}$ and $R^{1c}$ are each as defined herein. In certain embodiments, in any one of the formulae provided herein, $R^{5e}$ is —$OC(O)SR^{1a}$, wherein $R^{1a}$ is as defined herein. In certain embodiments, in any one of the formulae provided herein, $R^{5e}$ is —$OC(NR^{1a})NR^{1b}R^{1c}$, wherein $R^{1a}$, $R^{1b}$, and $R^{1c}$ are each as defined herein. In certain embodiments, in any one of the formulae provided herein, $R^{5e}$ is —$OC(S)R^{1a}$, wherein $R^{1a}$ is as defined herein. In certain embodiments, in any one of the formulae provided herein, $R^{5e}$ is —$OC(S)OR^{1a}$, wherein $R^{1a}$ is as defined herein. In certain embodiments, in any one of the formulae provided herein, $R^{5e}$ is —$OC(S)NR^{1b}R^{1c}$, wherein $R^{1b}$ and $R^{1c}$ are each as defined herein. In certain embodiments, in any one of the formulae provided herein, $R^{5e}$ is —$OS(O)R^{1a}$, wherein $R^{1a}$ is as defined herein. In certain embodiments, in any one of the formulae provided herein, $R^{5e}$ is —$OS(O)_2R^{1a}$, wherein $R^{1a}$ is as defined herein. In certain embodiments, in any one of the formulae provided herein, $R^{5e}$ is —$OS(O)NR^{1b}R^{1c}$, wherein $R^{1b}$ and $R^{1c}$ are each as defined herein. In certain embodiments, in any one of the formulae provided herein, $R^{5e}$ is —$OS(O)_2NR^{1b}R^{1c}$, wherein $R^{1b}$ and $R^{1c}$ are each as defined herein. In certain embodiments, in any one of the formulae provided herein, $R^{5e}$ is —$NR^{1b}R^{1c}$ wherein $R^{1b}$ and $R^{1c}$ are each as defined herein. In certain embodiments, in any one of the formulae provided herein, $R^{5e}$ is —$NR^{1a}C(O)R^{1d}$, wherein $R^{1a}$ and $R^{1d}$ are each as defined herein. In certain embodiments, in any one of the formulae provided herein, $R^{5e}$ is —$NR^{1a}C(O)OR^{1d}$, wherein $R^{1a}$ and $R^{1d}$ are each as defined herein. In certain embodiments, in any one of the formulae provided herein, $R^{5e}$ is —$NR^{1a}C(O)NR^{1b}R^{1c}$, wherein $R^{1b}$ and $R^{1c}$ are each as defined herein. In certain embodiments, in any one of the formulae provided herein, $R^{5e}$ is —$NR^{1a}C(O)SR^{1d}$, wherein $R^{1a}$ and $R^{1d}$ are each as defined herein. In certain embodiments, in any one of the formulae provided herein, $R^{5e}$ is —$NR^{1a}C(NR^{1d})NR^{1b}R^{1c}$, wherein $R^{1a}$, $R^{1b}$, $R^{1c}$, and $R^{1d}$ are each as defined herein. In certain embodiments, in any one of the formulae provided herein, $R^{5e}$ is —$NR^{1a}C(S)R^{1d}$, wherein $R^{1a}$ and $R^{1d}$ are each as defined herein. In certain embodiments, in any one of the formulae provided herein, $R^{5e}$ is —$NR^{1a}C(S)OR^{1d}$, wherein $R^{1a}$ and $R^{1d}$ are each as defined herein. In certain embodiments, in any one of the formulae provided herein, $R^{5e}$ is —$NR^{1a}C(S)NR^{1b}R^{1c}$, wherein $R^{1a}$, $R^{1b}$, and $R^{1c}$ are each as defined herein. In certain embodiments, in any one of the formulae provided herein, $R^{5e}$ is —$NR^{1a}S(O)R^{1d}$, wherein $R^{1a}$ and $R^{1d}$ are each as defined herein. In certain embodiments, in any one of the formulae provided herein, $R^{5e}$ is —$NR^{1a}S(O)_2R^{1d}$, wherein $R^{1a}$ and $R^{1d}$ are each as defined herein. In certain embodiments, in any one of the formulae provided herein, $R^{5e}$ is —$NR^{1a}S(O)NR^{1b}R^{1c}$, wherein $R^{1a}$, $R^{1b}$, and $R^{1c}$ are each as defined herein. In certain embodiments, in any one of the formulae provided herein, $R^{5e}$ is —$NR^{1a}S(O)_2NR^{1b}R^{1c}$, wherein $R^{1a}$, $R^{1b}$, and $R^{1c}$ are each as defined herein. In certain embodiments, in any one of the formulae provided herein, $R^{5e}$ is —$SR^{1a}$, wherein $R^{1a}$ is as defined herein. In certain embodiments, in any one of the formulae provided herein, $R^{5e}$ is —$S(O)R^{1a}$, wherein $R^{1a}$ is as defined herein. In certain embodiments, in any one of the formulae provided herein, $R^{5e}$ is —$S(O)_2R^{1a}$, wherein $R^{1a}$ is as defined herein. In certain embodiments, in any one of the formulae provided herein, $R^{5e}$ is —$S(O)NR^{1b}R^{1c}$, wherein $R^{1b}$ and $R^{1c}$ are each as defined herein. In certain embodiments, in any one of the formulae provided herein, $R^{5e}$ is —$S(O)_2NR^{1b}R^{1c}$, wherein $R^{1b}$ and $R^{1c}$ are each as defined herein.

In certain embodiments, in any one of the formulae provided herein, $R^{5e}$ is (i) hydrogen, cyano, or halo; (ii) $C_{1-6}$ alkyl or $C_{6-14}$ aryl, each optionally substituted with one or more substituents Q; or (iii) —$OR^{1a}$, —$NR^{1b}R^c$, or —$S(O)_2R^{1a}$, wherein each $R^{1a}$, $R^{1b}$, and $R^{1c}$ is as defined herein. In certain embodiments, in any one of the formulae provided herein, $R^{5e}$ is hydrogen, cyano, fluoro, chloro, bromo, methyl, ethyl, fluoromethyl, difluoromethyl, trifluoromethyl, 1-cyano-1,1-difluoromethyl, 1,1-difluoro-2-hydroxyethyl, 1,1-difluoro-2-hydroxy-2-methylpropyl, methylaminomethyl, 2-aminomethylphenyl, 2-(2-aminoethyl)phenyl, 2-methyl-aminomethylphenyl, 2-dimethylaminomethylphenyl, hydroxyl, methoxy, amino, or methylsulfonyl. In certain embodiments, in any one of the formulae provided herein, $R^{5e}$ is hydrogen.

In one embodiment, provided herein is a compound of Formula (III):

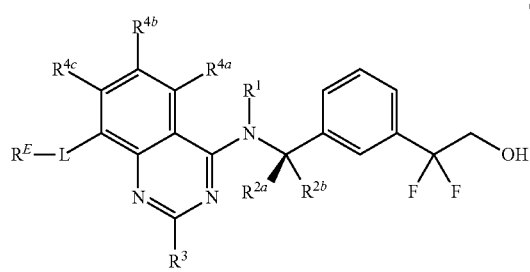

(III)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{4a}$, $R^{4b}$, $R^{4c}$, $R^E$, and L are each as defined herein.

In another embodiment, provided herein is a compound of Formula (IV):

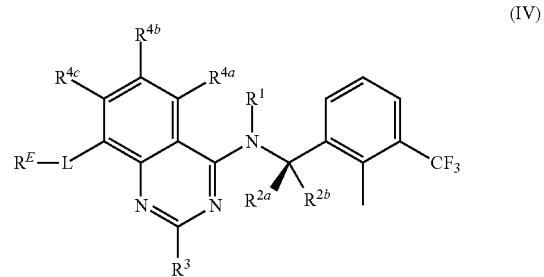

(IV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{4a}$, $R^{4b}$, $R^{4C}$, $R^E$, and L are each as defined herein.

In yet another embodiment, provided herein is a compound of Formula (V):

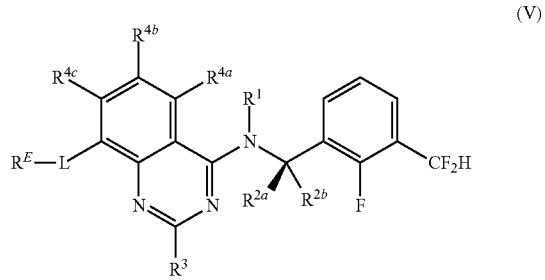

(V)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{4a}$, $R^{4b}$, $R^{4c}$, $R^E$, and L are each as defined herein.

In still another embodiment, provided herein is a compound of Formula (VI):

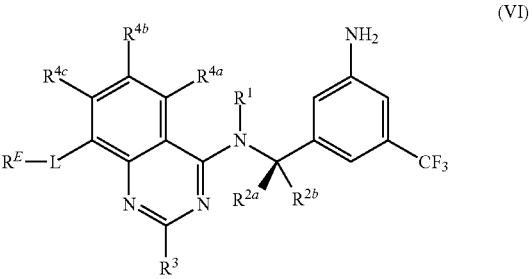

(VI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{4a}$, $R^{4b}$, $R^{4c}$, $R^E$, and L are each as defined herein.

In certain embodiments, in any one of the formulae provided herein, $R^1$ is hydrogen. In certain embodiments, in any one of the formulae provided herein, $R^1$ is $C_{1-6}$ alkyl, optionally substituted with one or more substituents Q. In certain embodiments, in any one of the formulae provided herein, $R^1$ is $C_{1-6}$ heteroalkyl, optionally substituted with one or more substituents Q. In certain embodiments, in any one of the formulae provided herein, $R^1$ is $C_{2-6}$ alkenyl, optionally substituted with one or more substituents Q. In certain embodiments, in any one of the formulae provided herein, $R^1$ is $C_{2-6}$ alkynyl, optionally substituted with one or more substituents Q. In certain embodiments, in any one of the formulae provided herein, $R^1$ is $C_{3-10}$ cycloalkyl, optionally substituted with one or more substituents Q. In certain embodiments, in any one of the formulae provided herein, $R^1$ is $C_{6-14}$ aryl, optionally substituted with one or more substituents Q. In certain embodiments, in any one of the formulae provided herein, $R^1$ is $C_{7-15}$ aralkyl, optionally substituted with one or more substituents Q. In certain embodiments, in any one of the formulae provided herein, $R^1$ is heteroaryl, optionally substituted with one or more substituents Q. In certain embodiments, in any one of the formulae provided herein, $R^1$ is heterocyclyl, optionally substituted with one or more substituents Q.

In certain embodiments, in any one of the formulae provided herein, $R^{2a}$ is hydrogen. In certain embodiments, in any one of the formulae provided herein, $R^{2a}$ is deuterium. In certain embodiments, in any one of the formulae provided herein, $R^{2a}$ is halo. In certain embodiments, in any one of the formulae provided herein, $R^{2a}$ is $C_{1-6}$ alkyl, optionally substituted with one or more substituents Q. In certain embodiments, in any one of the formulae provided herein, $R^{2a}$ is methyl, optionally substituted with one or more substituents Q. In certain embodiments, in any one of the formulae provided herein, $R^{2a}$ is methyl. In certain embodiments, in any one of the formulae provided herein, $R^{2a}$ is $C_{1-6}$ heteroalkyl, optionally substituted with one or more substituents Q. In certain embodiments, in any one of the formulae provided herein, $R^{2a}$ is $C_{2-6}$ alkenyl, optionally substituted with one or more substituents Q. In certain embodiments, in any one of the formulae provided herein, $R^{2a}$ is $C_{2-6}$ alkynyl, optionally substituted with one or more substituents Q. In certain embodiments, in any one of the formulae provided herein, $R^{2a}$ is $C_{3-10}$ cycloalkyl, optionally substituted with one or more substituents Q. In certain embodiments, in any one of the formulae provided herein, $R^{2a}$ is $C_{6-14}$ aryl, optionally substituted with one or more substituents Q. In certain embodiments, in any one of the formulae provided herein, $R^{2a}$ is $C_{7-15}$ aralkyl, optionally substituted with one or more substituents Q. In certain embodiments, in any one of the formulae provided herein, $R^{2a}$ is heteroaryl, optionally substituted with one or more substituents Q. In certain embodiments, in any one of the formulae provided herein, $R^{2a}$ is heterocyclyl, optionally substituted with one or more substituents Q.

In certain embodiments, in any one of the formulae provided herein, $R^{2b}$ is hydrogen. In certain embodiments, in any one of the formulae provided herein, $R^{2b}$ is deuterium. In certain embodiments, in any one of the formulae provided herein, $R^{2b}$ is halo. In certain embodiments, in any one of the formulae provided herein, $R^{2b}$ is $C_{1-6}$ alkyl, optionally substituted with one or more substituents Q. In certain embodiments, in any one of the formulae provided herein, $R^{2b}$ is methyl, optionally substituted with one or more substituents Q. In certain embodiments, in any one of the formulae provided herein, $R^{2b}$ is methyl. In certain embodiments, in any one of the formulae provided herein, $R^{2b}$ is $C_{1-6}$ heteroalkyl, optionally substituted with one or more substituents Q. In certain embodiments, in any one of the formulae provided herein, $R^{2b}$ is $C_{2-6}$ alkenyl, optionally substituted with one or more substituents Q. In certain embodiments, in any one of the formulae provided herein, $R^{2b}$ is $C_{2-6}$ alkynyl, optionally substituted with one or more substituents Q. In certain embodiments, in any one of the formulae provided herein, $R^{2b}$ is $C_{3-10}$ cycloalkyl, optionally substituted with one or more substituents Q. In certain embodiments, in any one of the formulae provided herein, $R^{2b}$ is $C_{6-14}$ aryl, optionally substituted with one or more substituents Q. In certain embodiments, in any one of the formulae provided herein, $R^{2b}$ is $C_{7-15}$ aralkyl, optionally substituted with one or more substituents Q. In certain embodiments, in any one of the formulae provided herein, $R^{2b}$ is heteroaryl, optionally substituted with one or more substituents Q. In certain embodiments, in any one of the formulae provided herein, $R^{2b}$ is heterocyclyl, optionally substituted with one or more substituents Q.

In certain embodiments, in any one of the formulae provided herein, $R^{2a}$ is hydrogen and $R^{2b}$ is $C_{1-6}$ alkyl, optionally substituted with one or more substituents Q. In certain embodiments, in any one of the formulae provided herein, $R^{2a}$ is hydrogen and $R^{2b}$ is methyl. In certain embodiments, in any one of the formulae provided herein, $R^{2a}$ is $C_{1-6}$ alkyl, optionally substituted with one or more substituents Q; and $R^{2b}$ is hydrogen. In certain embodiments, in any one of the formulae provided herein, $R^{2a}$ is methyl and $R^{2b}$ is hydrogen.

In certain embodiments, in any one of the formulae provided herein, $R^3$ is hydrogen. In certain embodiments, in any one of the formulae provided herein, $R^3$ is deuterium. In certain embodiments, in any one of the formulae provided herein, $R^3$ is cyano. In certain embodiments, in any one of the formulae provided herein, $R^3$ is halo. In certain embodiments, in any one of the formulae provided herein, $R^3$ is fluoro or chloro. In certain embodiments, in any one of the formulae provided herein, $R^3$ is fluoro. In certain embodiments, in any one of the formulae provided herein, $R^3$ is nitro.

In certain embodiments, in any one of the formulae provided herein, $R^3$ is $C_{1-6}$ alkyl, optionally substituted with one or more substituents Q. In certain embodiments, in any one of the formulae provided herein, $R^3$ is methyl, ethyl, or propyl, each optionally substituted with one or more substituents Q. In certain embodiments, in any one of the formulae provided herein, $R^3$ is methyl, trifluoromethyl, ethyl, isopropyl, methylaminomethyl, or dimethylaminomethyl. In certain embodiments, in any one of the formulae provided herein, $R^3$ is methyl. In certain embodiments, in any one of the formulae provided herein, $R^3$ is $C_{1-6}$ heteroalkyl, optionally substituted with one or more substituents Q. In certain embodiments, in any one of the formulae provided herein, $R^3$ is $C_{2-6}$ alkenyl, optionally substituted with one or more substituents Q. In certain embodiments, in any one of the formulae provided herein, $R^3$ is $C_{2-6}$ alkynyl, optionally substituted with one or more substituents Q. In certain embodiments, in any one of the formulae provided herein, $R^3$ is $C_{3-10}$ cycloalkyl, optionally substituted with one or more substituents Q. In certain embodiments, in any one of the formulae provided herein, $R^3$ is $C_{6-14}$ aryl, optionally substituted with one or more substituents Q. In certain embodiments, in any one of the formulae provided herein, $R^3$ is $C_{7-15}$ aralkyl, optionally substituted with one or more substituents Q. In certain embodiments, in any one of the formulae provided herein, $R^3$ is heteroaryl, optionally substituted with one or more substituents Q. In certain embodiments, in any one of the formulae provided herein, $R^3$ is heterocyclyl, optionally substituted with one or more substituents Q.

In certain embodiments, in any one of the formulae provided herein, $R^3$ is —C(O)$R^{1a}$, wherein $R^{1a}$ is as defined herein. In certain embodiments, in any one of the formulae provided herein, $R^3$ is —C(O)O$R^{1a}$, wherein $R^{1a}$ is as defined herein. In certain embodiments, in any one of the formulae provided herein, $R^3$ is —C(O)N$R^{1b}R^{1c}$, wherein $R^{1b}$ and $R^{1c}$ are each as defined herein. In certain embodiments, in any one of the formulae provided herein, $R^3$ is —C(O)S$R^{1a}$, wherein $R^{1a}$ is as defined herein. In certain embodiments, in any one of the formulae provided herein, $R^3$ is —C(N$R^{1a}$)N$R^{1b}R^{1c}$, wherein $R^{1a}$, $R^{1b}$, and $R^{1c}$ are each as defined herein. In certain embodiments, in any one of the formulae provided herein, $R^3$ is —C(S)$R^{1a}$, wherein $R^{1a}$ is as defined herein. In certain embodiments, in any one of the formulae provided herein, $R^3$ is —C(S)O$R^{1a}$, wherein $R^{1a}$ is as defined herein. In certain embodiments, in any one of the formulae provided herein, $R^3$ is —C(S)N$R^{1b}R^{1c}$, wherein $R^{1b}$ and $R^{1c}$ are each as defined herein. In certain embodiments, in any one of the formulae provided herein, $R^3$ is —O$R^{1a}$, wherein $R^{1a}$ is as defined herein. In certain embodiments, in any one of the formulae provided herein, $R^3$ is —OC(O)$R^{1a}$, wherein $R^{1a}$ is as defined herein. In certain embodiments, in any one of the formulae provided herein, $R^3$ is —OC(O)O$R^{1a}$, wherein $R^{1a}$ is as defined herein. In certain embodiments, in any one of the formulae provided herein, $R^3$ is —OC(O)N$R^{1b}R^{1c}$, wherein $R^{1b}$ and $R^{1c}$ are each as defined herein. In certain embodiments, in any one of the formulae provided herein, $R^3$ is —OC(O)S$R^{1a}$, wherein $R^{1a}$ is as defined herein. In certain embodiments, in any one of the formulae provided herein, $R^3$ is —OC(N$R^{1a}$)N$R^{1b}R^{1c}$, wherein $R^{1a}$, $R^{1b}$, and $R^{1c}$ are each as defined herein. In certain embodiments, in any one of the formulae provided herein, $R^3$ is —OC(S)$R^{1a}$, wherein $R^{1a}$ is as defined herein. In certain embodiments, in any one of the formulae provided herein, $R^3$ is —OC(S)O$R^{1a}$, wherein $R^{1a}$ is as defined herein. In certain embodiments, in any one of the formulae provided herein, $R^3$ is —OC(S)N$R^{1b}R^{1c}$, wherein $R^{1b}$ and $R^{1c}$ are each as defined herein. In certain embodiments, in any one of the formulae provided herein, $R^3$ is —OS(O)$R^{1a}$, wherein $R^{1a}$ is as defined herein. In certain embodiments, in any one of the formulae provided herein, $R^3$ is —OS(O)$_2R^{1a}$, wherein $R^{1a}$ is as defined herein. In certain embodiments, in any one of the formulae provided herein, $R^3$ is —OS(O)N$R^{1b}R^{1c}$, wherein $R^{1b}$ and $R^{1c}$ are each as defined herein. In certain embodiments, in any one of the formulae provided herein, $R^3$ is —OS(O)$_2$N$R^{1b}R^{1c}$, wherein $R^{1b}$ and $R^{1c}$ are each as defined herein. In certain embodiments, in any one of the formulae provided herein, $R^3$ is —N$R^{1b}R^{1c}$ wherein $R^{1b}$ and $R^{1c}$ are each as defined herein. In certain embodiments, in any one of the formulae provided herein, $R^3$ is dimethylamino. In certain embodiments, in any one of the formulae provided herein, $R^3$ is —N$R^{1a}$C(O)$R^{1d}$, wherein $R^{1a}$ and $R^{1d}$ are each as defined herein. In certain embodiments, in any one of the formulae provided herein, $R^3$ is —N$R^{1a}$C(O)O$R^{1d}$, wherein $R^{1a}$ and $R^{1d}$ are each as defined herein. In certain embodiments, in any one of the formulae provided herein, $R^3$ is —N$R^{1a}$C(O)N$R^{1b}R^{1c}$, wherein $R^{1b}$ and $R^{1c}$ are each as defined herein. In certain embodiments, in any one of the formulae provided herein, $R^3$ is —N$R^{1a}$C(O)S$R^{1d}$, wherein $R^{1a}$ and $R^{1d}$ are each as defined herein. In certain embodiments, in any one of the formulae provided herein, $R^3$ is —N$R^{1a}$C(N$R^d$)N$R^{1b}R^{1c}$, wherein $R^{1a}$, $R^{1b}$, $R^{1c}$, and $R^{1d}$ are each as defined herein. In certain embodiments, in any one of the formulae provided herein, $R^3$ is —N$R^{1a}$C(S)$R^{1d}$, wherein $R^{1a}$ and $R^{1d}$ are each as defined herein. In certain embodiments, in any one of the formulae provided herein, $R^3$ is —N$R^{1a}$C(S)O$R^{1d}$, wherein $R^{1a}$ and $R^{1d}$ are each as defined herein. In certain embodiments, in any one of the formulae provided herein, $R^3$ is —N$R^{1a}$C(S)N$R^{1b}R^{1c}$, wherein $R^{1a}$, $R^{1b}$, and $R^{1c}$ are each as defined herein. In certain embodiments, in any one of the formulae provided herein, $R^3$ is —N$R^{1a}$S(O)$R^{1d}$, wherein $R^{1a}$ and $R^{1d}$ are each as defined herein. In certain embodiments, in any one of the formulae provided herein, $R^3$ is —N$R^{1a}$S(O)$_2R^{1d}$, wherein $R^{1a}$ and $R^{1d}$ are each as defined herein. In certain embodiments, in any one of the formulae provided herein, $R^3$ is —N$R^{1a}$S(O)N$R^{1b}R^{1c}$, wherein $R^{1a}$, $R^{1b}$, and $R^{1c}$ are each as defined herein. In certain embodiments, in any one of the formulae provided herein, $R^3$ is —N$R^{1a}$S(O)$_2$N$R^{1b}R^{1c}$, wherein $R^{1a}$, $R^{1b}$, and $R^{1c}$ are each as defined herein. In certain embodiments, in any one of the formulae provided herein, $R^3$ is —S$R^{1a}$, wherein $R^{1a}$ is as defined herein. In certain embodiments, in any one of the formulae provided herein, $R^3$ is —S(O)$R^{1a}$, wherein $R^{1a}$ is as defined herein. In certain embodiments, in any one of the formulae provided herein, $R^3$ is —S(O)$_2R^{1a}$, wherein $R^{1a}$ is as defined herein. In certain embodiments, in any one of the formulae provided herein, $R^3$ is —S(O)N$R^{1b}R^{1c}$, wherein $R^{1b}$ and $R^{1c}$ are each as defined herein. In certain embodiments, in any one of the formulae provided herein, $R^3$ is —S(O)$_2$N$R^{1b}R^{1c}$, wherein $R^{1b}$ and $R^{1c}$ are each as defined herein.

In certain embodiments, in any one of the formulae provided herein, $R^3$ is hydrogen, methyl, trifluoromethyl, or dimethylamino. In certain embodiments, in any one of the formulae provided herein, $R^3$ is methyl.

In certain embodiments, in any one of the formulae provided herein, $R^{4a}$ is hydrogen. In certain embodiments, in any one of the formulae provided herein, $R^{4a}$ is deuterium. In certain embodiments, in any one of the formulae provided herein, $R^{4a}$ is cyano. In certain embodiments, in any one of the formulae provided herein, $R^{4a}$ is halo. In certain embodiments, in any one of the formulae provided herein, $R^{4a}$ is fluoro or chloro. In certain embodiments, in any one of the formulae provided herein, $R^{4a}$ is nitro.

In certain embodiments, in any one of the formulae provided herein, $R^{4a}$ is $C_{1-6}$ alkyl, optionally substituted with one or more substituents Q. In certain embodiments, in any one of the formulae provided herein, $R^{4a}$ is methyl. In certain embodiments, in any one of the formulae provided herein, $R^{4a}$ is $C_{1-6}$ heteroalkyl, optionally substituted with one or more substituents Q. In certain embodiments, in any one of the formulae provided herein, $R^{4a}$ is $C_{2-6}$ alkenyl, optionally substituted with one or more substituents Q. In certain embodiments, in any one of the formulae provided herein, $R^{4a}$ is $C_{2-6}$ alkynyl, optionally substituted with one or more substituents Q. In certain embodiments, in any one of the formulae provided herein, $R^{4a}$ is $C_{3-10}$ cycloalkyl, optionally substituted with one or more substituents Q. In certain embodiments, in any one of the formulae provided herein, $R^{4a}$ is $C_{6-14}$ aryl, optionally substituted with one or more substituents Q. In certain embodiments, in any one of the formulae provided herein, $R^{4a}$ is $C_{7-15}$ aralkyl, optionally substituted with one or more substituents Q. In certain embodiments, in any one of the formulae provided herein, $R^{4a}$ is heteroaryl, optionally substituted with one or more substituents Q. In certain embodiments, in any one of the formulae provided herein, $R^{4a}$ is heterocyclyl, optionally substituted with one or more substituents Q.

In certain embodiments, in any one of the formulae provided herein, $R^{4a}$ is —C(O)$R^{1a}$, wherein $R^{1a}$ is as defined herein. In certain embodiments, in any one of the formulae provided herein, $R^{4a}$ is —C(O)O$R^{1a}$, wherein $R^{1a}$ is as defined herein. In certain embodiments, in any one of the formulae provided herein, $R^{4a}$ is —C(O)N$R^{1b}R^{1c}$, wherein $R^{1b}$ and $R^{1c}$ are each as defined herein. In certain embodiments, in any one of the formulae provided herein, $R^{4a}$ is —C(O)S$R^{1a}$, wherein $R^{1a}$ is as defined herein. In certain embodiments, in any one of the formulae provided herein, $R^{4a}$ is —C(N$R^{1a}$)N$R^{1b}R^{1c}$, wherein $R^{1a}$, $R^{1b}$, and $R^{1c}$ are each as defined herein. In certain embodiments, in any one of the formulae provided herein, $R^{4a}$ is —C(S)$R^{1a}$, wherein $R^{1a}$ is as defined herein. In certain embodiments, in any one of the formulae provided herein, $R^{4a}$ is —C(S)O$R^{1a}$, wherein $R^{1a}$ is as defined herein. In certain embodiments, in any one of the formulae provided herein, $R^{4a}$ is —C(S)N$R^{1b}R^{1c}$, wherein $R^{1b}$ and $R^{1c}$ are each as defined herein. In certain embodiments, in any one of the formulae provided herein, $R^{4a}$ is —O$R^{1a}$, wherein $R^{1a}$ is as defined herein. In certain embodiments, in any one of the formulae provided herein, $R^{4a}$ is —OC(O)$R^{1a}$, wherein $R^{1a}$ is as defined herein. In certain embodiments, in any one of the formulae provided herein, $R^{4a}$ is —OC(O)O$R^{1a}$, wherein $R^{1a}$ is as defined herein. In certain embodiments, in any one of the formulae provided herein, $R^{4a}$ is —OC(O)N$R^{1b}R^{1c}$, wherein $R^{1b}$ and $R^{1c}$ are each as defined herein. In certain embodiments, in any one of the formulae provided herein, $R^{4a}$ is —OC(O)S$R^{1a}$, wherein $R^{1a}$ is as defined herein. In certain embodiments, in any one of the formulae provided herein, $R^{4a}$ is —OC(N$R^{1a}$)N$R^{1b}R^{1c}$, wherein $R^{1a}$, $R^{1b}$, and $R^{1c}$ are each as defined herein. In certain embodiments, in any one of the formulae provided herein, $R^{4a}$ is —OC(S)$R^{1a}$, wherein $R^{1a}$ is as defined herein. In certain embodiments, in any one of the formulae provided herein, $R^{4a}$ is —OC(S)O$R^{1a}$, wherein $R^{1a}$ is as defined herein. In certain embodiments, in any one of the formulae provided herein, $R^{4a}$ is —OC(S)N$R^{1b}R^{1c}$, wherein $R^{1b}$ and $R^{1c}$ are each as defined herein. In certain embodiments, in any one of the formulae provided herein, $R^{4a}$ is —OS(O)$R^{1a}$, wherein $R^{1a}$ is as defined herein. In certain embodiments, in any one of the formulae provided herein, $R^{4a}$ is —OS(O)$_2R^{1a}$, wherein $R^{1a}$ is as defined herein. In certain embodiments, in any one of the formulae provided herein, $R^{4a}$ is —OS(O)N$R^{1b}R^{1c}$, wherein $R^{1b}$ and $R^{1c}$ are each as defined herein. In certain embodiments, in any one of the formulae provided herein, $R^{4a}$ is —OS(O)$_2$N$R^{1b}R^{1c}$, wherein $R^{1b}$ and $R^{1c}$ are each as defined herein. In certain embodiments, in any one of the formulae provided herein, $R^{4a}$ is —N$R^{1b}R^{1c}$ wherein $R^{1b}$ and $R^{1c}$ are each as defined herein. In certain embodiments, in any one of the formulae provided herein, $R^{4a}$ is —N$R^{1a}$C(O)$R^{1d}$, wherein $R^{1a}$ and $R^{1d}$ are each as defined herein. In certain embodiments, in any one of the formulae provided herein, $R^{4a}$ is —N$R^{1a}$C(O)O$R^{1d}$, wherein $R^{1a}$ and $R^{1d}$ are each as defined herein. In certain embodiments, in any one of the formulae provided herein, $R^{4a}$ is —N$R^{1a}$C(O)N$R^{1b}R^{1c}$, wherein $R^{1b}$ and $R^{1c}$ are each as defined herein. In certain embodiments, in any one of the formulae provided herein, $R^{4a}$ is —N$R^{1a}$C(O)S$R^{1d}$, wherein $R^{1a}$ and $R^{1d}$ are each as defined herein. In certain embodiments, in any one of the formulae provided herein, $R^{4a}$ is —N$R^{1a}$C(N$R^{1d}$)N$R^{1b}R^{1c}$, wherein $R^{1a}$, $R^{1b}$, $R^{1c}$, and $R^{1d}$ are each as defined herein. In certain embodiments, in any one of the formulae provided herein, $R^{4a}$ is —N$R^{1a}$C(S)$R^{1d}$, wherein $R^{1a}$ and $R^{1d}$ are each as defined herein. In certain embodiments, in any one of the formulae provided herein, $R^{4a}$ is —N$R^{1a}$C(S)O$R^{1d}$, wherein $R^{1a}$ and $R^{1d}$ are each as defined herein. In certain embodiments, in any one of the formulae provided herein, $R^{4a}$ is —N$R^{1a}$C(S)N$R^{1b}R^{1c}$, wherein $R^{1a}$, $R^{1b}$, and $R^{1c}$ are each as defined herein. In certain embodiments, in any one of the formulae provided herein, $R^{4a}$ is —N$R^{1a}$S(O)$R^{1d}$, wherein $R^{1a}$ and $R^{1d}$ are each as defined herein. In certain embodiments, in any one of the formulae provided herein, $R^{4a}$ is —N$R^{1a}$S(O)$_2R^{1d}$, wherein $R^{1a}$ and $R^{1d}$ are each as defined herein. In certain embodiments, in any one of the formulae provided herein, $R^{4a}$ is —N$R^{1a}$S(O)N$R^{1b}R^{1c}$, wherein $R^{1a}$, $R^{1b}$, and $R^{1c}$ are each as defined herein. In certain embodiments, in any one of the formulae provided herein, $R^{4a}$ is —N$R^{1a}$S(O)$_2$N$R^{1b}R^{1c}$, wherein $R^{1a}$, $R^{1b}$, and $R^{1c}$ are each as defined herein. In certain embodiments, in any one of the formulae provided herein, $R^{4a}$ is —S$R^{1a}$, wherein $R^{1a}$ is as defined herein. In certain embodiments, in any one of the formulae provided herein, $R^{4a}$ is —S(O)$R^{1a}$, wherein $R^{1a}$ is as defined herein. In certain embodiments, in any one of the formulae provided herein, $R^{4a}$ is —S(O)$_2R^{1a}$, wherein $R^{1a}$ is as defined herein. In certain embodiments, in any one of the formulae provided herein, $R^{4a}$ is —S(O)N$R^{1b}R^{1c}$, wherein $R^{1b}$ and $R^{1c}$ are each as defined herein. In certain embodiments, in any one of the formulae provided herein, $R^{4a}$ is —S(O)$_2$N$R^{1b}R^{1c}$, wherein $R^{1b}$ and $R^{1c}$ are each as defined herein.

In certain embodiments, in any one of the formulae provided herein, $R^{4b}$ is hydrogen. In certain embodiments, in any one of the formulae provided herein, $R^{4b}$ is deuterium. In certain embodiments, in any one of the formulae provided herein, $R^{4b}$ is cyano. In certain embodiments, in any one of the formulae provided herein, $R^{4b}$ is halo. In certain embodiments, in any one of the formulae provided herein, $R^{4b}$ is fluoro or chloro. In certain embodiments, in any one of the formulae provided herein, $R^{4b}$ is nitro.

In certain embodiments, in any one of the formulae provided herein, $R^{4b}$ is $C_{1-6}$ alkyl, optionally substituted with one or more substituents Q. In certain embodiments, in any one of the formulae provided herein, $R^{4b}$ is $C_{1-6}$ heteroalkyl, optionally substituted with one or more substituents Q. In certain embodiments, in any one of the formulae provided herein, $R^{4b}$ is $C_{2-6}$ alkenyl, optionally substituted with one or more substituents Q. In certain embodiments, in any one of the formulae provided herein, $R^{4b}$ is $C_{2-6}$ alkynyl, optionally substituted with one or more substituents Q. In certain embodiments, in any one of the formulae provided herein, $R^{4b}$ is $C_{3-10}$ cycloalkyl, optionally substituted with one or more substituents Q. In certain embodiments, in any one of the formulae provided herein, $R^{4b}$ is $C_{6-14}$ aryl, optionally substituted with one or more substituents Q. In certain embodiments, in any one of the formulae provided herein, $R^{4b}$ is $C_{7-15}$ aralkyl, optionally substituted with one or more substituents Q. In certain embodiments, in any one of the formulae provided herein, $R^{4b}$ is heteroaryl, optionally substituted with one or more substituents Q. In certain embodiments, in any one of the formulae provided herein, $R^{4b}$ is monocyclic heteroaryl, optionally substituted with one or more substituents Q. In certain embodiments, in any one of the formulae provided herein, $R^{4b}$ is 5- or 6-membered heteroaryl, each optionally substituted with one or more substituents Q. In certain embodiments, in any one of the formulae provided herein, $R^{4b}$ is bicyclic heteroaryl, optionally substituted with one or more substituents Q. In certain embodiments, in any one of the formulae provided herein, $R^{4b}$ is 5,5-, 5,6-, or 6,6-fused heteroaryl, each optionally substituted with one or more substituents Q.

In certain embodiments, in any one of the formulae provided herein, $R^{4b}$ is heterocyclyl, optionally substituted with one or more substituents Q. In certain embodiments, in any one of the formulae provided herein, $R^{4b}$ is monocyclic heterocyclyl, optionally substituted with one or more substituents Q. In certain embodiments, in any one of the formulae provided herein, $R^{4b}$ is 3-, 4-. 5-, 6-, or 7-membered heterocyclyl, each optionally substituted with one or more substituents Q. In certain embodiments, in any one of the formulae provided herein, $R^{4b}$ is 3-membered heterocyclyl, optionally substituted with one or more substituents Q. In certain embodiments, in any one of the formulae provided herein, $R^{4b}$ is 4-membered heterocyclyl, optionally substituted with one or more substituents Q. In certain embodiments, in any one of the formulae provided herein, $R^{4b}$ is 5-membered heterocyclyl, optionally substituted with one or more substituents Q. In certain embodiments, in any one of the formulae provided herein, $R^{4b}$ is 6-membered heterocyclyl, optionally substituted with one or more substituents Q. In certain embodiments, in any one of the formulae provided herein, $R^{4b}$ is 7-membered heterocyclyl, optionally substituted with one or more substituents Q. In certain embodiments, in any one of the formulae provided herein, $R^{4b}$ is pyrrolidinyl, morpholinyl, piperidinyl, piperazinyl, or 1,4-diazepanyl, each optionally substituted with one or more substituents Q. In certain embodiments, in any one of the formulae provided herein, $R^{4b}$ is bicyclic heterocyclyl, optionally substituted with one or more substituents Q. In certain embodiments, in any one of the formulae provided herein, $R^{4b}$ is bridged heterocyclyl, optionally substituted with one or more substituents Q. In certain embodiments, in any one of the formulae provided herein, $R^{4b}$ is fused heterocyclyl, optionally substituted with one or more substituents Q. In certain embodiments, in any one of the formulae provided herein, $R^{4b}$ is 4,4-, 5,5-, 5,6-, or 6,6-fused heterocyclyl, each optionally substituted with one or more substituents Q. In certain embodiments, in any one of the formulae provided herein, $R^{4b}$ is 4,4-fused heterocyclyl, optionally substituted with one or more substituents Q. In certain embodiments, in any one of the formulae provided herein, $R^{4b}$ is 5,5-fused heterocyclyl, optionally substituted with one or more substituents Q. In certain embodiments, in any one of the formulae provided herein, $R^{4b}$ is 5,6-fused heterocyclyl, optionally substituted with one or more substituents Q. In certain embodiments, in any one of the formulae provided herein, $R^{4b}$ is 6,6-fused heterocyclyl, optionally substituted with one or more substituents Q. In certain embodiments, in any one of the formulae provided herein, $R^{4b}$ is 5,6,7,8-tetrahydroimidazo[1,5-a]pyrazinyl or 4,5,6,7-tetrahydropyrazolo[1,5-a]pyrazinyl, each optionally substituted with one or more substituents Q. In certain embodiments, in any one of the formulae provided herein, $R^{4b}$ is spiro heterocyclyl, optionally substituted with one or more substituents Q. In certain embodiments, in any one of the formulae provided herein, $R^{4b}$ is 1-acetyl-3-methoxy-pyrrolidine-3-yl, morpholin-4-yl, piperazin-1-yl, 4-(1-methylpyrazol-4-yl)piperazin-1-yl, 3,3-difluoro-1,4-diazepan-1-yl, 1,3-dimethyl-5,6,7,8-tetrahydroimidazo[1,5-a]pyrazin-7-yl, or 4,5,6,7-tetrahydropyrazolo[1,5-a]-pyrazin-5-yl.

In certain embodiments, in any one of the formulae provided herein, $R^{4b}$ is —C(O)$R^{1a}$, wherein $R^{1a}$ is as defined herein. In certain embodiments, in any one of the formulae provided herein, $R^{4b}$ is —C(O)O$R^{1a}$, wherein $R^{1a}$ is as defined herein. In certain embodiments, in any one of the formulae provided herein, $R^{4b}$ is —C(O)NR$^{1b}$R$^{1c}$, wherein $R^{1b}$ and $R^{1c}$ are each as defined herein. In certain embodiments, in any one of the formulae provided herein, $R^{4b}$ is —C(O)S$R^{1a}$, wherein $R^{1a}$ is as defined herein. In certain embodiments, in any one of the formulae provided herein, $R^{4b}$ is —C(NR$^{1a}$)NR$^{1b}$R$^{1c}$, wherein $R^{1a}$, $R^{1b}$, and $R^{1c}$ are each as defined herein. In certain embodiments, in any one of the formulae provided herein, $R^{4b}$ is —C(S)$R^{1a}$, wherein $R^{1a}$ is as defined herein. In certain embodiments, in any one of the formulae provided herein, $R^{4b}$ is —C(S)O$R^{1a}$, wherein $R^{1a}$ is as defined herein. In certain embodiments, in any one of the formulae provided herein, $R^{4b}$ is —C(S)NR$^{1b}$R$^{1c}$, wherein $R^{1b}$ and $R^{1c}$ are each as defined herein. In certain embodiments, in any one of the formulae provided herein, $R^{4b}$ is —OR$^{1a}$, wherein $R^{1a}$ is as defined herein. In certain embodiments, in any one of the formulae provided herein, $R^{4b}$ is $C_{1-6}$ alkoxy, optionally substituted with one or more substituents Q. In certain embodiments, in any one of the formulae provided herein, $R^{4b}$ is methoxy. In certain embodiments, in any one of the formulae provided herein, $R^{4b}$ is —OC(O)$R^{1a}$, wherein $R^{1a}$ is as defined herein. In certain embodiments, in any one of the formulae provided herein, $R^{4b}$ is —OC(O)O$R^{1a}$, wherein $R^{1a}$ is as defined herein. In certain embodiments, in any one of the formulae provided herein, $R^{4b}$ is —OC(O)NR$^{1b}$R$^{1c}$, wherein $R^{1b}$ and $R^{1c}$ are each as defined herein. In certain embodiments, in any one of the formulae provided herein, $R^{4b}$ is —OC(O)S$R^{1a}$, wherein $R^{1a}$ is as defined herein. In certain embodiments, in any one of the formulae provided herein, $R^{4b}$ is —OC(NR$^{1a}$)NR$^{1b}$R$^{1c}$, wherein $R^{1a}$, $R^{1b}$, and $R^{1c}$ are each as defined herein. In certain embodiments, in any one of the formulae provided herein, $R^{4b}$ is —OC(S)$R^{1a}$, wherein $R^{1a}$ is as defined herein. In certain embodiments, in any one of the formulae provided herein, $R^{4b}$ is —OC(S)O$R^{1a}$, wherein $R^{1a}$ is as defined herein. In certain embodiments, in any one of the formulae provided herein, $R^{4b}$ is —OC(S)NR$^{1b}$R$^{1c}$, wherein $R^{1b}$ and $R^{1c}$ are each as defined herein. In certain embodiments, in any one of the formulae provided herein, $R^{4b}$ is —OS(O)$R^{1a}$, wherein $R^{1a}$ is as defined herein. In certain embodiments, in any one of the formulae provided herein, $R^{4b}$ is —OS(O)$_2$R$^{1a}$, wherein $R^{1a}$ is as defined herein. In certain embodiments, in any one of the formulae provided herein, $R^{4b}$ is —OS(O)NR$^{1b}$R$^{1c}$, wherein $R^{1b}$ and $R^{1c}$ are each as defined herein. In certain embodiments, in any one of the formulae provided herein, $R^{4b}$ is —OS(O)$_2$NR$^{1b}$R$^{1c}$, wherein $R^{1b}$ and $R^{1c}$ are each as defined herein. In certain embodiments, in any one of the formulae provided herein, $R^{4b}$ is —NR$^{1b}$R$^{1c}$ wherein $R^{1b}$ and $R^{1c}$ are each as defined herein. In certain embodiments, in any one of the formulae provided herein, $R^{4b}$ is —NR$^{1a}$C(O)R$^{1d}$, wherein $R^{1a}$ and $R^{1d}$ are each as defined herein. In certain embodiments, in any one of the formulae provided herein, $R^{4b}$ is —NR$^{1a}$C(O)OR$^{1d}$, wherein $R^{1a}$ and $R^{1d}$ are each as defined herein. In certain embodiments, in any one of the formulae provided herein, $R^{4b}$ is —NR$^{1a}$C(O)NR$^{1b}$R$^{1c}$, wherein $R^{1b}$ and $R^{1c}$ are each as defined herein. In certain embodiments, in any one of the formulae provided herein, $R^{4b}$ is —NR$^{1a}$C(O)SR$^{1d}$, wherein $R^{1a}$ and $R^{1d}$ are each as defined herein. In certain embodiments, in any one of the formulae provided herein, $R^{4b}$ is —NR$^{1a}$C(NR$^{1d}$)NR$^{1b}$R$^{1c}$, wherein $R^{1a}$, $R^{1b}$, $R^{1c}$, and $R^{1d}$ are each as defined herein. In certain embodiments, in any one of the formulae provided herein, $R^{4b}$ is —NR$^{1a}$C(S)R$^{1d}$, wherein $R^{1a}$ and $R^{1d}$ are each as defined herein. In certain embodiments, in any one of the formulae provided herein, $R^{4b}$ is —NR$^{1a}$C(S)OR$^{1d}$, wherein $R^{1a}$ and $R^{1d}$ are each as defined herein. In certain embodiments, in any one of the formulae provided herein, $R^{4b}$ is —NR$^{1a}$C(S)NR$^{1b}$R$^{1c}$, wherein $R^{1a}$, $R^{1b}$, and $R^{1c}$ are each as defined herein. In certain embodiments, in any one of the formulae provided herein, $R^{4b}$ is —NR$^{1a}$S(O)R$^{1d}$, wherein $R^{1a}$ and $R^{1d}$ are each as defined herein. In certain embodiments, in any one of the formulae provided herein, $R^{4b}$ is —NR$^{1a}$S(O)$_2$R$^{1d}$, wherein $R^{1a}$ and $R^{1d}$ are each as defined herein. In certain embodiments, in any one of the formulae provided herein, $R^{4b}$ is —NR$^{1a}$S(O)NR$^{1b}$R$^{1c}$, wherein $R^{1a}$, $R^{1b}$, and $R^{1c}$ are each as defined herein. In certain embodiments, in any one of the formulae provided herein, $R^{4b}$ is —NR$^{1a}$S(O)$_2$NR$^{1b}$R$^{1c}$, wherein $R^{1a}$, $R^{1b}$, and $R^{1c}$ are each as defined herein. In certain embodiments, in any one of the formulae provided herein, $R^{4b}$ is —SR$^{1a}$, wherein $R^{1a}$ is as defined herein. In certain embodiments, in any one of the formulae provided herein, $R^{4b}$ is —S(O)R$^{1a}$, wherein $R^{1a}$ is as defined herein. In certain embodiments, in any one of the formulae provided herein, $R^{4b}$ is —S(O)$_2$R$^{1a}$, wherein $R^{1a}$ is as defined herein. In certain embodiments, in any one of the formulae provided herein, $R^{4b}$ is —S(O)NR$^{1b}$R$^{1c}$, wherein $R^{1b}$ and $R^{1c}$ are each as defined herein. In certain embodiments, in any one of the formulae provided herein, $R^{4b}$ is —S(O)$_2$NR$^{1b}$R$^{1c}$, wherein $R^{1b}$ and $R^{1c}$ are each as defined herein.

In certain embodiments, in any one of the formulae provided herein, $R^{4b}$ is cyclopropyl, cyclobutyl, cyclohexyl, cyclohexenyl, bicyclo[1.1.1]pentanyl, bicyclo[2.2.2]octanyl, methoxy, tetrahydrofuryloxy, or pyrrolidinyloxy, each of which is optionally substituted with one, two, or three substituents, wherein each substituent is independently fluoro, oxo, imino, methyl, difluoromethyl, hydroxycarbonylmethyl, dimethylcarbamoylmethyl, isopropyl, tetrahydrofur-3-yl, acetyl, propionyl, 2-methoxyacetyl, 2-dimethylaminoacetyl, cyclopropyl-carbonyl, 3-cyanoazetidin-1-ylcarbonyl, 3-fluoroazetidin-1-ylcarbonyl, 3-methoxyazetidin-1-yl-carbonyl, 3-hydroxypyrrolidin-1-ylcarbonyl, morpholin-4-ylcarbonyl, 4-methylpiperazin-1-yl-carbonyl, 4-(2-methoxyethyl)piperazin-1-ylcarbonyl, hydroxycarbonyl, ethoxycarbonyl, tert-butoxycarbonyl, dimethylcarbamoyl, (methyl)(ethyl)carbamoyl, (2-hydroxyethyl)(methyl)-carbamoyl, (2-hydroxypropyl)(methyl)carbamoyl, (2-hydroxy-2-methylpropyl)(methyl)-carbamoyl, (2,3-dihydroxypropyl)(methyl)carbamoyl, (2-methoxyethyl)(methyl)carbamoyl, (methyl)(oxetan-3-yl)carbamoyl, (methyl)(tetrahydrofur-3-yl)carbamoyl, hydroxyl, or acetoxy.

In certain embodiments, in any one of the formulae provided herein, $R^{4b}$ is 1-methylcyclopropyl, 1-fluoromethylcyclopropyl, 1-difluoromethylcyclopropyl, 3-fluoro-cyclobutyl, 3,3-difluorocyclobutyl, 4-hydroxycyclohexyl, 4-hydroxycarbonylcyclohexyl, 4-ethoxy-carbonylcyclohexyl, 4-(3-cyanoazetidin-1-ylcarbonyl)cyclohexyl, 4-(3-fluoroazetidin-1-yl-carbonyl)cyclohexyl, 4-(3-methoxyazetidin-1-ylcarbonyl)cyclohexyl, 4-(3-hydroxypyrrolidin-1-yl)carbonylcyclohexyl, 4-morpholin-4-ylcarbonylcyclohexyl, 4-(4-methylpiperazin-1-yl)-carbonylcyclohexyl, 4-(4-(2-methoxyethyl)piperazin-1-yl)carbonylcyclohexyl, 4-dimethyl-carbamoylcyclohexyl, 4-(methyl)(ethyl)carbamoylcyclohexyl, 4-(2-hydroxyethyl)(methyl)-carbamoylcyclohexyl, 4-(2-hydroxypropyl)(methyl)carbamoylcyclohexyl, 4-(2-hydroxy-2-methylpropyl)(methyl)carbamoylcyclohexyl, 4-(2,3-dihydroxypropyl)(methyl)carbamoylcyclohexyl, 4-(2-methoxyethyl)(methyl)carbamoylcyclohexyl, 4-(methyl)(oxetan-3-yl)carbamoylcyclohexyl, 4-(methyl)(tetrahydrofur-3-yl)carbamoylcyclohexyl, 4-acetoxy-1-hydroxycyclohexyl, 1,4-dihydroxycyclohexyl, 4-hydroxycarbonyl-1-hydroxycyclohexyl, 4-ethoxycarbonyl-1-hydroxycyclohexyl, 4-dimethylcarbamoyl-1-hydroxycyclohexyl, 4-(2-hydroxyethyl)(methyl)carbamoyl-1-hydroxycyclohexyl, 4-(2-hydroxypropyl)(methyl)-carbamoyl-1-hydroxycyclohexyl, bicyclo[1.1.1]pentan-1-yl, 4-fluorobicyclo[2.2.2]octan-1-yl, 3-methyltetrahydrofuran-3-yl, piperidin-4-yl, 1-isopropylpiperidin-4-yl, 1-(hydroxycarbonyl-methyl)piperidin-4-yl, 1-(dimethylcarbamoylmethyl)piperidin-4-yl, 1-tetrahydrofur-3-yl-piperidin-4-yl, 1-acetylpiperidin-4-yl, 1-(2-methoxyacetyl)piperidin-4-yl, 1-(2-dimethylamino-acetyl)piperidin-4-yl, 1-tert-butoxycarbonylpiperidin-4-yl, 4-hydroxypiperidin-4-yl, 1-acetyl-4-hydroxypiperidin-4-yl, 1-(2-methoxyacetyl)-4-hydroxypiperidin-4-yl, 4-hydroxy-1-tert-butoxy-carbonylpiperidin-4-yl, 1-dimethylcarbamoyl-4-hydroxypiperidin-4-yl, tetrahydropyran-4-yl, tetrahydrothiopyran-4-yl, 1-oxotetrahydrothiopyran-4-yl, 1,1-dioxotetrahydrothiopyran-4-yl, 1-oxo-1-iminotetrahydrothiopyran-4-yl, 1,2,3,6-tetrahydropyridin-4-yl, 3,6-dihydropyran-4-yl, 3,6-dihydrothiopyran-4-yl, 1-oxo-3,6-dihydrothiopyran-4-yl, 1,1-dioxo-3,6-dihydrothiopyran-4-yl, 1-oxo-1-imino-3,6-dihydrothiopyran-4-yl, 6-hydroxy-2-azaspiro[3.3]heptan-6-yl, 2-hydroxy-7-azaspiro[3.5]nonan-2-yl, methoxy, tetrahydrofur-3-yloxy, (R)-tetrahydrofur-3-yloxy, (S)-tetra-hydrofur-3-yloxy, pyrrolidin-3-yloxy, 1-acetylpyrrolidin-3-yloxy, 1-propionylpyrrolidin-3-yloxy, 1-cyclopropylcarbonylpyrrolidin-3-yloxy, or 1-tert-butoxycarbonylpyrrolidin-3-yloxy.

In certain embodiments, in any one of the formulae provided herein, $R^{4c}$ is hydrogen. In certain embodiments, in any one of the formulae provided herein, $R^{4c}$ is deuterium. In certain embodiments, in any one of the formulae provided herein, $R^{4c}$ is cyano. In certain embodiments, in any one of the formulae provided herein, $R^{4c}$ is halo. In certain embodiments, in any one of the formulae provided herein, $R^{4c}$ is fluoro or chloro. In certain embodiments, in any one of the formulae provided herein, $R^{4c}$ is fluoro. In certain embodiments, in any one of the formulae provided herein, $R^{4c}$ is nitro.

In certain embodiments, in any one of the formulae provided herein, $R^{4c}$ is $C_{1-6}$ alkyl, optionally substituted with one or more substituents Q. In certain embodiments, in any one of the formulae provided herein, $R^{4c}$ is methyl, optionally substituted with one or more substituents Q. In certain embodiments, in any one of the formulae provided herein, $R^{4c}$ is methyl. In certain embodiments, in any one of the formulae provided herein, $R^{4c}$ is $C_{1-6}$ heteroalkyl, optionally substituted with one or more substituents Q. In certain embodiments, in any one of the formulae provided herein, $R^{4c}$ is $C_{2-6}$ alkenyl, optionally substituted with one or more substituents Q. In certain embodiments, in any one of the formulae provided herein, $R^{4c}$ is $C_{2-6}$ alkynyl, optionally substituted with one or more substituents Q. In certain embodiments, in any one of the formulae provided herein, $R^{4c}$ is $C_{3-10}$ cycloalkyl, optionally substituted with one or more substituents Q. In certain embodiments, in any one of the formulae provided herein, $R^{4c}$ is $C_{6-14}$ aryl, optionally substituted with one or more substituents Q. In certain embodiments, in any one of the formulae provided herein, $R^{4c}$ is $C_{7-15}$ aralkyl, optionally substituted with one or more substituents Q. In certain embodiments, in any one of the formulae provided herein, $R^{4c}$ is heteroaryl, optionally substituted with one or more substituents Q. In certain embodiments, in any one of the formulae provided herein, $R^{4c}$ is heterocyclyl, optionally substituted with one or more substituents Q.

In certain embodiments, in any one of the formulae provided herein, $R^{4c}$ is —C(O)R$^{1a}$, wherein $R^{1a}$ is as defined herein. In certain embodiments, in any one of the formulae provided herein, $R^{4c}$ is —C(O)OR$^{1a}$, wherein $R^{1a}$ is as defined herein. In certain embodiments, in any one of the formulae provided herein, $R^{4c}$ is —C(O)NR$^{1b}$R$^{1c}$, wherein $R^{1b}$ and $R^{1c}$ are each as defined herein. In certain embodiments, in any one of the formulae provided herein, $R^{4c}$ is —C(O)SR$^{1a}$, wherein $R^{1a}$ is as defined herein. In certain embodiments, in any one of the formulae provided herein, $R^{4c}$ is —C(NR$^{1a}$)NR$^{1b}$R$^{1c}$, wherein R$^{1a}$, R$^{1b}$, and R$^{1c}$ are each as defined herein. In certain embodiments, in any one of the formulae provided herein, R$^{4c}$ is —C(S)R$^{1a}$, wherein R$^{1a}$ is as defined herein. In certain embodiments, in any one of the formulae provided herein, R$^{4c}$ is —C(S)OR$^{1a}$, wherein R$^{1a}$ is as defined herein. In certain embodiments, in any one of the formulae provided herein, R$^{4c}$ is —C(S)NR$^{1b}$R$^{1c}$, wherein R$^{1b}$ and R$^{1c}$ are each as defined herein. In certain embodiments, in any one of the formulae provided herein, R$^{4c}$ is —OR$^{1a}$, wherein R$^{1a}$ is as defined herein. In certain embodiments, in any one of the formulae provided herein, R$^{4c}$ is $C_{1-6}$ alkoxy, optionally substituted with one or more substituents Q. In certain embodiments, in any one of the formulae provided herein, R$^{4c}$ is methoxy. In certain embodiments, in any one of the formulae provided herein, R$^{4c}$ is —OC(O)R$^{1a}$, wherein R$^{1a}$ is as defined herein. In certain embodiments, in any one of the formulae provided herein, R$^{4c}$ is —OC(O)OR$^{1a}$, wherein R$^{1a}$ is as defined herein. In certain embodiments, in any one of the formulae provided herein, R$^{4c}$ is —OC(O)NR$^{1b}$R$^{1c}$, wherein R$^{1b}$ and R$^{1c}$ are each as defined herein. In certain embodiments, in any one of the formulae provided herein, R$^{4c}$ is —OC(O)SR$^{1a}$, wherein R$^{1a}$ is as defined herein. In certain embodiments, in any one of the formulae provided herein, R$^{4c}$ is —OC(NR$^{1a}$)NR$^{1b}$R$^{1c}$, wherein R$^{1a}$, R$^{1b}$, and R$^{1c}$ are each as defined herein. In certain embodiments, in any one of the formulae provided herein, R$^{4c}$ is —OC(S)R$^{1a}$, wherein R$^{1a}$ is as defined herein. In certain embodiments, in any one of the formulae provided herein, R$^{4c}$ is —OC(S)OR$^{1a}$, wherein R$^{1a}$ is as defined herein. In certain embodiments, in any one of the formulae provided herein, R$^{4c}$ is —OC(S)NR$^{1b}$R$^{1c}$, wherein R$^{1b}$ and R$^{1c}$ are each as defined herein. In certain embodiments, in any one of the formulae provided herein, R$^{4c}$ is —OS(O)R$^{1a}$, wherein R$^{1a}$ is as defined herein. In certain embodiments, in any one of the formulae provided herein, R$^{4c}$ is —OS(O)$_2$R$^{1a}$, wherein R$^{1a}$ is as defined herein. In certain embodiments, in any one of the formulae provided herein, R$^{4c}$ is —OS(O)NR$^{1b}$R$^{1c}$, wherein R$^{1b}$ and R$^{1c}$ are each as defined herein. In certain embodiments, in any one of the formulae provided herein, R$^{4c}$ is —OS(O)$_2$NR$^{1b}$R$^{1c}$, wherein R$^{1b}$ and R$^{1c}$ are each as defined herein. In certain embodiments, in any one of the formulae provided herein, R$^{4c}$ is —NR$^{1b}$R$^{1c}$, wherein R$^{1b}$ and R$^{1c}$ are each as defined herein. In certain embodiments, in any one of the formulae provided herein, R$^{4c}$ is —NR$^{1a}$C(O)R$^{1d}$, wherein R$^{1a}$ and R$^{1d}$ are each as defined herein. In certain embodiments, in any one of the formulae provided herein, R$^{4c}$ is —NR$^{1a}$C(O)OR$^{1d}$, wherein R$^{1a}$ and R$^{1d}$ are each as defined herein. In certain embodiments, in any one of the formulae provided herein, R$^{4c}$ is —NR$^{1a}$C(O)NR$^{1b}$R$^{1c}$, wherein R$^{1b}$ and R$^{1c}$ are each as defined herein. In certain embodiments, in any one of the formulae provided herein, R$^{4c}$ is —NR$^{1a}$C(O)SR$^{1d}$, wherein R$^{1a}$ and R$^{1d}$ are each as defined herein. In certain embodiments, in any one of the formulae provided herein, R$^{4c}$ is —NR$^{1a}$C(NR$^{1d}$)NR$^{1b}$R$^{1c}$, wherein R$^{1a}$, R$^{1b}$, R$^{1c}$, and R$^{1d}$ are each as defined herein. In certain embodiments, in any one of the formulae provided herein, R$^{4c}$ is —NR$^{1a}$C(S)R$^{1d}$, wherein R$^{1a}$ and R$^{1d}$ are each as defined herein. In certain embodiments, in any one of the formulae provided herein, R$^{4c}$ is —NR$^{1a}$C(S)OR$^{1d}$, wherein R$^{1a}$ and R$^{1d}$ are each as defined herein. In certain embodiments, in any one of the formulae provided herein, R$^{4c}$ is —NR$^{1a}$C(S)NR$^{1b}$R$^{1c}$, wherein R$^{1a}$, R$^{1b}$, and R$^{1c}$ are each as defined herein. In certain embodiments, in any one of the formulae provided herein, R$^{4c}$ is —NR$^{1a}$S(O)R$^{1d}$, wherein R$^{1a}$ and R$^{1d}$ are each as defined herein. In certain embodiments, in any one of the formulae provided herein, R$^{4c}$ is —NR$^{1a}$S(O)$_2$R$^{1d}$, wherein R$^{1a}$ and R$^{1d}$ are each as defined herein. In certain embodiments, in any one of the formulae provided herein, R$^{4c}$ is —NR$^{1a}$S(O)NR$^{1b}$R$^{1c}$, wherein R$^{1a}$, R$^{1b}$, and R$^{1c}$ are each as defined herein. In certain embodiments, in any one of the formulae provided herein, R$^{4c}$ is —NR$^{1a}$S(O)$_2$NR$^{1b}$R$^{1c}$, wherein R$^{1a}$, R$^{1b}$, and R$^{1c}$ are each as defined herein. In certain embodiments, in any one of the formulae provided herein, R$^{4c}$ is —SR$^{1a}$, wherein R$^{1a}$ is as defined herein. In certain embodiments, in any one of the formulae provided herein, R$^{4c}$ is —S(O)R$^{1a}$, wherein R$^{1a}$ is as defined herein. In certain embodiments, in any one of the formulae provided herein, R$^{4c}$ is —S(O)$_2$R$^{1a}$, wherein R$^{1a}$ is as defined herein. In certain embodiments, in any one of the formulae provided herein, R$^{4c}$ is —S(O)NR$^{1b}$R$^{1c}$, wherein R$^{1b}$ and R$^{1c}$ are each as defined herein. In certain embodiments, in any one of the formulae provided herein, R$^{4c}$ is —S(O)$_2$NR$^{1b}$R$^{1c}$, wherein R$^{1b}$ and R$^{1c}$ are each as defined herein.

In certain embodiments, in any one of the formulae provided herein, R$^{4c}$ is hydrogen, fluoro, methyl, or methoxy. In certain embodiments, in any one of the formulae provided herein, R$^{4c}$ is methoxy.

All combinations of the embodiments provided herein for the groups in the formulae described herein are within the scope of this disclosure.

In one embodiment, provided herein is a compound of Formula (VII):

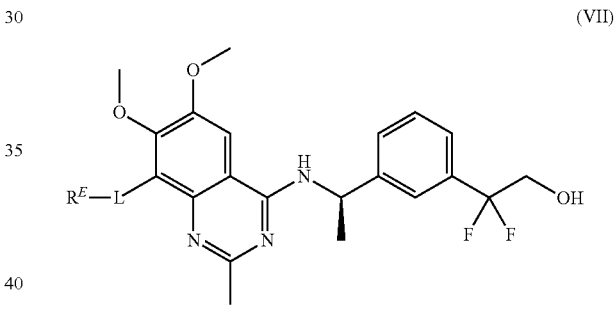

(VII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein R$^E$ and L are each as defined herein.

In another embodiment, provided herein is a compound of Formula (VIII):

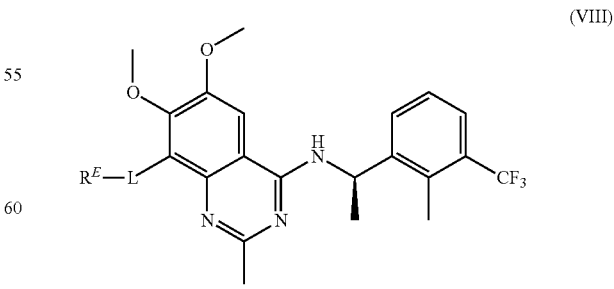

(VIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^E$ and L are each as defined herein.

In yet another embodiment, provided herein is a compound of Formula (IX):

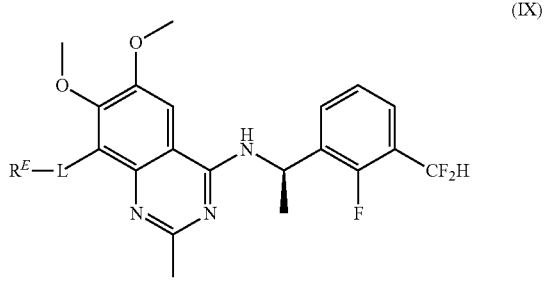

(IX)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^E$ and L are each as defined herein.

In still another embodiment, provided herein is a compound of Formula (X):

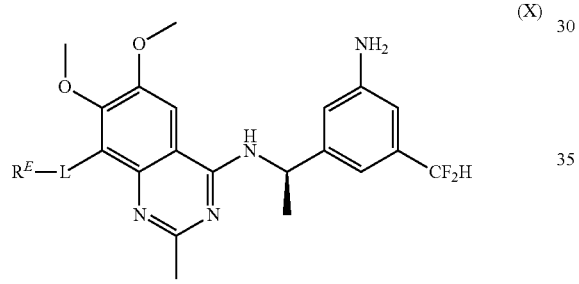

(X)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^E$ and L are each as defined herein.

In certain embodiments, in any one of the formulae provided herein, $R^E$ is a moiety of a cereblon (CRBN) E3 ligand, an inhibitors-of-apoptosis protein (IAP) E3 ligand, a mouse double minute 2 homolog (MDM2) E3 ligand, or a von Hippel-Lindau (VHL) E3 ligand.

In certain embodiments, in any one of the formulae provided herein, $R^E$ is a moiety of a CRBN E3 ligand.

In certain embodiments, $R^E$ is a moiety having the structure of Formula (EC-I):

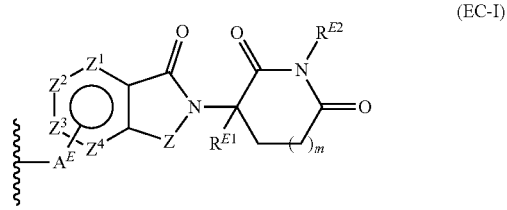

(EC-I)

or an enantiomer, a mixture of enantiomers, a diastereomer, a mixture of two or more diastereomers, a tautomer, a mixture of two or more tautomers, or an isotopic variant thereof;

wherein:

$A^E$ is a bond, —O—, —N($R^{1b}$)—, —S—, $C_{1-6}$ alkylene, $C_{1-6}$ heteroalkylene, $C_{2-6}$ alkenylene, $C_{2-6}$ heteroalkenylene, $C_{2-6}$ alkynylene, $C_{2-6}$ heteroalkynylene, $C_{3-10}$ cycloalkylene, $C_{6-14}$ arylene, $C_{7-15}$ aralkylene, heteroarylene, heterocyclylene, $C_{1-6}$ heteroalkylene-$C_{6-14}$ arylene, $C_{1-6}$ heteroalkylene-heterocyclylene, or $C_{2-6}$ alkynylene-heterocyclylene;

Z is —$CH_2$— or —C(O)—;

one of $Z^1$, $Z^2$, $Z^3$, and $Z^4$ is —C= and the remaining three of $Z^1$, $Z^2$, $Z^3$, and $Z^4$ are each independently —C($R^{E5}$)=; or $Z^t$ is a bond; one of $Z^2$, $Z^3$, and $Z^4$ is —C=, and the remaining two of $Z^2$, $Z^3$, and $Z^4$ are each independently —C($R^{E5}$)= or —S—;

m is an integer of 0, 1, or 2;

$R^{E1}$ is hydrogen, deuterium, halo, or $C_{1-6}$ alkyl;

$R^{E2}$ is hydrogen or $C_{1-6}$ alkyl;

each $R^{E4}$ is independently (i) deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^c$, or —S(O)$_2$N$R^{1b}R^{1c}$;

each $R^{E5}$ is independently hydrogen or $R^{E4}$; and $R^{1a}$, $R^{1b}$, $R^{1c}$, and $R^{1d}$ are each as defined herein;

wherein each alkyl, heteroalkyl, alkylene, heteroalkylene, alkenyl, alkenylene, heteroalkenylene, alkynyl, alkynylene, heteroalkynylene, cycloalkyl, cycloalkylene, aryl, arylene, aralkyl, aralkylene, heteroaryl, heteroarylene, heterocyclyl, and heterocyclylene is optionally substituted with one or more, in one embodiment, one, two, three, or four, substituents Q.

In certain embodiments, $R^E$ is a moiety having the structure of Formula (EC-II):

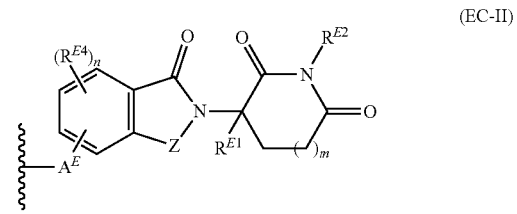

(EC-II)

or an enantiomer, a mixture of enantiomers, a diastereomer, a mixture of two or more diastereomers, a tautomer, a mixture of two or more tautomers, or an isotopic variant thereof; wherein n is an integer of 0, 1, 2, or 3; and $A^E$, $R^{E1}$, $R^{E2}$, $R^{E4}$, Z, and m are each as defined herein.

In certain embodiments, $R^E$ is a moiety having the structure of Formula (EC-III):

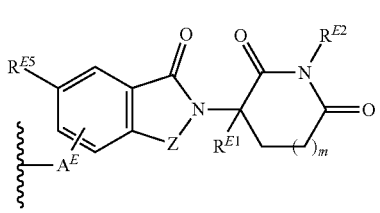

(EC-III)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E5}$, Z, and m are each as defined herein. In one embodiment, $R^{E5}$ is hydrogen or fluoro.

In certain embodiments, $R^E$ is a moiety having the structure of Formula (EC-IV):

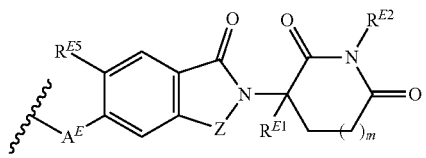

(EC-IV)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E5}$, Z, and m are each as defined herein. In one embodiment, $R^{E5}$ is hydrogen or fluoro.

In certain embodiments, $R^E$ is a moiety having the structure of Formula (EC-V):

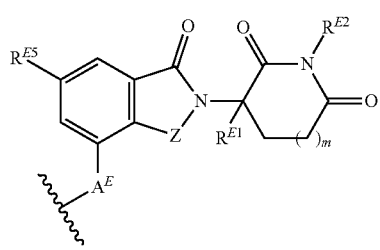

(EC-V)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E5}$, Z, and m are each as defined herein. In one embodiment, $R^{E5}$ is hydrogen or fluoro.

In certain embodiments, $R^E$ is a moiety having the structure of Formula (EC-VI):

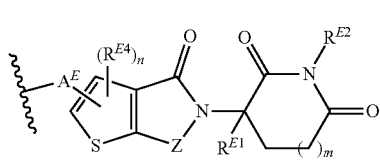

(EC-VI)

or an enantiomer, a mixture of enantiomers, a diastereomer, a mixture of two or more diastereomers, a tautomer, a mixture of two or more tautomers, or an isotopic variant thereof; wherein n is an integer of 0 or 1; and $A^E$, $R^{E1}$, $R^{E2}$, $R^{E4}$, Z, and m are each as defined herein.

In certain embodiments, $R^E$ is a moiety having the structure of Formula (EC-VII):

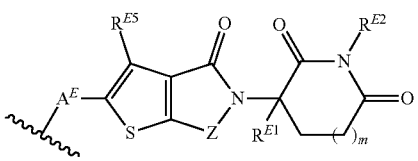

(EC-VII)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E5}$, Z, and m are each as defined herein. In one embodiment, $R^{E5}$ is hydrogen or fluoro.

In certain embodiments, $R^E$ is a moiety having the structure of Formula (EC-VIII):

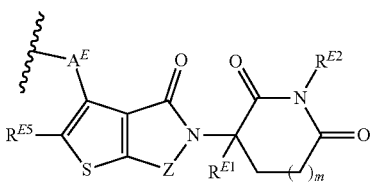

(EC-VIII)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E5}$, Z, and m are each as defined herein. In one embodiment, $R^{E5}$ is hydrogen or fluoro.

In certain embodiments, $R^E$ is a moiety having the structure of Formula (EC-IX):

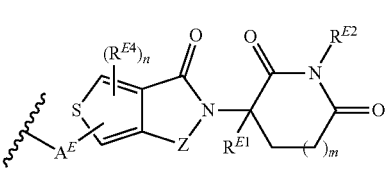

(EC-IX)

or an enantiomer, a mixture of enantiomers, a diastereomer, a mixture of two or more diastereomers, a tautomer, a mixture of two or more tautomers, or an isotopic variant thereof; wherein n is an integer of 0 or 1; and $A^E$, $R^{E1}$, $R^{E2}$, $R^{E4}$, Z, and m are each as defined herein.

In certain embodiments, $R^E$ is a moiety having the structure of Formula (EC-X):

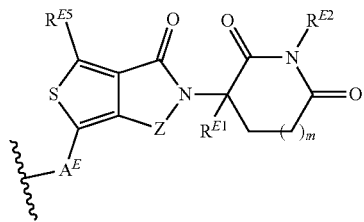

(EC-X)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E5}$, Z, and m are each as defined herein. In one embodiment, $R^{E5}$ is hydrogen or fluoro.

In certain embodiments, $R^E$ is a moiety having the structure of Formula (EC-XI):

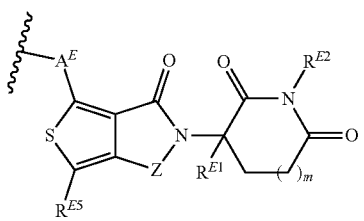

(EC-XI)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E5}$, Z, and m are each as defined herein. In one embodiment, $R^{E5}$ is hydrogen or fluoro.

In certain embodiments, $R^E$ is a moiety having the structure of Formula (EC-XII):

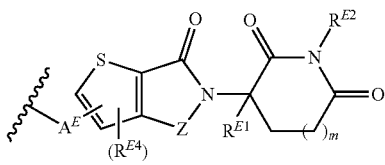

(EC-XII)

or an enantiomer, a mixture of enantiomers, a diastereomer, a mixture of two or more diastereomers, a tautomer, a mixture of two or more tautomers, or an isotopic variant thereof; wherein n is an integer of 0 or 1; and $A^E$, $R^{E1}$, $R^{E2}$, $R^{E4}$, Z, and m are each as defined herein.

In certain embodiments, $R^E$ is a moiety having the structure of Formula (EC-XIII):

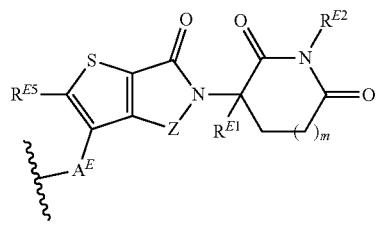

(EC-XIII)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E5}$, Z, and m are each as defined herein. In one embodiment, $R^{E5}$ is hydrogen or fluoro.

In certain embodiments, $R^E$ is a moiety having the structure of Formula (EC-XIV):

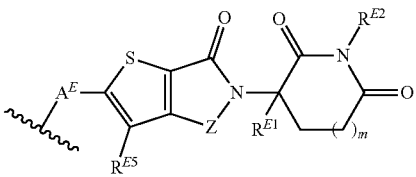

(EC-XIV)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E5}$, Z, and m are each as defined herein. In one embodiment, $R^{E5}$ is hydrogen or fluoro.

In certain embodiments, $R^E$ is a moiety having the structure of Formula (EC-XV):

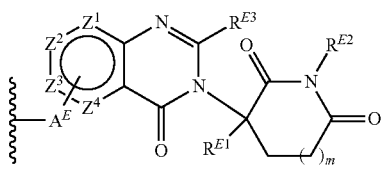

(EC-XV)

or an enantiomer, a mixture of enantiomers, a diastereomer, a mixture of two or more diastereomers, a tautomer, a mixture of two or more tautomers, or an isotopic variant thereof; wherein $R^{E3}$ is hydrogen, deuterium, halo, or $C_{1-6}$ alkyl, optionally substituted with one or more, in one embodiment, one, two, three, or four, substituents Q; and $A^E$, $R^{E1}$, $R^{E2}$, $Z^1$, $Z^2$, $Z^3$, $Z^4$, and m are each as defined herein.

In certain embodiments, $R^E$ is a moiety having the structure of Formula (EC-XVI):

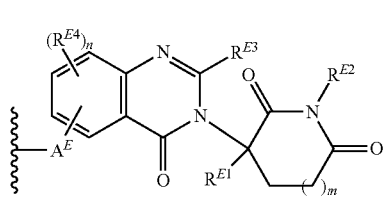

(EC-XVI)

or an enantiomer, a mixture of enantiomers, a diastereomer, a mixture of two or more diastereomers, a tautomer, a mixture of two or more tautomers, or an isotopic variant thereof; wherein n is an integer of 0, 1, 2, or 3; and $A^E$, $R^{E1}$, $R^{E2}$, $R^{E3}$, $R^{E4}$, and m are each as defined herein.

In certain embodiments, $R^E$ is a moiety having the structure of Formula (EC-XVII):

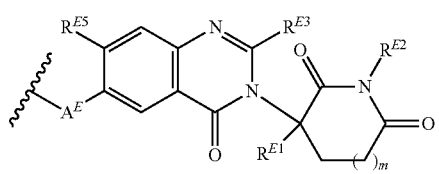

(EC-XVII)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E3}$, $R^{E5}$, and m are each as defined herein. In one embodiment, $R^{E5}$ is hydrogen or fluoro.

In certain embodiments, $R^E$ is a moiety having the structure of Formula (EC-XVIII):

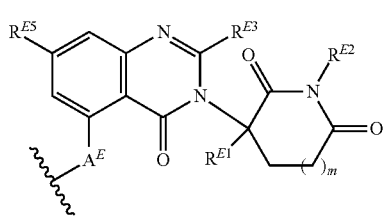

(EC-XVIII)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E3}$, $R^{E5}$, and m are each as defined herein. In one embodiment, $R^{E5}$ is hydrogen or fluoro.

In certain embodiments, $R^E$ is a moiety having the structure of Formula (EC-XIX):

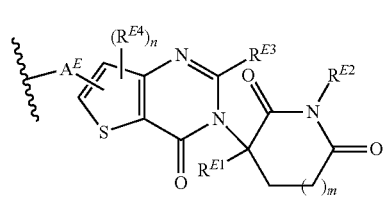

(EC-XIX)

or an enantiomer, a mixture of enantiomers, a diastereomer, a mixture of two or more diastereomers, a tautomer, a mixture of two or more tautomers, or an isotopic variant thereof; wherein n is an integer of 0 or 1; and $A^E$, $R^{E1}$, $R^{E2}$, $R^{E3}$, $R^{E4}$, and m are each as defined herein.

In certain embodiments, $R^E$ is a moiety having the structure of Formula (EC-XX):

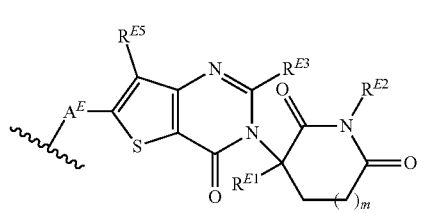

(EC-XX)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E3}$, $R^{E5}$, and m are each as defined herein. In one embodiment, $R^{E5}$ is hydrogen or fluoro.

In certain embodiments, $R^E$ is a moiety having the structure of Formula (EC-XXI):

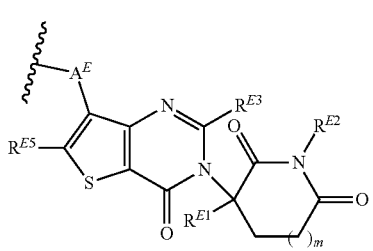

(EC-XXI)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E3}$, $R^{E5}$, and m are each as defined herein. In one embodiment, $R^{E5}$ is hydrogen or fluoro.

In certain embodiments, $R^E$ is a moiety having the structure of Formula (EC-XXII):

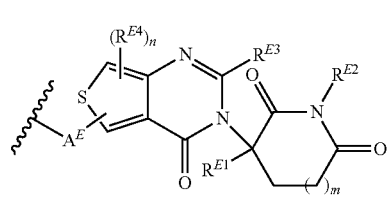
(EC-XXII)

or an enantiomer, a mixture of enantiomers, a diastereomer, a mixture of two or more diastereomers, a tautomer, a mixture of two or more tautomers, or an isotopic variant thereof; wherein n is an integer of 0 or 1; and $A^E$, $R^{E1}$, $R^{E2}$, $R^{E3}$, $R^{E4}$, and m are each as defined herein.

In certain embodiments, $R^E$ is a moiety having the structure of Formula (EC-XXIII):

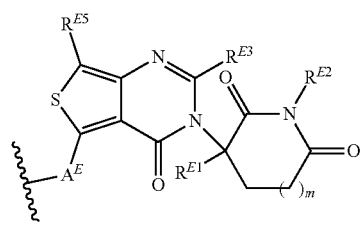
(EC-XXIII)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E3}$, $R^{E5}$, and m are each as defined herein. In one embodiment, $R^{E5}$ is hydrogen or fluoro.

In certain embodiments, $R^E$ is a moiety having the structure of Formula (EC-XXIV):

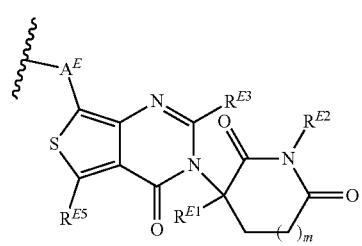
(EC-XXIV)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E3}$, $R^{E5}$, and m are each as defined herein. In one embodiment, $R^{E5}$ is hydrogen or fluoro.

In certain embodiments, $R^E$ is a moiety having the structure of Formula (EC-XXV):

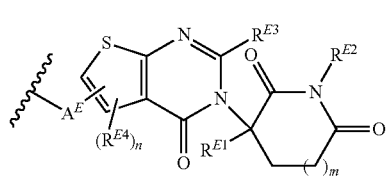
(EC-XXV)

or an enantiomer, a mixture of enantiomers, a diastereomer, a mixture of two or more diastereomers, a tautomer, a mixture of two or more tautomers, or an isotopic variant thereof; wherein n is an integer of 0 or 1; and $A^E$, $R^{E1}$, $R^{E2}$, $R^{E3}$, $R^{E4}$, and m are each as defined herein.

In certain embodiments, $R^E$ is a moiety having the structure of Formula (EC-XXVI):

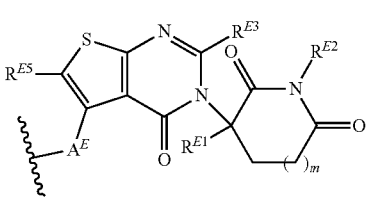
(EC-XXVI)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E3}$, $R^{E5}$, and m are each as defined herein. In one embodiment, $R^{E5}$ is hydrogen or fluoro.

In certain embodiments, $R^E$ is a moiety having the structure of Formula (EC-XXVII):

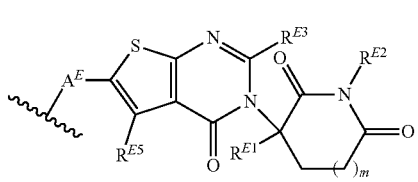
(EC-XXVII)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E3}$, $R^{E5}$, and m are each as defined herein. In one embodiment, $R^{E5}$ is hydrogen or fluoro.

In certain embodiments, $R^E$ is a moiety having the structure of Formula (EC-XXVIII):

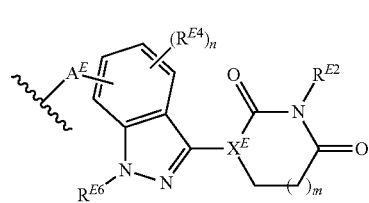

(EC-XXVIII)

or an enantiomer, a mixture of enantiomers, a diastereomer, a mixture of two or more diastereomers, a tautomer, a mixture of two or more tautomers, or an isotopic variant thereof;

wherein:

$R^{E6}$ is (i) hydrogen; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents Q; or (iii) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$X^E$ is C($R^{E1}$) or N; and $A^E$, $R^{E1}$, $R^{E2}$, $R^{E4}$, m, and n are each as defined herein.

In certain embodiments, $R^E$ is a moiety having the structure of Formula (EC-XXIX):

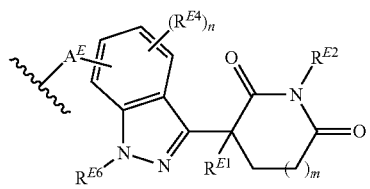

(EC-XXIX)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E4}$, $R^{E6}$, m, and n are each as defined herein.

In certain embodiments, $R^E$ is a moiety having the structure of Formula (EC-XXX):

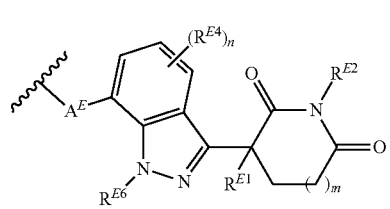

(EC-XXX)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E4}$, $R^{E6}$, m, and n are each as defined herein.

In certain embodiments, $R^E$ is a moiety having the structure of Formula (EC-XXXI):

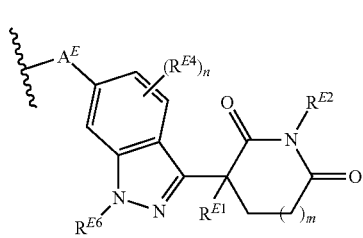

(EC-XXXI)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E4}$, $R^{E6}$, m, and n are each as defined herein.

In certain embodiments, $R^E$ is a moiety having the structure of Formula (EC-XXXII):

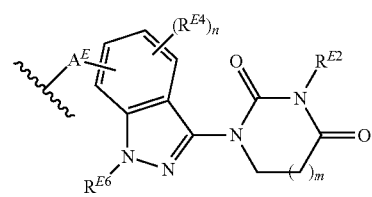

(EC-XXXII)

or an enantiomer, a mixture of enantiomers, a diastereomer, a mixture of two or more diastereomers, a tautomer, a mixture of two or more tautomers, or an isotopic variant thereof; wherein $A^E$, $R^{E2}$, $R^{E4}$, $R^{E6}$, m, and n are each as defined herein.

In certain embodiments, $R^E$ is a moiety having the structure of Formula (EC-XXXIII):

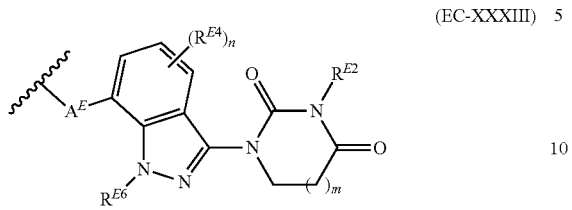

(EC-XXXIII)

or an enantiomer, a mixture of enantiomers, a diastereomer, a mixture of two or more diastereomers, a tautomer, a mixture of two or more tautomers, or an isotopic variant thereof; wherein $A^E$, $R^{E2}$, $R^{E4}$, $R^{E6}$, m, and n are each as defined herein.

In certain embodiments, $R^E$ is a moiety having the structure of Formula (EC-XXXIV):

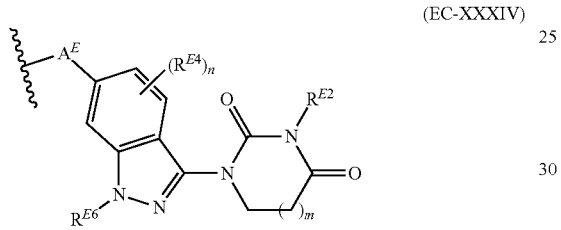

(EC-XXXIV)

or an enantiomer, a mixture of enantiomers, a diastereomer, a mixture of two or more diastereomers, a tautomer, a mixture of two or more tautomers, or an isotopic variant thereof; wherein $A^E$, $R^{E2}$, $R^{E4}$, $R^{E6}$, m, and n are each as defined herein.

In certain embodiments, $R^E$ is a moiety having the structure of Formula (EC-XXXV):

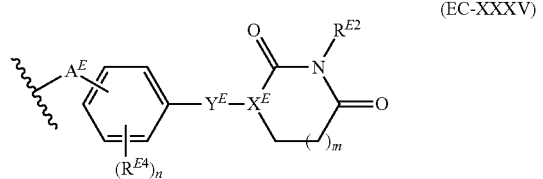

(EC-XXXV)

or an enantiomer, a mixture of enantiomers, a diastereomer, a mixture of two or more diastereomers, a tautomer, a mixture of two or more tautomers, or an isotopic variant thereof; wherein:

$Y^E$ is a bond, $C_{1-6}$ alkylene, —O—, —S—, —S(O)—, —S(O$_2$)—, or —N($R^{E7}$)—;

$R^{E7}$ is hydrogen or $C_{1-6}$ alkyl; and $A^E$, $R^{E2}$, $R^{E4}$, $X^E$, m, and n are each as defined herein.

In certain embodiments, $R^E$ is a moiety having the structure of Formula (EC-XXXVI):

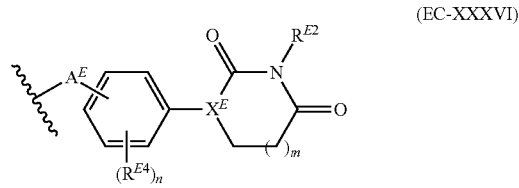

(EC-XXXVI)

or an enantiomer, a mixture of enantiomers, a diastereomer, a mixture of two or more diastereomers, a tautomer, a mixture of two or more tautomers, or an isotopic variant thereof; wherein $A^E$, $R^{E2}$, $R^{E4}$, $X^E$, m, and n are each as defined herein.

In certain embodiments, $R^E$ is a moiety having the structure of Formula (EC-XXXVII):

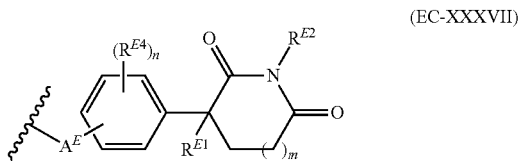

(EC-XXXVII)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E4}$, m, and n are each as defined herein.

In certain embodiments, $R^E$ is a moiety having the structure of Formula (EC-XXXVIII):

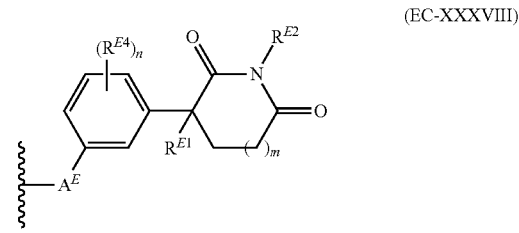

(EC-XXXVIII)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E4}$, m, and n are each as defined herein.

In certain embodiments, $R^E$ is a moiety having the structure of Formula (EC-XXXIX):

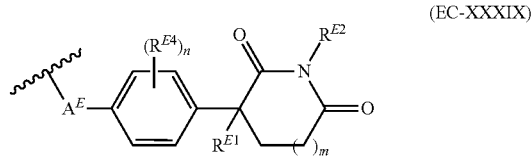

(EC-XXXIX)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E4}$, m, and n are each as defined herein.

In certain embodiments, $R^E$ is a moiety having the structure of Formula (EC-XL):

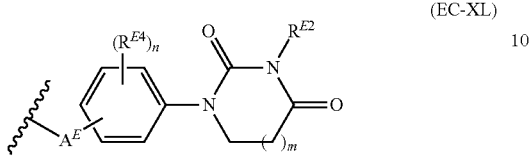

(EC-XL)

or an enantiomer, a mixture of enantiomers, a diastereomer, a mixture of two or more diastereomers, a tautomer, a mixture of two or more tautomers, or an isotopic variant thereof; wherein $A^E$, $R^{E2}$, $R^{E4}$, m, and n are each as defined herein.

In certain embodiments, $R^E$ is a moiety having the structure of Formula (EC-XLI):

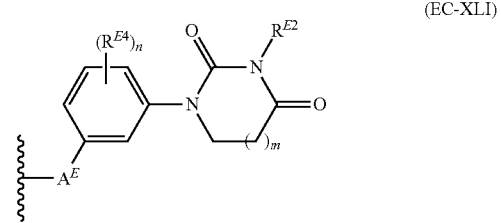

(EC-XLI)

or an enantiomer, a mixture of enantiomers, a diastereomer, a mixture of two or more diastereomers, a tautomer, a mixture of two or more tautomers, or an isotopic variant thereof; wherein $A^E$, $R^{E2}$, $R^{E4}$, m, and n are each as defined herein.

In certain embodiments, $R^E$ is a moiety having the structure of Formula (EC-XLII):

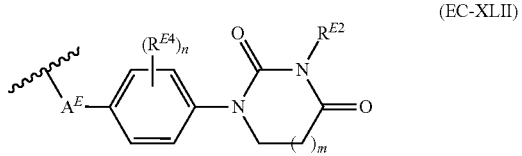

(EC-XLII)

or an enantiomer, a mixture of enantiomers, a diastereomer, a mixture of two or more diastereomers, a tautomer, a mixture of two or more tautomers, or an isotopic variant thereof; wherein $A^E$, $R^{E2}$, $R^{E4}$, m, and n are each as defined herein.

In certain embodiments, $R^E$ is a moiety having the structure of Formula (EC-XLIII):

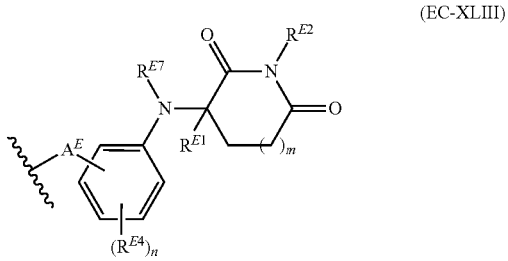

(EC-XLIII)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E4}$, $R^{E7}$, m, and n are each as defined herein.

In certain embodiments, $R^E$ is a moiety having the structure of Formula (EC-XLIV):

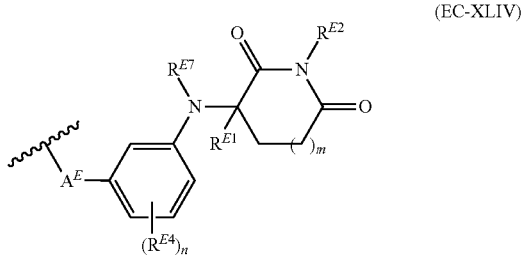

(EC-XLIV)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E4}$, $R^{E7}$, m, and n are each as defined herein.

In certain embodiments, $R^E$ is a moiety having the structure of Formula (EC-XLV):

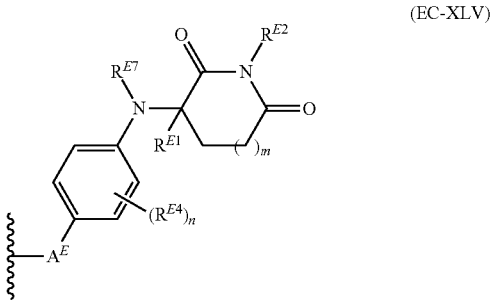

(EC-XLV)

or an enantiomer, a mixture of enantiomers, a diastereomer, a mixture of two or more diastereomers, a tautomer, a mixture of two or more tautomers, or an isotopic variant thereof; wherein $A^E$, $R^{E1}$, $R^{E2}$, $R^{E4}$, $R^{E7}$, m, and n are each as defined herein.

In certain embodiments, $R^E$ is a moiety of an E3 ubiquitin ligase binder disclosed in U.S. Pat. No. 9,938,302 B2; U.S. Pat. No. 10,336,771 B2; U.S. Pat. No. 10,406,165 B2; U.S. Pat. No. 10,513,515 B2; US 2019/0322682 A1; US 2020/

0000814 A1; US 2020/0148663 A1; US 2020/0369679 A1; and WO 2019/173224 A1; the disclosure of each of which is incorporated herein by reference in its entirety. In certain embodiments, $R^E$ is a moiety of an E3 ubiquitin ligase binder disclosed in U.S. Pat. No. 9,938,302 B2, in one embodiment, one of compounds 1 to 57 disclosed therein in cols. 108 to 137, which are incorporated herein by reference in their entireties. In certain embodiments, $R^E$ is a moiety of an E3 ubiquitin ligase binder disclosed in U.S. Pat. No. 10,336,771 B2, in one embodiment, one of compounds 1 to 57 and 64 to 66 disclosed therein in cols. 113 to 161 and 169 to 172, which are incorporated herein by reference in their entireties. In certain embodiments, $R^E$ is a moiety of an E3 ubiquitin ligase binder disclosed in U.S. Pat. No. 10,406,165 B2, in one embodiment, one of compounds 1 to 27 disclosed therein in cols. 40 to 64, which are incorporated herein by reference in their entireties. In certain embodiments, $R^E$ is a moiety of an E3 ubiquitin ligase binder disclosed in U.S. Pat. No. 10,513,515 B2, in one embodiment, one of compounds 1 to 5, 7 to 12, 14 to 16, 19, 23, and 27 disclosed therein in cols. 97 to 104, 106 to 112, 114 to 117, 122, 126, and 132, which are incorporated herein by reference in their entireties. In certain embodiments, $R^E$ is a moiety of an E3 ubiquitin ligase binder disclosed in US 2019/0322682 A1, in one embodiment, one of compounds 1 to 15 disclosed therein on pages 31 to 36, which are incorporated herein by reference in their entireties. In certain embodiments, $R^E$ is a moiety of an E3 ubiquitin ligase binder disclosed in US 2020/0000814 A1, in one embodiment, one of compounds 1 to 21 disclosed therein on pages 26 to 41, which are incorporated herein by reference in their entireties. In certain embodiments, $R^E$ is a moiety of an E3 ubiquitin ligase binder disclosed in US 2020/0148663 A1, in one embodiment, one of compounds 1 to 21 disclosed therein on pages 18 to 34, which are incorporated herein by reference in their entireties. In certain embodiments, $R^E$ is a moiety of an E3 ubiquitin ligase binder disclosed in US 2020/0369679 A1, in one embodiment, one of compounds I-1 to I-106 and II-1 to II-164 disclosed therein on pages 50 to 101, which are incorporated herein by reference in their entireties. In certain embodiments, $R^E$ is a moiety of an E3 ubiquitin ligase binder disclosed in WO 2019/173224 A1, in one embodiment, one of compounds 1 to 3 disclosed therein on pages 62 to 65 and the compounds disclosed therein on page 78, which are incorporated herein by reference in their entireties.

In certain embodiments, $R^E$ is a moiety of an E3 ubiquitin ligase binder disclosed in US 2020/0199073 A1, the disclosure of which is incorporated herein by reference in its entirety. In certain embodiments, $R^E$ is a moiety of an E3 ubiquitin ligase binder disclosed in US Application No. US 2020/0199073 A1, in one embodiment, one of compounds 1 to 291 disclosed therein on pages 118 to 193, which are incorporated herein by reference in their entireties.

In certain embodiments, in any one of Formulae (EC-I) to (EC-XXVII),
$A^E$ is a bond, —O—, —N($R^{1b}$)—, $C_{2-6}$ alkynylene, heterocyclylene, $C_{1-6}$ heteroalkylene-$C_{6-14}$ arylene, or $C_{2-6}$ alkynylene-heterocyclylene, where each heteroalkylene, alkynylene, arylene, and heterocyclylene is optionally substituted with one or more, in one embodiment, one, two, three, or four, substituents Q;
Z, if present, is —CH$_2$— or —C(O)—;
m is an integer of 0, 1, or 2;
$R^{E1}$ and $R^{E2}$ are each hydrogen; and
$R^{E5}$, if present, is independently hydrogen or fluoro.

In certain embodiments, in any one of Formulae (EC-I) to (EC-XXVII),
$A^E$ is a bond, —O—, —NH—, ethynediyl, piperidindiyl, piperazindiyl, (phendiyl)oxymethanediyl, or (piperidindiyl)ethynediyl;
Z, if present, is —CH$_2$— or —C(O)—;
m is an integer of 0, 1, or 2;
$R^{E1}$ and $R^{E2}$ are each hydrogen; and
$R^{E5}$, if present, is independently hydrogen or fluoro.

In certain embodiments, in any one of Formulae (EC-I) to (EC-XXVII),
$A^E$ is a bond, —NH—, piperidin-1,3-diyl, piperidin-1,4-diyl, piperaz-1,4-diyl, (phen-1,4-diyl)oxymethanediyl, or (piperidin-1,4-diyl)ethynediyl;
Z, if present, is —CH$_2$— or —C(O)—;
m is an integer of 0, 1, or 2;
$R^{E1}$ and $R^{E2}$ are each hydrogen; and
$R^{E5}$, if present, is independently hydrogen or fluoro.

In one embodiment, in a compound of any one of the formulae provided herein, $R^E$ is a moiety having the structure of Formula (EC-I), or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula (EC-II), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-III), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-IV), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-V), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-VI), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-VII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-VIII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-IX), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-X), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XI), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XIII), or an enantiomer, a mixture of enantiomers, a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula (EC-XIV), or an enantiomer, a mixture of enantiomers, a diastereomer, a mixture of two or more diastereomers, a tautomer, a mixture of two or more tautomers, or an isotopic variant thereof.

In one embodiment, in a compound of any one of the formulae provided herein, $R^E$ is a moiety having the structure of Formula (EC-XV), or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula (EC-XVI), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XVII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XVIII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XIX), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XX), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXI), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXIII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXIV), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXV), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXVI), or an enantiomer, a mixture of enantiomers, a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula (EC-XXVII), or an enantiomer, a mixture of enantiomers, a diastereomer, a mixture of two or more diastereomers, a tautomer, a mixture of two or more tautomers, or an isotopic variant thereof.

In one embodiment, in a compound of any one of the formulae provided herein, $R^E$ is a moiety having the structure of Formula (EC-XXVIII), or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula (EC-XXIX), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXX), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXXI), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXXII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXXIII), or an enantiomer, a mixture of enantiomers, a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula (EC-XXXIV), or an enantiomer, a mixture of enantiomers, a diastereomer, a mixture of two or more diastereomers, a tautomer, a mixture of two or more tautomers, or an isotopic variant thereof.

In one embodiment, in a compound of any one of the formulae provided herein, $R^E$ is a moiety having the structure of Formula (EC-XXXV), or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula (EC-XXXVI), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXXVII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXXVIII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XXXIX), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XL), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XLI), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XLII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XLIII), or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EC-XLIV), or an enantiomer, a mixture of enantiomers, a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula (EC-XLV), or an enantiomer, a mixture of enantiomers, a diastereomer, a mixture of two or more diastereomers, a tautomer, a mixture of two or more tautomers, or an isotopic variant thereof.

In certain embodiments, $R^E$ is a moiety having the structure of:

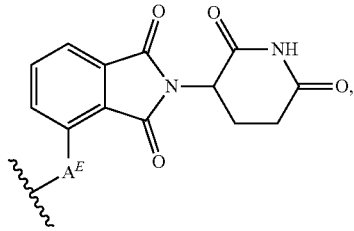

EC-1

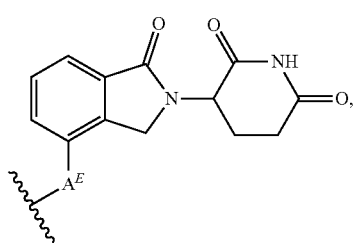

EC-2

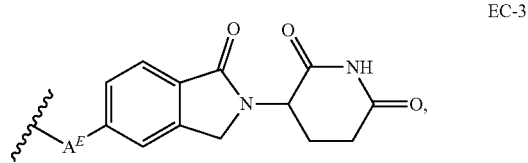

EC-3

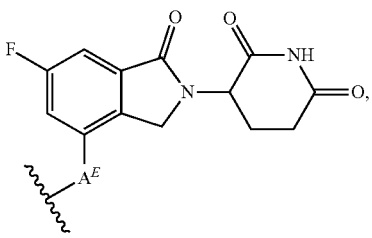

EC-4

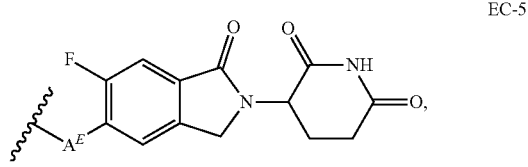

EC-5

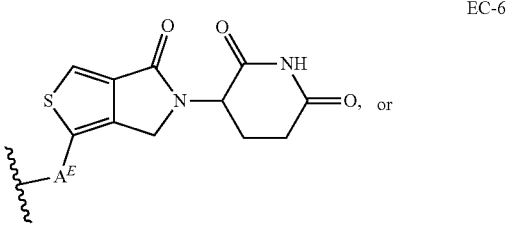

EC-6

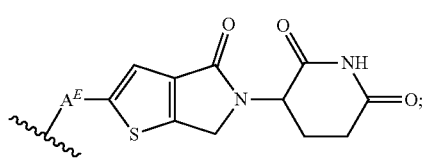

EC-7 or an enantiomer, a mixture of enantiomers, a diastereomer, a mixture of two or more diastereomers, a tautomer, a mixture of two or more tautomers, or an isotopic variant thereof; wherein $A^E$ is as defined herein.

In one embodiment, in any one of Formulae EC-1 to EC-7, $A^E$ is a bond, —O—, —NH—, ethynediyl, piperidindiyl, piperazindiyl, (phendiyl)oxymethanediyl, or (piperidindiyl)-ethynediyl. In another embodiment, in any one of Formulae EC-1 to EC-7, $A^E$ is a bond. In yet another embodiment, in any one of Formulae EC-1 to EC-7, $A^E$ is —O—. In yet another embodiment, in any one of Formulae EC-1 to EC-7, $A^E$ is —NH—. In yet another embodiment, in any one of Formulae EC-1 to EC-7, $A^E$ is ethynediyl. In yet another embodiment, in any one of Formulae EC-1 to EC-7, $A^E$ is piperidindiyl. In yet another embodiment, in any one of Formulae EC-1 to EC-7, $A^E$ is piperazindiyl. In yet another embodiment, in any one of Formulae EC-1 to EC-7, $A^E$ is (phendiyl)oxymethanediyl. In still another embodiment, in any one of Formulae EC-1 to EC-7, $A^E$ is (piperidindiyl)ethynyl.

In one embodiment, in any one of Formulae EC-1 to EC-7, $A^E$ is a bond, —O—, —NH—, ethynediyl, piperidin-1,3-diyl, piperidin-1,4-diyl, piperazin-1,4-diyl, (phen-1,4-diyl)-oxymethanediyl, or (piperidin-1,4-diyl)ethynediyl. In another embodiment, in any one of Formulae EC-1 to EC-7, $A^E$ is piperidin-1,3-diyl. In yet another embodiment, in any one of Formulae EC-1 to EC-7, $A^E$ is piperidin-1,4-diyl. In yet another embodiment, in any one of Formulae EC-1 to EC-7, $A^E$ is piperazin-1,4-diyl. In yet another embodiment, in any one of Formulae EC-1 to EC-7, $A^E$ is (phen-1,4-diyl)oxymethanediyl. In still another embodiment, in any one of Formulae EC-1 to EC-7, $A^E$ is (piperidin-1,4-diyl)ethynediyl.

In one embodiment, in a compound of any one of the formulae provided herein, $R^E$ is a moiety having the structure of Formula EC-1, or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula EC-2, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-3, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-4, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-5, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-6, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-7, or an enantiomer, a mixture of enantiomers, a diastereomer, a mixture of two or more diastereomers, a tautomer, a mixture of two or more tautomers, or an isotopic variant thereof.

In certain embodiments, $R^E$ is a moiety having the structure of:

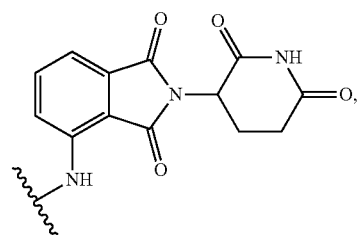

EC-8

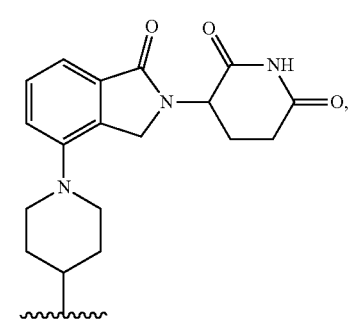

EC-9

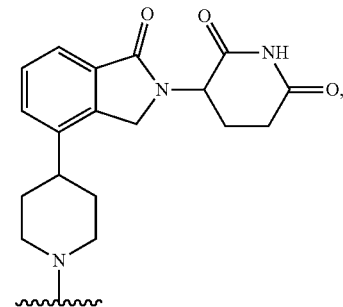

EC-10

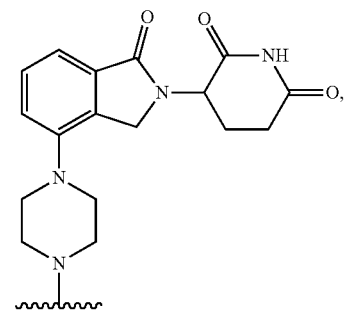

EC-11

EC-12
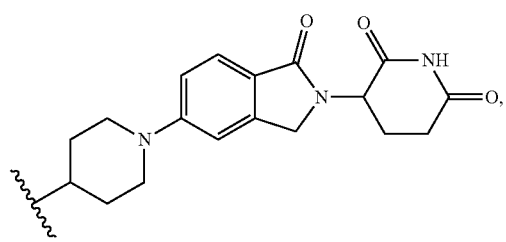
EC-13
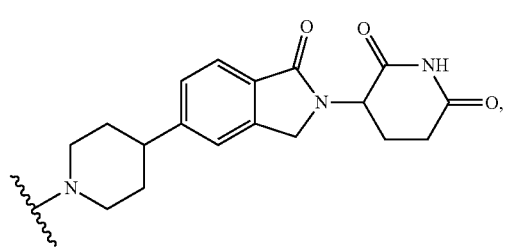
EC-14
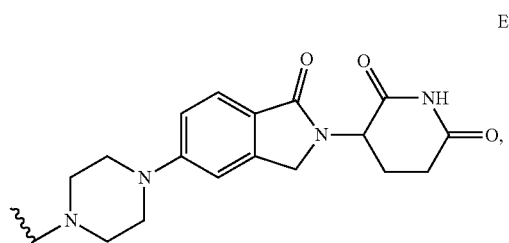
EC-15
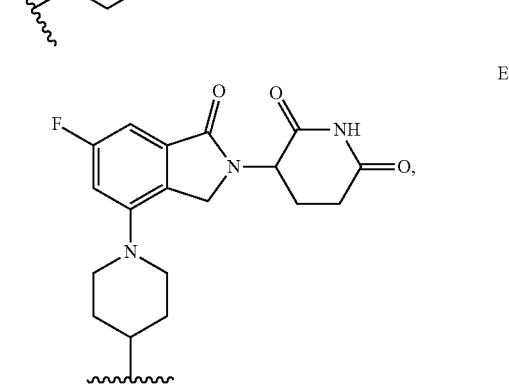
EC-16
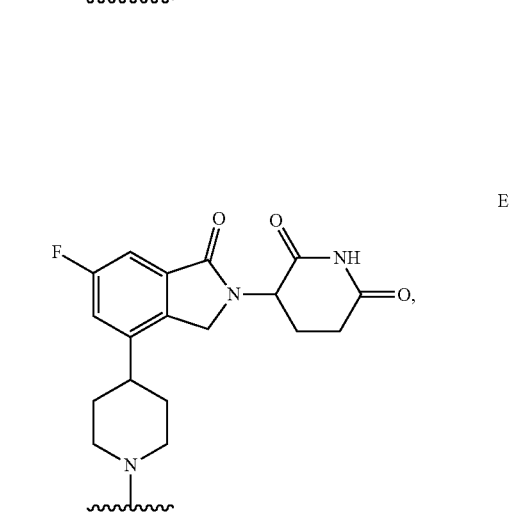
EC-17
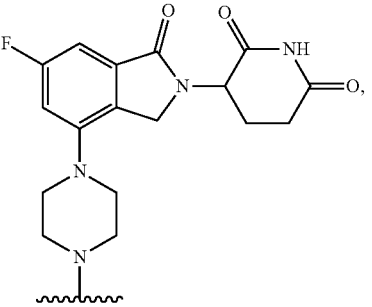
EC-18
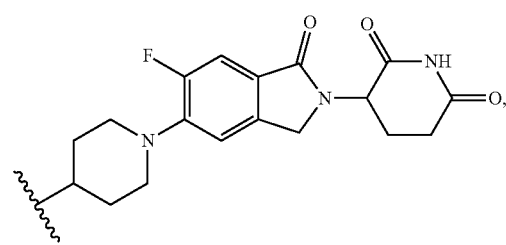
EC-19
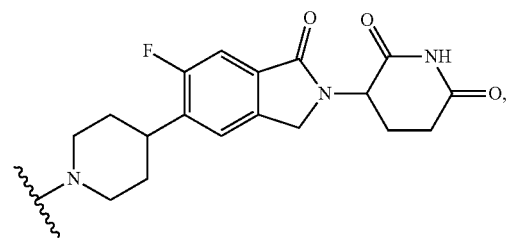
EC-20
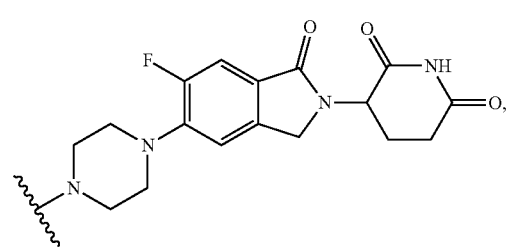
EC-21
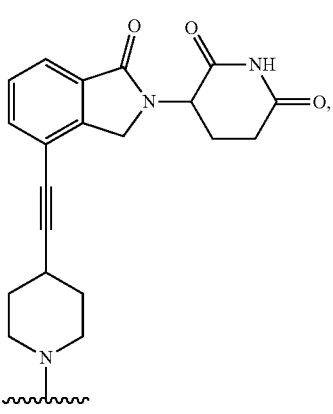

-continued

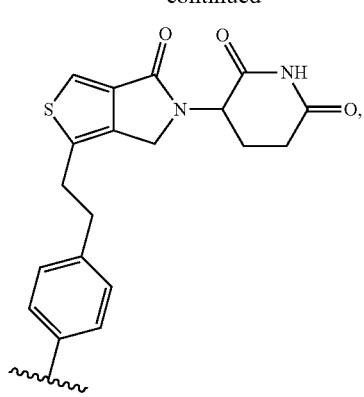

EC-22

EC-23

EC-24 or an enantiomer, a mixture of enantiomers, a tautomer, a mixture of two or more tautomers, or an isotopic variant thereof.

In one embodiment, in a compound of any one of the formulae provided herein, $R^E$ is a moiety having the structure of Formula EC-8, or an enantiomer, a mixture of enantiomers, a tautomer, a mixture of two or more tautomers, or an isotopic variant thereof. In another embodiment, in a compound of any one of the formulae provided herein, $R^E$ is a moiety having the structure of Formula EC-9, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-10, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-11, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-12, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-13, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-14, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-15, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-16, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-17, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-18, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-19, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-20, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-21, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-22, or an enantiomer, a mixture of enantiomers, a tautomer, a mixture of two or more tautomers, or an isotopic variant thereof. In yet another embodiment, in a compound of any one of the formulae provided herein, $R^E$ is a moiety having the structure of Formula EC-23, or an enantiomer, a mixture of enantiomers, a tautomer, a mixture of two or more tautomers, or an isotopic variant thereof. In still another embodiment, in a compound of any one of the formulae provided herein, $R^E$ is a moiety having the structure of Formula EC-24, or an enantiomer, a mixture of enantiomers, a tautomer, a mixture of two or more tautomers, or an isotopic variant thereof.

In certain embodiments, $R^E$ is a moiety having the structure of:

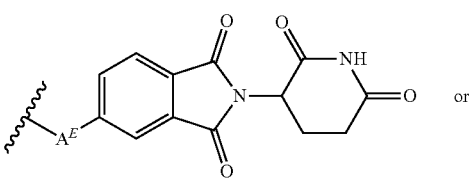

EC-25 or

EC-26

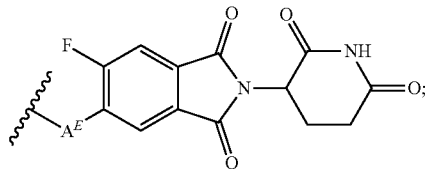

or an enantiomer, a mixture of enantiomers, a diastereomer, a mixture of two or more diastereomers, a tautomer, a mixture of two or more tautomers, or an isotopic variant thereof; wherein $A^E$ is as defined herein.

In one embodiment, in Formula EC-25 or EC-26, $A^E$ is a bond, —O—, —NH—, ethynediyl, piperidindiyl, piperazindiyl, (phendiyl)oxymethanediyl, or (piperidindiyl)ethynediyl. In another embodiment, in Formula EC-25 or EC-26, $A^E$ is a bond. In yet another embodiment, in Formula EC-25 or EC-26, $A^E$ is —O—. In yet another embodiment, in Formula EC-25 or EC-26, $A^E$ is —NH—. In yet another embodiment, in Formula EC-25 or EC-26, $A^E$ is ethynediyl. In yet another embodiment, in Formula EC-25 or EC-26, $A^E$ is piperidindiyl. In yet another embodiment, in Formula EC-25 or EC-26, $A^E$ is piperazindiyl. In yet another embodiment, in Formula EC-25 or EC-26, $A^E$ is (phendiyl)oxymethanediyl. In still another embodiment, in Formula EC-25 or EC-26, $A^E$ is (piperidindiyl)ethynyl.

In one embodiment, in Formula EC-25 or EC-26, $A^E$ is a bond, —O—, —NH—, ethynediyl, piperidin-1,3-diyl, piperidin-1,4-diyl, piperazin-1,4-diyl, (phen-1,4-diyl)oxymethanediyl, or (piperidin-1,4-diyl)ethynediyl. In another embodiment, in Formula EC-25 or EC-26, $A^E$ is piperidin-1,3-diyl. In yet another embodiment, in Formula EC-25 or EC-26, $A^E$ is piperidin-1,4-diyl. In yet another embodiment, in Formula EC-25 or EC-26, $A^E$ is piperazin-1,4-diyl. In yet another embodiment, in Formula EC-25 or EC-26, $A^E$ is (phen-1,4-diyl)oxy-methanediyl. In still another embodiment, in Formula EC-25 or EC-26, $A^E$ is (piperidin-1,4-diyl)ethynediyl.

In one embodiment, in a compound of any one of the formulae provided herein, $R^E$ is a moiety having the structure of Formula EC-25, or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula EC-26, or an enantiomer, a mixture of enantiomers, a diastereomer, a mixture of two or more diastereomers, a tautomer, a mixture of two or more tautomers, or an isotopic variant thereof.

In certain embodiments, $R^E$ is a moiety having the structure of:

EC-27

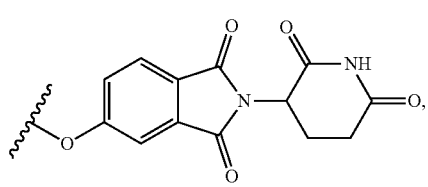

EC-28

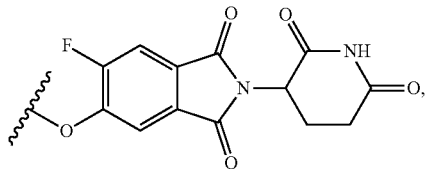

or an enantiomer, a mixture of enantiomers, a tautomer, a mixture of two or more tautomers, or an isotopic variant thereof.

In one embodiment, in a compound of any one of the formulae provided herein, $R^E$ is a moiety having the structure of Formula EC-27, or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula EC-28, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-29, or an enantiomer, a mixture of enantiomers, a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula EC-30, or an enantiomer, a mixture of enantiomers, a diastereomer, a mixture of two or more diastereomers, a tautomer, a mixture of two or more tautomers, or an isotopic variant thereof.

In certain embodiments, $R^E$ is a moiety having the structure of:

EC-31

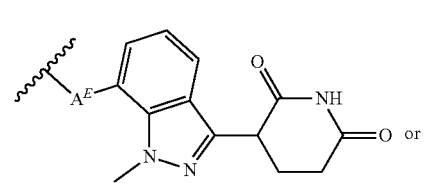

-continued

EC-32

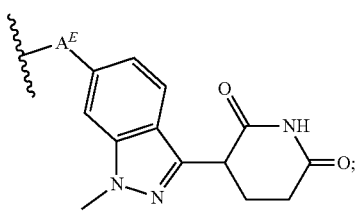

or an enantiomer, a mixture of enantiomers, a tautomer, a mixture of two or more tautomers, or an isotopic variant thereof; wherein $A^E$ is as defined herein.

In one embodiment, in Formula EC-31 or EC-32, $A^E$ is a bond, —O—, —NH—, ethynediyl, piperidindiyl, piperazindiyl, (phendiyl)oxymethanediyl, or (piperidindiyl)ethynediyl. In another embodiment, in Formula EC-31 or EC-32, $A^E$ is a bond. In yet another embodiment, in Formula EC-25 or EC-26, $A^E$ is —O—. In yet another embodiment, in Formula EC-31 or EC-32, $A^E$ is —NH—. In yet another embodiment, in Formula EC-31 or EC-32, $A^E$ is ethynediyl. In yet another embodiment, in Formula EC-31 or EC-32, $A^E$ is piperidindiyl. In yet another embodiment, in Formula EC-31 or EC-32, $A^E$ is piperazindiyl. In yet another embodiment, in Formula EC-31 or EC-32, $A^E$ is (phendiyl)oxymethanediyl. In still another embodiment, in Formula EC-31 or EC-32, $A^E$ is (piperidindiyl)ethynyl.

In one embodiment, in Formula EC-31 or EC-32, $A^E$ is a bond, —O—, —NH—, ethynediyl, piperidin-1,3-diyl, piperidin-1,4-diyl, piperazin-1,4-diyl, (phen-1,4-diyl)oxymethanediyl, (piperidin-1,4-diyl)ethynediyl,

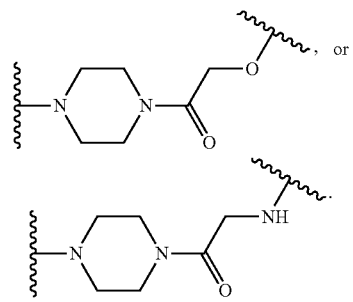

In another embodiment, in Formula EC-31 or EC-32, $A^E$ is piperidin-1,3-diyl. In yet another embodiment, in Formula EC-25 or EC-26, $A^E$ is piperidin-1,4-diyl. In yet another embodiment, in Formula EC-31 or EC-32, $A^E$ is piperazin-1,4-diyl. In yet another embodiment, in Formula EC-31 or EC-32, $A^E$ is (phen-1,4-diyl)oxy-methanediyl. In yet another embodiment, in Formula EC-31 or EC-32, $A^E$ is (piperidin-1,4-diyl)ethynediyl. In yet another embodiment, in Formula EC-31 or EC-32, $A^E$ is

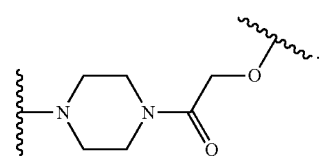 [SMILES: *OCC(=O)N1CCN(*)CC1]

In still another embodiment, in Formula EC-31 or EC-32, $A^E$ is

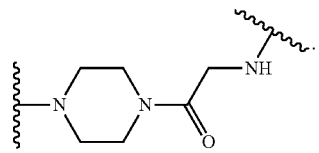 [SMILES: *NCC(=O)N1CCN(*)CC1]

In one embodiment, in a compound of any one of the formulae provided herein, $R^E$ is a moiety having the structure of Formula EC-31, or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula EC-32, or an enantiomer, a mixture of enantiomers, a diastereomer, a mixture of two or more diastereomers, a tautomer, a mixture of two or more tautomers, or an isotopic variant thereof.

In certain embodiments, $R^E$ is a moiety having the structure of.

EC-33

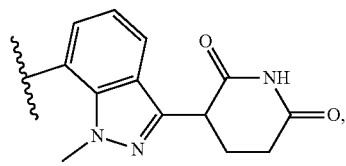

EC-34

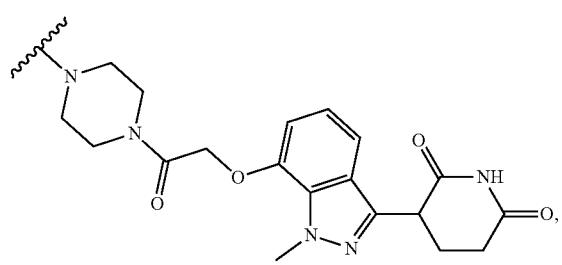

EC-35

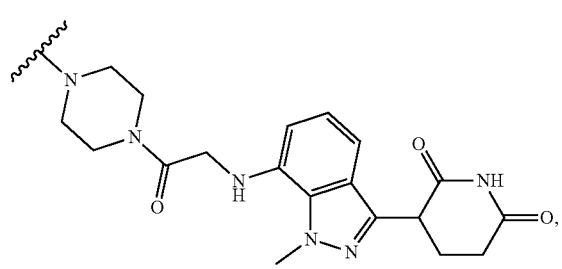

EC-36

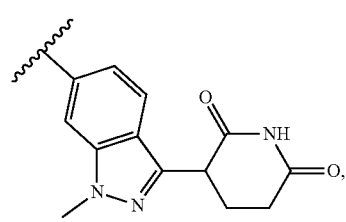

-continued

EC-37

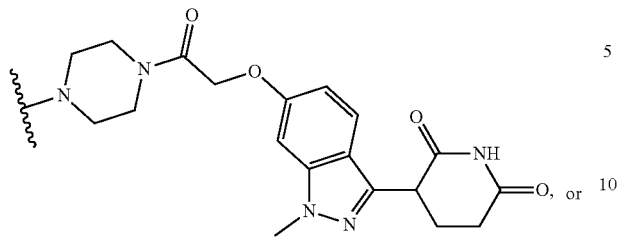

EC-38

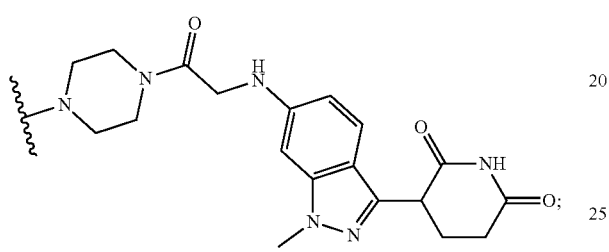

or an enantiomer, a mixture of enantiomers, a tautomer, a mixture of two or more tautomers, or an isotopic variant thereof.

In one embodiment, in a compound of any one of the formulae provided herein, $R^E$ is a moiety having the structure of Formula EC-33, or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula EC-34, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-35, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-36, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-37, or an enantiomer, a mixture of enantiomers, a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula EC-38, or an enantiomer, a mixture of enantiomers, a diastereomer, a mixture of two or more diastereomers, a tautomer, a mixture of two or more tautomers, or an isotopic variant thereof.

In certain embodiments, $R^E$ is a moiety having the structure of:

EC-39

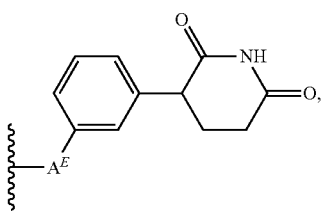

EC-40

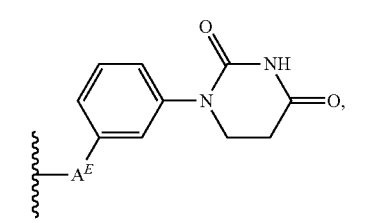

EC-41

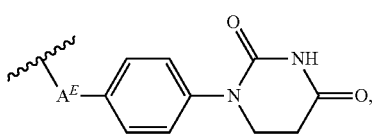

EC-42

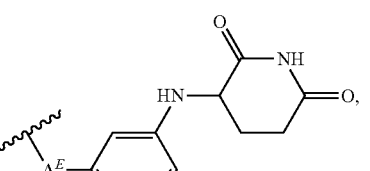

EC-43

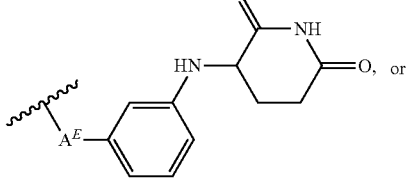

EC-44

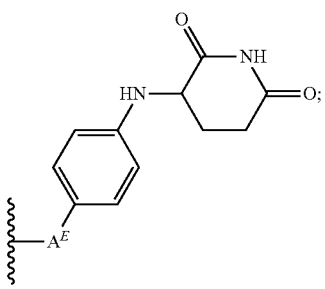

or an enantiomer, a mixture of enantiomers, a tautomer, a mixture of two or more tautomers, or an isotopic variant thereof; wherein $A^E$ is as defined herein.

In one embodiment, in Formula EC-39 to EC-44, $A^E$ is a bond, —O—, —NH—, ethynediyl, piperidindiyl, piperazindiyl, (phendiyl)oxymethanediyl, or (piperidindiyl)ethynediyl. In another embodiment, in Formula EC-39 to EC-44, $A^E$ is a bond. In yet another embodiment, in Formula EC-39 to EC-44, $A^E$ is —O—. In yet another embodiment, in Formula EC-39 to EC-44, $A^E$ is —NH—. In yet another embodiment, in Formula EC-39 to EC-44, $A^E$ is ethynediyl. In yet another embodiment, in Formula EC-39 to EC-44, $A^E$ is piperidindiyl. In yet another embodiment, in Formula EC-39 to EC-44, $A^E$ is piperazindiyl. In yet another embodiment, in Formula EC-39 to EC-44, $A^E$ is (phendiyl)oxymethanediyl. In still another embodiment, in Formula EC-39 to EC-44, $A^E$ is (piperidindiyl)ethynyl.

In one embodiment, in Formula EC-39 to EC-44, $A^E$ is a bond, —O—, —NH—, ethynediyl, piperidin-1,3-diyl, piperidin-1,4-diyl, piperazin-1,4-diyl, (phen-1,4-diyl)oxymethanediyl, (piperidin-1,4-diyl)ethynediyl,

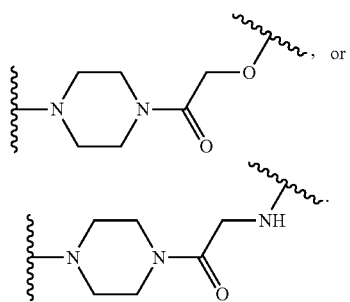

In another embodiment, in Formula EC-39 to EC-44, $A^E$ is piperidin-1,3-diyl. In yet another embodiment, in Formula EC-39 to EC-44, $A^E$ is piperidin-1,4-diyl. In yet another embodiment, in Formula EC-39 to EC-44, $A^E$ is piperazin-1,4-diyl. In yet another embodiment, in Formula EC-39 to EC-44, $A^E$ is (phen-1,4-diyl)oxy-methanediyl. In yet another embodiment, in Formula EC-39 to EC-44, $A^E$ is (piperidin-1,4-diyl)ethynediyl. In yet another embodiment, in Formula EC-39 to EC-44, $A^E$ is

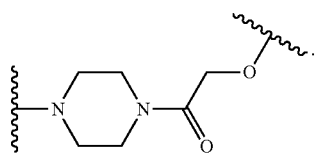 [SMILES: *OCC(=O)N1CCN(*)CC1]

In still another embodiment, in Formula EC-39 to EC-44, $A^E$ is

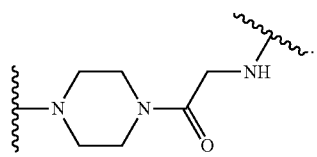 [SMILES: *NCC(=O)N1CCN(*)CC1]

In one embodiment, in a compound of any one of the formulae provided herein, $R^E$ is a moiety having the structure of Formula EC-39, or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula EC-40, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-41, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-42, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-43, or an enantiomer, a mixture of enantiomers, a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula EC-44, or an enantiomer, a mixture of enantiomers, a diastereomer, a mixture of two or more diastereomers, a tautomer, a mixture of two or more tautomers, or an isotopic variant thereof.

In certain embodiments, $R^E$ is a moiety having the structure of:

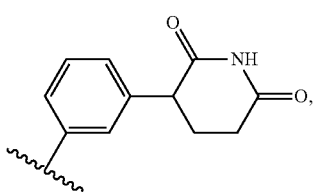

EC-45

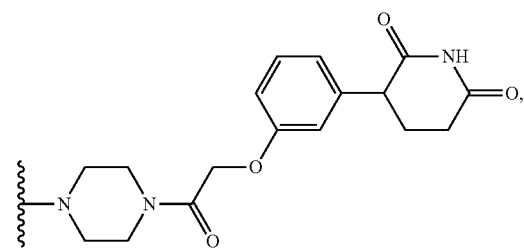

EC-46

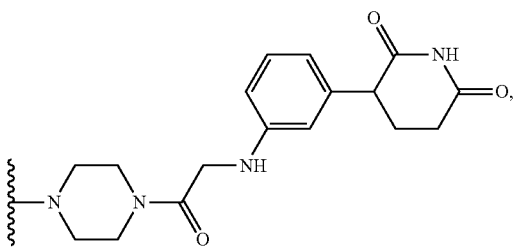

EC-47

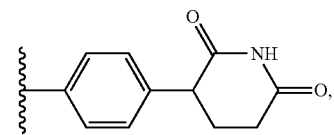

EC-48

-continued

EC-49
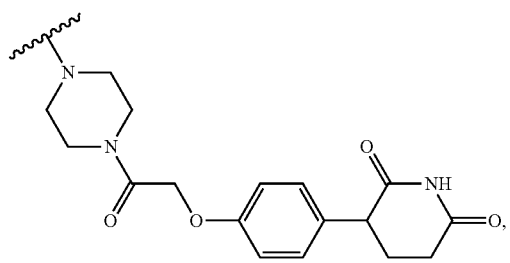

EC-50
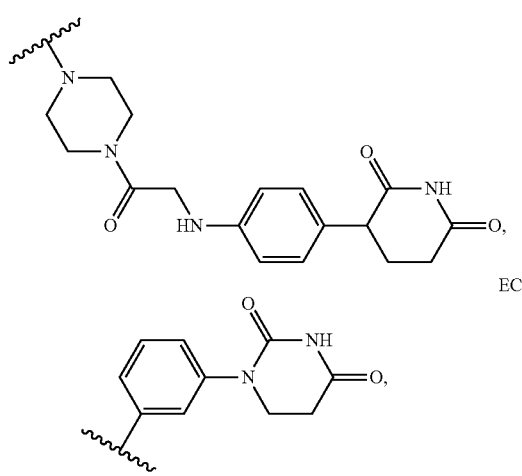

EC-51

EC-52

EC-53

EC-54

EC-55
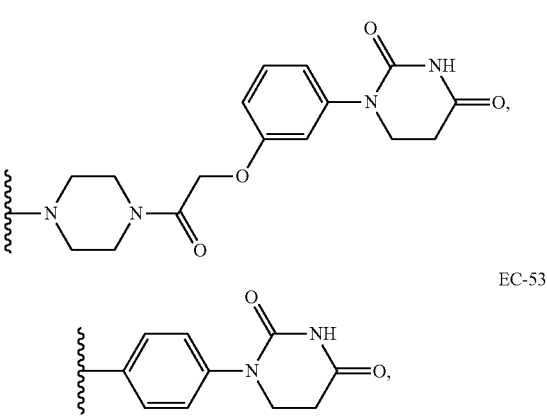
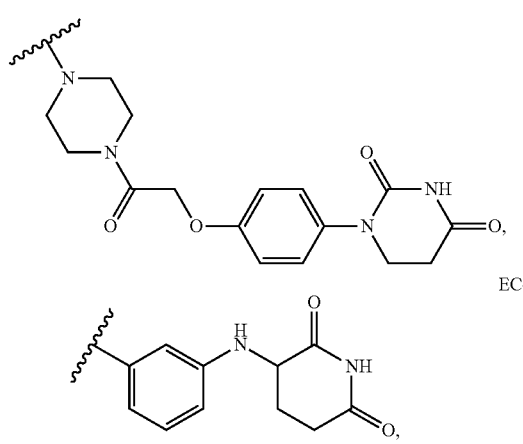

-continued

EC-56
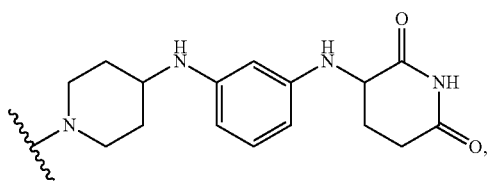

EC-57
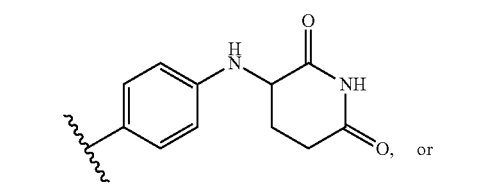
or

EC-58
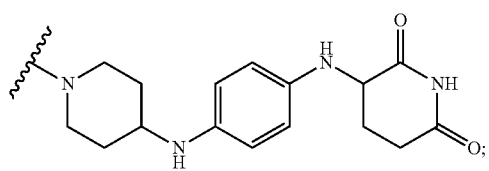

or an enantiomer, a mixture of enantiomers, a tautomer, a mixture of two or more tautomers, or an isotopic variant thereof.

In one embodiment, in a compound of any one of the formulae provided herein, $R^E$ is a moiety having the structure of Formula EC-45, or an enantiomer, a mixture of enantiomers, a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula EC-46, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-47, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-48, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-49, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-50, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-51, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-52, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-53, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-54, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-55, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-56, or an enantiomer, a mixture of enantiomers, a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EC-57, or an enantiomer, a mixture of enantiomers, a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula EC-58, or an enantiomer, a mixture of enantiomers, a diastereomer, a mixture of two or more diastereomers, a tautomer, a mixture of two or more tautomers, or an isotopic variant thereof.

In certain embodiments, in any one of the formulae provided herein, $R^E$ is a moiety of an IAP E3 ligand.

In certain embodiments, $R^E$ is a moiety having the structure of Formula (EI-I):

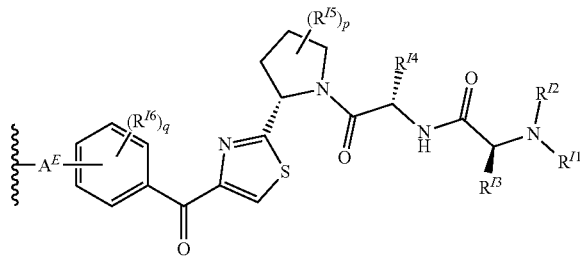

(EI-I)

or a diastereomer, a mixture of two or more diastereomers, a tautomer, a mixture of two or more tautomers, or an isotopic variant thereof; wherein:

$R^{I1}$ and $R^{I2}$ are each independently hydrogen, $C_{1-6}$ alkyl, or $C_{3-10}$ cycloalkyl;

$R^{I3}$ and $R^{I4}$ are each independently $C_{1-6}$ alkyl, $C_{3-10}$ cycloalkyl, or heterocyclyl;

each $R^{I5}$ and $R^{I6}$ is independently (i) deuterium, cyano, halo, nitro, or oxo; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^c$, or —S(O)$_2$NR$^{1b}$R$^{1c}$;

p is an integer of 0, 1, 2, 4, or 5;

q is an integer of 0, 1, 2, 3, or 4; and each $R^{1a}$, $R^{1b}$, $R^{1c}$, $R^{1d}$, and $A^E$ is as defined herein;

wherein each alkyl, heteroalkyl, alkenyl, alkynyl, cycloalkyl, aryl, aralkyl, heteroaryl, and heterocyclyl is optionally substituted with one or more, in one embodiment, one, two, three, or four, substituents Q.

In certain embodiments, $R^E$ is a moiety having the structure of Formula (EI-II):

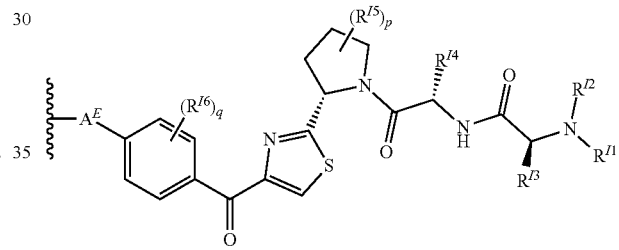

(EI-II)

or a diastereomer, a mixture of two or more diastereomers, a tautomer, a mixture of two or more tautomers, or an isotopic variant thereof; wherein $R^{I1}$, $R^{I2}$, $R^{I3}$, $R^{I4}$, $R^{I5}$, $R^{I6}$, $A^E$, p, and q are each as defined herein.

In certain embodiments, $R^E$ is a moiety having the structure of Formula (EI-III):

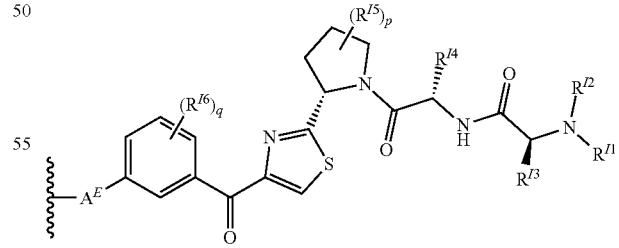

(EI-III)

or a diastereomer, a mixture of two or more diastereomers, a tautomer, a mixture of two or more tautomers, or an isotopic variant thereof; wherein $R^{I1}$, $R^{I2}$, $R^{I3}$, $R^{I4}$, $R^{I5}$, $R^{I6}$, $A^E$, p, and q are each as defined herein.

In one embodiment, in Formula (EI-I), (EI-II), or (EI-III), $R^{I1}$ is hydrogen; $R^{I2}$ is $C_{1-6}$ alkyl; $R^{I3}$ is $C_{1-6}$ alkyl; $R^{I4}$ is $C_{1-6}$ alkyl or $C_{3-10}$ cycloalkyl; $R^{I5}$ is —OR$^{1a}$; $R^{I6}$ is halo; and p and q are each independently an integer of 0 or 1. In another embodiment, in Formula (EI-I), (EI-II), or (EI-III), $R^{J1}$ is hydrogen; $R^{J2}$ is $C_{1-6}$ alkyl; $R^{J3}$ is $C_{1-6}$ alkyl; $R^{J4}$ is $C_{3-10}$ cycloalkyl; $R^{J5}$ is $-OR^{1a}$; $R^{J6}$ is halo; and p and q are each independently an integer of 0 or 1. In yet another embodiment, in Formula (EI-I), (EI-II), or (EI-III), $R^{J1}$ is hydrogen; $R^{J2}$ and $R^{J3}$ are each methyl; $R^{J4}$ is cyclohexyl; $R^{J5}$ is hydroxyl; $R^{J6}$ is fluoro; and p and q are each independently an integer of 0 or 1.

In certain embodiments, $R^E$ is a moiety having the structure of Formula (EI-IV):

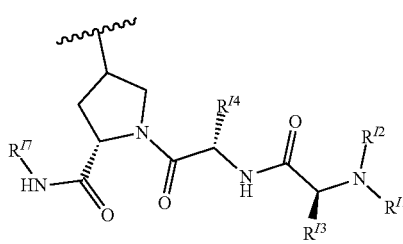

(EI-IV)

or a diastereomer, a mixture of two or more diastereomers, a tautomer, a mixture of two or more tautomers, or an isotopic variant thereof; wherein $R^{J7}$ is $C_{3-10}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q; and $R^{J1}$, $R^{J2}$, $R^{J3}$, and $R^{J4}$ are each as defined herein.

In one embodiment, in Formula (EI-IV), $R^{J1}$ is hydrogen; $R^{J2}$ is $C_{1-6}$ alkyl; $R^{J3}$ is $C_{1-6}$ alkyl; $R^{J4}$ is $C_{1-6}$ alkyl or $C_{3-10}$ cycloalkyl; and $R^{J7}$ is $C_{3-10}$ cycloalkyl or $C_{6-14}$ aryl. In another embodiment, in Formula (EI-IV), $R^{J1}$ is hydrogen; $R^{J2}$ is $C_{1-6}$ alkyl; $R^{J3}$ is $C_{1-6}$ alkyl; $R^{J4}$ is $C_{3-10}$ cycloalkyl; and $R^{J7}$ is $C_{3-10}$ cycloalkyl or $C_{6-14}$ aryl. In yet another embodiment, in Formula (EI-IV), $R^{J1}$ is hydrogen; $R^{J2}$ is methyl; $R^{J3}$ is methyl; $R^{J4}$ is cyclohexyl; and $R^{J7}$ is 1,2,3,4-tetrahydronaphthalenyl. In still another embodiment, in Formula (EI-IV), $R^{J1}$ is hydrogen; $R^{J2}$ is methyl; $R^{J3}$ is methyl; $R^{J4}$ is cyclohexyl; and $R^{J7}$ is 1,2,3,4-tetrahydronaphthalen-1-yl.

In certain embodiments, $R^E$ is a moiety having the structure of Formula (EI-V):

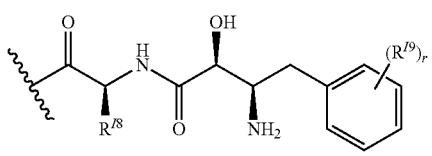

(EI-V)

or a diastereomer, a mixture of two or more diastereomers, a tautomer, a mixture of two or more tautomers, or an isotopic variant thereof; wherein:

$R^{J8}$ is $C_{1-6}$ alkyl, $C_{3-10}$ cycloalkyl, or heterocyclyl;

each $R^{J9}$ is independently (i) deuterium, cyano, halo, nitro, or oxo; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $-C(O)R^{1a}$, $-C(O)OR^{1a}$, $-C(O)NR^{1b}R^{1c}$, $-C(O)SR^{1a}$, $-C(NR^{1a})NR^{1b}R^{1c}$, $-C(S)R^{1a}$, $-C(S)OR^{1a}$, $-C(S)NR^{1b}R^{1c}$, $-OR^{1a}$, $-OC(O)R^{1a}$, $-OC(O)OR^{1a}$, $-OC(O)NR^{1b}R^{1c}$, $-OC(O)SR^{1a}$, $-OC(NR^{1a})$ $NR^{1b}R^{1c}$, $-OC(S)R^{1a}$, $-OC(S)OR^{1a}$, $-OC(S)$ $NR^{1b}R^{1c}$, $-OS(O)R^{1a}$, $-OS(O)_2R^{1a}$, $-OS(O)$ $NR^{1b}R^{1c}$, $-OS(O)_2NR^{1b}R^{1c}$, $-NR^{1b}R^{1c}$, $-NR^{1a}C(O)R^{1d}$, $-NR^{1a}C(O)OR^{1d}$, $-NR^{1a}C(O)NR^{1b}R^{1c}$, $-NR^{1a}C(O)SR^{1d}$, $-NR^{1a}C(NR^{1d})NR^{1b}R^{1c}$, $-NR^{1a}C(S)R^{1d}$, $-NR^{1a}C(S)OR^{1d}$, $-NR^{1a}C(S)$ $NR^{1b}R^{1c}$, $-NR^{1a}S(O)R^{1d}$, $-NR^{1a}S(O)_2R^{1d}$, $-NR^{1a}S(O)NR^{1b}R^{1c}$, $-NR^{1a}S(O)_2NR^{1b}R^{1c}$, $-SR^{1a}$, $-S(O)R^{1a}$, $-S(O)_2R^{1a}$, $-S(O)NR^{1b}R^{1c}$ or $-S(O)_2NR^{1b}R^{1c}$;

r is an integer of 0, 1, 2, 4, or 5; and each $R^{1a}$, $R^{1b}$, $R^{1c}$, and $R^{1d}$ is as defined herein;

wherein each alkyl, heteroalkyl, alkenyl, alkynyl, cycloalkyl, aryl, aralkyl, heteroaryl, and heterocyclyl is optionally substituted with one or more, in one embodiment, one, two, three, or four, substituents Q.

In one embodiment, in Formula (EI-V), $R^{J8}$ is $C_{1-6}$ alkyl or $C_{3-10}$ cycloalkyl; and r is an integer of 0 or 1. In another embodiment, in Formula (EI-V), $R^{J8}$ is $C_{1-6}$ alkyl and r is an integer of 0. In yet another embodiment, in Formula (EI-V), $R^{J8}$ is isobutyl and r is an integer of 0.

In one embodiment, in a compound of any one of the formulae provided herein, $R^E$ is a moiety having the structure of Formula (EI-I), or a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula (EI-II), or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EI-III), or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EI-IV), or a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula (EI-V), or a diastereomer, a mixture of two or more diastereomers, a tautomer, a mixture of two or more tautomers, or an isotopic variant thereof.

In certain embodiments, $R^E$ is a moiety of an IAP E3 ligand having the structure of:

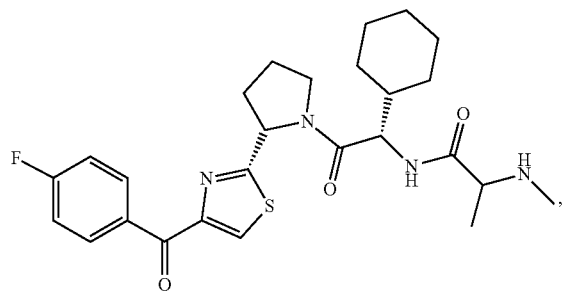

EI-1

-continued

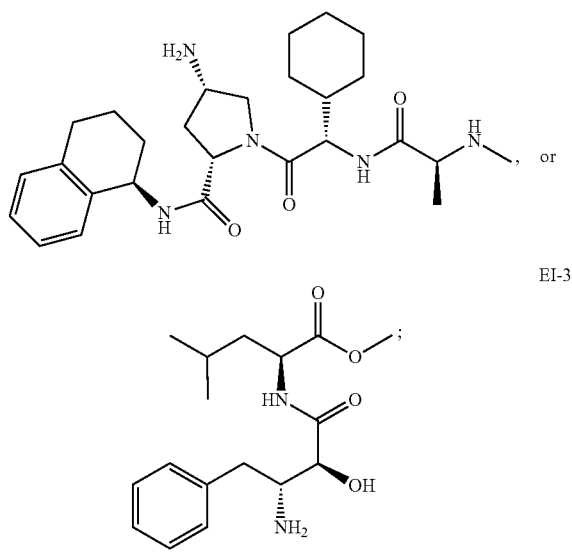

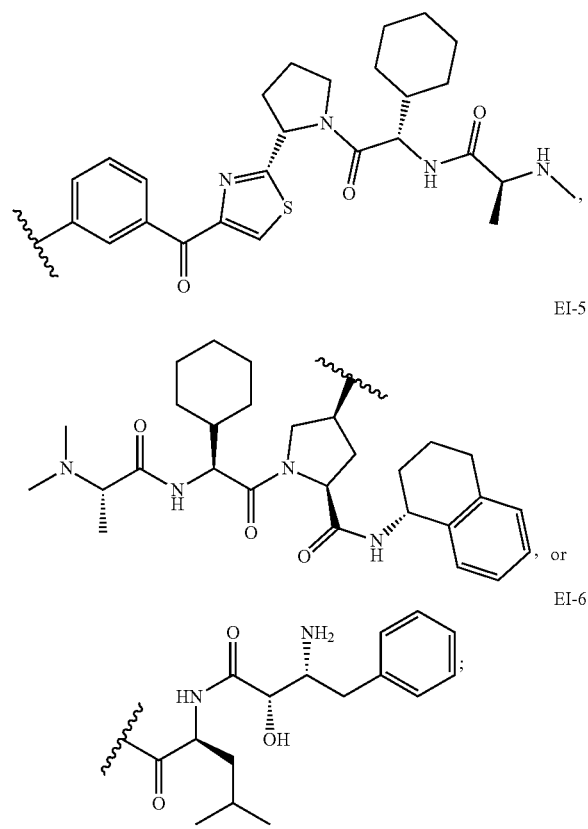

or a diastereomer, a mixture of two or more diastereomers, a tautomer, a mixture of two or more tautomers, or an isotopic variant thereof.

In certain embodiments, $R^E$ is a moiety having the structure of:

or a diastereomer, a mixture of two or more diastereomers, a tautomer, a mixture of two or more tautomers, or an isotopic variant thereof.

In one embodiment, in a compound of any one of the formulae provided herein, $R^E$ is a moiety of compound EI-1, or a diastereomer, a mixture of two or more diastereomers, a tautomer, a mixture of two or more tautomers, or an isotopic variant thereof. In another embodiment, in a compound of any one of the formulae provided herein, $R^E$ is a moiety of compound EI-2, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EI-3, or a diastereomer, a mixture of two or more diastereomers, a tautomer, a mixture of two or more tautomers, or an isotopic variant thereof.

In one embodiment, in a compound of any one of the formulae provided herein, $R^E$ is a moiety having the structure of Formula EI-4, or a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula EI-5, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EI-6, or a diastereomer, a mixture of two or more diastereomers, a tautomer, a mixture of two or more tautomers, or an isotopic variant thereof.

In certain embodiments, in any one of the formulae provided herein, $R^E$ is a moiety of an MDM2 E3 ligand.

In certain embodiments, $R^E$ is a moiety having the structure of Formula (EM-I):

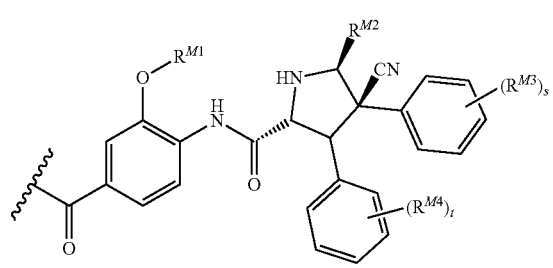

(EM-I)

or a diastereomer, a mixture of two or more diastereomers, a tautomer, a mixture of two or more tautomers, or an isotopic variant thereof; wherein:

$R^{M1}$ and $R^{M2}$ are each independently $C_{1-6}$ alkyl or $C_{3-10}$ cycloalkyl;

each $R^{M3}$ and $R^{M4}$ is independently (i) deuterium, cyano, halo, nitro, or oxo; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{b}R^{c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

s and t are each independently an integer of 0, 1, 2, 3, 4, or 5; and each R$^{1a}$, R$^{1b}$, R$^{1c}$, and R$^{1d}$ is as defined herein;

wherein each alkyl, heteroalkyl, alkenyl, alkynyl, cycloalkyl, aryl, aralkyl, heteroaryl, and heterocyclyl is optionally substituted with one or more, in one embodiment, one, two, three, or four, substituents Q.

In one embodiment, in Formula (EM-I), R$^{M1}$ and R$^{M2}$ are each independently C$_{1-6}$ alkyl; each R$^{M3}$ and R$^{M4}$ is independently deuterium or halo; and s and t are each independently an integer of 0, 1, or 2. In another embodiment, in Formula (EM-I), R$^{M1}$ and R$^{M2}$ are each independently methyl or 2,2-dimethylpropyl; each R$^{M3}$ and R$^{M4}$ is independently fluoro or chloro; and s and t are each independently an integer of 2.

In certain embodiments, R$^E$ is a moiety having the structure of Formula (EM-II):

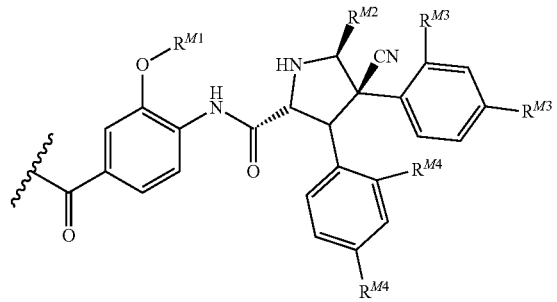

(EM-II)

or a diastereomer, a mixture of two or more diastereomers, a tautomer, a mixture of two or more tautomers, or an isotopic variant thereof; wherein R$^{M1}$, R$^{M2}$, R$^{M3}$, and R$^{M4}$ are each as defined herein.

In one embodiment, in Formula (EM-II), R$^{M1}$ and R$^{M2}$ are each independently C$_{1-6}$ alkyl; and each R$^{M3}$ and R$^{M4}$ is independently deuterium or halo. In another embodiment, in Formula (EM-II), R$^{M1}$ and R$^{M2}$ are each independently methyl or 2,2-dimethylpropyl; and each R$^{M3}$ and R$^{M4}$ is independently fluoro or chloro.

In certain embodiments, R$^E$ is a moiety having the structure of Formula (EM-III):

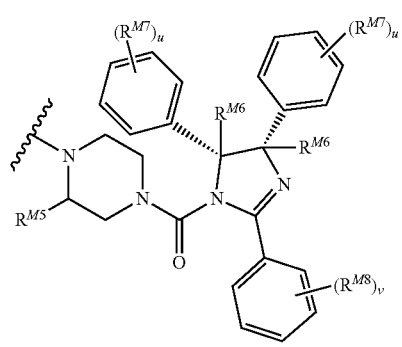

(EM-III)

or a diastereomer, a mixture of two or more diastereomers, a tautomer, a mixture of two or more tautomers, or an isotopic variant thereof; wherein:

R$^{M5}$ is hydrogen or oxo;

each R$^{M6}$ is independently hydrogen, deuterium, or C$_{1-6}$ alkyl; and each R$^{M7}$ and R$^{M8}$ is independently (i) deuterium, cyano, halo, nitro, or oxo; (ii) C$_{1-6}$ alkyl, C$_{1-6}$ heteroalkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

each u and v is independently an integer of 0, 1, 2, 3, 4, or 5; and each R$^{1a}$, R$^{1b}$, R$^{1c}$, and R$^{1d}$ is as defined herein;

wherein each alkyl, heteroalkyl, alkenyl, alkynyl, cycloalkyl, aryl, aralkyl, heteroaryl, and heterocyclyl is optionally substituted with one or more, in one embodiment, one, two, three, or four, substituents Q.

In one embodiment, in Formula (EM-III), R$^{M5}$ is hydrogen or oxo; each R$^{M6}$ is independently hydrogen, deuterium, or C$_{1-6}$ alkyl; each R$^{M7}$ is independently halo; each R$^{M8}$ is independently C$_{1-6}$ alkyl or —OC$_{1-6}$ alkyl; and each u and v is independently an integer of 0, 1, or 2. In another embodiment, in Formula (EM-III), R$^{M5}$ is hydrogen or oxo; each R$^{M6}$ is independently hydrogen or methyl; each R$^{M7}$ is chloro; each R$^{M8}$ is independently tert-butyl, methoxy, ethoxy, or isopropoxy; u is an integer of 0 or 1; and v is an integer of 1 or 2. In yet another embodiment, in Formula (EM-III), R$^{M5}$ is hydrogen or oxo; each R$^{M6}$ is independently hydrogen or methyl; each R$^{M7}$ is chloro; each R$^{M8}$ is independently tert-butyl, methoxy, ethoxy, or isopropoxy; u is an integer of 1; and v is an integer of 2.

In certain embodiments, R$^E$ is a moiety having the structure of Formula (EM-IV):

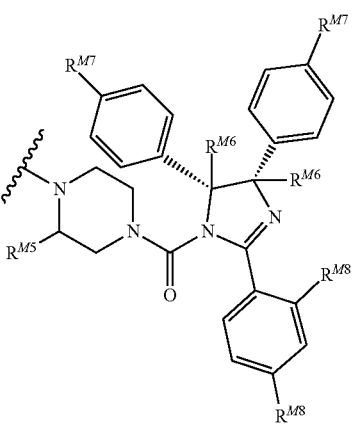

(EM-IV)

or a diastereomer, a mixture of two or more diastereomers, a tautomer, a mixture of two or more tautomers, or an isotopic variant thereof; wherein each $R^{M5}$, $R^{M6}$, $R^{M7}$, and $R^{M8}$ is as defined herein.

In one embodiment, in Formula (EM-IV), $R^{M5}$ is hydrogen or oxo; each $R^{M6}$ is independently hydrogen, deuterium, or $C_{1-6}$ alkyl; each $R^{M7}$ is independently halo; and each $R^{M8}$ is independently $C_{1-6}$ alkyl or $-OC_{1-6}$ alkyl. In another embodiment, in Formula (EM-IV), $R^{M5}$ is hydrogen or oxo; each $R^{M6}$ is independently hydrogen or methyl; each $R^{M7}$ is chloro; and each $R^{M8}$ is independently tert-butyl, methoxy, ethoxy, or isopropoxy.

In one embodiment, in a compound of any one of the formulae provided herein, $R^E$ is a moiety having the structure of Formula (EM-I), or a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula (EM-II), or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EM-III), or a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula (EM-IV), or a diastereomer, a mixture of two or more diastereomers, a tautomer, a mixture of two or more tautomers, or an isotopic variant thereof.

In certain embodiments, $R^E$ is a moiety of an MDM2 E3 ligand having the structure of:

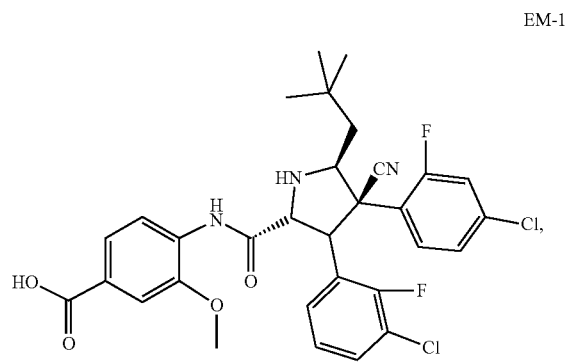

EM-1

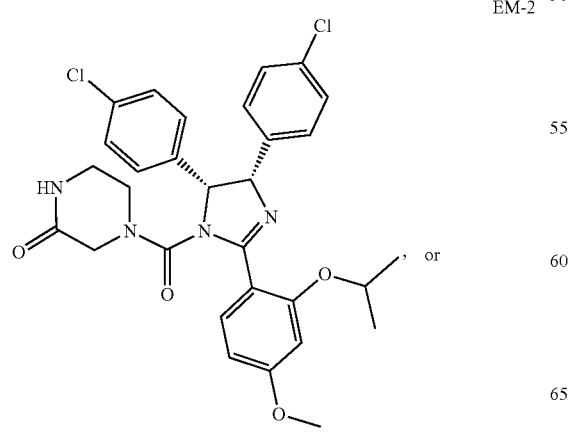

EM-2

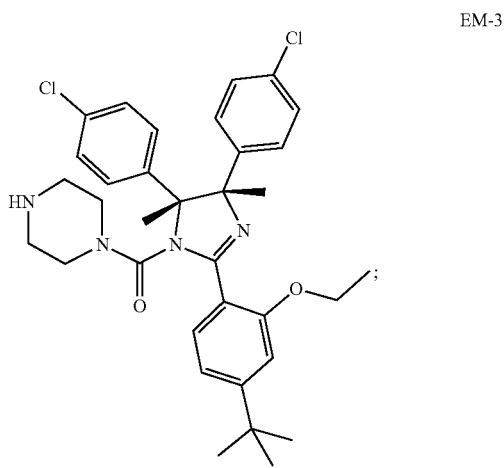

EM-3 or a diastereomer, a mixture of two or more diastereomers, a tautomer, a mixture of two or more tautomers, or an isotopic variant thereof.

In one embodiment, in a compound of any one of the formulae provided herein, $R^E$ is a moiety of compound EM-1, or a diastereomer, a mixture of two or more diastereomers, a tautomer, a mixture of two or more tautomers, or an isotopic variant thereof. In another embodiment, in a compound of any one of the formulae provided herein, $R^E$ is a moiety of compound EM-2, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety of compound EM-3, or a diastereomer, a mixture of two or more diastereomers, a tautomer, a mixture of two or more tautomers, or an isotopic variant thereof.

In certain embodiments, $R^E$ is a moiety having the structure of:

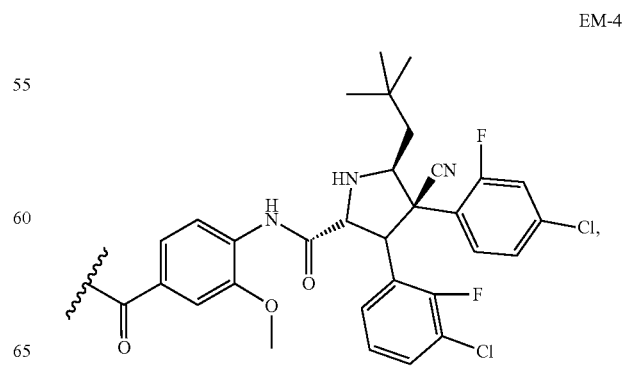

EM-4

-continued

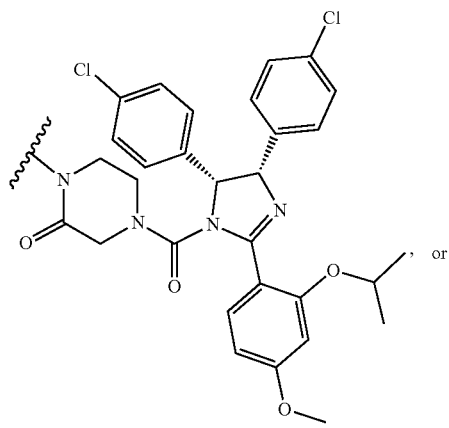

EM-5

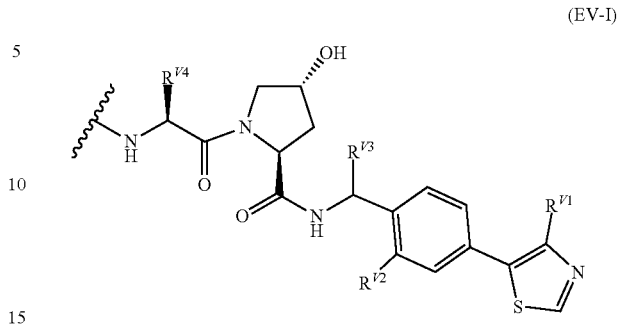

EM-6 or a diastereomer, a mixture of two or more diastereomers, a tautomer, a mixture of two or more tautomers, or an isotopic variant thereof.

In one embodiment, in a compound of any one of the formulae provided herein, $R^E$ is a moiety having the structure of Formula EM-4, or a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula EM-5, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EM-6, or a diastereomer, a mixture of two or more diastereomers, a tautomer, a mixture of two or more tautomers, or an isotopic variant thereof.

In certain embodiments, in any one of the formulae provided herein, $R^E$ is a moiety of a VHL E3 ligand.

In certain embodiments, $R^E$ has the structure of Formula (EV-I):

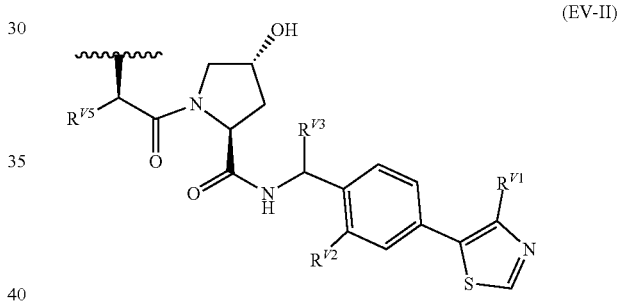

(EV-I)

or a diastereomer, a mixture of two or more diastereomers, a tautomer, a mixture of two or more tautomers, or an isotopic variant thereof; wherein:
  $R^{V1}$, $R^{V3}$, and $R^{V4}$ are each independently hydrogen, deuterium, $C_{1-6}$ alkyl, or $C_{3-10}$ cycloalkyl; and
  $R^{V2}$ is hydrogen, deuterium, halo, hydroxyl, —$OC_{1-6}$ alkyl, or —$OC_{3-10}$ cycloalkyl;
  wherein each alkyl and cycloalkyl is optionally substituted with one or more, in one embodiment, one, two, three, or four, substituents Q.

In certain embodiments, $R^E$ has the structure of Formula (EV-II):

(EV-II)

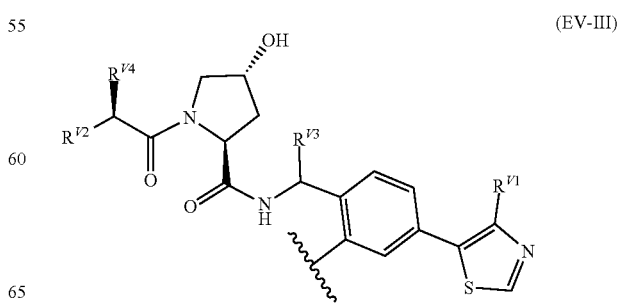

or a diastereomer, a mixture of two or more diastereomers, a tautomer, a mixture of two or more tautomers, or an isotopic variant thereof; wherein:
  $R^{V5}$ is —NHC(O)$C_{1-6}$ alkyl, —NHC(O)$C_{3-10}$ cycloalkyl, or heterocyclyl, wherein the alkyl, cycloalkyl, and heterocyclyl are each optionally substituted with one or more, in one embodiment, one, two, three, or four, substituents Q; and
  $R^{V1}$, $R^{V2}$, and $R^{V3}$ are each as defined herein.

In certain embodiments, $R^E$ has the structure of Formula (EV-III):

(EV-III)

or a diastereomer, a mixture of two or more diastereomers, a tautomer, a mixture of two or more tautomers, or an isotopic variant thereof; wherein $R^{V1}$, $R^{V3}$, $R^{V4}$, and $R^{V5}$ are each as defined herein.

In certain embodiments, in any one of Formulae (EV-I) to (EV-III), $R^{V1}$ is methyl;

$R^{V2}$, if present, is hydrogen;

$R^{V3}$ is hydrogen;

$R^{V4}$, if present, is propyl, butyl, or cyclopropyl; and $R^{V5}$, if present, is acetamido, cyclopropamido, or isoindolinyl;

wherein the propyl, butyl, cyclopropyl, acetamido, cyclopropamido, and isoindolinyl are each optionally substituted with cyano, fluoro, or trifluoromethyl.

In certain embodiments, in any one of Formulae (EV-I) to (EV-III), $R^{V1}$ is methyl;

$R^{V2}$, if present, is hydrogen;

$R^{V3}$ is hydrogen;

$R^{V4}$, if present, is isopropyl, tert-butyl, cyclopropyl, 1-fluorocyclopropyl, or 1-trifuloromethylcyclopropyl; and $R^{V5}$, if present, is acetamido, cyclopropamido, 1-cyanocyclopropamido, 1-fluorocyclopropamido, or 1-oxoisoindolin-2-yl.

In one embodiment, in a compound of any one of the formulae provided herein, $R^E$ is a moiety having the structure of Formula (EV-I), or a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula (EV-II), or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula (EV-III), or a diastereomer, a mixture of two or more diastereomers, a tautomer, a mixture of two or more tautomers, or an isotopic variant thereof.

In certain embodiments, $R^E$ is a moiety of a VHL E3 ligand having the structure of:

EV-1

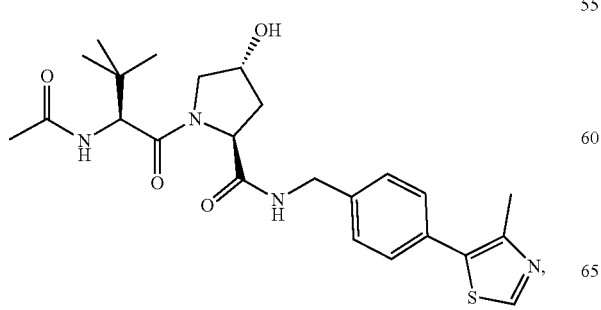

EV-2

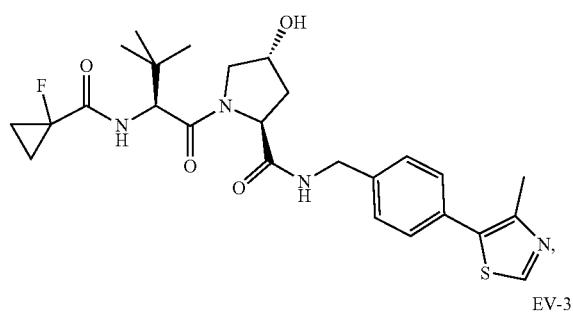

EV-3

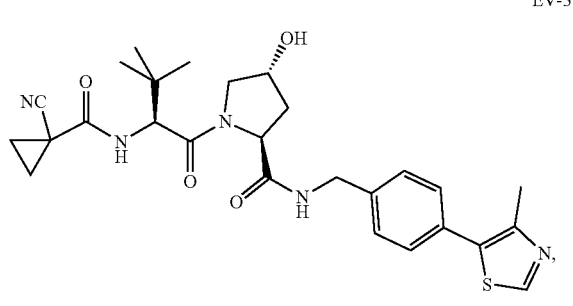

EV-4

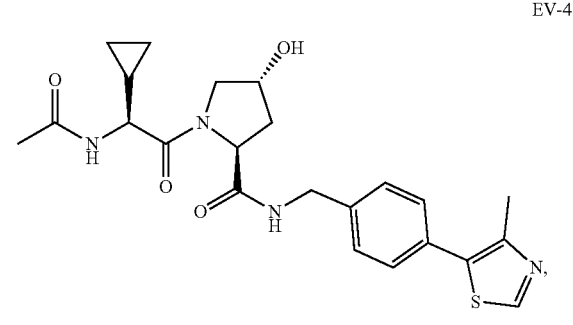

EV-5

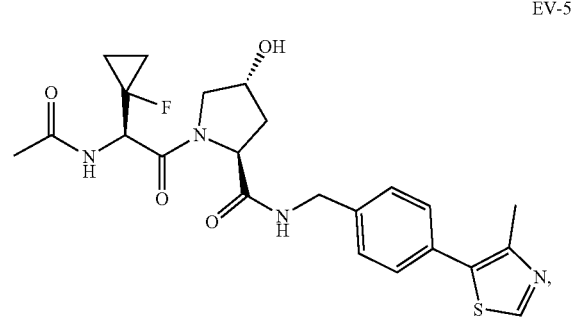

EV-6

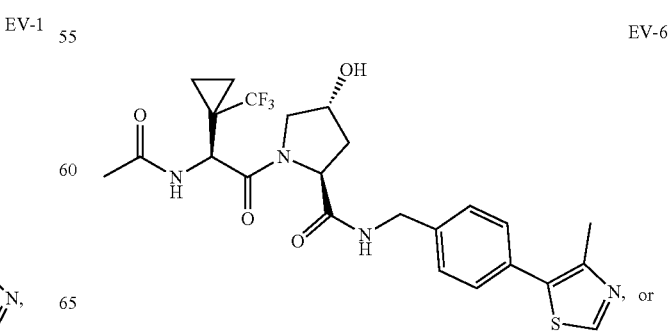

or

-continued

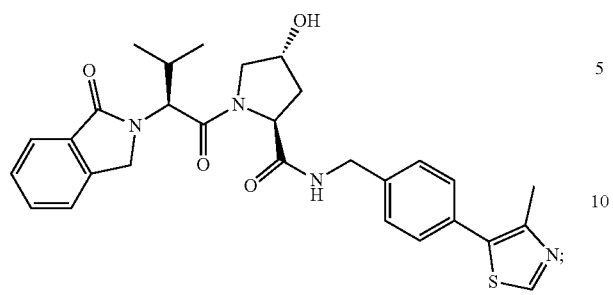
EV-7 or a diastereomer, a mixture of two or more diastereomers, a tautomer, a mixture of two or more tautomers, or an isotopic variant thereof.

In one embodiment, in a compound of any one of the formulae provided herein, $R^E$ is a moiety of compound EV-1, or a diastereomer, a mixture of two or more diastereomers, a tautomer, a mixture of two or more tautomers, or an isotopic variant thereof. In another embodiment, in a compound of any one of the formulae provided herein, $R^E$ is a moiety of compound EV-2, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety of compound EV-3, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety of compound EV-4, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety of compound EV-5, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety of compound EV-6, or a diastereomer, a mixture of two or more diastereomers, a tautomer, a mixture of two or more tautomers, or an isotopic variant thereof. In still another embodiment, in a compound of any one of the formulae provided herein, $R^E$ is a moiety of compound EV-7, or a diastereomer, a mixture of two or more diastereomers, a tautomer, a mixture of two or more tautomers, or an isotopic variant thereof.

In certain embodiments, $R^E$ is a moiety having the structure of:

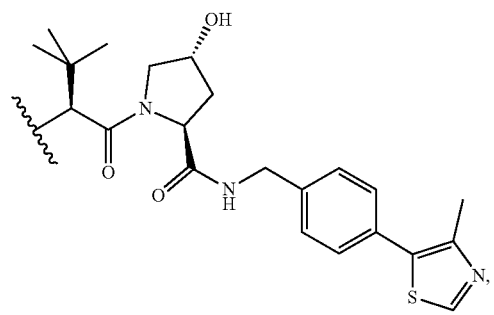
EV-8

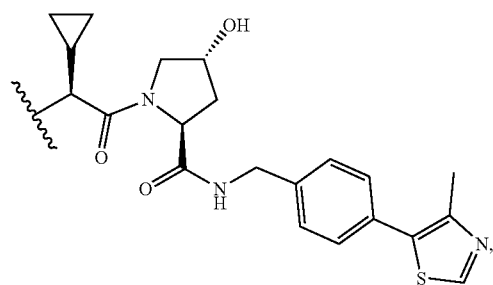
EV-9

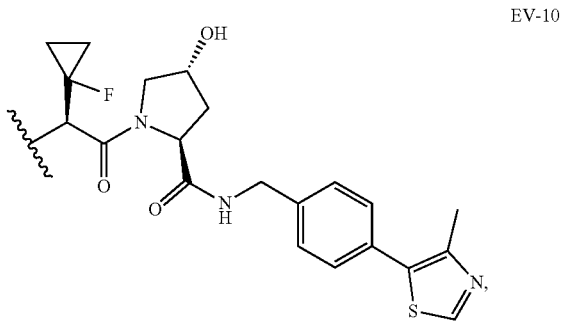
EV-10

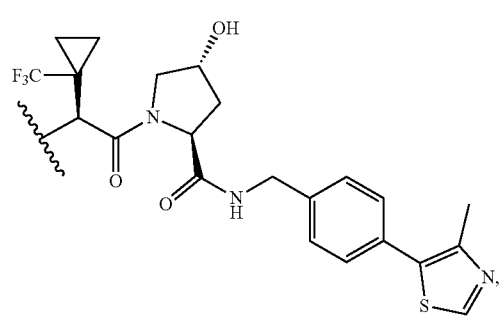
EV-11

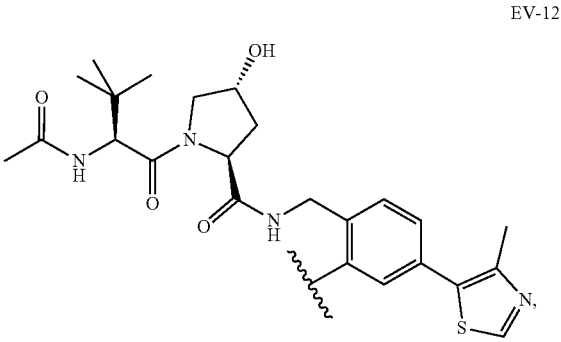
EV-12

EV-13

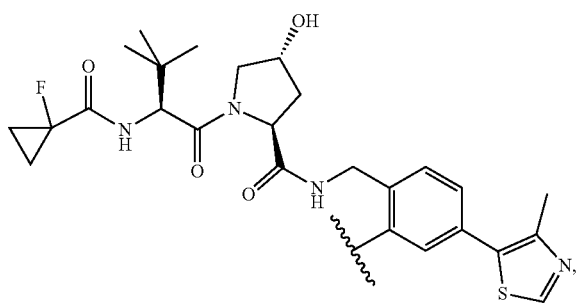

EV-14

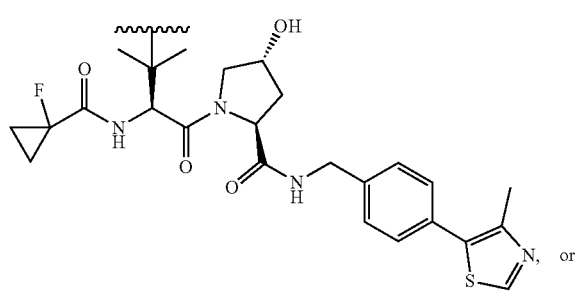

EV-15

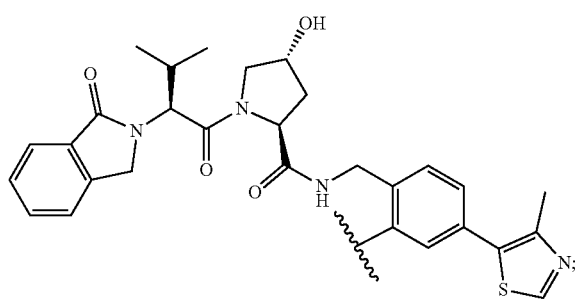

or a diastereomer, a mixture of two or more diastereomers, a tautomer, a mixture of two or more tautomers, or an isotopic variant thereof.

In certain embodiments, $R^E$ is a moiety having the structure of:

EV-8

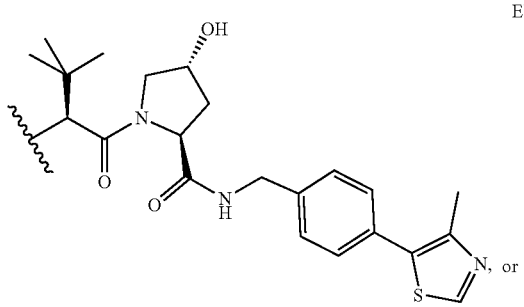

EV-12

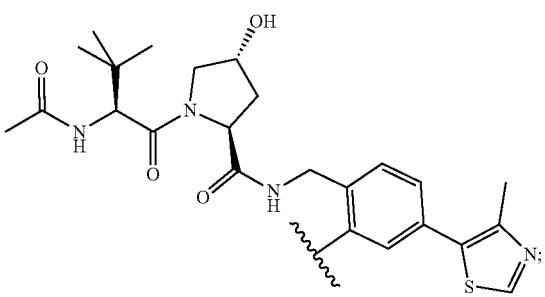

or a diastereomer, a mixture of two or more diastereomers, a tautomer, a mixture of two or more tautomers, or an isotopic variant thereof.

In one embodiment, in a compound of any one of the formulae provided herein, $R^E$ is a moiety having the structure of Formula EV-8, or a diastereomer, a mixture of two or more diastereomers, a tautomer, a mixture of two or more tautomers, or an isotopic variant thereof. In another embodiment, in a compound of any one of the formulae provided herein, $R^E$ is a moiety having the structure of Formula EV-9, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EV-10, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EV-11, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EV-12, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EV-13, or a diastereomer, a mixture of two or more diastereomers, a tautomer, a mixture of two or more tautomers, or an isotopic variant thereof. In yet another embodiment, in a compound of any one of the formulae provided herein, $R^E$ is a moiety having the structure of Formula EV-14, or a diastereomer, a mixture of two or more diastereomers, a tautomer, a mixture of two or more tautomers, or an isotopic variant thereof. In still another embodiment, in a compound of any one of the formulae provided herein, $R^E$ is a moiety having the structure of Formula EV-15, or a diastereomer, a mixture of two or more diastereomers, a tautomer, a mixture of two or more tautomers, or an isotopic variant thereof.

In one embodiment, provided herein is a compound of Formula (XI):

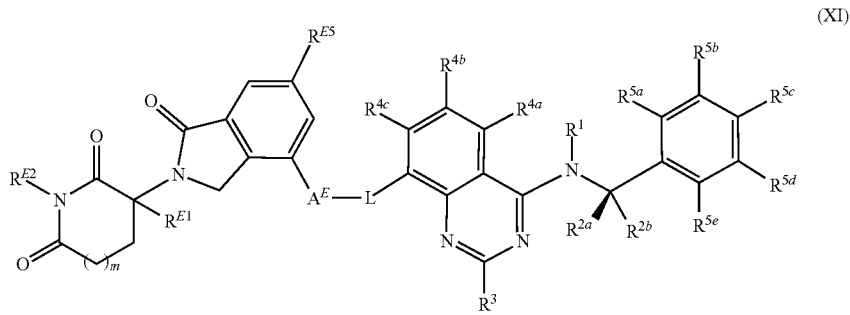

(XI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{4a}$, $R^{4b}$, $R^{4c}$, $R^{5a}$, $R^{5b}$, $R^{5c}$, $R^{5d}$, $R^{5e}$, $R^{E1}$, $R^{E2}$, $R^{E5}$, $A^E$, L, and m are each as defined herein. In one embodiment, $R^{E5}$ is hydrogen or fluoro.

In another embodiment, provided herein is a compound of Formula (XII):

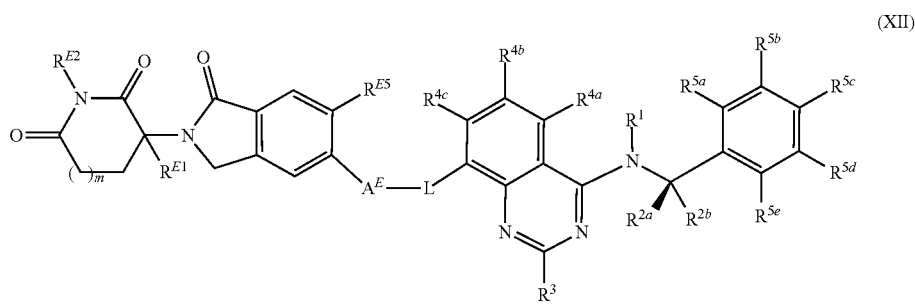

(XII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{4a}$, $R^{4b}$, $R^{4c}$, $R^{5a}$, $R^{5b}$, $R^{5c}$, $R^{5d}$, $R^{5e}$, $R^{E1}$, $R^{E2}$, $R^{E5}$, $A^E$, L, and m are each as defined herein. In one embodiment, $R^{E5}$ is hydrogen or fluoro.

In yet another embodiment, provided herein is a compound of Formula (XIII):

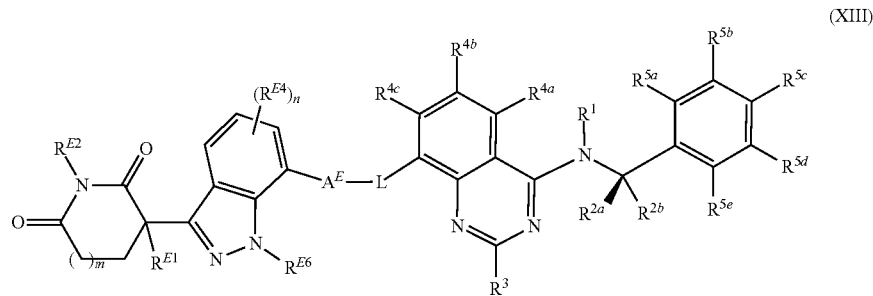

(XIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{4a}$, $R^{4b}$, $R^{4c}$, $R^{5a}$, $R^{5b}$, $R^{5c}$, $R^{5d}$, $R^{5e}$, $R^{E1}$, $R^{E2}$, $R^{E4}$, $R^{E6}$, $A^E$, L, m, and n are each as defined herein.

In yet another embodiment, provided herein is a compound of Formula (XIV):

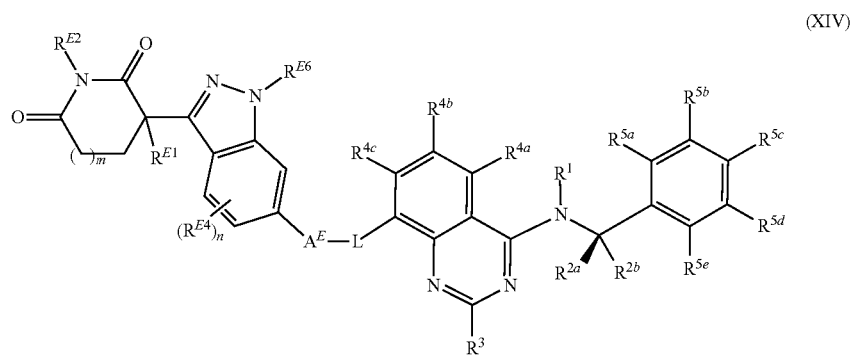

(XIV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{4a}$, $R^{4b}$, $R^{4c}$, $R^{5a}$, $R^{5b}$, $R^{5c}$, $R^{5d}$, $R^{5e}$, $R^{E1}$, $R^{E2}$, $R^{E4}$, $R^{E6}$, $A^E$, L, m, and n are each as defined herein.

In yet another embodiment, provided herein is a compound of Formula (XV):

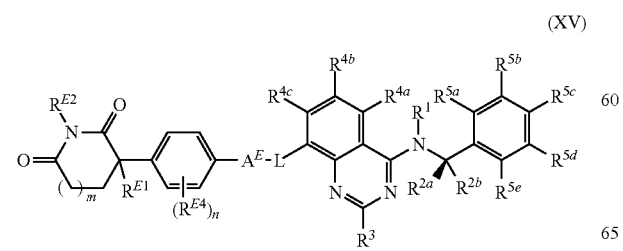

(XV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^3$, $R^{2a}$, $R^{2b}$, $R^{4a}$, $R^{4b}$, $R^{4c}$, $R^{5a}$, $R^{5b}$, $R^{5c}$, $R^{5d}$, $R^{5e}$, $R^{E1}$, $R^{E2}$, $R^{E4}$, $A^E$, L, m, and n are each as defined herein.

In still another embodiment, provided herein is a compound of Formula (XVI):

(XVI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; wherein $R^1$, $R^{2a}$, $R^{2b}$, $R^{3a}$, $R^{4a}$, $R^{4c}$, $R^{4d}$, $R^{5a}$, $R^{5b}$, $R^{5c}$, $R^{5d}$, $R^{5e}$, $R^{E1}$, $R^{E2}$, $R^{E4}$, A, $A^E$, L, m, and n are each as defined herein.

In certain embodiments, in any one of the formulae provided herein, L is a linker having the structure of —$Z^L$—($R^L$—$Z^L$)$_z$— wherein:

each $R^L$ is independently $C_{1-10}$ alkylene, $C_{2-10}$ alkenylene, $C_{2-10}$ alkynylene, $C_{3-10}$ cycloalkylene, $C_{6-14}$ arylene, heteroarylene, or heterocyclylene, each of which is optionally substituted with one or more, in one embodiment, one, two, three, or four, substituents Q;

each $Z^L$ is independently a bond, —C(O)—, —C(O)O—, —C(O)NR$^{1b}$—, —C(O)S—, —C(NR$^{1a}$)NR$^{1b}$—, —C(S)—, —C(S)O—, —C(S)NR$^{1b}$—, —O—, —OC(O)O—, —OC(O)NR$^{1b}$—, —OC(O)S—, —OC(NR$^{1a}$)NR$^{1b}$—, —OC(S)O—, —OC(S)NR$^{1b}$—, —OS(O)—, —OS(O)$_2$—, —OS(O)NR$^{1b}$—, —OS(O)$_2$NR$^{1b}$—, —NR$^{1b}$—, —NR$^{1a}$C(O)NR$^{1b}$—, —NR$^{1a}$C(O)S—, —NR$^{1a}$C(NR$^{1d}$)NR$^{1b}$—, —NR$^{1a}$C(S)NR$^{1b}$—, —NR$^{1a}$S(O)NR$^{1b}$—, —NR$^{1a}$S(O)$_2$NR$^{1b}$—, —S—, —S(O)—, —S(O)$_2$—, —S(O)NR$^{1b}$—, or —S(O)$_2$NR$^{1b}$—; where each $R^{1a}$, $R^{1b}$, and $R^{1d}$ is as defined herein; and z is an integer of 1, 2, 3, 4, 5, 6, 7, 8, 9, or 10.

In certain embodiments, each $R^L$ is independently $C_{1-10}$ alkylene, $C_{2-10}$ alkynylene, $C_{3-10}$ cycloalkylene, $C_{6-14}$ arylene, heteroarylene, or heterocyclylene, each optionally substituted with one or more, in one embodiment, one, two, three, or four, substituents Q; each $Z^L$ is independently a bond, —C(O)—, —C(O)NR$^{1b}$—, —C(NR$^{1a}$)NR$^{1b}$—, —O—, —OC(O)NR$^{1b}$—, —NR$^{1b}$—, —R$^{1a}$C(O)NR$^{1b}$—, —NR$^{1a}$C(NR$^{1d}$)R$^{1b}$—, —NR$^{1a}$S(O)NR$^{1b}$—, —NR$^{1a}$S(O)$_2$NR$^{1b}$—, —S—, —S(O)—, —S(O)$_2$—, —S(O)NR$^{1b}$—, or —S(O)$_2$NR$^{1b}$—; and z is an integer of 1, 2, 3, 4, 5, 6, 7, 8, 9, or 10; where each $R^{1a}$, $R^{1b}$, and $R^{1d}$ is as defined herein.

In certain embodiments, each $R^L$ is independently $C_{1-10}$ alkylene, $C_{2-10}$ alkynylene, $C_{3-10}$ cycloalkylene, $C_{6-14}$ arylene, heteroarylene, or heterocyclylene, each optionally substituted with one or more, in one embodiment, one, two, three, or four, substituents Q; each $Z^L$ is independently a bond, —C(O)—, —C(O)NR$^{1b}$—, —O—, —OC(O)NR$^{1b}$—, —NR$^{1b}$—, —NR$^{1a}$C(O)NR$^{1b}$—, or —NR$^{1a}$C(NR$^{1d}$)NR$^{1b}$—; and z is an integer of 1, 2, 3, 4, 5, 6, 7, or 8; where each $R^{1a}$, $R^{1b}$, and $R^{1d}$ is as defined herein.

In certain embodiments, each $R^L$ is independently methanediyl, ethanediyl, propanediyl, butanediyl, pentanediyl, hexanediyl, heptanediyl, octanediyl, nonanediyl, decanediyl, ethynediyl, cyclobutanediyl, cyclopentanediyl, cyclohexanediyl, cycloheptanediyl, bicyclo[2.2.2]octanediyl, phendiyl, pyrazoldiyl, imidazoldiyl, tetrazoldiyl, pyrimidindiyl, 5,6,7,8,9,10-hexahydrocycloocta[d]-pyridazindiyl, 1,3-dioxandiyl, piperazindiyl, piperidindiyl, or 3,9-diazaspiro[5.5]undecanediyl, each optionally substituted with one or more, in one embodiment, one, two, three, or four, substituents Q; each $Z^L$ is independently a bond, —C(O)—, —C(O)O—, —C(O)NH—, —OC(O)NH—, —O—, —NH—, —N(CH$_3$)—, or —NHC(O)NH—; and z is an integer of 1, 2, 3, 4, 5, 6, 7, or 8.

In certain embodiments, each $R^L$ is independently methanediyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, ethyne-1,2-diyl, cyclobutane-1,3-diyl, cyclopentane-1,3-diyl, cyclohexane-1,3-diyl, cyclohexane-1,4-diyl, cycloheptane-1,3-diyl, cycloheptane-1,4-diyl, bicyclo[2.2.2]octane-1,4-diyl, phen-1,3-diyl, phen-1,4-diyl, pyrazol-1,3-diyl, pyrazol-1,4-diyl, imidazol-1,4-diyl, 1,2,3-triazol-1,4-diyl, pyrimidin-2,4-diyl, pyrimidin-2,5-diyl, 5,6,7,8,9,10-hexahydrocycloocta[d]-pyridazin-1,7-diyl, pyrazolidin-1,3-diyl, pyrazolidin-1,4-diyl, 1,3-dioxan-2,5-diyl, piperazin-1,4-diyl, piperidin-1,3-diyl, piperidin-1,4-diyl, or 3,9-diazaspiro[5.5]-undecane-3,9-diyl, each optionally substituted with one or more, in one embodiment, one, two, three, or four, substituents Q; each $Z^L$ is independently a bond, —C(O)—, —C(O)O—, —C(O)NH—, —OC(O)NH—, —O—, —NH—, —N(CH$_3$)—, or —NHC(O)NH—; and z is an integer of 1, 2, 3, 4, 5, 6, 7, or 8.

In certain embodiments, L is:

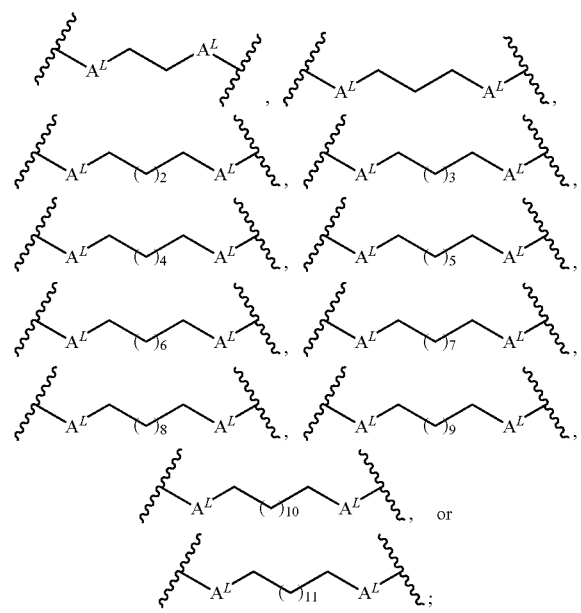

wherein each $A^L$ is independently a bond, —O—, —NH—, or —N(CH$_3$)—.

In certain embodiments, L is:

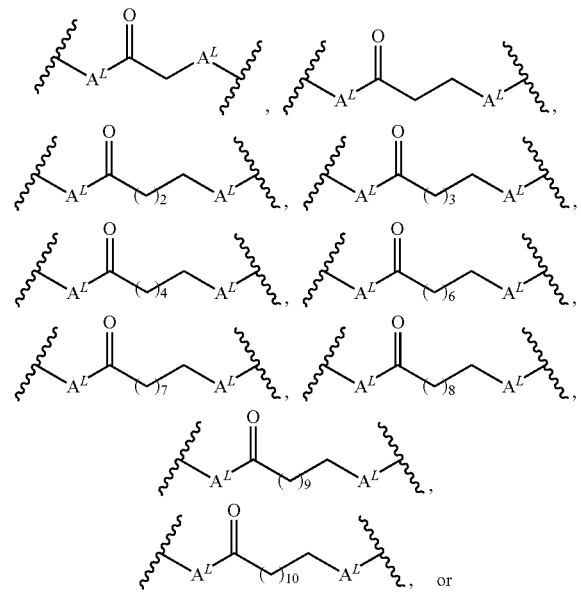

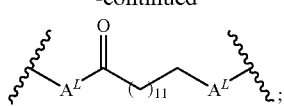

wherein each $A^L$ is independently a bond, —O—, —NH—, or —N(CH$_3$)—.

In certain embodiments, L is:

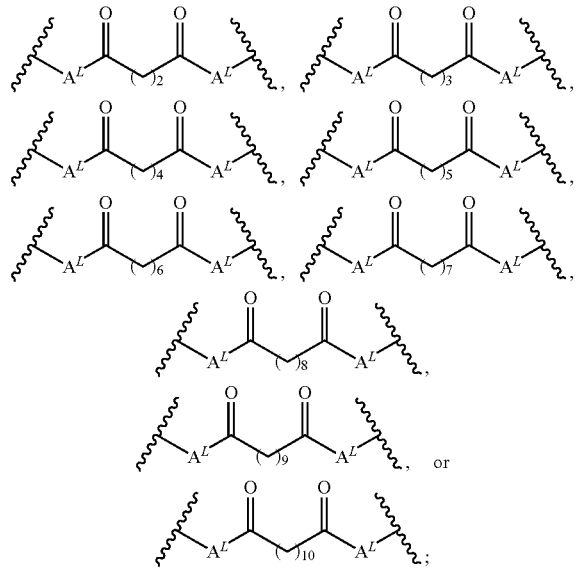

wherein each $A^L$ is independently a bond, —O—, —NH—, or —N(CH$_3$)—.

In certain embodiments, L is:

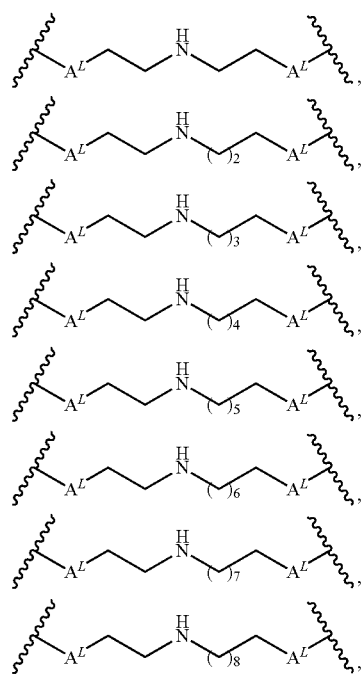

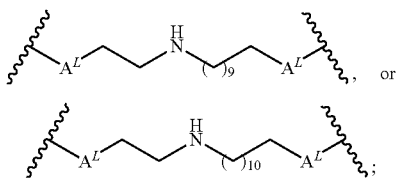

wherein each $A^L$ is independently a bond, —O—, —NH—, or —N(CH$_3$)—; and wherein each amino (NH) group is optionally substituted with methyl.

In certain embodiments, L is:

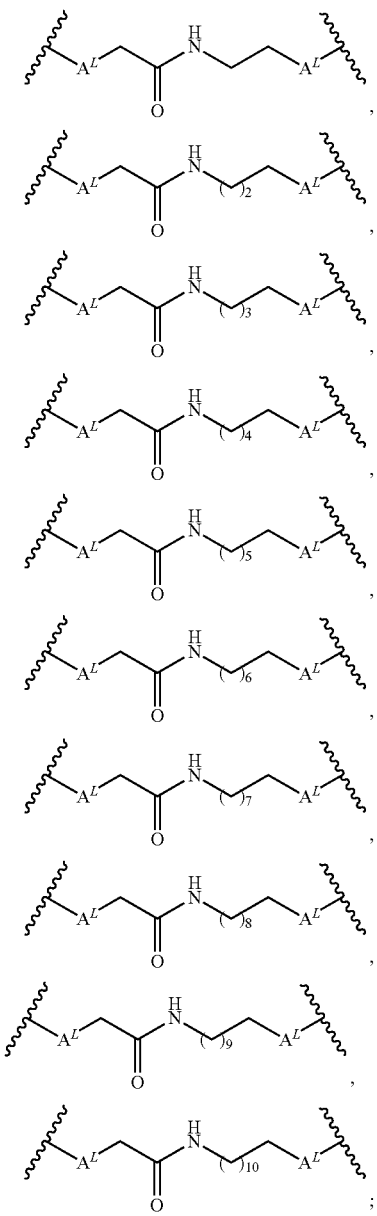

wherein each $A^L$ is independently a bond, —O—, —NH—, or —N(CH$_3$)—; and wherein each amino (NH) group is optionally substituted with methyl.

In certain embodiments, L is:
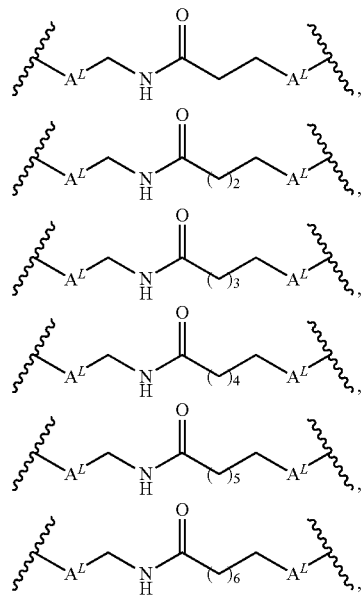
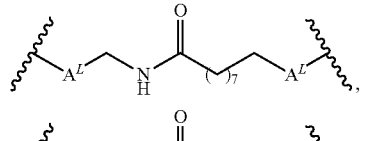
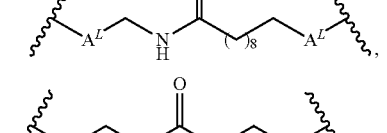
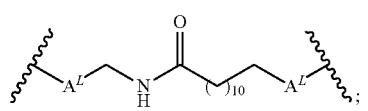
wherein each $A^L$ is independently a bond, —O—, —NH—, or —N(CH$_3$)—; and wherein each amino group (NH) is optionally substituted with methyl.
In certain embodiments, L is:
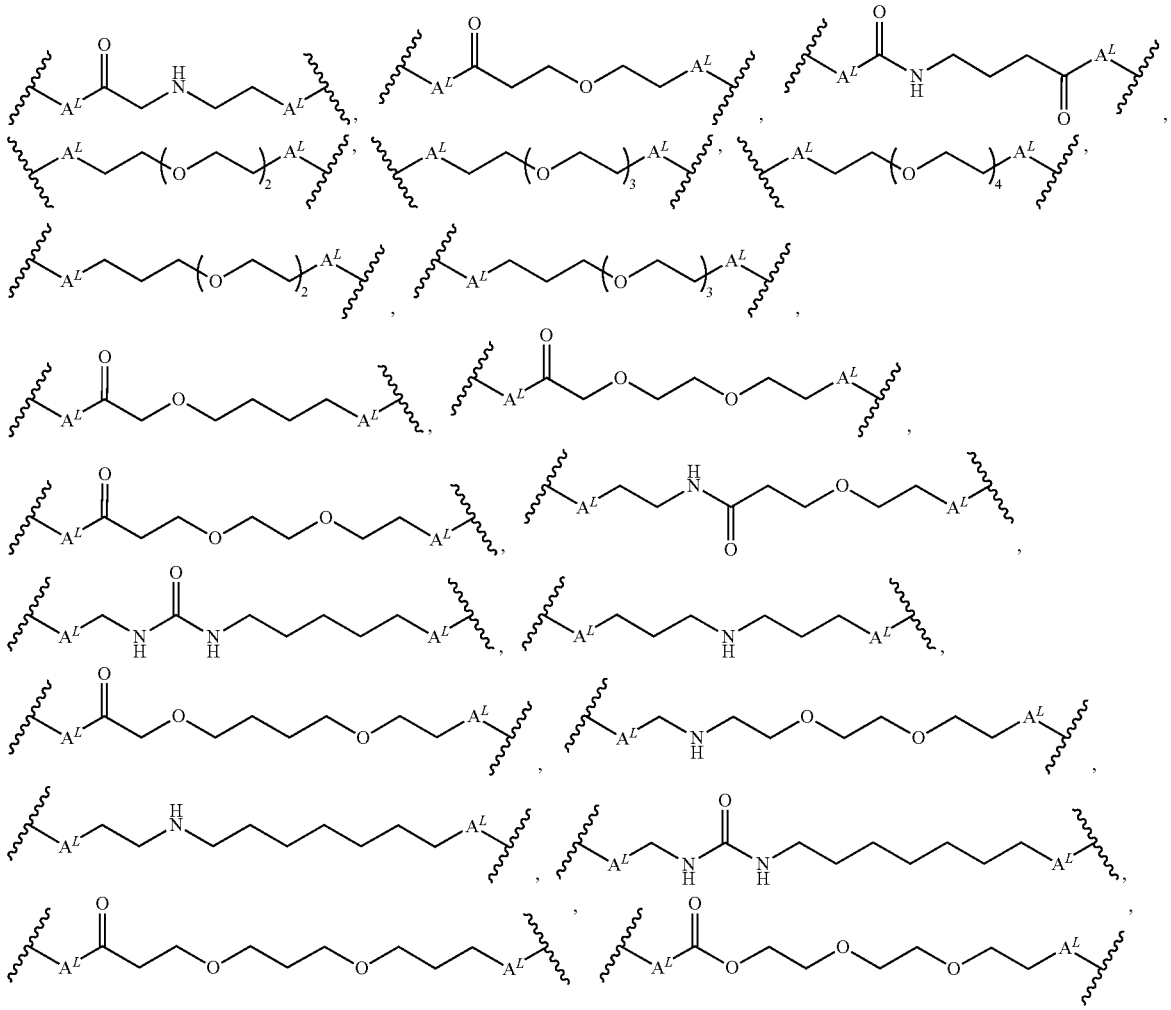

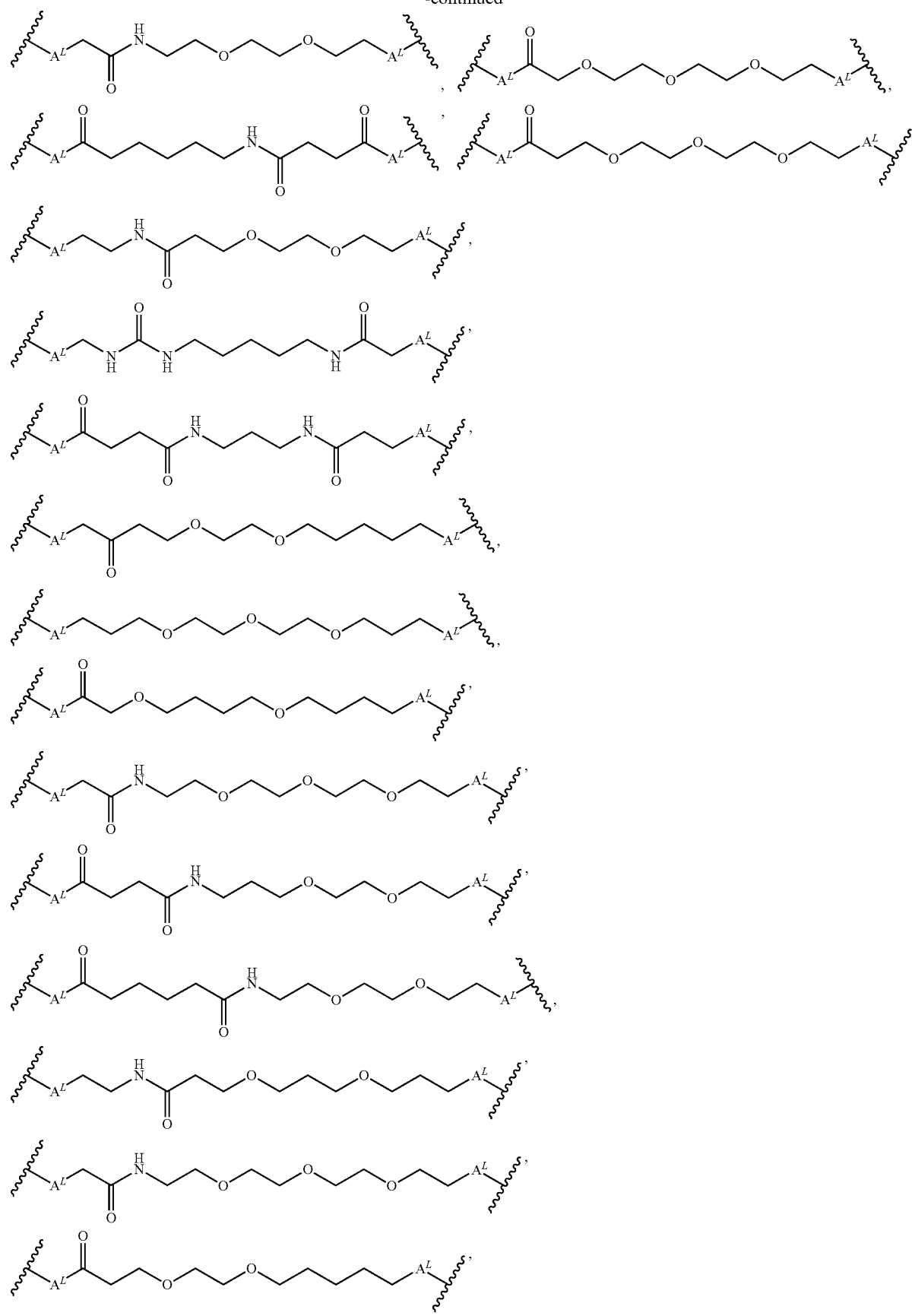

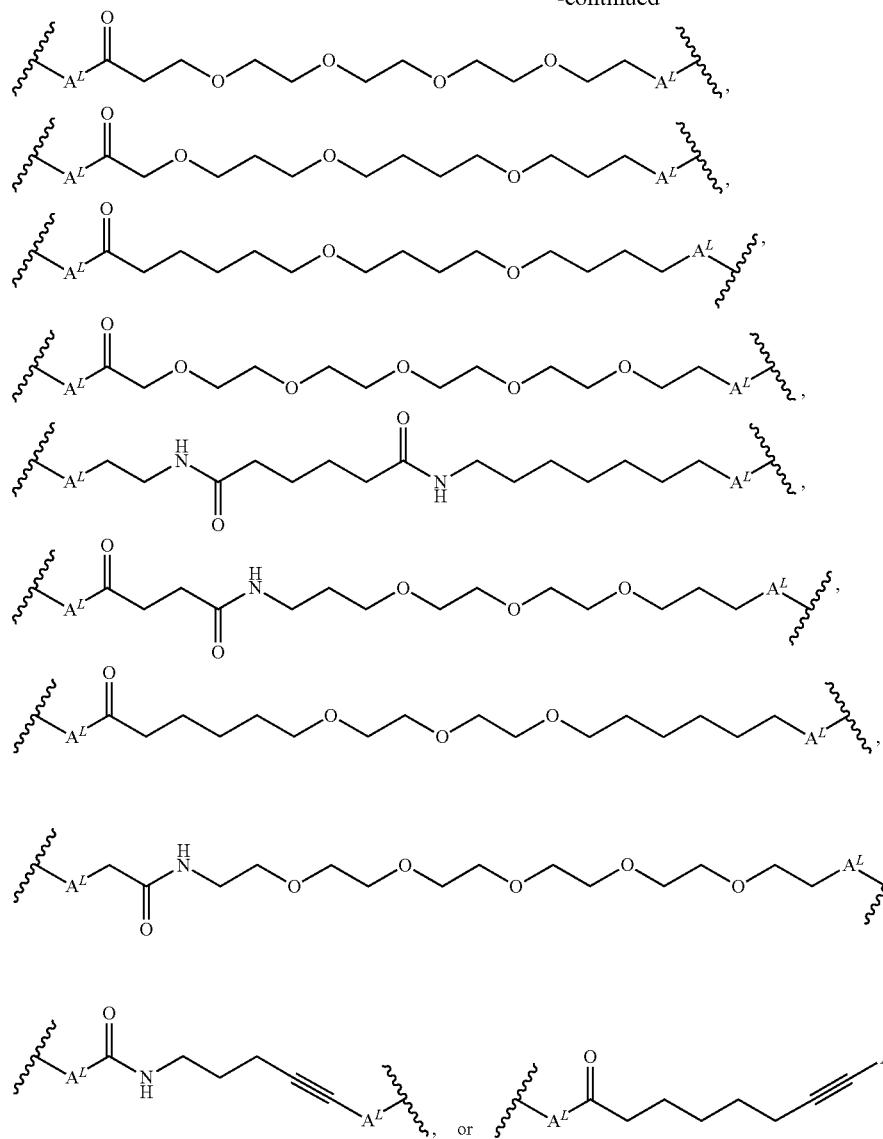
wherein each $A^L$ is independently a bond, —O—, —NH—, or —N(CH$_3$)—; and wherein each amino (NH) group is optionally substituted with methyl.
In certain embodiments, L is:
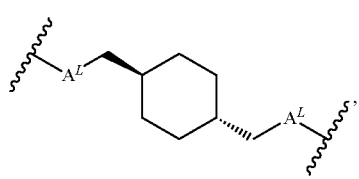
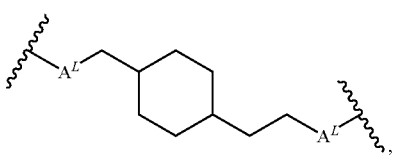
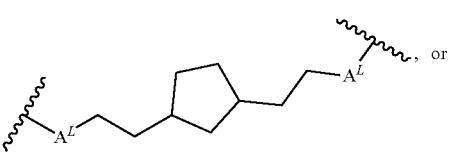

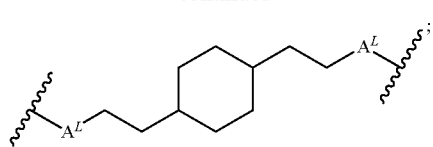
wherein each $A^L$ is independently a bond, —O—, —NH—, or —N(CH$_3$)—.
In certain embodiments, L is:
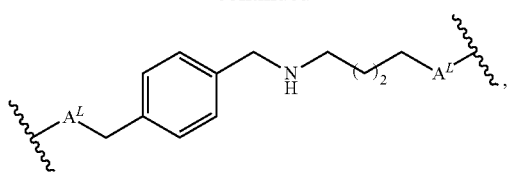
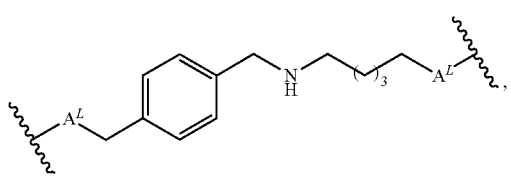
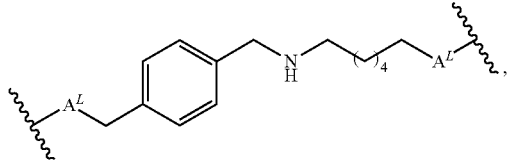
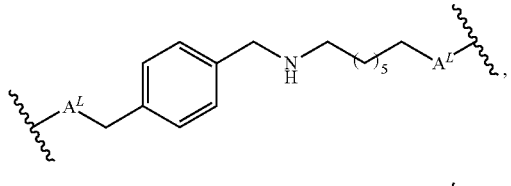
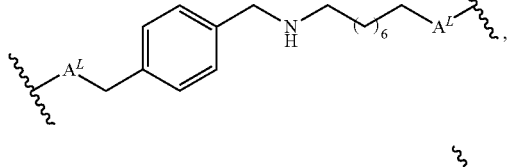
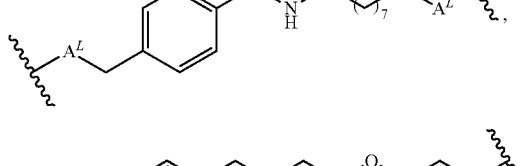
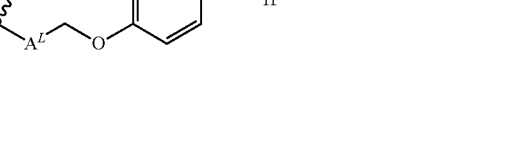
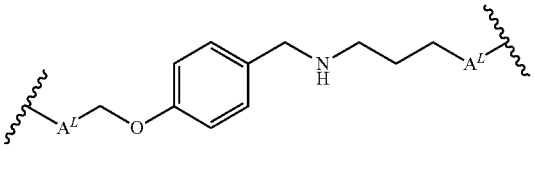
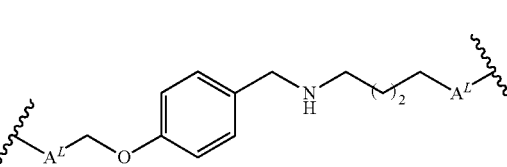
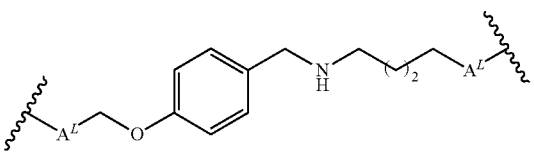

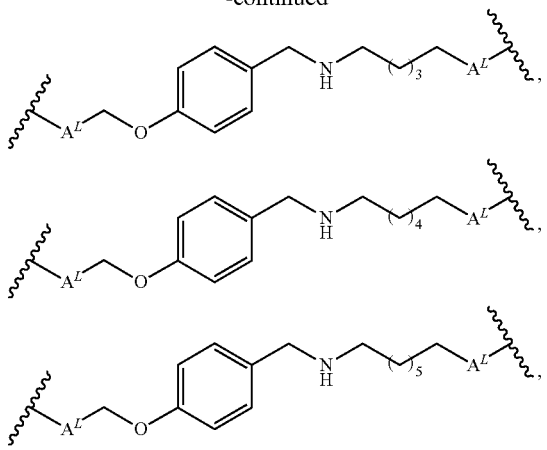
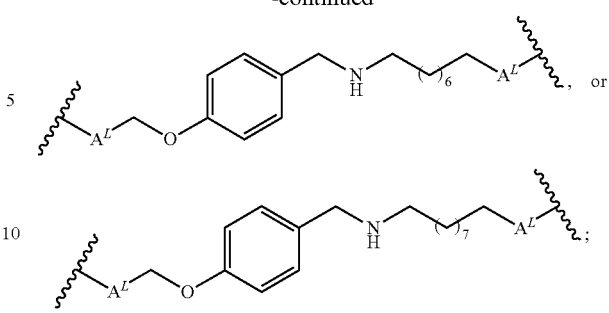
wherein each $A^L$ is independently a bond, —O—, —NH—, or —N(CH$_3$)—; and wherein each amino group (NH) is optionally substituted with methyl.
In certain embodiments, L is:
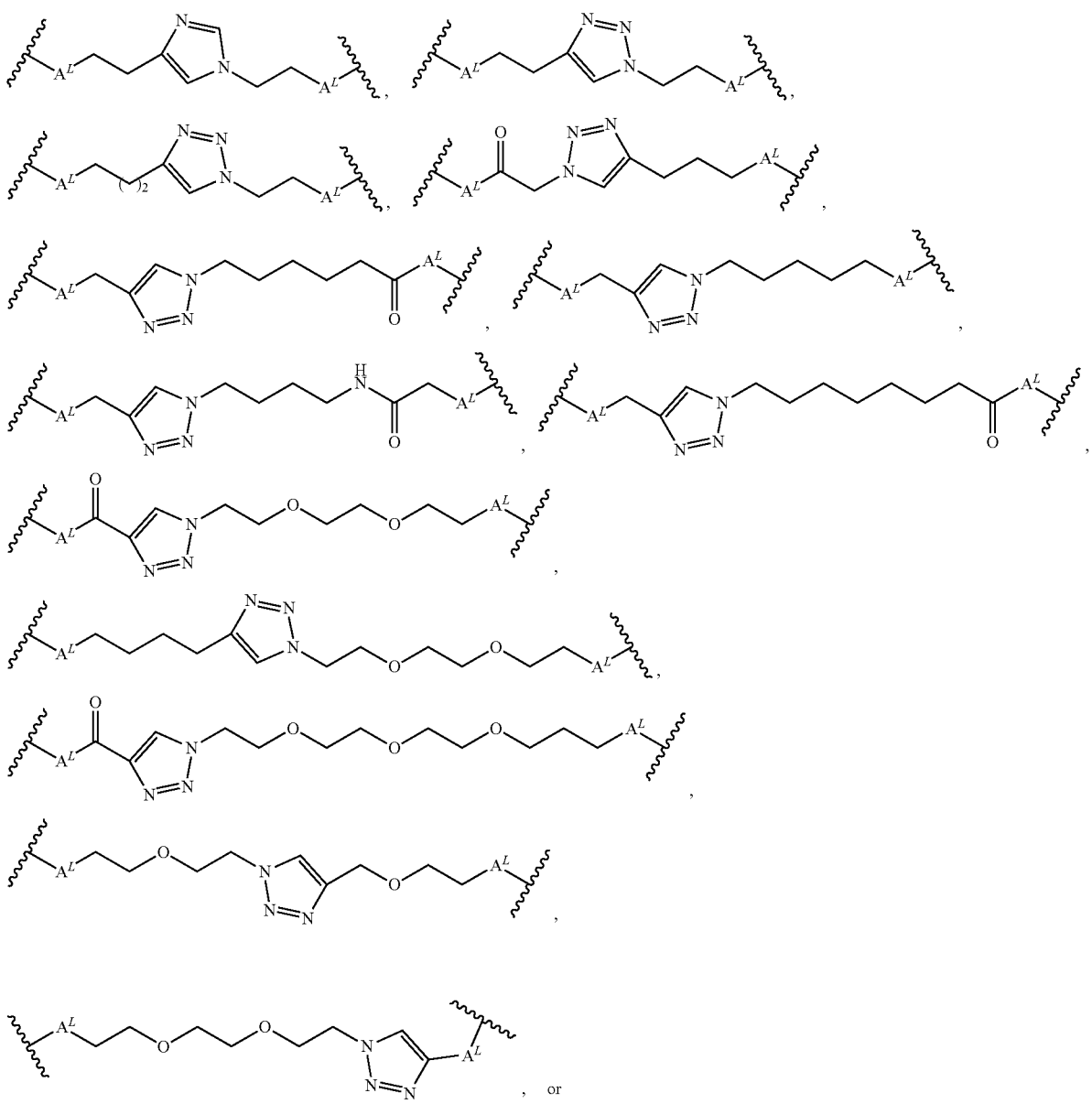
, or

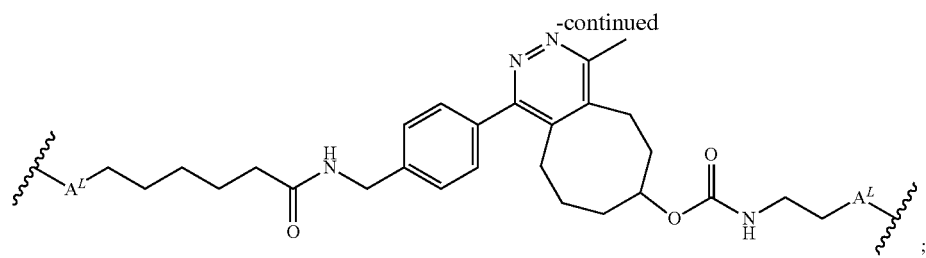
wherein each $A^L$ is independently a bond, —O—, —NH—, or —N(CH$_3$)—; and wherein each amino group (NH) is optionally substituted with methyl.
In certain embodiments, L is:
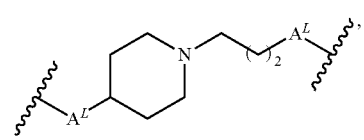
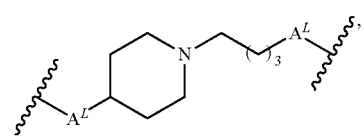
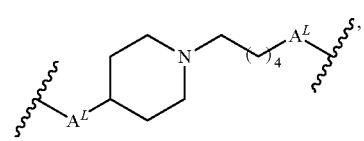
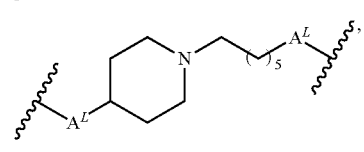
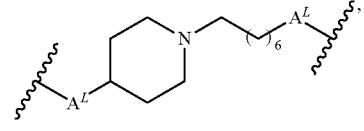
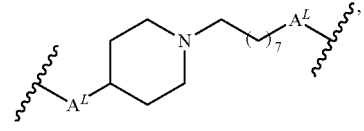
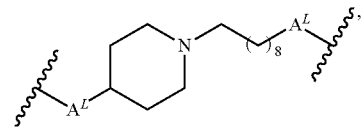
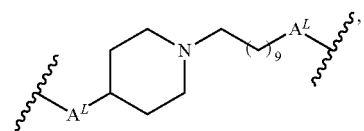
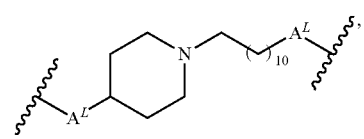
-continued
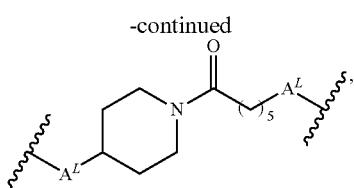
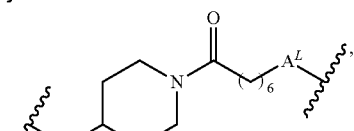
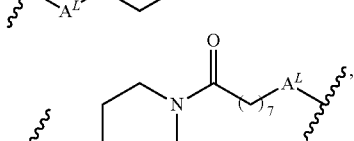
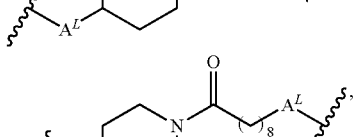
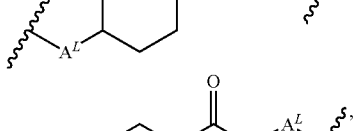
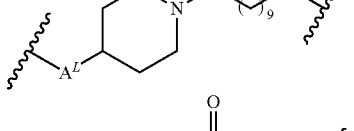
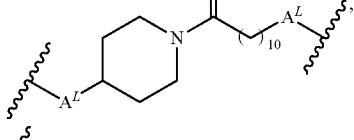
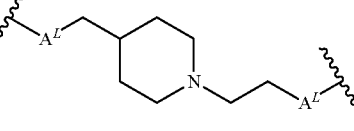
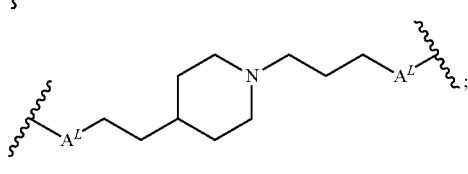

wherein each $A^L$ is independently a bond, —O—, —NH—, or —N(CH$_3$)—.
In certain embodiments, L is:
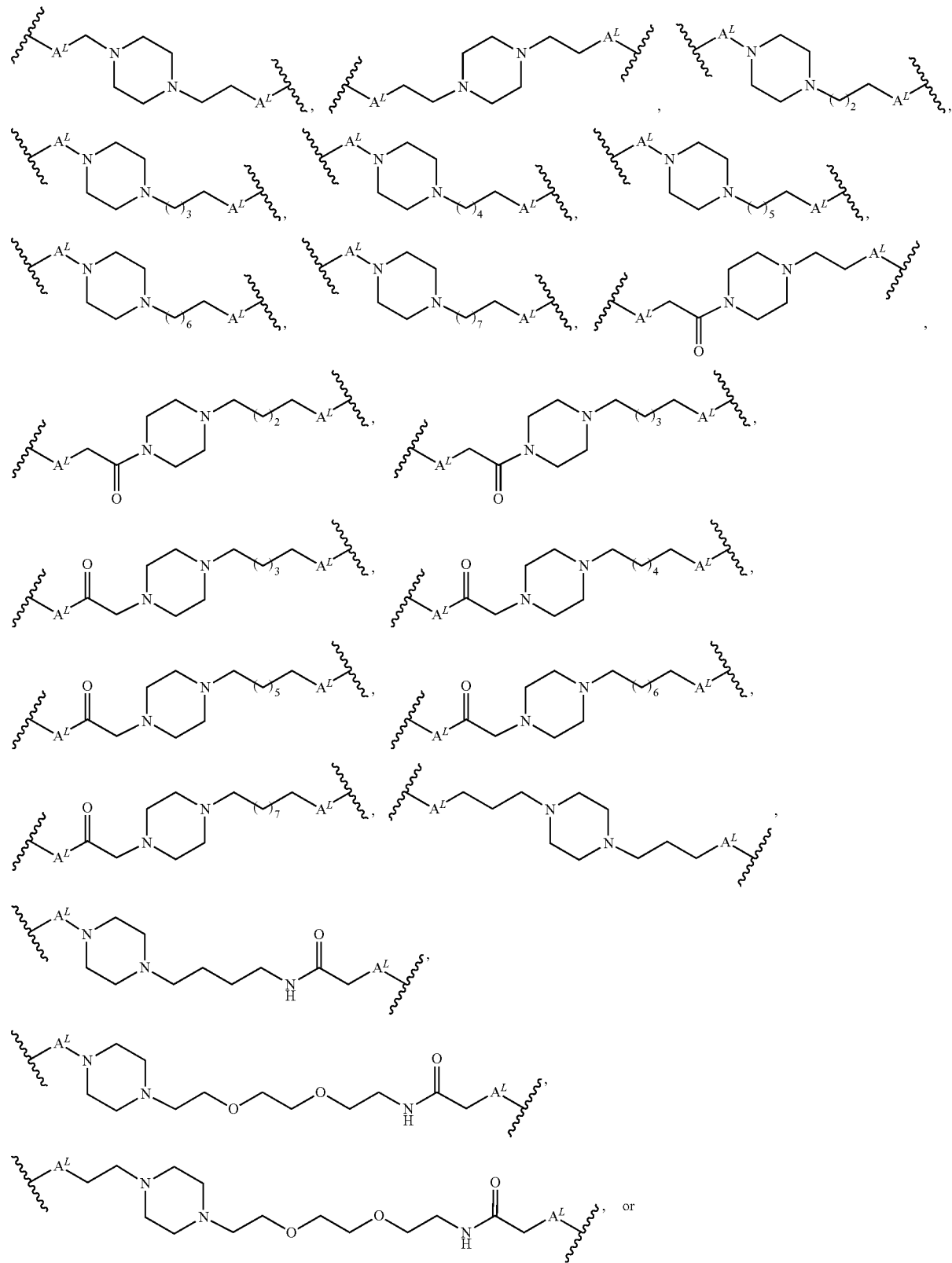

-continued
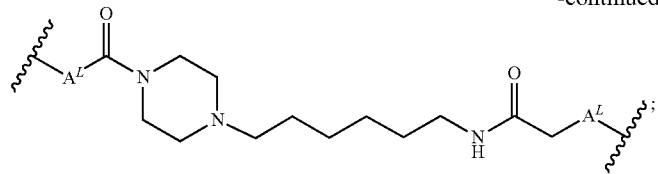
wherein each $A^L$ is independently a bond, —O—, —NH—, or —N(CH$_3$)—; and wherein each amino group (NH) is optionally substituted with methyl.
In certain embodiments, L is:
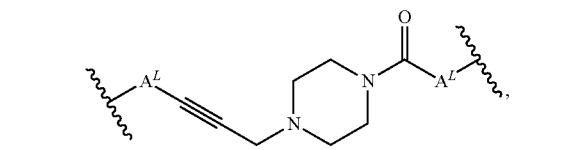
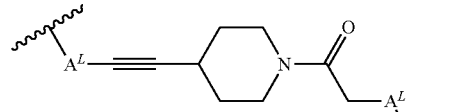
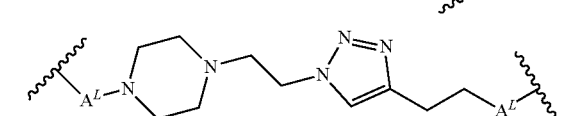
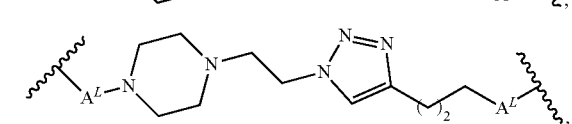
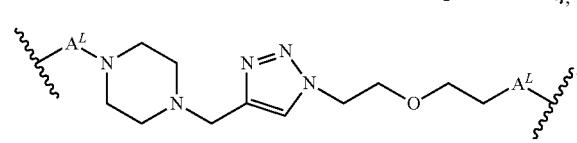
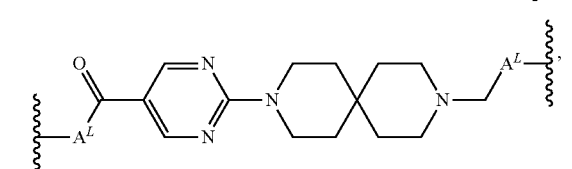
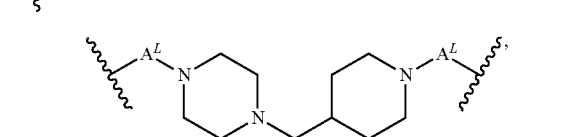
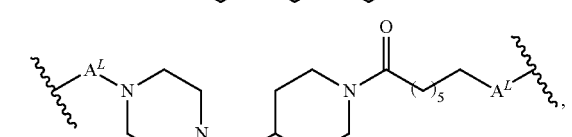
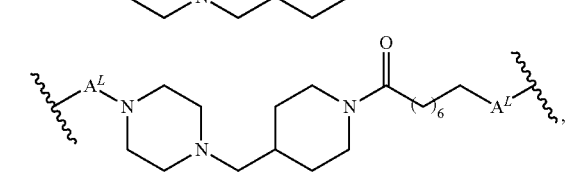
-continued
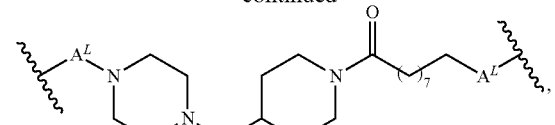
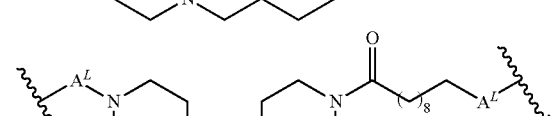
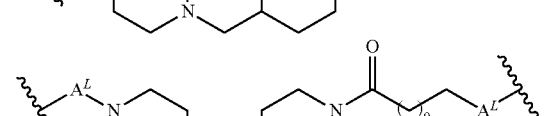
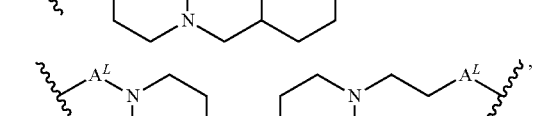
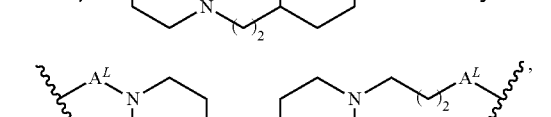
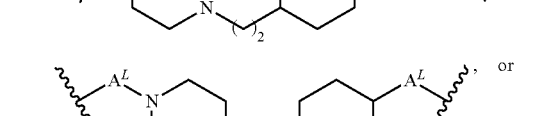
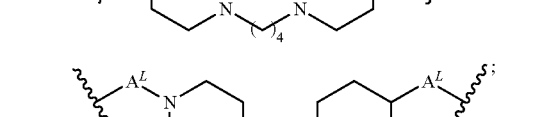
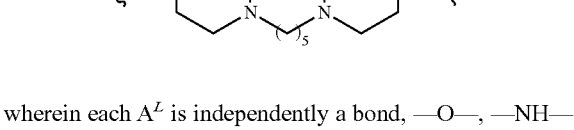
wherein each $A^L$ is independently a bond, —O—, —NH—, or —N(CH$_3$)—; and wherein each amino group is optionally substituted with methyl.
In certain embodiments, L is:
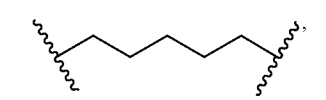
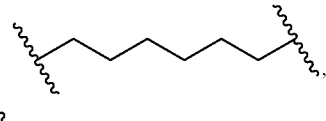

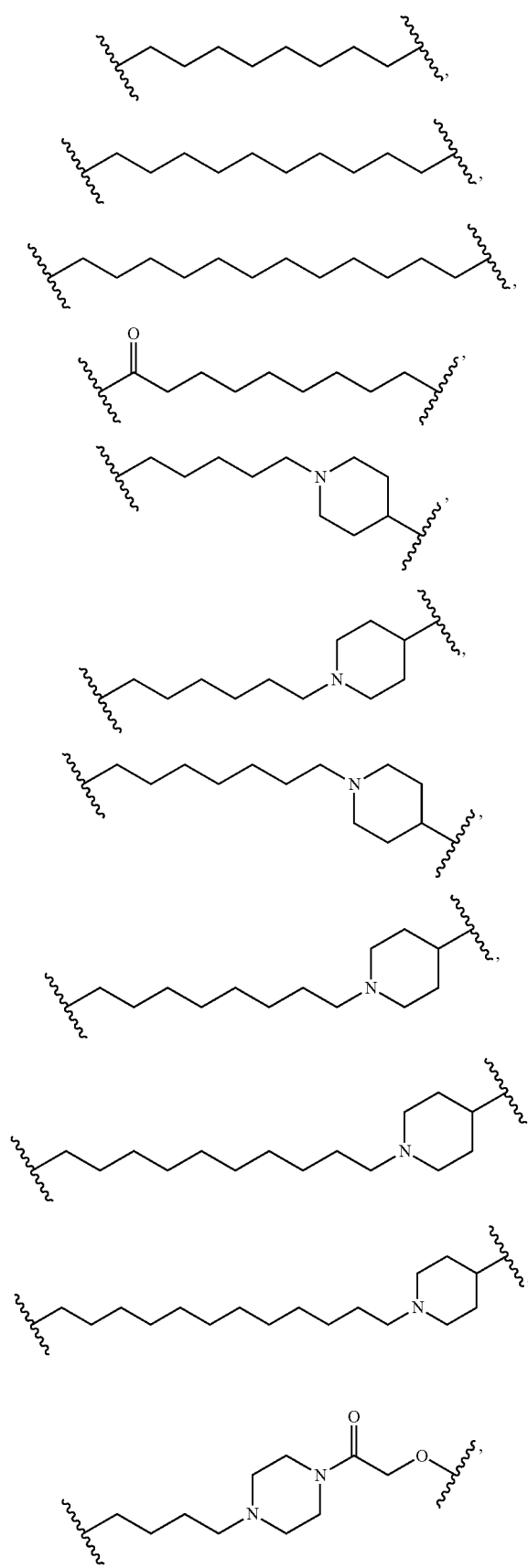
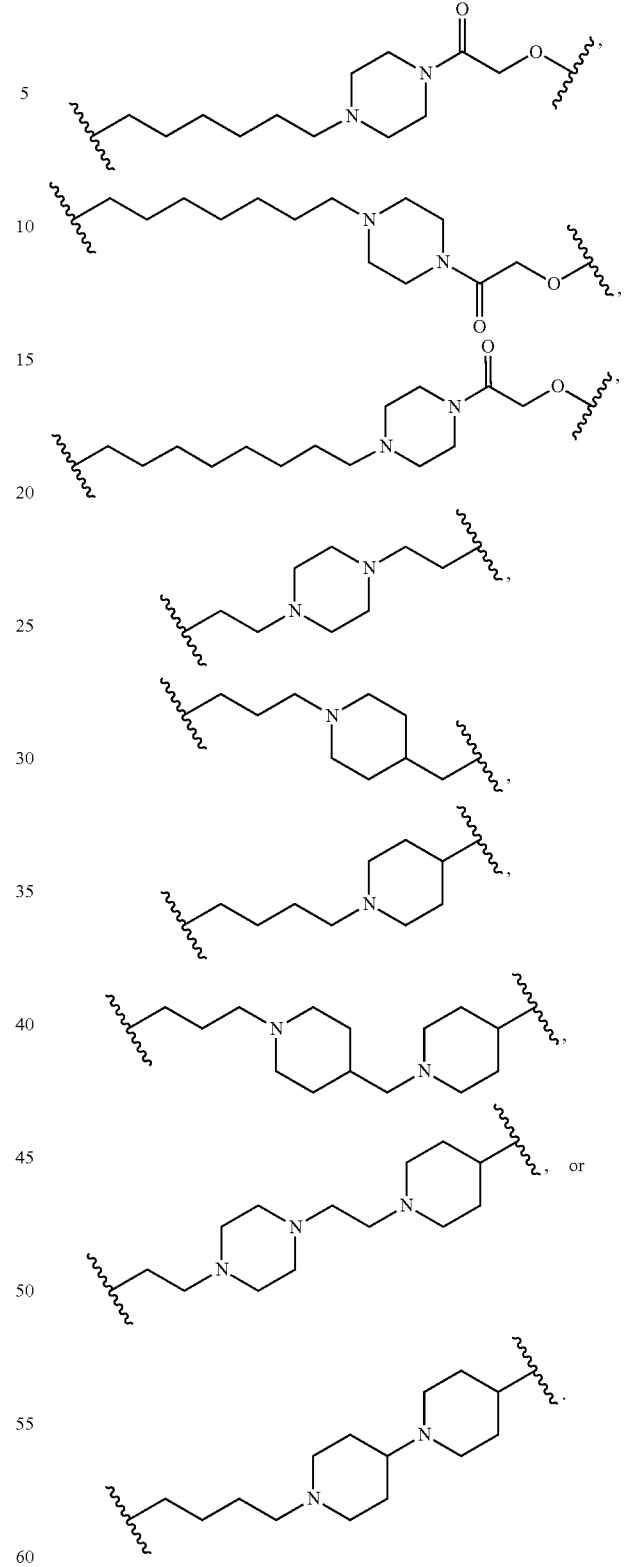
In one embodiment, provided herein is a compound of:
3-(4-(1-(6-(4-(((R)-1-(3-amino-5-(trifluoromethyl)phenyl)ethyl)amino)-6,7-dimethoxy-2-methylquinazolin-8-yl)hexyl)piperidin-4-yl)-6-fluoro-1-oxoisoindolin-2-yl)-piperidine-2,6-dione A101;

3-(5-(4-(7-(4-(((R)-1-(3-(1,1-difluoro-2-hydroxyethyl)phenyl)ethyl)amino)-6,7-dimethoxy-2-methylquinazolin-8-yl)heptyl)piperazin-1-yl)-6-fluoro-1-oxoisoindolin-2-yl)piperidine-2,6-dione A102;

3-(4-(1-(6-(4-(((S)-1-(3-amino-5-(trifluoromethyl)phenyl)ethyl)amino)-6,7-dimethoxy-2-methylquinazolin-8-yl)hexyl)piperidin-4-yl)-6-fluoro-1-oxoisoindolin-2-yl)-piperidine-2,6-dione A103;

3-(4-(1-(7-(4-(((R)-1-(3-(1,1-difluoro-2-hydroxyethyl)phenyl)ethyl)amino)-6,7-dimethoxy-2-methylquinazolin-8-yl)heptyl)piperidin-4-yl)-6-fluoro-1-oxoisoindolin-2-yl)piperidine-2,6-dione A104;

3-(4-(1-(8-(4-(((R)-1-(3-amino-5-(trifluoromethyl)phenyl)ethyl)amino)-6,7-dimethoxy-2-methylquinazolin-8-yl)octyl)piperidin-4-yl)-6-fluoro-1-oxoisoindolin-2-yl)-piperidine-2,6-dione A105;

3-(4-(1-(10-(4-(((R)-1-(3-amino-5-(trifluoromethyl)phenyl)ethyl)amino)-6,7-dimethoxy-2-methylquinazolin-8-yl)decyl)piperidin-4-yl)-6-fluoro-1-oxoisoindolin-2-yl)-piperidine-2,6-dione A106;

3-(4-(1-(12-(4-(((R)-1-(3-amino-5-(trifluoromethyl)phenyl)ethyl)amino)-6,7-dimethoxy-2-methylquinazolin-8-yl)dodecyl)piperidin-4-yl)-6-fluoro-1-oxoisoindolin-2-yl)piperidine-2,6-dione A107;

3-(4-(1-(12-(4-(((S)-1-(3-amino-5-(trifluoromethyl)phenyl)ethyl)amino)-6,7-dimethoxy-2-methylquinazolin-8-yl)dodecyl)piperidin-4-yl)-6-fluoro-1-oxoisoindolin-2-yl)piperidine-2,6-dione A108;

3-(5-(4-(7-(4-(((R)-1-(3-(1,1-difluoro-2-hydroxyethyl)phenyl)ethyl)amino)-6,7-dimethoxy-2-methylquinazolin-8-yl)heptyl)piperazin-1-yl)-6-fluoro-1-oxoisoindolin-2-yl)piperidine-2,6-dione A109;

3-(4-(1-(10-(4-(((S)-1-(3-amino-5-(trifluoromethyl)phenyl)ethyl)amino)-6,7-dimethoxy-2-methylquinazolin-8-yl)decyl)piperidin-4-yl)-6-fluoro-1-oxoisoindolin-2-yl)-piperidine-2,6-dione A110;

3-(4-(1-(8-(4-(((S)-1-(3-amino-5-(trifluoromethyl)phenyl)ethyl)amino)-6,7-dimethoxy-2-methylquinazolin-8-yl)octyl)piperidin-4-yl)-6-fluoro-1-oxoisoindolin-2-yl)-piperidine-2,6-dione A111;

3-(4-((4-(((7-(6,7-dimethoxy-2-methyl-4-(((S)-1-(4-(2-((methylamino)methyl)-phenyl)thiophen-2-yl)ethyl)amino)quinazolin-8-yl)heptyl)amino)methyl)benzyl)oxy)-1-oxoisoindolin-2-yl)piperidine-2,6-dione A112;

3-(4-((4-(((7-(6,7-dimethoxy-2-methyl-4-(((R)-1-(4-(2-((methylamino)methyl)-phenyl)thiophen-2-yl)ethyl)amino)quinazolin-8-yl)heptyl)amino)methyl)benzyl)oxy)-1-oxoisoindolin-2-yl)piperidine-2,6-dione A113;

3-(5-(1-(7-(4-(((S)-1-(3-(1,1-difluoro-2-hydroxyethyl)phenyl)ethyl)amino)-6,7-dimethoxy-2-methylquinazolin-8-yl)heptyl)piperidin-4-yl)-6-fluoro-1-oxoisoindolin-2-yl)piperidine-2,6-dione A114;

3-(6-(1-(7-(6,7-dimethoxy-2-methyl-4-(((R)-1-(4-(2-((methylamino)methyl)-phenyl)thiophen-2-yl)ethyl)amino)quinazolin-8-yl)heptyl)piperidin-4-yl)-1-oxoisoindolin-2-yl)piperidine-2,6-dione A115;

3-(6-(1-(7-(6,7-dimethoxy-2-methyl-4-(((S)-1-(4-(2-((methylamino)methyl)-phenyl)thiophen-2-yl)ethyl)amino)quinazolin-8-yl)heptyl)piperidin-4-yl)-1-oxoisoindolin-2-yl)piperidine-2,6-dione A116;

3-(4-(1-(7-(4-(((S)-1-(3-(1,1-difluoro-2-hydroxyethyl)phenyl)ethyl)amino)-6,7-dimethoxy-2-methylquinazolin-8-yl)heptyl)piperidin-4-yl)-6-fluoro-1-oxoisoindolin-2-yl)piperidine-2,6-dione A117;

3-(4-((4-(((7-(4-(((R)-1-(3-bromophenyl)ethyl)amino)-6,7-dimethoxy-2-methyl-quinazolin-8-yl)heptyl)amino)methyl)benzyl)oxy)-1-oxoisoindolin-2-yl)piperidine-2,6-dione A118;

3-(5-(1-(5-(4-(((R)-1-(3-(1,1-difluoro-2-hydroxyethyl)phenyl)ethyl)amino)-6,7-dimethoxy-2-methylquinazolin-8-yl)pentyl)piperidin-4-yl)-6-fluoro-1-oxoisoindolin-2-yl)piperidine-2,6-dione A119;

3-(5-(1-(6-(4-(((R)-1-(3-(1,1-difluoro-2-hydroxyethyl)phenyl)ethyl)amino)-6,7-dimethoxy-2-methylquinazolin-8-yl)hexyl)piperidin-4-yl)-6-fluoro-1-oxoisoindolin-2-yl)piperidine-2,6-dione A120;

3-(5-(1-((1-(3-(4-(((R)-1-(3-(1,1-difluoro-2-hydroxyethyl)phenyl)ethyl)amino)-6,7-dimethoxy-2-methylquinazolin-8-yl)propyl)piperidin-4-yl)methyl)piperidin-4-yl)-6-fluoro-1-oxoisoindolin-2-yl)piperidine-2,6-dione A121;

3-(5-(1'-(4-(4-(((R)-1-(3-(1,1-difluoro-2-hydroxyethyl)phenyl)ethyl)amino)-6,7-dimethoxy-2-methylquinazolin-8-yl)butyl)-[1,4'-bipiperidin]-4-yl)-6-fluoro-1-oxoisoindolin-2-yl)piperidine-2,6-dione A122; or 3-(5-(1-(2-(4-(2-(4-(((R)-1-(3-(1,1-difluoro-2-hydroxyethyl)phenyl)ethyl)amino)-6,7-dimethoxy-2-methylquinazolin-8-yl)ethyl)piperazin-1-yl)ethyl)piperidin-4-yl)-6-fluoro-1-oxoisoindolin-2-yl)piperidine-2,6-dione A123;

or an enantiomer, a mixture of enantiomers, a tautomer, a mixture of two or more tautomers, or an isotopic variant thereof, or a pharmaceutically acceptable salt, solvate, hydrate, or prodrug thereof.

In another embodiment, provided herein is a compound of:

3-(7-(2-(4-(4-(4-(((R)-1-(3-(1,1-difluoro-2-hydroxyethyl)phenyl)ethyl)amino)-6,7-dimethoxy-2-methylquinazolin-8-yl)butyl)piperazin-1-yl)-2-oxoethoxy)-1-methyl-1H-indazol-3-yl)piperidine-2,6-dione A201;

3-(6-(2-(4-(4-(4-(((R)-1-(3-(1,1-difluoro-2-hydroxyethyl)phenyl)ethyl)amino)-6,7-dimethoxy-2-methylquinazolin-8-yl)butyl)piperazin-1-yl)-2-oxoethoxy)-1-methyl-1H-indazol-3-yl)piperidine-2,6-dione A202;

3-(7-(2-(4-(6-(4-(((R)-1-(3-(1,1-difluoro-2-hydroxyethyl)phenyl)ethyl)amino)-6,7-dimethoxy-2-methylquinazolin-8-yl)hexyl)piperazin-1-yl)-2-oxoethoxy)-1-methyl-1H-indazol-3-yl)piperidine-2,6-dione A203;

3-(6-(2-(4-(6-(4-(((R)-1-(3-(1,1-difluoro-2-hydroxyethyl)phenyl)ethyl)amino)-6,7-dimethoxy-2-methylquinazolin-8-yl)hexyl)piperazin-1-yl)-2-oxoethoxy)-1-methyl-1H-indazol-3-yl)piperidine-2,6-dione A204;

3-(7-(2-(4-(8-(4-(((R)-1-(3-(1,1-difluoro-2-hydroxyethyl)phenyl)ethyl)amino)-6,7-dimethoxy-2-methylquinazolin-8-yl)octyl)piperazin-1-yl)-2-oxoethoxy)-1-methyl-1H-indazol-3-yl)piperidine-2,6-dione A205; or 3-(6-(2-(4-(8-(4-(((R)-1-(3-(1,1-difluoro-2-hydroxyethyl)phenyl)ethyl)amino)-6,7-dimethoxy-2-methylquinazolin-8-yl)octyl)piperazin-1-yl)-2-oxoethoxy)-1-methyl-1H-indazol-3-yl)piperidine-2,6-dione A206;

or an enantiomer, a mixture of enantiomers, a tautomer, a mixture of two or more tautomers, or an isotopic variant thereof, or a pharmaceutically acceptable salt, solvate, hydrate, or prodrug thereof.

In yet another embodiment, provided herein is a compound of:

3-(3-(2-(4-(4-(4-(((R)-1-(3-(1,1-difluoro-2-hydroxyethyl)phenyl)ethyl)amino)-6,7-dimethoxy-2-methylquinazolin-8-yl)butyl)piperazin-1-yl)-2-oxoethoxy)phenyl)piperidine-2,6-dione A301;

3-(4-(2-(4-(4-(4-(((R)-1-(3-(1,1-difluoro-2-hydroxyethyl)
  phenyl)ethyl)amino)-6,7-dimethoxy-2-methylquinazolin-
  8-yl)butyl)piperazin-1-yl)-2-oxoethoxy)phenyl)piperi-
  dine-2,6-dione A302;
3-(3-(2-(4-(6-(4-(((R)-1-(3-(1,1-difluoro-2-hydroxyethyl)
  phenyl)ethyl)amino)-6,7-dimethoxy-2-methylquinazolin-
  8-yl)hexyl)piperazin-1-yl)-2-oxoethoxy)phenyl)piperi-
  dine-2,6-dione A303;
3-(4-(2-(4-(6-(4-(((R)-1-(3-(1,1-difluoro-2-hydroxyethyl)
  phenyl)ethyl)amino)-6,7-dimethoxy-2-methylquinazolin-
  8-yl)hexyl)piperazin-1-yl)-2-oxoethoxy)phenyl)piperi-
  dine-2,6-dione A304;
3-(3-(2-(4-(8-(4-(((R)-1-(3-(1,1-difluoro-2-hydroxyethyl)
  phenyl)ethyl)amino)-6,7-dimethoxy-2-methylquinazolin-
  8-yl)octyl)piperazin-1-yl)-2-oxoethoxy)phenyl)piperi-
  dine-2,6-dione A305; or
3-(4-(2-(4-(8-(4-(((R)-1-(3-(1,1-difluoro-2-hydroxyethyl)
  phenyl)ethyl)amino)-6,7-dimethoxy-2-methylquinazolin-
  8-yl)octyl)piperazin-1-yl)-2-oxoethoxy)phenyl)piperi-
  dine-2,6-dione A306;
or an enantiomer, a mixture of enantiomers, a tautomer, a mixture of two or more tautomers, or an isotopic variant thereof, or a pharmaceutically acceptable salt, solvate, hydrate, or prodrug thereof.

In yet another embodiment, provided herein is a compound of:
(2S,4R)-1-((S)-2-(9-(6,7-dimethoxy-2-methyl-4-(((S)-1-(4-
  (2-((methylamino)-methyl)phenyl)thiophen-2-yl)ethyl)
  amino)quinazolin-8-yl)nonanamido)-3,3-dimethylbu-
  tanoyl)-4-hydroxy-N-(4-(4-methylthiazol-5-yl)benzyl)
  pyrrolidine-2-carboxamide A401; or
(2S,4R)-1-((S)-2-(9-(6,7-dimethoxy-2-methyl-4-(((R)-1-(4-
  (2-((methylamino)-methyl)phenyl)thiophen-2-yl)ethyl)
  amino)quinazolin-8-yl)nonanamido)-3,3-dimethylbu-
  tanoyl)-4-hydroxy-N-(4-(4-methylthiazol-5-yl)benzyl)
  pyrrolidine-2-carboxamide A402;
or a diastereomer, a mixture of two or more diastereomers, a tautomer, a mixture of two or more tautomers, or an isotopic variant thereof; or a pharmaceutically acceptable salt, solvate, hydrate, or prodrug thereof.

In still another embodiment, provided herein is a compound of:
3-(4-(1-(7-((4-(((R)-1-(3-amino-5-(trifluoromethyl)phenyl)
  ethyl)amino)-2-methyl-6-(((S)-tetrahydrofuran-3-yl)oxy)
  quinazolin-7-yl)oxy)heptyl)piperidin-4-yl)-6-fluoro-1-
  oxoisoindolin-2-yl)piperidine-2,6-dione B101;
3-(5-(1-(11-((4-(((R)-1-(3-bromophenyl)ethyl)amino)-6-
  methoxy-2-methyl-quinazolin-7-yl)oxy)undecanoyl)pip-
  eridin-4-yl)-6-fluoro-1-oxoisoindolin-2-yl)piperidine-2,
  6-dione B102;
3-(6-((7-((4-(((R)-1-(3-bromophenyl)ethyl)amino)-6-
  methoxy-2-methyl-quinazolin-7-yl)oxy)heptyl)amino)-1-
  oxo-3,4-dihydroisoquinolin-2(1H)-yl)piperidine-2,6-di-
  one B103;
3-(5-((9-((4-(((R)-1-(3-bromophenyl)ethyl)amino)-6-
  methoxy-2-methyl-quinazolin-7-yl)oxy)nonyl)amino)-1-
  oxo-3,4-dihydroisoquinolin-2(1H)-yl)piperidine-2,6-di-
  one B104;
3-(5-((7-((4-(((R)-1-(3-bromophenyl)ethyl)amino)-6-
  methoxy-2-methyl-quinazolin-7-yl)oxy)heptyl)amino)-1-
  oxo-3,4-dihydroisoquinolin-2(1H)-yl)piperidine-2,6-di-
  one B105;
3-(5-((11-((4-(((R)-1-(3-bromophenyl)ethyl)amino)-6-
  methoxy-2-methyl-quinazolin-7-yl)oxy)undecyl)amino)-
  1-oxo-3,4-dihydroisoquinolin-2(1H)-yl)piperidine-2,6-
  dione B106;
3-(6-((9-((4-(((R)-1-(3-bromophenyl)ethyl)amino)-6-
  methoxy-2-methyl-quinazolin-7-yl)oxy)nonyl)amino)-1-
  oxo-3,4-dihydroisoquinolin-2(1H)-yl)piperidine-2,6-di-
  one B107; or
3-(6-((11-((4-(((R)-1-(3-Bromophenyl)ethyl)amino)-6-
  methoxy-2-methyl-quinazolin-7-yl)oxy)undecyl)amino)-
  1-oxo-3,4-dihydroisoquinolin-2(1H)-yl)piperidine-2,6-
  dione B108;
or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, a compound provided herein is deuterium-enriched. In certain embodiments, a compound provided herein is carbon-13 enriched. In certain embodiments, a compound provided herein is carbon-14 enriched. In certain embodiments, a compound provided herein contains one or more less prevalent isotopes for other elements, including, but not limited to, $^{15}$N for nitrogen; $^{17}$O or $^{18}$O for oxygen, and $^{34}$S, $^{35}$S, or $^{36}$S for sulfur.

In certain embodiments, a compound provided herein has an isotopic enrichment factor of no less than about 5, no less than about 10, no less than about 20, no less than about 50, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 6,410 for deuterium and 90 for carbon-13.

In certain embodiments, a compound provided herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy. In certain embodiments, at least one of the atoms of a compound provided herein, as specified as deuterium-enriched, has deuterium enrichment of no less than about 50%, no less than about 70%, no less than about 80%, no less than about 90%, or no less than about 98%.

In certain embodiments, a compound provided herein is isolated or purified. In certain embodiments, a compound provided herein has a purity of at least about 90%, at least about 95%, at least about 98%, at least about 99%, or at least about 99.5% by weight.

The compounds provided herein are intended to encompass all possible stereoisomers unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contains an aromatic moiety. It follows that a single compound may exhibit more than one type of isomerism.

A compound provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for the compound that undergoes epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When a compound provided herein contains an acidic or basic moiety, it can also be provided as a pharmaceutically acceptable salt. See, Berge et al., *J. Pharm. Sci.* 1977, 66, 1-19; *Handbook of Pharmaceutical Salts: Properties, Selection, and Use,* 2nd ed.; Stahl and Wermuth Eds.; John Wiley & Sons, 2011. In certain embodiments, a pharmaceutically acceptable salt of a compound provided herein is a solvate. In certain embodiments, a pharmaceutically acceptable salt of a compound provided herein is a hydrate.

Suitable acids for use in the preparation of pharmaceutically acceptable salts of a compound provided herein include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of a compound provided herein include, but are not limited to, inorganic bases, such as magnesium hydroxide, calcium hydroxide, potassium hydroxide, zinc hydroxide, and sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

A compound provided herein may also be provided as a prodrug, which is a functional derivative of the compound and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis.

Pharmaceutical Compositions

In one embodiment, provided herein is a pharmaceutical composition, comprising a compound provided herein, e.g., a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

The pharmaceutical composition provided herein can be formulated in various dosage forms, including, but not limited to, dosage forms for oral, parenteral, and topical administration. The pharmaceutical composition can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art. See, e.g., *Remington: The Science and Practice of Pharmacy,* supra; *Modified-Release Drug Delivery Technology,* 2nd ed.; Rathbone et al., Eds.; Drugs and the Pharmaceutical Sciences 184; CRC Press: Boca Raton, F L, 2008.

In one embodiment, the pharmaceutical composition provided herein is formulated in a dosage form for oral administration. In another embodiment, the pharmaceutical composition provided herein is formulated in a dosage form for parenteral administration. In yet another embodiment, the pharmaceutical composition provided herein is formulated in a dosage form for intravenous administration. In yet another embodiment, the pharmaceutical composition provided herein is formulated in a dosage form for intramuscular administration. In yet another embodiment, the pharmaceutical composition provided herein is formulated in a dosage form for subcutaneous administration. In still another embodiment, the pharmaceutical composition provided herein is formulated in a dosage form for topical administration.

The pharmaceutical composition provided herein can be provided in a unit-dosage form or multiple-dosage form. A unit-dosage form, as used herein, refers to physically discrete a unit suitable for administration to a subject, and packaged individually as is known in the art. Each unit-dose contains a predetermined quantity of an active ingredient(s)

(e.g., a compound provided herein) sufficient to produce the desired therapeutic effect, in association with the required pharmaceutical excipient(s). Examples of a unit-dosage form include, but are not limited to, an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of a multiple-dosage form include, are not limited to, a vial, bottle of tablets or capsules, or bottle of pints or gallons.

The pharmaceutical composition provided herein can be administered at once or multiple times at intervals of time. It is understood that the precise dosage and duration of treatment may vary with the age, weight, and condition of the subject being treated, and may be determined empirically using known testing protocols or by extrapolation from in vivo or in vitro test or diagnostic data. It is further understood that for any particular individual, specific dosage regimens should be adjusted over time according to the subject's need and the professional judgment of the person administering or supervising the administration of the pharmaceutical composition.

A. Oral Administration

The pharmaceutical composition provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical composition can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500®); gelatin; sugars, such as sucrose, glucose, dextrose, molasses, and lactose; natural and synthetic gums, such as acacia, alginic acid, alginates, extract of Irish moss, Panwar gum, Ghatti gum, mucilage of isabgol husks, carboxymethylcellulose, methylcellulose, polyvinylpyrrolidone (PVP), VEEGUM®, larch arabinogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); and microcrystalline celluloses, such as AVICEL® PH-101, AVICEL® PH-103, AVICEL® PH-105, and AVICEL® RC-581. Suitable fillers include, but are not limited to, talc, calcium carbonate, microcrystalline cellulose, powdered cellulose, dextrates, kaolin, mannitol, silicic acid, sorbitol, starch, and pre-gelatinized starch. The amount of a binder or filler in the pharmaceutical composition provided herein varies upon the type of formulation, and is readily discernible to those of ordinary skill in the art. The binder or filler may be present from about 50 to about 99% by weight in the pharmaceutical composition provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical composition provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and VEEGUM® HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; and algins. The amount of a disintegrant in the pharmaceutical composition provided herein varies upon the type of formulation, and is readily discernible to those of ordinary skill in the art. The pharmaceutical composition provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, such as peanut oil, cottonseed oil, sunflower oil, sesame oil, olive oil, corn oil, and soybean oil; zinc stearate; ethyl oleate; ethyl laureate; agar; starch; lycopodium; and silica or silica gels, such as AEROSIL® 200 and CAB-O-SIL®. The amount of a lubricant in the pharmaceutical composition provided herein varies upon the type of formulation, and is readily discernible to those of ordinary skill in the art. The pharmaceutical compositions provided herein may contain about 0.1 to about 5% by weight of a lubricant.

Suitable glidants include, but are not limited to, colloidal silicon dioxide, CAB-O-SIL®, and asbestos-free talc. Suitable coloring agents include, but are not limited to, any of the approved, certified, water soluble FD&C dyes, and water insoluble FD&C dyes suspended on alumina hydrate, and color lakes. A color lake is a combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, VEEGUM®, acacia, sodium carboxymethylcellulose, hydroxypropyl methylcellulose, and polyvinylpyrrolidone. Suitable preservatives include, but are not limited to, glycerin, methyl and propylparaben, benzoic add, and sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical composition provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredient(s) from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from an active ingredient(s) in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical composition provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient(s). The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409, 239; and 4,410,545. The capsules may also be coated as known by those of skill in the art in order to modify or sustain dissolution of the active ingredient(s).

The pharmaceutical composition provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing an active ingredient (s), and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These dosage forms can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical composition provided herein for oral administration can be also provided in the forms of liposomes, micelles, microspheres, or nanosystems. Micellar dosage forms can be prepared as described in U.S. Pat. No. 6,350,458.

The pharmaceutical composition provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the dosage forms described herein.

The pharmaceutical composition provided herein for oral administration can be formulated as immediate or modified release dosage forms, including delayed-, sustained, pulsed-, controlled, targeted-, and programmed-release forms.

B. Parenteral Administration

The pharmaceutical composition provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical composition provided herein for parenteral administration can be formulated in any dosage forms that are suitable for parenteral administration, including, but not limited to, solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science. See, e.g., *Remington: The Science and Practice of Pharmacy, supra.*

The pharmaceutical composition provided herein for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringer's injection, isotonic dextrose injection, sterile water injection, dextrose and lactated Ringer's injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants include those described herein, such as bisulfite and sodium metabisulfite. Suitable local anesthetics include, but are not limited to, procaine hydrochloride. Suitable suspending and dispersing agents include those described herein, such as sodium carboxymethylcellulose, hydroxypropyl methylcellulose, and polyvinylpyrrolidone. Suitable emulsifying agents include those described herein, such as polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®).

When the pharmaceutical composition provided herein is formulated for multiple dosage administration, multiple dosage parenteral formulations must contain an antimicrobial agent at bacteriostatic or fungistatic concentrations. All parenteral formulations must be sterile, as known and practiced in the art.

In one embodiment, the pharmaceutical composition for parenteral administration is provided as a ready-to-use sterile solution. In another embodiment, the pharmaceutical composition is provided as a sterile dry soluble product, including a lyophilized powder and hypodermic tablet, to be reconstituted with a vehicle prior to use. In yet another embodiment, the pharmaceutical composition is provided as a ready-to-use sterile suspension. In yet another embodiment, the pharmaceutical composition is provided as a sterile dry insoluble product to be reconstituted with a vehicle prior to use. In still another embodiment, the pharmaceutical composition is provided as a ready-to-use sterile emulsion.

The pharmaceutical composition provided herein for parenteral administration can be formulated as immediate or modified release dosage forms, including delayed-, sustained, pulsed-, controlled, targeted-, and programmed-release forms.

The pharmaceutical composition provided herein for parenteral administration can be formulated as a suspension, solid, semi-solid, or thixotropic liquid, for administration as an implanted depot. In one embodiment, the pharmaceutical composition provided herein are dispersed in a solid inner matrix, which is surrounded by an outer polymeric membrane that is insoluble in body fluids but allows the active ingredient(s) in the pharmaceutical composition to diffuse through.

Suitable inner matrixes include, but are not limited to, polymethylmethacrylate, polybutylmethacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers (such as hydrogels of esters of acrylic and methacrylic acid), collagen, cross-linked polyvinyl alcohol, and cross-linked partially hydrolyzed polyvinyl acetate.

Suitable outer polymeric membranes include, but are not limited to, polyethylene, polypropylene, ethylene/propylene copolymers, ethylene/ethyl acrylate copolymers, ethylene/vinyl acetate copolymers, silicone rubbers, polydimethylsiloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical composition provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical composition provided herein can be formulated in any dosage forms that are suitable for topical administration for local or systemic effect, including, but not limited to, emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulations of the pharmaceutical composition provided herein can also comprise liposomes, micelles, microspheres, and nanosystems.

Pharmaceutically acceptable carriers and excipients suitable for use in the topical formulations include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical composition can also be administered topically by electroporation, iontophoresis, phonophoresis, sonophoresis, or microneedle or needle-free injection, such as POWDERJECT™ and BIOJECT™.

The pharmaceutical composition provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid. See, e.g., *Remington: The Science and Practice of Pharmacy*, supra. These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical composition provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with an active ingredient(s); and antioxidants as described herein, including bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical composition provided herein can be administered ophthalmically in the forms of solutions, suspensions, ointments, emulsions, gel-forming solutions, powders for solutions, gels, ocular inserts, and implants.

The pharmaceutical composition provided herein can be administered intranasally or by inhalation to the respiratory tract. The pharmaceutical composition can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical composition can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of an active ingredient(s); a propellant as solvent; and/or a surfactant, such as sorbitan trioleate, oleic acid, or an oligolactic acid.

The pharmaceutical composition provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical composition provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical composition provided herein for inhaled/intranasal administration can further comprise a suitable flavor, such as menthol and levomenthol; and/or sweeteners, such as saccharin and saccharin sodium.

The pharmaceutical composition provided herein for topical administration can be formulated to be immediate release or modified release, including delayed-, sustained-, pulsed-, controlled-, targeted, and programmed release.

D. Modified Release

The pharmaceutical composition provided herein can be formulated as a modified release dosage form. As used herein, the term "modified release" refers to a dosage form in which the rate or place of release of an active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical composition in modified release dosage forms can be prepared using a variety of modified release devices and methods known to those skilled in the art, including, but not limited to, matrix-controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

1. Matrix Controlled Release Devices

The pharmaceutical composition provided herein in a modified release dosage form can be fabricated using a matrix-controlled release device known to those skilled in the art. See, e.g., Takada et al. in *Encyclopedia of Controlled Drug Delivery*, Mathiowitz Ed.; Wiley, 1999; Vol. 2.

In certain embodiments, the pharmaceutical composition provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum Ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical composition provided herein is formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix-controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical composition provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical composition provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical composition in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, e.g., *Remington: The Science and Practice of Pharmacy, supra*; Santus and Baker, *J. Controlled Release*, 1995, 35, 1-21; Verma et al., *Drug Dev. Ind. Pharm.*, 2000, 26, 695-708; Verma et al., *J. Controlled Release*, 2002, 79, 7-27.

In certain embodiments, the pharmaceutical composition provided herein is formulated as an AMT controlled-release dosage form, which comprises an asymmetric osmotic membrane that coats a core comprising the active ingredient(s) and other pharmaceutically acceptable excipients or carriers. See, e.g., U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical composition provided herein is formulated as an ESC controlled-release dosage form, which comprises an osmotic membrane that coats a core comprising the active ingredient(s), a hydroxyethyl cellulose, and other pharmaceutically acceptable excipients or carriers.

3. Multiparticulate Controlled Release Devices

The pharmaceutical composition provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, e.g., *Multiparticulate Oral Drug Delivery*; Ghebre-Sellassie Eds.; Drugs and the Pharmaceutical Sciences 65; CRC Press: 1994; and *Pharmaceutical Palletization Technology*; Ghebre-Sellassie Eds.; Drugs and the Pharmaceutical Sciences 37; CRC Press: 1989.

Other excipients or carriers as described herein can be blended with the pharmaceutical composition to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical composition provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method of treating, preventing, or ameliorating one or more symptoms of a disorder, disease, or condition mediated by a son of sevenless homolog 1 (SOS1) in a subject, comprising administering to the subject in need thereof a therapeutically effective amount of a compound provided herein, e.g., a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the disorder, disease, or condition mediated by an SOS1 is a proliferative disease.

In another embodiment, provided herein is a method of treating, preventing, or ameliorating one or more symptoms of a disorder, disease, or condition mediated by a RAS in a subject, comprising administering to the subject in need thereof a therapeutically effective amount of a compound provided herein, e.g., a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the disorder, disease, or condition mediated by a RAS is a proliferative disease. In certain embodiments, the RAS is a KRAS. In certain embodiments, the RAS is a HRAS. In certain embodiments, the RAS is an NRAS.

In yet another embodiment, provided herein is a method of treating, preventing, or ameliorating one or more symptoms of a proliferative disease in a subject, comprising administering to the subject in need thereof a therapeutically effective amount of a compound provided herein, e.g., a compound of Formula (I), or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the proliferative disease is cancer. In certain embodiments, the cancer is a solid tumor. In certain embodiments, the cancer is colon cancer, colorectal cancer, lung cancer, or pancreatic cancer. In certain embodiments, the cancer is colon cancer. In certain embodiments, the cancer is colorectal cancer. In certain embodiments, the cancer is lung cancer. In certain embodiments, the cancer is non-small cell lung cancer (NSCLC). In certain embodiments, the cancer is pancreatic cancer. In certain embodiments, the cancer is an unresectable solid tumor. In certain embodiments, the cancer is a hematologic malignancy.

In certain embodiments, the cancer is refractory and/or relapsed. In certain embodiments, the cancer is refractory. In certain embodiments, the cancer is relapsed. In certain embodiments, the cancer is metastatic. In certain embodiments, the cancer is unresectable. In certain embodiments, the cancer is metastatic.

In certain embodiments, the cancer is drug-resistant. In certain embodiment, the cancer is multidrug-resistant. In certain embodiments, the cancer is resistant to a chemotherapy. In certain embodiments, the cancer is resistant to an immunotherapy. In certain embodiments, the cancer is resistant to a standard therapy for the cancer.

In certain embodiments, the cancer bears a KRAS mutation. In certain embodiments, the cancer bears a KRAS mutation at the G12 or G13 position. In certain embodiments, the cancer bears a KRAS mutation of G12C, G12D, G12V, G12A, G12S, or G12R. In certain embodiments, the cancer bears a KRAS mutation of G12C. In certain embodiments, the cancer bears a KRAS mutation of G12D. In certain embodiments, the cancer bears a KRAS mutation of G12V. In certain embodiments, the cancer bears a KRAS mutation of G12A. In certain embodiments, the cancer bears a KRAS mutation of G12S. In certain embodiments, the cancer bears a KRAS mutation of G12R. In certain embodiments, the cancer bears a KRAS mutation at the G13 position. In certain embodiments, the cancer bears a KRAS mutation of G13D.

In certain embodiments, the cancer is a solid tumor with a KRAS mutation. In certain embodiments, the cancer is a solid tumor with a KRAS mutation at the G12 or G13 position. In certain embodiments, the cancer is a solid tumor with a KRAS mutation of G12C, G12D, G12V, G12A, G12S, or G12R. In certain embodiments, the cancer is a solid tumor with a KRAS mutation of G12C. In certain embodiments, the cancer is a solid tumor with a KRAS mutation of G12D. In certain embodiments, the cancer is a solid tumor with a KRAS mutation of G12V. In certain embodiments, the cancer is a solid tumor with a KRAS mutation of G12A. In certain embodiments, the cancer is a solid tumor with a KRAS mutation of G12S. In certain embodiments, the cancer is a solid tumor with a KRAS mutation of G12R. In certain embodiments, the cancer is a solid tumor with a KRAS mutation at the G13 position. In certain embodiments, the cancer is a solid tumor with a KRAS mutation of G13D.

In certain embodiments, the subject is a mammal. In certain embodiments, the subject is a human.

In certain embodiments, the therapeutically effective amount of a compound provided herein is ranging from about 0.1 to about 100 mg/kg/day, from about 0.1 to about 50 mg/kg/day, from about 0.1 to about 60 mg/kg/day, from about 0.1 to about 50 mg/kg/day, from about 0.1 to about 25 mg/kg/day, from about 0.1 to about 20 mg/kg/day, from about 0.1 to about 15 mg/kg/day, from about 0.1 to about 10 mg/kg/day, or from about 0.1 to about 5 mg/kg/day. In one embodiment, the therapeutically effective amount of a compound provided herein is ranging from about 0.1 to about 100 mg/kg/day. In another embodiment, the therapeutically effective amount of a compound provided herein is ranging from about 0.1 to about 50 mg/kg/day. In yet another embodiment, the therapeutically effective amount of a compound provided herein is ranging from about 0.1 to about 60 mg/kg/day. In yet another embodiment, the therapeutically effective amount of a compound provided herein is ranging from about 0.1 to about 50 mg/kg/day. In yet another embodiment, the therapeutically effective amount of a compound provided herein is ranging from about 0.1 to about 25 mg/kg/day. In yet another embodiment, the therapeutically effective amount of a compound provided herein is ranging from about 0.1 to about 20 mg/kg/day. In yet another embodiment, the therapeutically effective amount of a compound provided herein is ranging from about 0.1 to about 15 mg/kg/day. In yet another embodiment, the therapeutically effective amount of a compound provided herein is ranging from about 0.1 to about 10 mg/kg/day. In still another embodiment, the therapeutically effective amount of a compound provided herein is ranging from about 0.1 to about 5 mg/kg/day.

It is understood that the administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both. For example, a dose of 1 mg/m²/day for a 65 kg human is approximately equal to 58 mg/kg/day.

Depending on the disorder, disease, or condition to be treated and the subject's condition, a compound provided herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A compound provided herein may be formulated in suitable dosage unit with a pharmaceutically acceptable excipient, carrier, adjuvant, or vehicle, appropriate for each route of administration.

In one embodiment, a compound provided herein is administered orally. In another embodiment, a compound provided herein is administered parenterally. In yet another embodiment, a compound provided herein is administered intravenously. In yet another embodiment, a compound provided herein is administered intramuscularly. In yet another embodiment, a compound provided herein is administered subcutaneously. In still another embodiment, a compound provided herein is administered topically.

A compound provided herein can be delivered as a single dose such as, e.g., a single bolus injection, or oral tablets or pills; or over time such as, e.g., continuous infusion over time or divided bolus doses over time. A compound provided herein can be administered repetitively, if necessary, for example, until the subject experiences stable disease or regression, or until the subject experiences disease progression or unacceptable toxicity.

A compound provided herein can be administered once daily (QD) or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of a compound provided herein is administration for one to six days per week, administration in cycles (e.g., daily administration for two to eight consecutive weeks, then a rest period with no administration for up to one week), or administration on alternate days.

In certain embodiments, a compound provided herein is cyclically administered to a subject. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

A compound provided herein can also be combined or used in combination with other therapeutic agents useful in the treatment and/or prevention of a condition, disorder, or disease described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 50 minutes, 65 minutes, 1 hour, 2 hours, 6 hours, 6 hours, 12 hours, 26 hours, 68 hours, 72 hours, 96 hours, 1 week, 2 weeks, 5 weeks, 6 weeks, 8 weeks, or 12 weeks before), concomitantly with, or subsequent to (e.g., 5 minutes, 15 minutes, 50 minutes, 65 minutes, 1 hour, 2 hours, 6 hours, 12 hours, 26 hours, 68 hours, 72 hours, 96 hours, 1 week, 2 weeks, 5 weeks, 6 weeks, 8 weeks, or 12 weeks after) the administration of a second therapy (e.g., a prophylactic or therapeutic agent) to the subject. Triple therapy is also contemplated herein.

The route of administration of a compound provided herein is independent of the route of administration of a second therapy. In one embodiment, a compound provided herein is administered orally. In another embodiment, a compound provided herein is administered intravenously. Thus, in accordance with these embodiments, a compound provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, a compound provided herein and a second therapy are administered by the same mode of administration, orally or by IV. In another embodiment, a compound provided herein is administered by one mode of administration, e.g., by IV, whereas the second agent (an anticancer agent) is administered by another mode of administration, e.g., orally.

In one embodiment, provided herein is a method of inhibiting the growth of a cell, comprising contacting the cell with a compound provided herein, e.g., a compound of Formula (I), or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In certain embodiments, the cell is a cancerous cell. In certain embodiments, the cell is a human cell. In certain embodiments, the cell is a human cancerous cell.

In certain embodiments, the cell is a cell of colon cancer, colorectal cancer, lung cancer, or pancreatic cancer. In certain embodiments, the cell is a cell of non-small cell lung cancer (NSCLC).

In certain embodiments, the cell is a cancerous cell bearing a KRAS mutation. In certain embodiments, the cell is a cancerous cell bearing a KRAS mutation at the G12 or G13 position. In certain embodiments, the cell is a cancerous cell bearing a KRAS mutation of G12C, G12D, G12V, G12A, G12S, or G12R. In certain embodiments, the cell is a cancerous cell bearing a KRAS mutation of G12C. In certain embodiments, the cell is a cancerous cell bearing a KRAS mutation of G12D. In certain embodiments, the cell is a cancerous cell bearing a KRAS mutation of G12V. In certain embodiments, the cell is a cancerous cell bearing a KRAS mutation of G12A. In certain embodiments, the cell is a cancerous cell bearing a KRAS mutation of G12S. In certain embodiments, the cell is a cancerous cell bearing a KRAS mutation of G12R. In certain embodiments, the cell is a cancerous cell bearing a KRAS mutation at the G13 position. In certain embodiments, the cell is a cancerous cell bearing a KRAS mutation of G13D.

In another embodiment, provided herein is a method of inducing degradation of an SOS1, comprising contacting the SOS1 with a compound provided herein, e.g., a compound of Formula (I), or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

A compound provided herein can also be provided as an article of manufacture using packaging materials well known to those of skill in the art. See, e.g., U.S. Pat. Nos. 5,525,907; 5,052,558; and 5,055,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein is a kit which, when used by a medical practitioner, can simplify the administration of an appropriate amount of a compound provided herein as an active ingredient to a subject. In certain embodiments, the kit provided herein includes a container and a dosage form of a compound provided herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, water for injection USP, sodium chloride injection, Ringer's injection, dextrose injection, dextrose and sodium chloride injection, and lactated Ringer's injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); mmol (millimoles); min (minute or minutes); h (hour or hours); ACN (acetonitrile); $Ac_2O$ (acetic anhydride); AcOH (acetic acid); Boc (tert-butoxycarbonyl); $Boc_2O$ (di-tert-butyl carbonate); BOP (benzotriazol-1-yloxytris-(dimethyl-amino)phosphonium hexafluorophosphate); DBU (1,8-diazabicyclo[5.4.0]undec-7-ene); DCM (dichloromethane); DIPEA (N,N-diisopropylethylamine); DMF (dimethylformamide); DMSO (dimethyl sulfoxide); EDCI (1-ethyl-3-(3-dimethylaminopropyl)carbodiimide); EtOAc (ethyl acetate); HOBt (hydroxybenzotriazole); LiHMDS (lithium bis(trimethylsilyl)amide); MeOH (methanol); $NaBH(OAc)_3$ (sodium triacetoxyborohydride); NFSI (N-fluoro-N-(phenyl-sulfonyl)benzenesulfonamide), $Pd(PPh_3)_2Cl_2$ (bis(triphenylphosphine)palladium(II) dichloride); $Pd(PPh_3)_4$ (palladium tetrakis(triphenylphosphine)); PE (petroleum ether); tBu (tert-butyl); TBME (tert-butyl methyl ether); TEA (triethylamine); THF (tetrahydrofuran); LCMS (liquid chromatography-mass spectrometry); MS (mass spectrometry); NMR (nuclear magnetic resonance); prep-HPLC (preparative high performance liquid chromatography); and prep-TLC (preparative thin layer chromatography).

For all of the following examples, standard work-up and purification methods known to those skilled in the art can be utilized. Unless otherwise indicated, all temperatures are expressed in ° C. (degrees Centigrade). All reactions are conducted at room temperature unless otherwise specified. Synthetic methodologies illustrated herein are intended to exemplify the applicable chemistry through the use of specific examples and are not indicative of the scope of the disclosure.

Example 1

Preparation of 3-(4-(1-(6-(4-(((R)-1-(3-amino-5-(trifluoromethyl)phenyl)ethyl)amino)-6,7-dimethoxy-2-methylquinazolin-8-yl)hexyl)piperidin-4-yl)-6-fluoro-1-oxoisoindolin-2-yl)-piperidine-2,6-dione A101

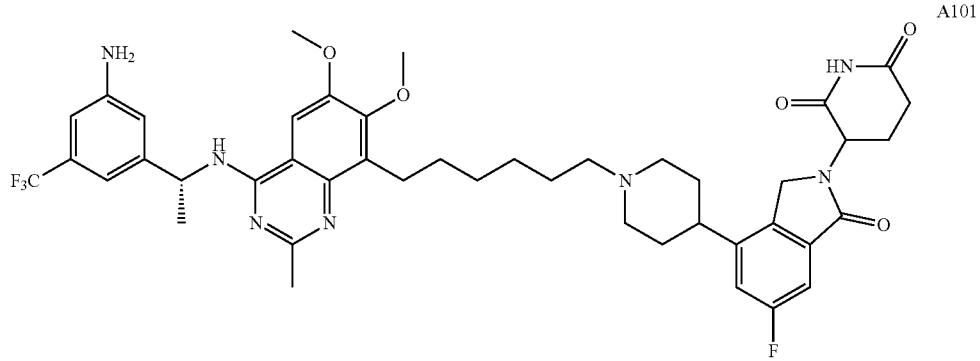 [SMILES: COc1cc2c(N[C@H](C)c3cc(N)cc(C(F)(F)F)c3)nc(C)nc2c(CCCCCCN2CCC(c3cc(F)cc4c3CN(C3CCC(=O)NC3=O)C4=O)CC2)c1OC]

Compound A101 was prepared as shown in Scheme 1.

Preparation of 3-iodo-4,5-dimethoxy-2-nitrobenzaldehyde 1.2. To 3-iodo-4,5-dimethoxybenzaldehyde 1.1 (62.9 g, 0.215 mol) at 0° C. was added nitric acid (250 mL) portionwise. The reaction mixture was stirred at 60° C. until it became clear. The reaction mixture was then cooled to room temperature and poured into ice-water. The resulting precipitates were collected by filtration and washed with PE/EtOAc (2/1) to afford compound 1.2 (53 g) in 73% yield. MS (ESI) m/z: 337.8 [M+H]$^+$.

Preparation of 3-iodo-4,5-dimethoxy-2-nitrobenzoic acid 1.3. To a solution of compound 1.2 (53 g, 0.157 mol) in AcOH (500 mL) was added sulfamic acid (45.8 g, 0.472 mol), followed by addition of sodium chlorite (21.2 g, 0.236 mol) in water (100 mL) slowly at 0° C. After stirred at 50° C. for 8 h, the reaction mixture was filtered and concentrated under reduced pressure to yield a crude product, which was purified with silica-gel column chromatography eluting with MeOH/DCM to afford compound 1.3 (27.4 g) in 50% yield. MS (ESI) m/z: 353.8 [M+H]$^+$.

Preparation of 2-amino-3-iodo-4,5-dimethoxybenzoic acid 1.4. To a solution of compound 1.3 (23.2 g, 66 mmol) in AcOH (150 mL) was added iron powder (14.7 g, 0.263 mol). After stirred at 60° C. for 2 h, the reaction mixture was filtered and concentrated under reduced pressure to afford compound 1.4, which was used directly in the next step without further purification. MS (ESI) m/z: 323.8 [M+H]$^+$.

Scheme 1

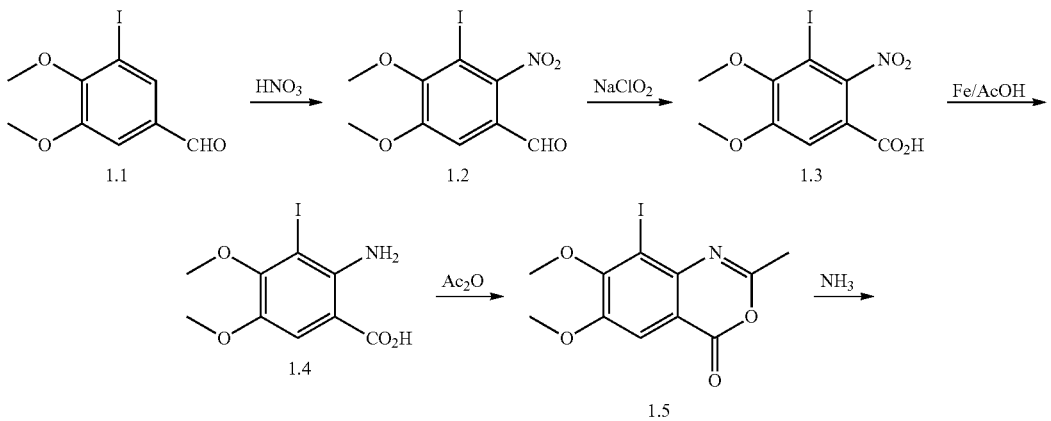

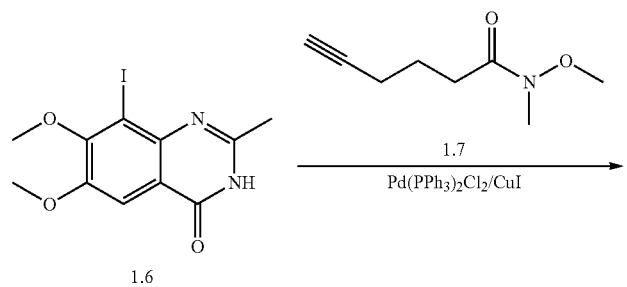

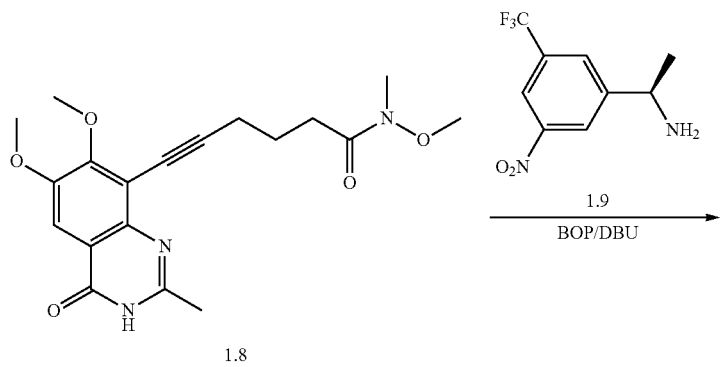

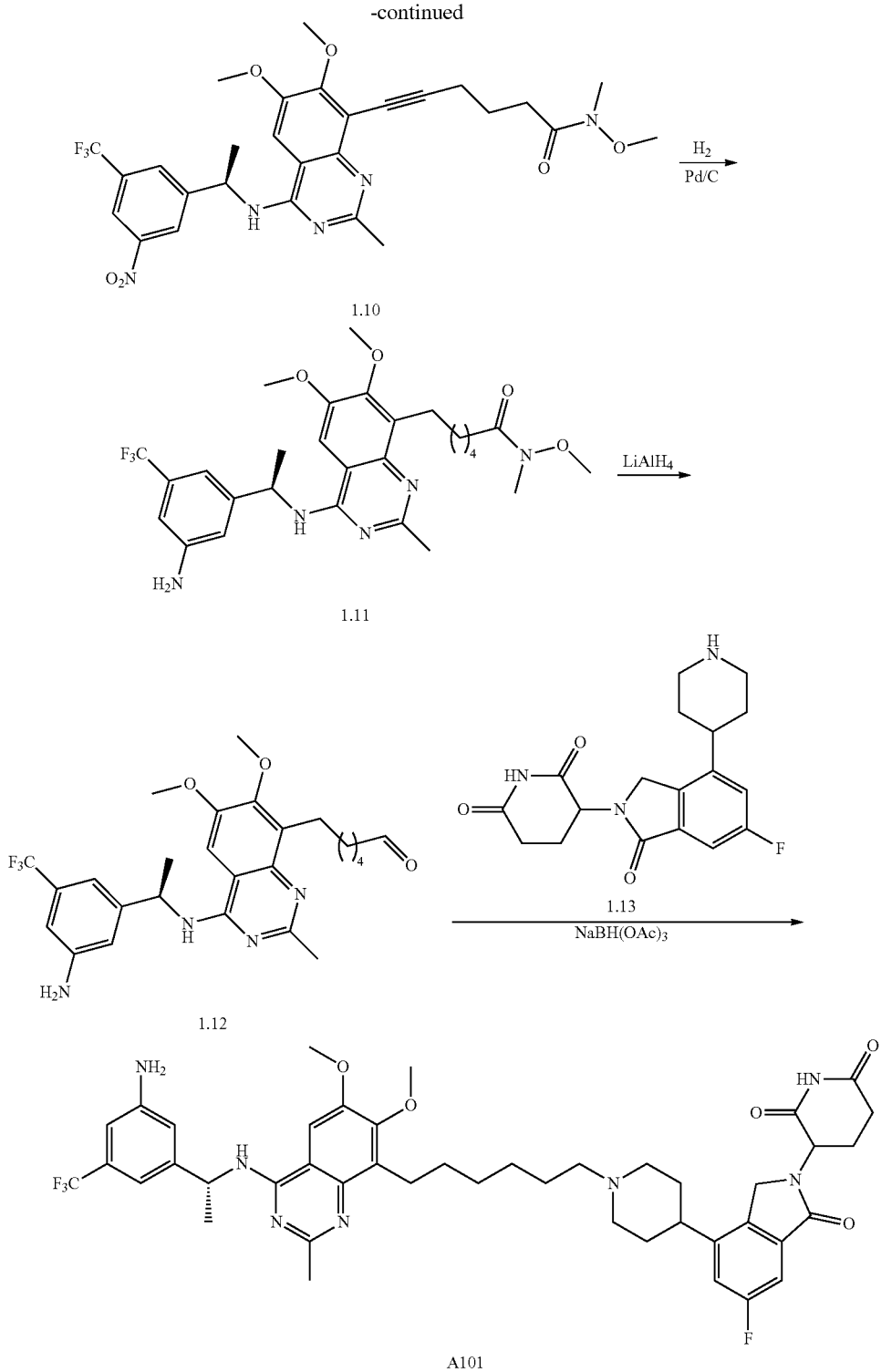

Preparation of 8-iodo-6,7-dimethoxy-2-methyl-4H-benzo[d][1,3]oxazin-4-one 1.5. A mixture of compound 1.4 and Ac$_2$O (250 mL) was stirred at 130° C. for 2 h. The reaction mixture was filtered and concentrated under reduced pressure to yield a crude product, which was purified by silica-gel column chromatography eluting with MeOH/DCM to afford compound 1.5 (8.7 g) in 39% yield. MS (ESI) m/z: 347.9 [M+H]$^+$.

Preparation of 8-iodo-6,7-dimethoxy-2-methylquinazolin-4(3H)-one 1.6. A mixture of compound 1.5 (9.69 g, 0.028 mol) and NH$_4$OH (150 mL) was stirred for 8 h, followed by addition of NaOH (10%), The reaction mixture was stirred until it became clear and then neutralized with AcOH to pH 7~8. The resulting precipitates were collected by filtration and purified by silica-gel column chromatography eluting with MeOH/DCM to afford compound 1.6 (7.2 g) in 75% yield. ¹H NMR (300 MHz, CDCl₃) δ 11.99 (s, 1H), 7.56 (s, 1H), 3.93 (s, 3H), 3.85 (s, 3H), 2.37 (s, 3H); MS (ESI) m/z: 346.9 [M+H]⁺.

Preparation of 6-(6,7-dimethoxy-2-methyl-4-oxo-3,4-dihydroquinazolin-8-yl)-N-methoxy-N-methylhex-5-ynamide 1.8. To a solution of compound 1.6 (500 mg, 1.44 mmol) in DMF (10 mL) were added N-methoxy-N-methylhex-5-ynamide 1.7 (672 mg, 4.34 mmol), CuI (55 mg, 0.289 mmol), Pd(PPh₃)₄ (105 mg, 0.145 mmol), and TEA (437 mg, 4.33 mmol). After stirred at 50° C. for 5 h under N₂, the reaction mixture was concentrated and then diluted with DCM. The organic layer was washed with aqueous NaHCO₃ and brine, dried over anhydrous Na₂SO₄, filtered, and concentrated under reduced pressure to yield a crude product, which was purified by silica-gel column chromatography eluting with MeOH in DCM to afford compound 1.8 (256 mg) in 48% yield. MS (ESI) m/z: 374.4 [M+H]⁺.

Preparation of (R)-6-(6,7-dimethoxy-2-methyl-4-((1-(3-nitro-5-(trifluoromethyl)-phenyl)ethyl)amino)quinazolin-8-yl)-N-methoxy-N-methylhex-5-ynamide 1.10. To a solution of compound 1.8 (256 mg, 0.686 mmol) in DMF (10 mL) were added DBU (313 mg, 2.06 mmol), BOP (455 mg, 1.03 mmol), and (R)-1-(3-nitro-5-(trifluoromethyl)phenyl)ethan-1-amine 1.9 (321 mg, 1.37 mmol). After stirred at 50° C. for 12 h, the reaction mixture was concentrated under reduced pressure and diluted with DCM. The organic layer was washed with water and brine, dried over anhydrous Na₂SO₄, filtered, and concentrated under reduced pressure to yield a crude product, which was purified by silica-gel column chromatography eluting with MeOH/DCM to afford compound 1.10 (135 mg) in 35% yield. MS (ESI) m/z: 590.5 [M+H]⁺.

Preparation of (R)-6-(4-((1-(3-amino-5-(trifluoromethyl)phenyl)ethyl)amino)-6,7-dimethoxy-2-methylquinazolin-8-yl)-N-methoxy-N-methylhexanamide 1.11. To a solution of compound 1.10 (135 mg, 0.229 mmol) in THF (10 mL) was added Pd/C (50 mg) under N₂. After stirred for 12 h under H₂, the reaction mixture was filtered and concentrated under reduced pressure to afford compound 1.11 (105 mg) in 71% yield. MS (ESI) m/z: 564.6 [M+H]⁺.

Preparation of (R)-5-(4-(1-methyl-4-((1-(2-methyl-3-(trifluoromethyl)phenyl)-ethyl)amino)phthalazin-6-yl)piperazin-1-yl)pentanal 1.12. To a solution of compound 1.11 (105 mg, 0.187 mmol) in THF (10 mL) was added 1 M LiAlH₄ in THF (0.37 mL, 0.373 mmol) at −70° C. After stirred at −70° C. for 1 h under N₂, the reaction was quenched with aqueous NH₄Cl (3 drops). The reaction mixture was filtered and concentrated under reduced pressure to afford compound 1.12, which was used directly in the next step without further purification. MS (ESI) m/z: 505.5 [M+H]⁺.

Preparation of 3-(4-(1-(6-(4-(((R)-1-(3-amino-5-(trifluoromethyl)phenyl)ethyl)-amino)-6,7-dimethoxy-2-methylquinazolin-8-yl)hexyl)piperidin-4-yl)-6-fluoro-1-oxoisoindolin-2-yl)-piperidine-2,6-dione A101. To a solution of compound 1.12 (0.187 mmol) and 3-(6-fluoro-1-oxo-4-(piperidin-4-yl)isoindolin-2-yl)piperidine-2,6-dione 1.13 (64 mg, 0.187 mmol) in MeOH (8 mL) and DCM (2 mL) was added NaBH(OAc)₃ (79 mg, 0.374 mmol). After stirred for 12 h, the reaction mixture was concentrated under reduced pressure to yield a crude product, which was purified by silica-gel column chromatography eluting with MeOH/DCM and further purified by reverse-phase prep-HPLC to afford compound A101 (58.5 mg) in 38% yield. ¹H NMR (400 MHz, DMSO-d₆) δ 11.00 (s, 1H), 8.00 (d, J=8.0 Hz, 1H), 7.66 (s, 1H), 7.41-7.34 (m, 2H), 6.87 (d, J=11.2 Hz, 2H), 6.69 (s, 1H), 5.59-5.52 (m, 3H), 5.13 (dd, J=5.2 Hz, 13.2 Hz, 1H), 4.52-4.31 (m, 2H), 3.94 (s, 3H), 3.81 (s, 3H), 3.02-2.96 (m, 5H), 2.93-2.87 (m, 1H), 2.67-2.58 (m, 3H), 2.45-2.41 (m, 1H), 2.39 (s, 3H), 2.37-2.32 (m, 1H), 2.06-1.99 (m, 4H), 1.75 (s, 4H), 1.55 (d, J=6.8 Hz, 3H), 1.46 (s, 2H), 1.34-1.30 (m, 4H); MS (ESI) m/z: 834.2 [M+H]⁺.

Example 2

Preparation of 3-(5-(4-(7-(4-(((R)-1-(3-(1,1-difluoro-2-hydroxyethyl)phenyl)ethyl)amino)-6,7-dimethoxy-2-methylquinazolin-8-yl)heptyl)piperazin-1-yl)-6-fluoro-1-oxoisoindolin-2-yl)-piperidine-2,6-dione A102

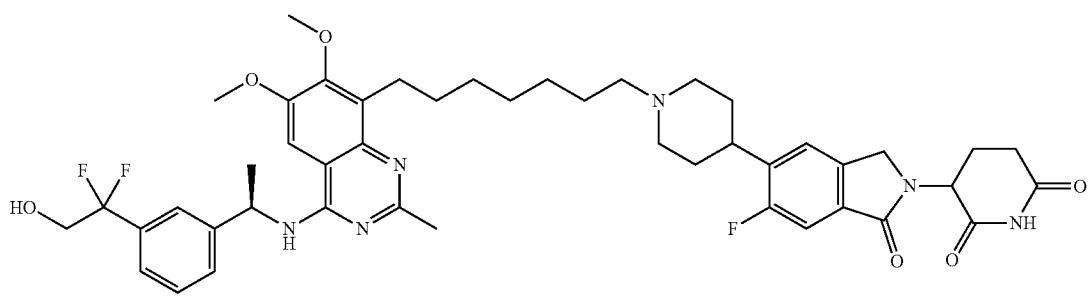

A102

Compound A102 was prepared as shown in Schemes 2A and 2B.

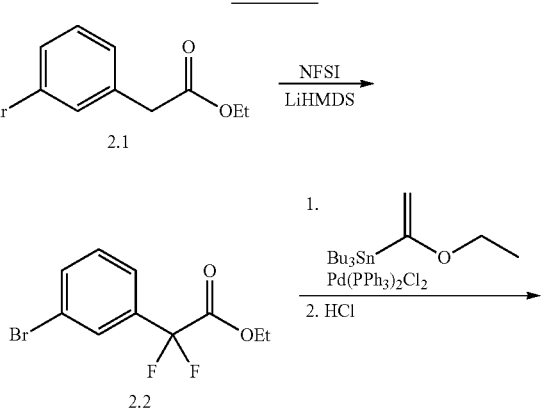

Scheme 2A

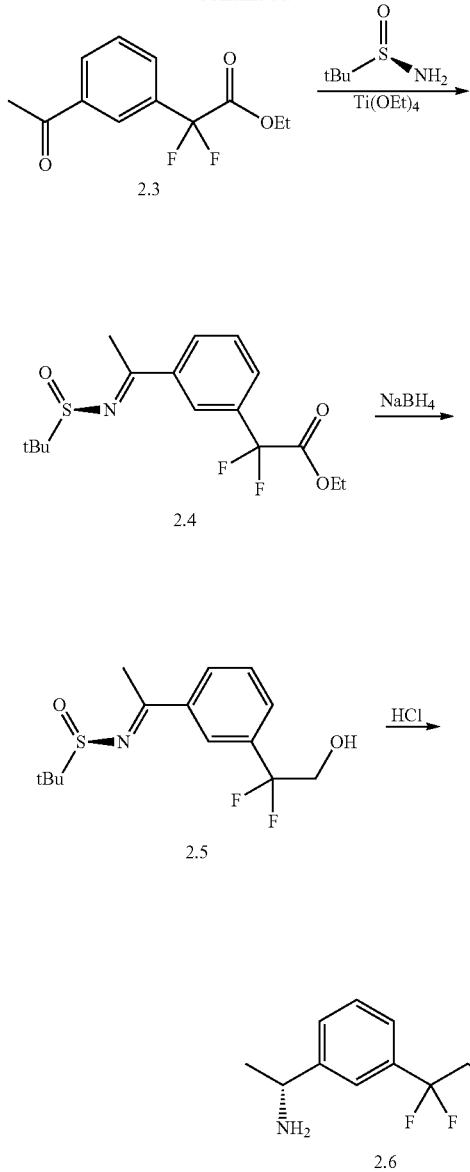

Preparation of ethyl 2-(3-bromophenyl)-2,2-difluoroacetate 2.2. To a solution of ethyl 2-(3-bromophenyl)acetate 2.1 (20 g, 80 mmol) in THF (100 mL) was added 1 M LiHMDS in THF (184 mL, 184 mmol) at −60° C. under N₂. After the mixture was stirred for 2 h, NFSI (57.2 g, 184 mmol) was added at −60° C. The reaction stirred at −60° C. for 4 h and then quenched with H₂O (200 mL). The reaction mixture was extracted with EtOAc (100 mL×3). The combined organic layers were dried over anhydrous Na₂SO₄, filtered, and concentrated under reduced pressure to yield a crude product, which was purified by silica-gel column chromatography eluting with EtOAc/PE to afford compound 2.2 (15.6 g) in 68% yield. ¹H NMR (400 MHz, CDCl₃) δ 7.78-7.74 (m, 1H), 7.83 (dd, J=8.0 Hz, 0.8 Hz, 1H), 7.54 (dd, J=8.0 Hz, 0.8 Hz, 1H), 7.33 (t, J=8.4 Hz, 1H), 4.32 (q, J=7.2 Hz, 2H), 1.31 (t, J=7.2 Hz, 3H).

Preparation of ethyl 2-(3-acetylphenyl)-2,2-difluoroacetate 2.3. To a solution of compound 2.2 (15.6 g, 55.9 mmol) and tributyl(1-ethoxyvinyl)stannane (24.2 g, 67.1 mmol) in dioxane (200 mL) was added Pd(Ph₃)₂Cl₂ (3.9 g, 5.59 mmol) under N₂. After stirred at 80° C. overnight, the reaction mixture was acidified to pH 2~3 with 6N HCl and stirred at room temperature for 2 h. The reaction mixture was diluted with water (200 mL) and extracted with EtOAc (100 mL×3). The combined organic layers were dried over anhydrous Na₂SO₄, filtered, and concentrated under reduced pressure to yield a crude product, which was purified by silica-gel column chromatography eluting with EtOAc/PE to afford compound 2.3 (7.5 g) in 57% yield. ¹H NMR (400 MHz, CDCl₃) δ 8.18 (s, 1H), 8.09 (d, J=7.6 Hz, 1H), 7.81 (d, J=7.2 Hz, 1H), 7.58 (t, J=7.6 Hz, 1H), 4.31 (q, J=7.2 Hz, 2H), 2.64 (s, 3H), 1.31 (t, J=7.2 Hz, 3H).

Preparation of (R,E)-2-(3-(1-((tert-butylsulfinyl)imino)ethyl)phenyl)-2,2-difluoroacetate 2.4. To a solution of compound 2.3 (7.5 g, 31 mmol) in THF (80 mL) were added (R)-2-methylpropane-2-sulfinamide (9.4 g, 77 mmol) and titanium ethoxide (28.3 g, 124 mmol). After stirred overnight, the reaction mixture was diluted with water (100 mL), filtered, and extracted with EtOAc (50 mL×3). The combined organic layers were dried over anhydrous Na₂SO₄, filtered, and concentrated under reduced pressure to yield a crude product, which was purified by silica-gel column chromatography eluting with EtOAc/PE to afford 2.4 (7.5 g) in 70% yield. MS (ESI) m/z: 346.1 [M+H]⁺.

Preparation of (R)—N—((R)-1-(3-(1,1-difluoro-2-hydroxyethyl)phenyl)ethyl)-2-methylpropane-2-sulfinamide 2.5. To a solution of compound 2.4 (7.5 g, 20 mmol) in THF (75 mL) and H₂O (1.5 mL) at −60° C. was added NaBH₄ (1.5 g, 40 mmol) under N₂. After stirred at −60° C. for 1 h, the reaction mixture was diluted with H₂O (100 mL) and extracted with EtOAc (50 mL×3). The combined organic layers were dried over anhydrous Na₂SO₄, filtered, and concentrated under reduced pressure to yield a crude product, which was purified by silica-gel column chromatography eluting with EtOAc/PE and further purified by reverse-phase column chromatography eluting with ACN/H₂O to afford compound 2.5 (4.2 g) in 63% yield. MS (ESI) m/z: 306.1 [M+H]⁺.

Preparation of (R)-2-(3-(1-aminoethyl)phenyl)-2,2-difluoroethan-1-ol 2.6. To a solution of compound 2.5 (4.2 g, 13.7 mmol) in DCM (40 mL) was added HCl in EtOAc (20 mL). After stirred for 1 h, the reaction mixture was concentrated under reduced pressure, diluted with H₂O (20 mL), and extracted with EtOAc (20 mL×3). The aqueous layer was then adjusted to pH 8~9 with saturated aqueous NaHCO₃ and extracted with DCM/MeOH (10:1) (40 mL×3). The combined organic layers were dried over anhydrous Na₂SO₄, filtered, and concentrated under reduced pressure to afford compound 2.6 (2 g) in 95% yield. MS (ESI) m/z: 202.1 [M+H]⁺.

Preparation of 7-(6,7-dimethoxy-2-methyl-4-oxo-3,4-dihydroquinazolin-8-yl)-N-methoxy-N-methylhept-6-ynamide 2.12. To a solution of 8-iodo-6,7-dimethoxy-2-methylquinazolin-4(3H)-one 1.6 (3 g, 8.67 mmol), N-methoxy-N-methylhept-6-ynamide 2.11 (5.86 g, 34.7 mmol), and TEA (3.07 g, 30.4 mmol) in DMF (40 mL) were added CuI (165 mg, 0.867 mmol) and Pd(PPh₃)₂Cl₂ (609 mg, 0.867 mmol) under N₂. After stirred at 50° C. for 4 h, the reaction mixture was concentrated under reduced pressure to yield a crude product, which was purified by silica-gel column chromatography eluting with EtOAc/DCM and further purified by reverse-phase column chromatography eluting with ACN/water to afford compound 2.12 (1.40 g) in 42% yield. MS (ESI) m/z: 388.2 [M+H]⁺.

Scheme 2B
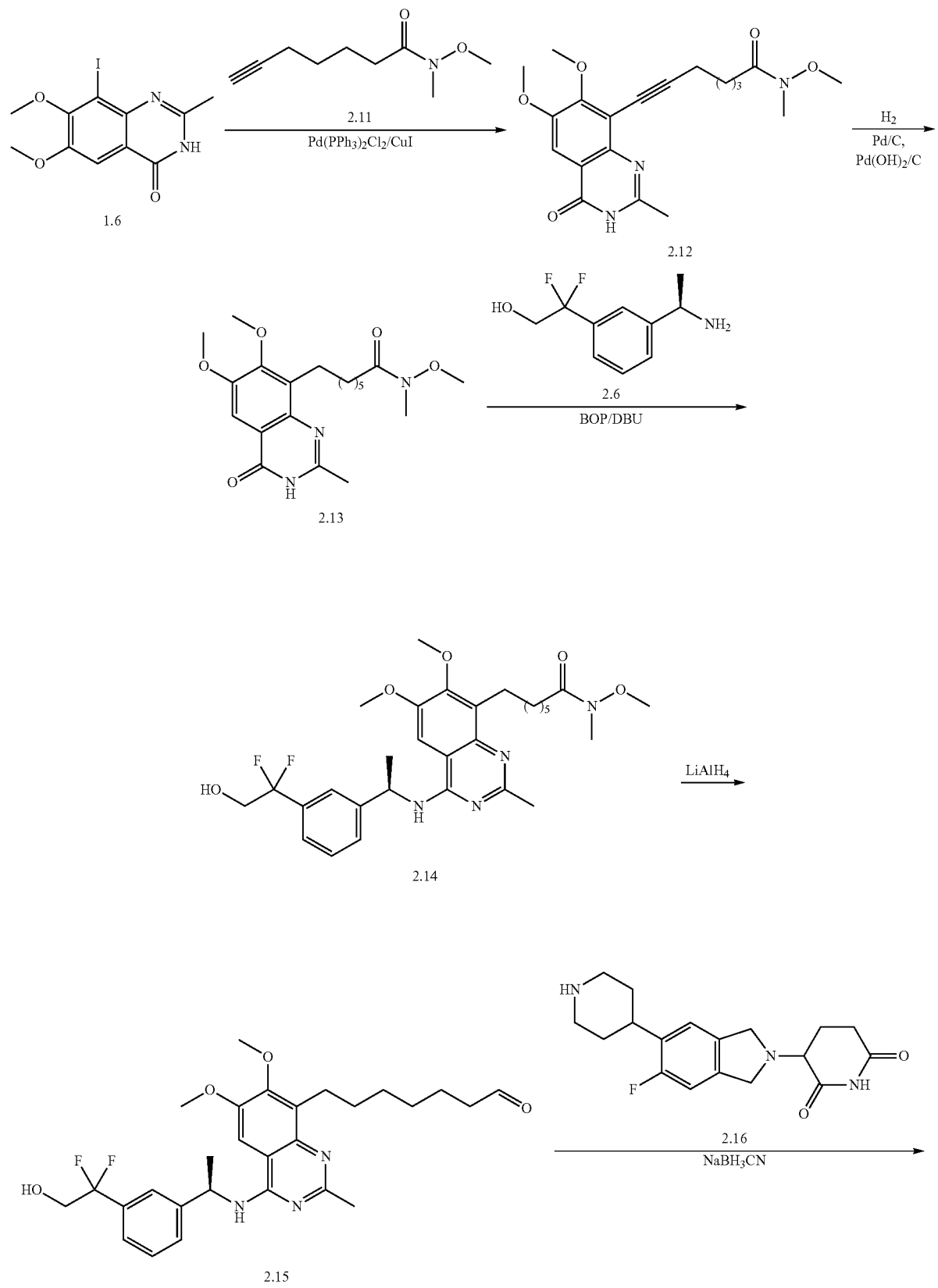

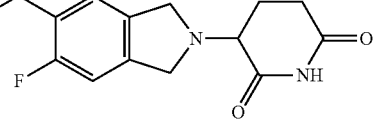
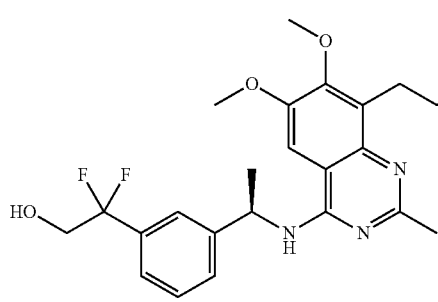

A102

Preparation of 7-(6,7-dimethoxy-2-methyl-4-oxo-3,4-dihydroquinazolin-8-yl)-N-methoxy-N-methylheptanamide 2.13. To the stirred solution of compound 2.12 (1.4 g, 3.62 mmol) in THF (30 mL) and MeOH (30 mL) were added Pd/C (400 mg) and Pd(OH)$_2$/C (400 mg) under N$_2$. After stirred under H$_2$ overnight, the reaction mixture was filtered and concentrated under reduced pressure to afford compound 2.13 (1.35 g) in 98% yield. MS (ESI) m/z: 392.2 [M+H]$^+$.

Preparation of (R)-7-(4-((1-(3-(1,1-difluoro-2-hydroxyethyl)phenyl)ethyl)amino)-6,7-dimethoxy-2-methylquinazolin-8-yl)-N-methoxy-N-methylheptanamide 2.14. To a solution of compound 2.13 (572 mg, 1.46 mmol) in DMF (10 mL) were added DBU (445 mg, 2.93 mmol) and BOP (970 mg, 2.19 mmol). After the mixture was stirred at room temperature for 2 h, (R)-2-(3-(1-aminoethyl)phenyl)-2,2-difluoroethan-1-ol 2.6 (733 mg, 3.65 mmol) was added. The reaction mixture was stirred at 50° C. overnight, and then cooled to room temperature, diluted with water (15 mL), extracted with EtOAc (3×25 mL). The combined organic layers were dried over anhydrous Na$_2$SO$_4$, filtered, and concentrated under reduced pressure to yield a crude product, which was purified by silica-gel column chromatography eluting with MeOH/DCM and further purified by prep-TLC with DCM/MeOH to afford compound 2.14 (350 mg) in 42% yield. MS (ESI) m/z: 575.3 [M+H]$^+$.

Preparation of (R)-7-(4-((1-(3-(1,1-difluoro-2-hydroxyethyl)phenyl)ethyl)amino)-6,7-dimethoxy-2-methylquinazolin-8-yl)heptanal 2.15. To a solution of compound 2.14 (200 mg, 0.348 mmol) in THF (20 mL) was added 1 M LiAlH$_4$ in THF (0.87 mL, 0.871 mmol) dropwise at −60° C. under N$_2$. After stirred at −60° C. for 1 h, the reaction was quenched with saturated aqueous NH$_4$Cl (2 mL), and the reaction mixture was diluted with water (15 mL) and extracted with EtOAc (3×15 mL). The combined organic layers were dried over anhydrous Na$_2$SO$_4$, filtered, and concentrated under reduced pressure to afford compound 2.15 (180 mg), which was used directly in the next step without further purification. MS (ESI) m/z: 516.3 [M+H]$^+$.

Preparation of 3-(5-(4-(7-(4-(((R)-1-(3-(1,1-difluoro-2-hydroxyethyl)phenyl)-ethyl)amino)-6,7-dimethoxy-2-methylquinazolin-8-yl)heptyl)piperazin-1-yl)-6-fluoro-1-oxo-isoindolin-2-yl)-piperidine-2,6-dione A102. To a solution of 3-(6-fluoro-1-oxo-5-(piperidin-4-yl)isoindolin-2-yl)piperidine-2,6-dione hydrochloride 2.16 (67 mg, 0.175 mmol) in DCM/MeOH (4:1, 3 mL) was added DIPEA (1 drop) to pH 7, followed by addition of compound 2.15 (90 mg, 0.175 mmol) in DCM/MeOH (4:1, 2 mL) and AcOH (1 drop). After the mixture was stirred for 30 min, NaBH$_3$CN (22 mg, 0.350 mmol) was added. The reaction mixture was stirred overnight, and then concentrated under reduced pressure to yield a crude product, which was purified by silica-gel column chromatography eluting with MeOH/DCM and further purified by reverse-phase prep-HPLC to afford compound A102 (21.6 mg). $^1$H NMR (400 MHz, DMSO-d$_6$) δ 10.98 (s, 1H), 8.17 (s, 1H), 8.05 (d, J=8.0 Hz, 1H), 7.65-7.56 (m, 4H), 7.48-7.35 (m, 3H), 5.70-5.65 (m, 1H), 5.10 (dd, J=5.2 Hz, 12.8 Hz, 1H), 4.43-4.25 (m, 2H), 3.94 (s, 3H), 3.87-3.80 (m, 5H), 3.05-2.80 (m, 6H), 2.67-2.57 (m, 2H), 2.40-2.30 (m, 6H), 2.10-1.98 (m, 3H), 1.76-1.72 (m, 4H), 1.60 (d, J=7.2 Hz, 3H), 1.53-1.41 (m, 4H), 1.35-1.25 (m, 6H); MS (ESI) m/z: 845.6 [M+H]$^+$.

Example 3

Preparation of 3-(6-(2-(4-(6-(4-(((R)-1-(3-(1,1-difluoro-2-hydroxyethyl)phenyl)ethyl)amino)-6,7-dimethoxy-2-methylquinazolin-8-yl)hexyl)piperazin-1-yl)-2-oxoethoxy)-1-methyl-1H-indazol-3-yl)piperidine-2,6-dione A204

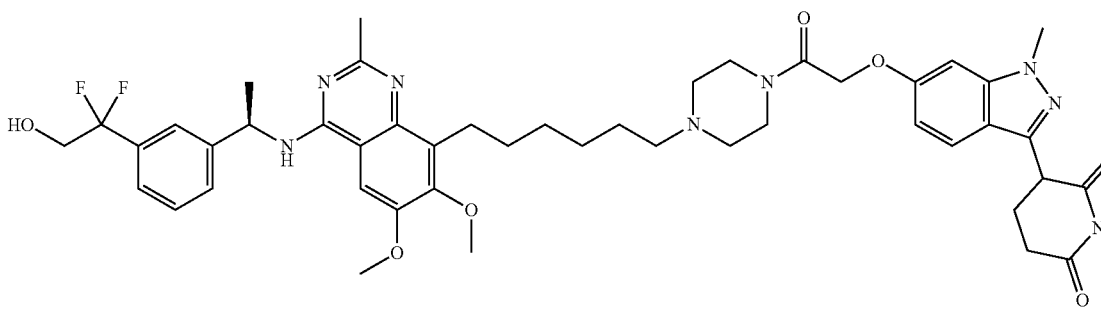

A204

Compound A204 was prepared as shown in Scheme 3.

Preparation of (R)-6-(4-((1-(3-(1,1-difluoro-2-hydroxyethyl)phenyl)ethyl)amino)-6,7-dimethoxy-2-methylquinazolin-8-yl)-N-methoxy-N-methylhexanamide 3.2. To a solution of 6-(6,7-dimethoxy-2-methyl-4-oxo-3,4-dihydroquinazolin-8-yl)-N-methoxy-N-methylhexanamide 3.1 (450 mg, 1.2 mmol) in DMF (5 mL) were added DBU (365 mg, 2.4 mmol) and BOP (796 mg, 1.8 mmol). After the mixture was stirred for 2 h, (R)-2-(3-(1-aminoethyl)phenyl)-2,2-difluoroethan-1-ol 2.6 (300 mg, 1.5 mmol) in DMF (2 mL) was added. The reaction mixture was stirred at 50° C. overnight, and then diluted with water (15 mL) and extracted with EtOAc (10 mL×3). The combined organic layers were dried over anhydrous Na$_2$SO$_4$, filtered, and concentrated under reduced pressure to yield a crude product, which was purified by silica-gel column chromatography eluting with MeOH/DCM to afford compound 3.2 (500 mg) in 74% yield. MS (ESI) m/z: 561.3 [M+H]$^+$.

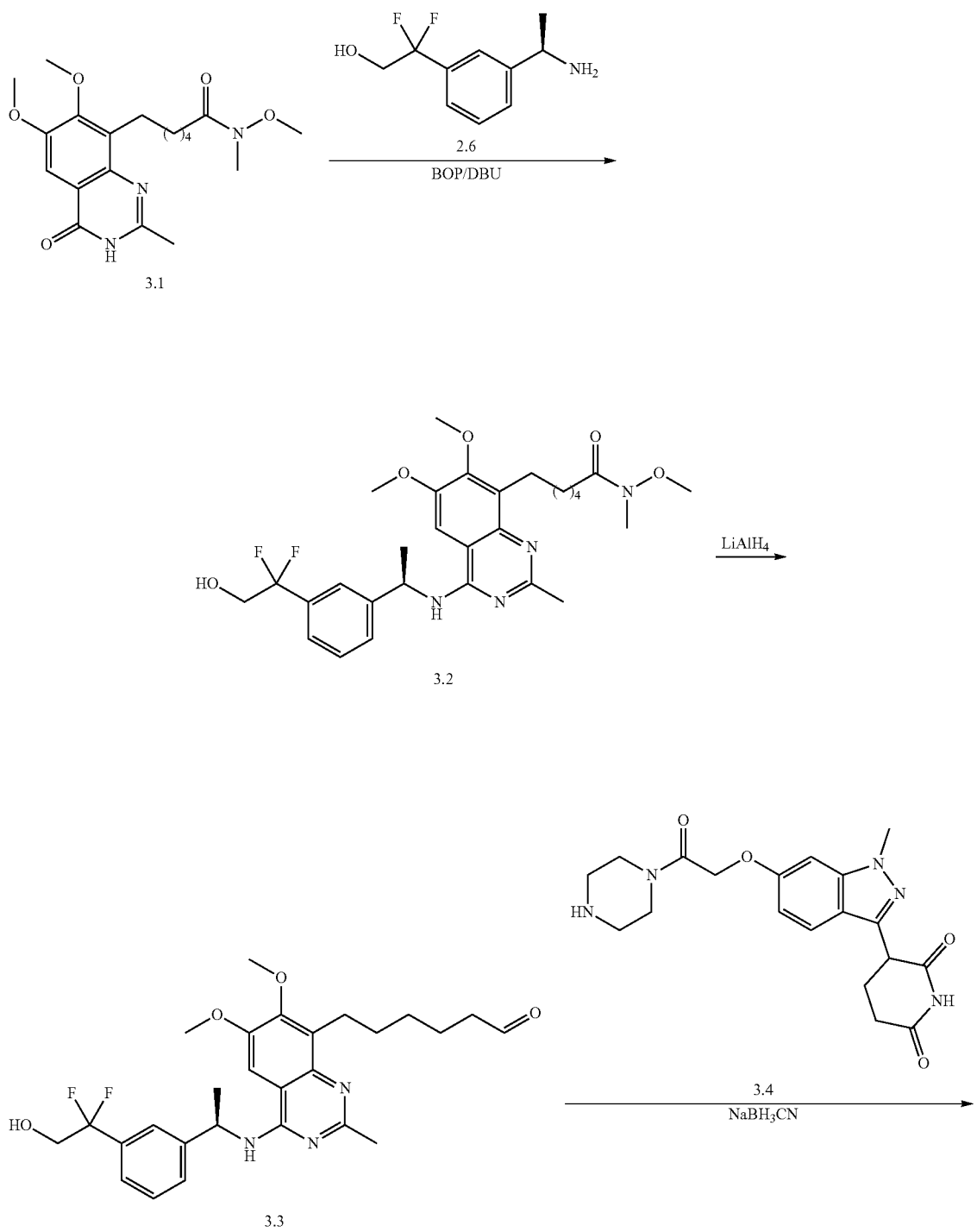

-continued

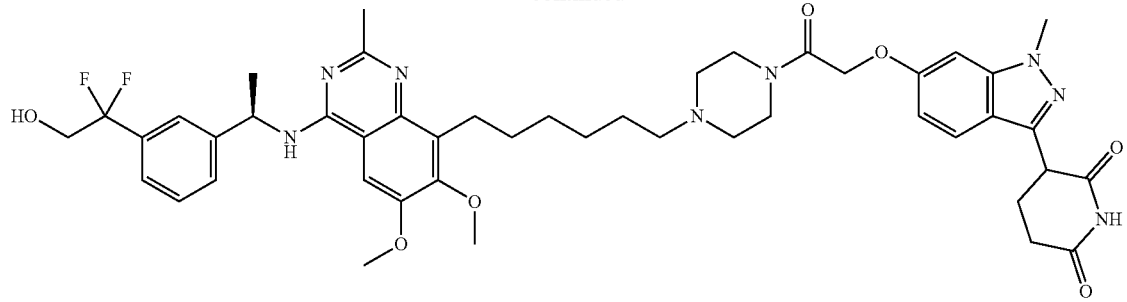

A204

Preparation of (R)-6-(4-((1-(3-(1,1-difluoro-2-hydroxyethyl)phenyl)ethyl)amino)-6,7-dimethoxy-2-methylquinazolin-8-yl)hexanal 3.3. To a solution of compound 3.2 (336 mg, 0.6 mmol) in THF was added 1 M LiAlH$_4$ in THF (1.5 mL, 1.5 mmol) dropwise under N$_2$ at −70° C. After stirred at −70° C. for 1 h, the reaction was quenched with saturated aqueous NH$_4$Cl and extracted with EtOAc (5 mL×3). The combined organic layers were dried over anhydrous Na$_2$SO$_4$, filtered, and concentrated under reduced pressure to afford compound 3.3 (300 mg), which was used directly in in the next step without further purification. MS (ESI) m/z: 502.3 [M+H]$^+$.

Preparation of 3-(6-(2-(4-(6-(4-(((R)-1-(3-(1,1-difluoro-2-hydroxyethyl)phenyl)-ethyl)amino)-6,7-dimethoxy-2-methylquinazolin-8-yl)hexyl)piperazin-1-yl)-2-oxoethoxy)-1-methyl-1H-indazol-3-yl)piperidine-2,6-dione A204. To a solution of compound 3.3 (300 mg) in DCM (10 mL) and MeOH (2 mL) was added 3-(1-methyl-6-(2-oxo-2-(piperazin-1-yl)ethoxy)-1H-indazol-3-yl)piperidine-2,6-dione 3.4 (170 mg, 0.6 mmol). After the mixture was stirred for 1 h, NaBH$_3$CN (75 mg, 1.2 mmol) and AcOH (a catalytic amount) were added. The reaction mixture was stirred overnight and then concentrated under reduced pressure to yield a crude product, which was purified by silica-gel column chromatography eluting with MeOH/DCM and purified by reverse-phase prep-HPLC to afford compound A204 (5 mg) in 1% yield. $^1$H NMR (400 MHz, DMSO-d$_6$) δ 10.86 (s, 1H), 8.27 (s, 1H), 8.07 (d, J=7.6 Hz, 1H), 7.65 (d, J=7.2 Hz, 2H), 7.58 (d, J=8.8 Hz, 2H), 7.44 (t, J=7.2 Hz, 1H), 7.37 (d, J=7.6 Hz, 1H), 7.05 (d, J=1.6 Hz, 1H), 6.78 (dd, J=2.0 Hz, 8.8 Hz, 1H), 5.70-5.64 (m, 1H), 4.87 (s, 2H), 4.31 (q, J=4.8 Hz, 1H), 3.95 (s, 3H), 3.92 (s, 3H), 3.89-3.84 (m, 2H), 3.78 (s, 3H), 3.46 (s, 4H), 2.99-2.94 (m, 2H), 2.68-2.56 (m, 2H), 2.38 (s, 5H), 2.33-2.25 (m, 6H), 2.21-2.13 (m, 1H), 1.62 (d, J=6.8 Hz, 3H), 1.52-1.47 (m, 2H), 1.46-1.40 (m, 2H), 1.33 (s, 4H); MS (ESI) m/z: 871.2 [M+H]$^+$.

Example 4

Preparation of 3-(3-(2-(4-(6-(4-(((R)-1-(3-(1,1-difluoro-2-hydroxyethyl)phenyl)ethyl)amino)-6,7-dimethoxy-2-methylquinazolin-8-yl)hexyl)piperazin-1-yl)-2-oxoethoxy)phenyl)piperidine-2,6-dione A303

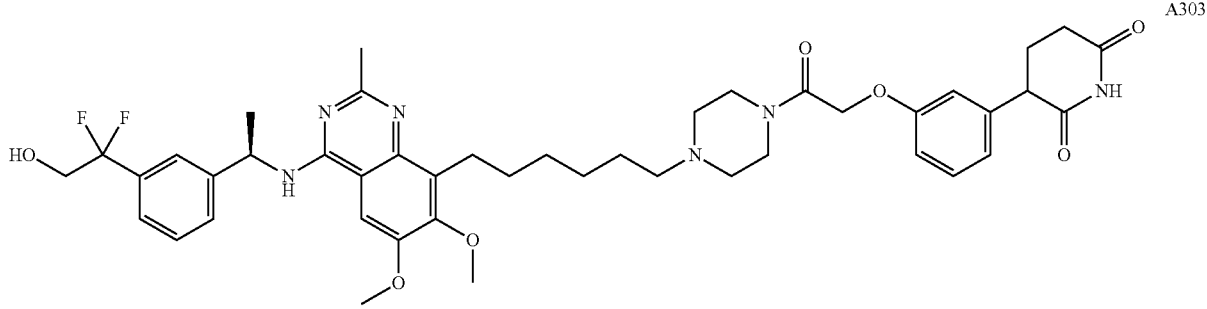 [SMILES: COc1cc2c(N[C@H](C)c3cccc(C(F)(F)CO)c3)nc(C)nc2c(CCCCCCN2CCN(C(=O)COc3cccc(C4CCC(=O)NC4=O)c3)CC2)c1OC]

A303

Compound A303 was prepared as shown in Scheme 4.
Preparation of 3-(3-(2-(4-(6-(4-(((R)-1-(3-(1,1-difluoro-2-hydroxyethyl)phenyl)-ethyl)amino)-6,7-dimethoxy-2-methylquinazolin-8-yl)hexyl)piperazin-1-yl)-2-oxoethoxy)-phenyl)piperidine-2,6-dione A303. To a solution of (R)-6-(4-((1-(3-(1,1-difluoro-2-hydroxy-ethyl)phenyl)ethyl)amino)-6,7-dimethoxy-2-methylquinazolin-8-yl)hexanal 3.3 (85 mg) in DCM (10 mL) and MeOH (2 mL) was added 3-(3-(2-oxo-2-(piperazin-1-yl)ethoxy)phenyl)piperidine-2,6-dione 4.1 (33 mg, 0.1 mmol). After the mixture was stirred for 1 h, NaBH$_3$CN (12.6 mg, 0.2 mmol) and AcOH (a catalytic amount) were added. The reaction mixture was stirred overnight and concentrated under reduced pressure to yield a crude product, which was purified by reverse-phase prep-HPLC to afford compound A303 (29.9 mg) in 37% yield. $^1$H NMR (400 MHz, DMSO-d$_6$) δ 10.81 (s, 1H), 8.14 (s, 1H), 8.05 (d, J=8.0 Hz, 1H), 7.64 (d, J=6.0 Hz, 2H), 7.57 (d, J=7.2 Hz, 1H), 7.43 (t, J=7.6 Hz, 1H), 7.36 (d, J=8.0 Hz, 1H), 7.25-7.21 (m, 1H), 6.81-6.79 (m, 3H), 5.67 (t, J=7.6

Hz, 1H), 5.59 (s, 1H), 4.76 (s, 2H), 3.94 (s, 3H), 3.83-3.82 (m, 2H), 3.80 (s, 4H), 3.42-3.43 (m, 4H), 2.96 (t, J=8.0 Hz, 2H), 2.69-2.58 (m, 2H), 2.38 (s, 3H), 2.35-2.32 (m, 2H), 2.28-2.16 (m, 5H), 2.05-2.00 (m, 1H), 1.61 (d, J=6.8 Hz, 3H), 1.53-1.49 (m, 2H), 1.43-1.41 (m, 2H), 1.36-1.29 (m, 4H); MS (ESI) m/z: 817.2 [M+H]⁺.
Scheme 4
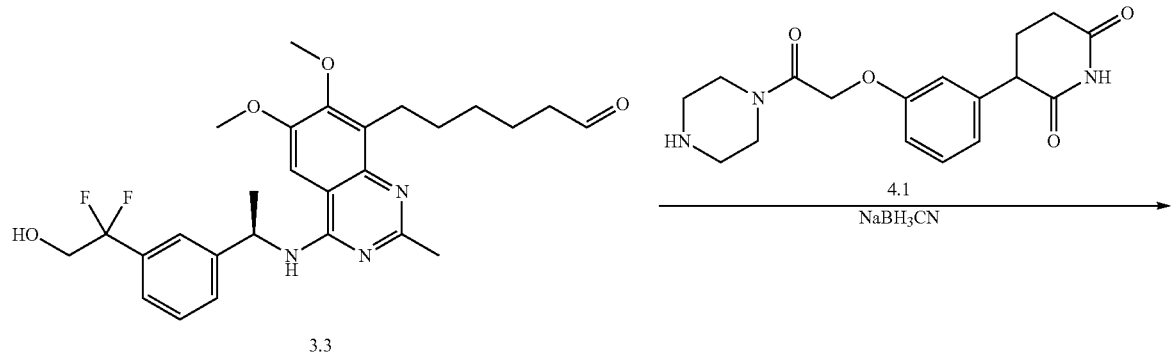
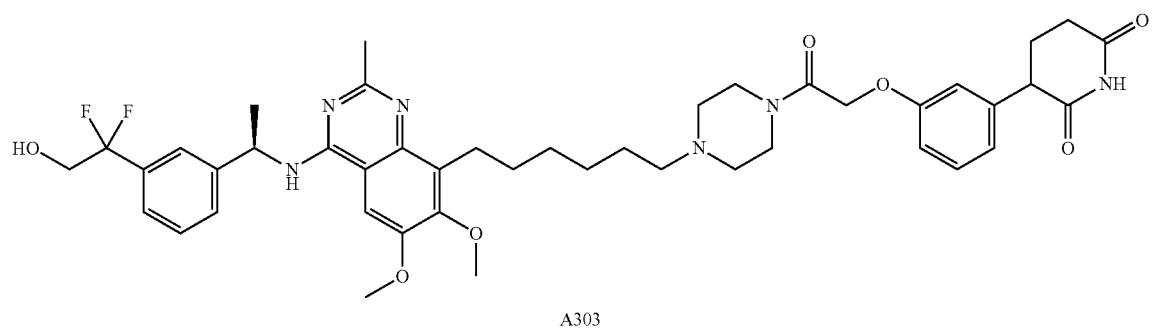
A303
40
Example 5
Preparation of (2S,4R)-1-((S)-2-(9-(6,7-dimethoxy-2-methyl-4-(((S)-1-(4-(2-((methylamino)-methyl)phenyl)thiophen-2-yl)ethyl)amino)quinazolin-8-yl)nonanamido)-3,3-dimethylbutanoyl)-4-hydroxy-N-(4-(4-methylthiazol-5-yl)benzyl)pyrrolidine-2-carboxamide A401
A401
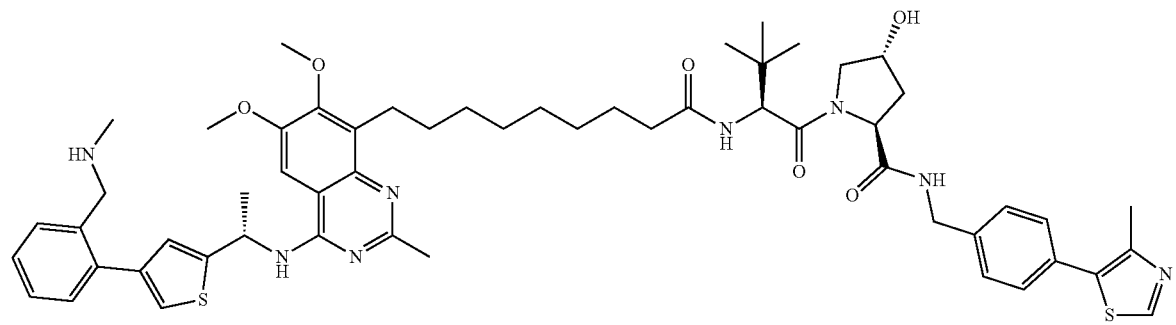

Compound A401 was prepared as shown in Schemes 5A and 5B.

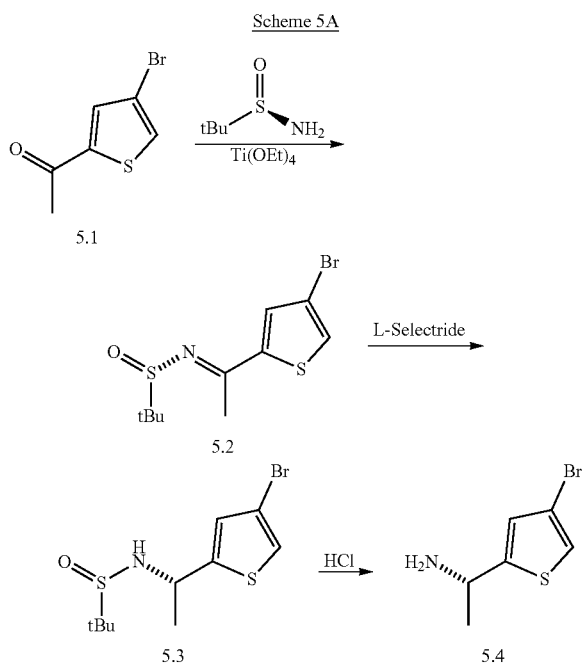

Preparation of (S,E)-N-(1-(4-bromothiophen-2-yl)ethylidene)-2-methylpropane-2-sulfinamide 5.2. To a solution of 1-(4-bromothiophen-2-yl)ethanone 5.1 (1 g, 4.88 mmol) in THF (10 mL) were added 2-methylpropane-2-sulfinamide (1.48 g, 12.2 mmol) and tetraethyl titanate (3.34 g, 14.6 mmol). After stirred at 70° C. for 16 h, the reaction mixture was diluted with $H_2O$ (10 mL) and extracted with EtOAc (20 mL×2). The combined organic layers were washed with brine, dried over anhydrous $Na_2SO_4$, filtered, and concentrated under reduced pressure to yield a crude product, which was purified by silica-gel column chromatography eluting with EtOAc/PE to afford compound 5.2 (1.17 g) in 78% yield. MS (ESI) m/z: 308.1 $[M+1]^+$.

Preparation of N—((S)-1-(4-bromothiophen-2-yl)ethyl)propane-2-sulfinamide 5.3. To a solution of compound 5.2 (8 g, 26 mmol) in THF (120 mL) at 0° C. was added 1N L-selectride (65 mL, 65 mmol) over 20 min. After completion, the reaction mixture was diluted with $H_2O$ (60 mL) and extracted with EtOAc (50 mL×3). The combined organic layers were dried over anhydrous $Na_2SO_4$, filtered, and concentrated under reduced pressure to yield a crude product, which was purified by silica-gel column chromatography eluting with EtOAc/PE to afford compound 5.3 (6.8 g) in 89% yield. MS (ESI) m/z: 294.0 $[M+H]^+$.

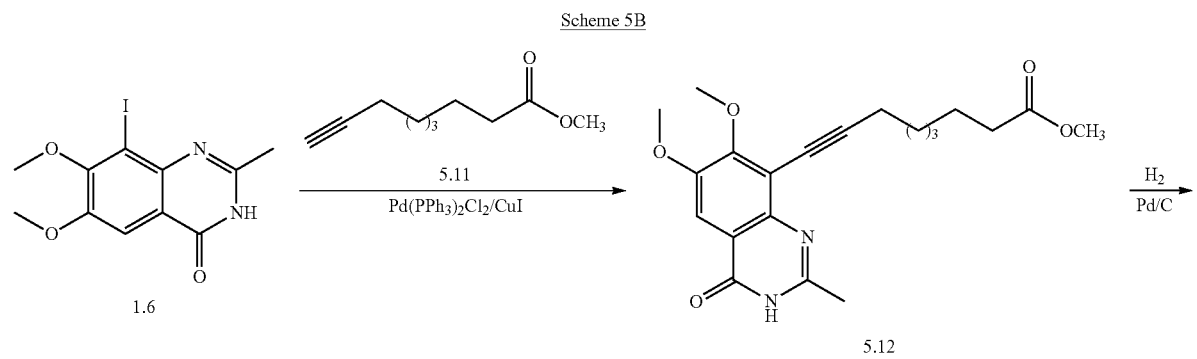

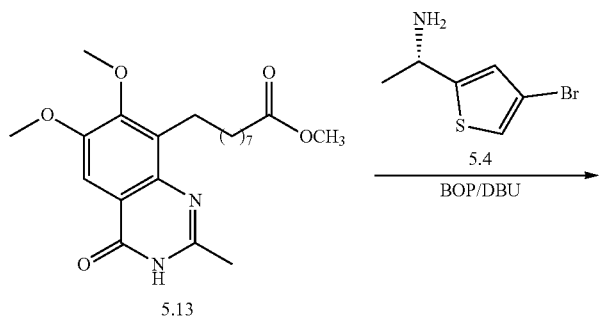

-continued
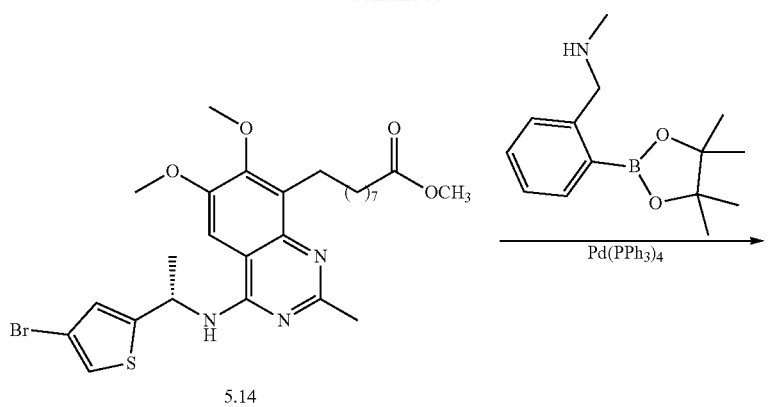
5.14
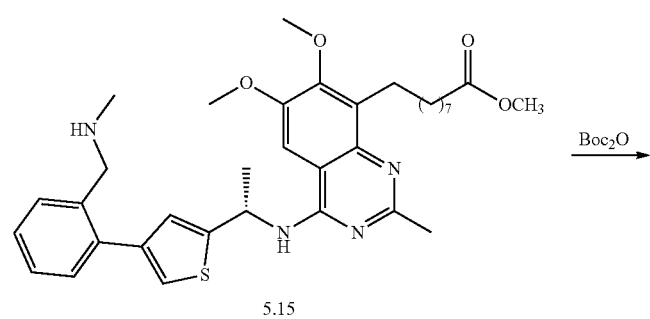
5.15
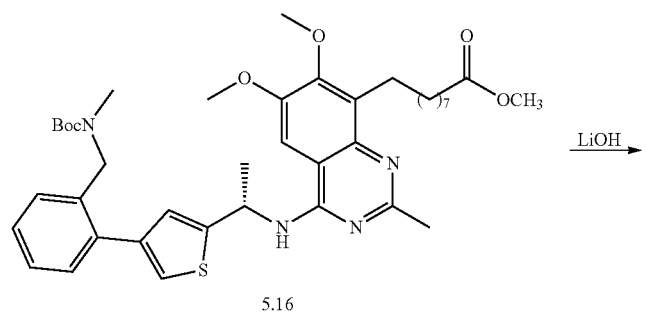
5.16
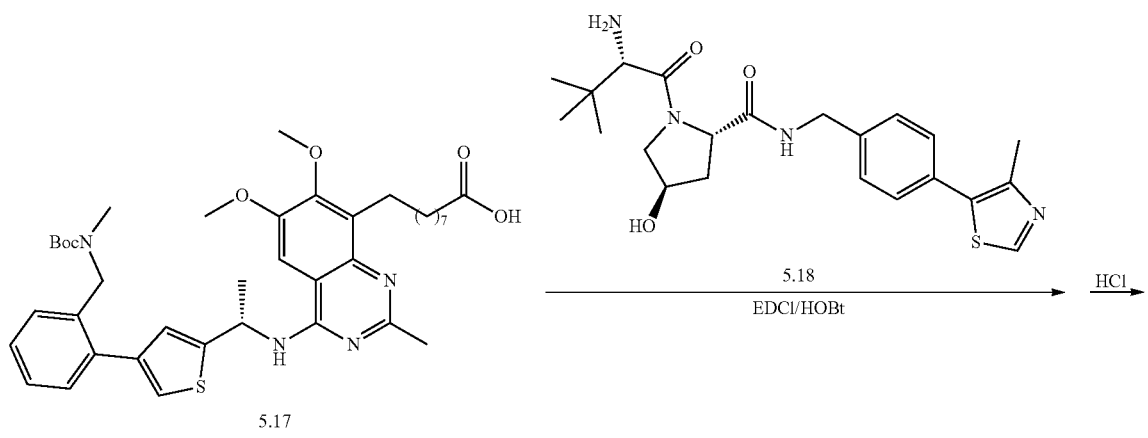
5.17
5.18

-continued

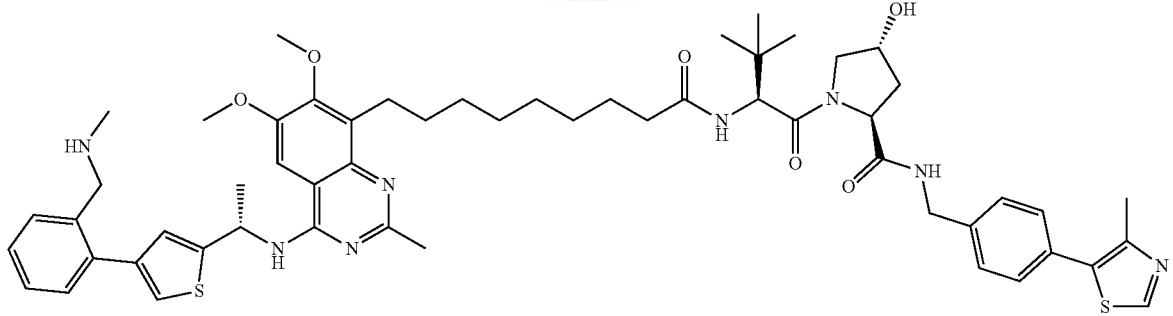

A401

Preparation of (S)-1-(4-bromothiophen-2-yl)ethanamine 5.4. To a solution of compound 5.3 (6.8 g, 23 mmol) in DCM (20 mL) at 0° C. was added HCl in EtOAc (5 mL). After stirred at 0° C. for 2 h, the reaction mixture was filtered and concentrated under reduced pressure to afford compound 5.4 (5 g), which was used directly in the next step without further purification. MS (ESI) m/z: 206.1 [M+H]$^+$.

Preparation of methyl 9-(6,7-dimethoxy-2-methyl-4-oxo-3,4-dihydroquinazolin-8-yl)non-8-ynoate 5.12. To a solution of 8-iodo-6,7-dimethoxy-2-methylquinazolin-4(3H)-one 1.6 (1.2 g, 3.47 mmol), methyl non-8-ynoate 5.11 (3 g, 17.3 mmol), and TEA (1 g, 10.4 mmol) in DMF (40 mL) were added Pd(PPh$_3$)$_2$Cl$_2$ (243 mg, 0.347 mmol) and CuI (66 mg, 0.347 mmol) under N$_2$. After stirred at 50° C. for 6 h under N$_2$, the reaction mixture was purified by reverse-phase column chromatography eluting with ACN/water to compound 5.12 (380 mg). MS (ESI) m/z: 387.2 [M+H]$^+$.

Preparation of methyl 9-(6,7-dimethoxy-2-methyl-4-oxo-3,4-dihydroquinazolin-8-yl)nonanoate 5.13. To a solution of compound 5.12 (380 mg, 0.98 mmol) in THF (8 mL) at was added Pd/C (200 mg). After stirred under H$_2$ overnight, the reaction mixture was filtered and concentrated under reduced pressure to yield a crude product, which was purified by silica gel column chromatography eluting with DCM/MeOH to afford compound 5.13 (300 mg) in 79% yield. MS (ESI) m/z: 391.2 [M+H]$^+$.

Preparation of (S)-methyl 9-(4-((1-(4-bromothiophen-2-yl)ethyl)amino)-6,7-dimethoxy-2-methylquinazolin-8-yl) nonanoate 5.14. To a solution of compound 5.13 (300 mg, 0.78 mmol) in DMF (6 mL) were added (S)-1-(4-bromothiophen-2-yl)ethanamine 5.4 (318 mg, 1.56 mmol), BOP (517 mg, 1.17 mmol), and DBU (237 mg, 1.56 mmol). After the mixture was stirred for 18 hours, another batch of compound 5.4 (318 mg, 1.56 mmol) was added. The reaction mixture was stirred at 50° C. for 18 h, and then diluted with water (20 mL) and extracted with EtOAc (50 mL×2). The combined organic layers were dried over anhydrous Na$_2$SO$_4$, filtered, and concentrated under reduced pressure to yield a crude product, which was purified by silica-gel column chromatography eluting with EtOAc/PE and further purified by prep-TLC eluting with EtOAc/PE to afford 5.14 (173 mg) in 38% yield. MS (ESI) m/z: 578.1 [M+H]$^+$.

Preparation of (S)-methyl 9-(6,7-dimethoxy-2-methyl-4-((1-(4-(2-((methyl-amino)methyl)phenyl)thiophen-2-yl) ethyl)amino)quinazolin-8-yl)nonanoate 5.15. To a solution of compound 5.14 (173 mg, 0.3 mmol) and N-methyl-1-(2-(4,4,5,5-tetramethyl-1,3,2-dioxa-borolan-2-yl)phenyl)methanamine (111 mg, 0.45 mmol) in dioxane (4 mL) and H$_2$O (1 mL) were added K$_2$CO$_3$ (124 mg, 0.9 mmol) and Pd(PPh$_3$)$_4$ (69 mg, 0.06 mmol). After stirred at 100° C. overnight under N$_2$, the reaction mixture was concentrated under reduced pressure to yield a crude product, which was purified by silica-gel column chromatography eluting with MeOH/DCM to afford compound 5.15 (70 mg) in 38% yield. MS (ESI) m/z: 619.3 [M+H]$^+$.

Preparation of (S)-methyl 9-(4-((1-(4-(2-(((tert-butoxycarbonyl)(methyl)amino)-methyl)phenyl)thiophen-2-yl) ethyl)amino)-6,7-dimethoxy-2-methylquinazolin-8-yl) nonanoate 5.16. To a solution of compound 5.15 (70 mg, 0.11 mmol) in THF (4 mL) were added Boc$_2$O (37 mg, 0.17 mmol) and TEA (17 mg, 0.17 mmol). After stirred overnight, the reaction mixture was diluted by water and extracted with EtOAc. The combined organic layers were dried over anhydrous Na$_2$SO$_4$, filtered, and concentrated under reduced pressure to yield a crude product, which was purified by silica-gel column chromatography eluting with MeOH/DCM to afford compound 5.16 (50 mg) in 63% yield. MS (ESI) m/z: 719.3 [M+H]$^+$.

Preparation of (S)-9-(4-((1-(4-(2-(((tert-butoxycarbonyl)(methyl)amino)methyl)-phenyl)thiophen-2-yl)ethyl) amino)-6,7-dimethoxy-2-methylquinazolin-8-yl)nonanoic acid 5.17. To a solution of compound 5.16 (50 mg, 0.07 mmol) in THF (4 mL), MeOH (1 mL), and H$_2$O (1 mL) was added LiOH (9 mg, 0.21 mmol). After stirred for 12 h, the reaction mixture was concentrated under reduced pressure, diluted with water (10 mL), and extracted with TBME. The aqueous layer was adjusted to pH 2~3 with 1N HCl and extracted with EtOAc. The combined organic layers were dried over anhydrous Na$_2$SO$_4$ and concentrated under reduced pressure to afford compound 5.17 (43 mg) in 88% yield. MS (ESI) m/z: 705.3 [M+H]$^+$.

Preparation of tert-butyl 2-(5-((S)-1-((8-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)-6,7-dimethoxy-2-methylquinazolin-4-yl) amino)ethyl)thiophen-3-yl)benzyl(methyl)-carbamate. To a solution of compound 5.17 (43 mg, 0.06 mmol) and (2S,4R)-1-((S)-2-amino-3,3-dimethylbutanoyl)-4-hydroxy-N-(4-(4-methylthiazol-5-yl)benzyl)pyrrolidine-2-carboxamide 4.18 (26 mg, 0.06 mmol) in DMF was added HOBt (16 mg, 0.12 mmol), EDCI (23 mg, 0.12 mmol), and DIPEA (23 mg, 0.18 mmol). After stirred overnight, the reaction mixture was concentrated under reduced pressure to yield a crude product, which was purified by silica-gel column chromatography eluting with MeOH/DCM and further purified by reverse-phase prep-HPLC to afford the title compound (28 mg) in 37% yield. MS (ESI) m/z: 1117.5 [M+H]$^+$.

Preparation of (2S,4R)-1-((S)-2-(9-(6,7-dimethoxy-2-methyl-4-(((S)-1-(4-(2-((methylamino)methyl)phenyl)thiophen-2-yl)ethyl)amino)quinazolin-8-yl)nonanamido)-3,3- dimethylbutanoyl)-4-hydroxy-N-(4-(4-methylthiazol-5-yl)benzyl)pyrrolidine-2-carboxamide A401. To a solution of tert-butyl 2-(5-(((S)-1-((8-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)-6,7-dimethoxy-2-methylquinazolin-4-yl)amino)ethyl)thiophen-3-yl)benzyl(methyl)-carbamate (28 mg, 0.025 mmol) in DCM (2 mL) was added HCl in EtOAc (2 mL). After stirred for 1 h, the reaction mixture was diluted with H₂O and extracted with EtOAc. The aqueous layer was lyophilized to afford compound A401 (18.5 mg) in 74% yield. $^1$H NMR (400 MHz, DMSO-$d_6$) δ 13.10 (s, 1H), 10.73 (s, 1H), 9.59 (s, 2H), 9.01 (s, 1H), 8.46-8.28 (m, 1H), 8.36 (s, 1H), 7.86-7.81 (m, 2H), 7.55 (s, 1H), 7.49-7.35 (m, 8H), 7.34-7.23 (m, 1H), 6.15 (t, J=7.2 Hz, 1H), 4.55-4.53 (m, 1H), 4.47-4.40 (m, 2H), 4.38-4.32 (m, 1H), 4.22 (dd, J=5.2, 15.2 Hz, 1H), 4.12 (t, J=6.0 Hz, 1H), 4.03 (s, 3H), 3.91 (s, 3H), 3.67-3.62 (m, 2H), 3.14-3.08 (m, 2H), 2.82 (s, 3H), 2.45 (s, 3H), 2.15-2.00 (m, 4H), 1.90-1.86 (m, 3H), 1.50-1.35 (m, 6H), 1.34-1.22 (m, 8H), 0.93 (s, 9H); MS (ESI) m/z: 1017.2 [M+H]⁺.

The following compounds were prepared similarly according to the synthetic procedures or methodologies exemplified herein.

3-(4-(1-(6-(4-(((S)-1-(3-Amino-5-(trifluoromethyl)phenyl)ethyl)amino)-6,7-dimethoxy-2-methylquinazolin-8-yl)hexyl)piperidin-4-yl)-6-fluoro-1-oxoisoindolin-2-yl)-piperidine-2,6-dione A103. $^1$H NMR (400 MHz, DMSO-$d_6$) δ 11.00 (s, 1H), 8.00 (d, J=8.0 Hz, 1H), 7.65 (s, 1H), 7.41-7.33 (m, 2H), 7.19 (s, 1H), 6.87 (d, J=12.0 Hz, 2H), 6.69 (s, 1H), 6.65 (s, 1H), 5.57 (t, J=7.2 Hz, 3H), 5.52 (s, 2H), 5.32 (t, J=5.2 Hz, 1H), 5.13 (dd, J=5.2, 13.2 Hz, 1H), 4.52-4.31 (m, 2H), 3.94 (s, 3H), 3.80 (s, 3H), 2.99-2.96 (m, 4H), 2.92-2.87 (m, 1H), 2.67-2.58 (m, 1H), 2.45-2.41 (m, 1H), 2.39 (s, 3H), 2.33-2.28 (m, 1H), 2.03-1.96 (m, 4H), 1.73 (s, 4H), 1.55 (d, J=6.8 Hz, 3H), 1.45 (s, 2H), 1.34-1.30 (m, 4H); MS (ESI) m/z: 834.5 [M+H]⁺.

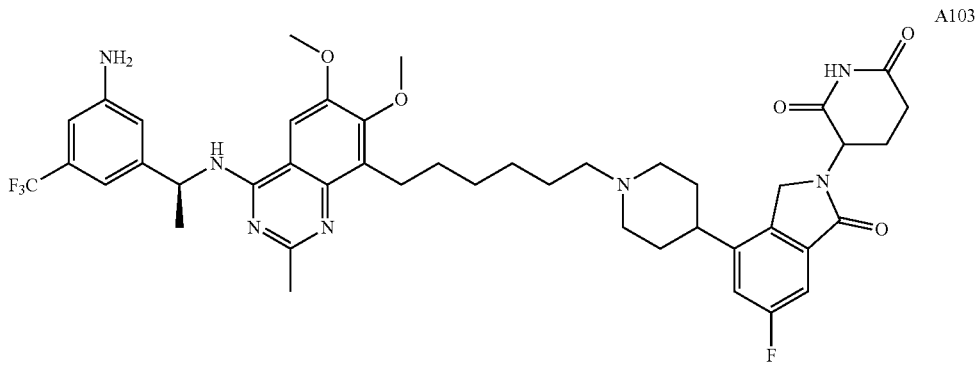 [SMILES: COc1cc2c(N[C@@H](C)c3cc(N)cc(C(F)(F)F)c3)nc(C)nc2c(CCCCCCN2CCC(c3cc(F)cc4c3CN(C3CCC(=O)NC3=O)C4=O)CC2)c1OC]

3-(4-(1-(7-(4-(((R)-1-(3-(1,1-Difluoro-2-hydroxyethyl)phenyl)ethyl)amino)-6,7-dimethoxy-2-methylquinazolin-8-yl)heptyl)piperidin-4-yl)-6-fluoro-1-oxoisoindolin-2-yl)-piperidine-2,6-dione A104. $^1$H NMR (400 MHz, DMSO-$d_6$) δ 11.00 (s, 1H), 8.16 (brs, 1H), 8.05 (d, J=8.0 Hz, 1H), 7.65-7.56 (m, 3H), 7.45-7.33 (m, 4H), 5.70-5.55 (m, 2H), 5.13 (dd, J=5.2, 13.2 Hz, 1H), 4.52-4.31 (m, 2H), 3.94 (s, 3H), 3.86-3.80 (m, 5H), 3.00-2.90 (m, 5H), 2.68-2.50 (m, 2H), 2.50-2.28 (m, 6H), 2.05-1.95 (m, 3H), 1.75-1.65 (m, 4H), 1.60 (d, J=6.8 Hz, 3H), 1.55-1.40 (m, 4H), 1.32-1.25 (m, 6H); MS (ESI) m/z: 845.6 [M+H]⁺.

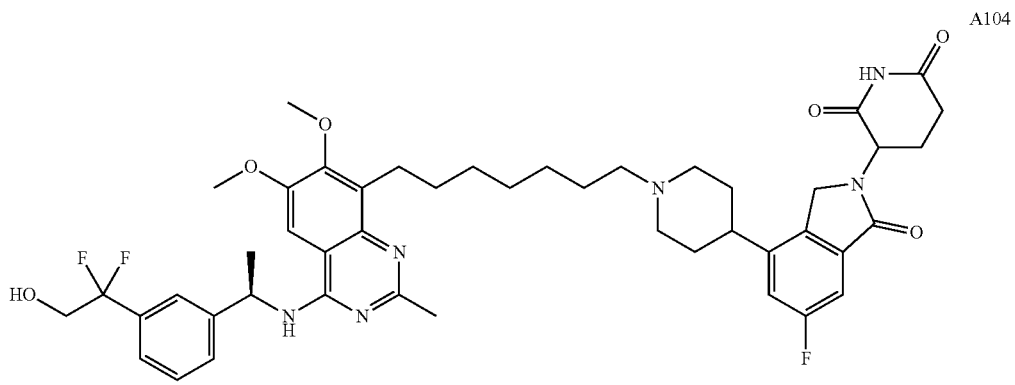 [SMILES: COc1cc2c(N[C@H](C)c3cccc(C(F)(F)CO)c3)nc(C)nc2c(CCCCCCCN2CCC(c3cc(F)cc4c3CN(C3CCC(=O)NC3=O)C4=O)CC2)c1OC]

3-(4-(1-(8-(4-(((R)-1-(3-Amino-5-(trifluoromethyl)phenyl)ethyl)amino)-6,7-dimethoxy-2-methylquinazolin-8-yl)octyl)piperidin-4-yl)-6-fluoro-1-oxoisoindolin-2-yl)-piperidine-2,6-dione A105. $^1$H NMR (400 MHz, DMSO-$d_6$) δ 11.00 (s, 1H), 8.17 (s, 2H), 7.99 (d, J=7.6 Hz, 1H), 7.65 (s, 1H), 7.41-7.33 (m, 2H), 6.88 (s, 1H), 6.85 (s, 1H), 6.69 (s, 1H), 5.60-5.35 (m, 3H), 5.14 (dd, J=5.2, 13.2 Hz, 1H), 4.53-4.30 (m, 2H), 3.94 (s, 3H), 3.80 (s, 3H), 3.05-2.90 (m, 5H), 2.70-2.55 (m, 2H), 2.45-2.30 (m, 6H), 2.10-1.95 (m, 3H), 1.80-1.70 (m, 4H), 1.60-1.40 (m, 7H), 1.35-1.20 (m, 8H); MS (ESI) m/z: 862.2 [M+H]⁺.

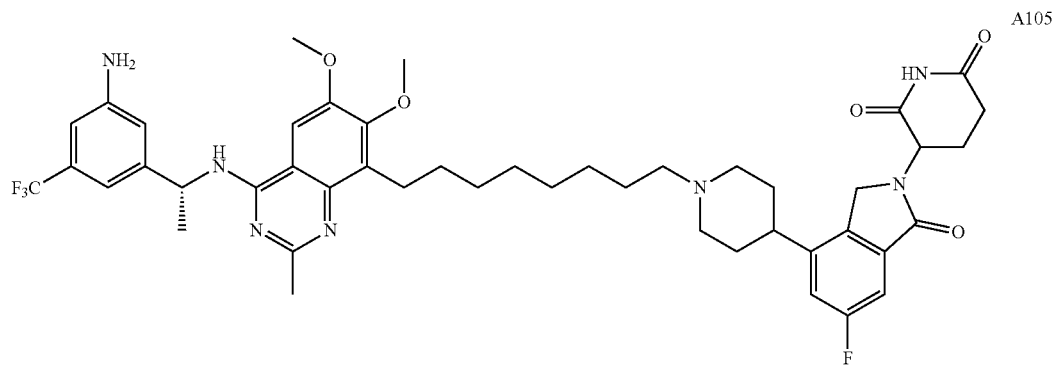 [SMILES: COc1cc2c(N[C@H](C)c3cc(N)cc(C(F)(F)F)c3)nc(C)nc2c(CCCCCCCCN2CCC(c3cc(F)cc4c3CN(C3CCC(=O)NC3=O)C4=O)CC2)c1OC]

3-(4-(1-(10-(4-(((R)-1-(3-Amino-5-(trifluoromethyl)phenyl)ethyl)amino)-6,7-dimethoxy-2-methylquinazolin-8-yl)decyl)piperidin-4-yl)-6-fluoro-1-oxoisoindolin-2-yl)-piperidine-2,6-dione A106. ¹H NMR (400 MHz, DMSO-d₆) δ 11.00 (s, 1H), 8.17 (s, 1H), 7.99 (d, J=8.0 Hz, 1H), 7.65 (s, 1H), 7.41-7.33 (m, 2H), 6.88 (s, 1H), 6.85 (s, 1H), 6.69 (s, 1H), 5.60-5.48 (m, 3H), 5.13 (dd, J=4.8 Hz, 13.2 Hz, 1H), 4.53-4.31 (m, 2H), 3.94 (s, 3H), 3.80 (s, 3H), 3.05-2.90 (m, 5H), 2.70-2.55 (m, 2H), 2.50-2.40 (m, 1H), 2.38 (s, 3H), 2.34-2.30 (m, 2H), 2.10-1.95 (m, 3H), 1.80-1.70 (m, 4H), 1.55 (d, J=6.8 Hz, 3H), 1.52-1.35 (m, 4H), 1.35-1.20 (m, 12H); MS (ESI) m/z: 890.2 [M+H]⁺.

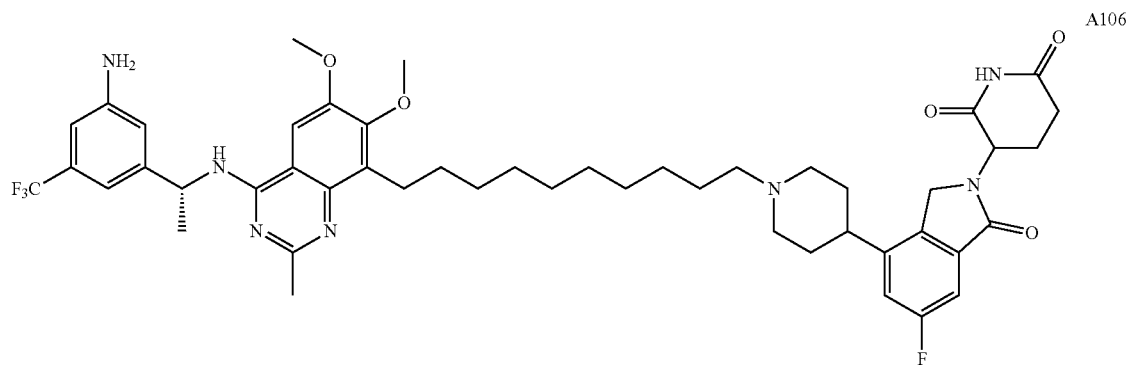 [SMILES: COc1cc2c(N[C@H](C)c3cc(N)cc(C(F)(F)F)c3)nc(C)nc2c(CCCCCCCCCCN2CCC(c3cc(F)cc4c3CN(C3CCC(=O)NC3=O)C4=O)CC2)c1OC]

3-(4-(1-(12-(4-(((R)-1-(3-Amino-5-(trifluoromethyl)phenyl)ethyl)amino)-6,7-dimethoxy-2-methylquinazolin-8-yl)dodecyl)piperidin-4-yl)-6-fluoro-1-oxoisoindolin-2-yl)-piperidine-2,6-dione A107. ¹H NMR (400 MHz, DMSO-d₆) δ 11.01 (s, 1H), 8.20 (s, 2H), 7.99 (d, J=8.0 Hz, 1H), 7.65 (s, 1H), 7.40-7.35 (m, 2H), 6.87 (d, J=11.2 Hz, 2H), 6.70 (s, 1H), 5.59-5.48 (m, 3H), 5.14 (dd, J=4.8 Hz, 12.8 Hz, 1H), 4.53-4.33 (m, 2H), 3.94 (s, 3H), 3.79 (s, 3H), 3.76-3.66 (m, 4H), 3.07 (d, J=11.2 Hz, 2H), 2.98-2.95 (m, 2H), 2.92-2.88 (m, 1H), 2.67-2.58 (m, 1H), 2.44-2.40 (m, 3H), 2.38 (s, 3H), 2.18-2.10 (m, 2H), 2.03-1.99 (m, 2H), 1.78 (s, 4H), 1.55 (d, J=6.8 Hz, 3H), 1.50-1.47 (m, 4H), 1.31-1.1.27 (m, 12H); MS (ESI) m/z: 918.3 [M+H]⁺.

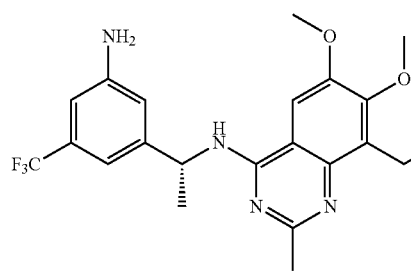
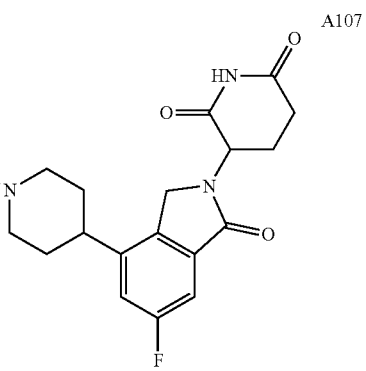

A107

3-(4-(1-(12-(4-(((S)-1-(3-Amino-5-(trifluoromethyl)phenyl)ethyl)amino)-6,7-dimethoxy-2-methylquinazolin-8-yl)dodecyl)piperidin-4-yl)-6-fluoro-1-oxoisoindolin-2-yl)-piperidine-2,6-dione A108. $^1$H NMR (400 MHz, DMSO-d$_6$) δ 11.01 (s, 1H), 8.14 (s, 1H), 7.99 (d, J=8.0 Hz, 1H), 7.65 (s, 1H), 7.39-7.37 (m, 2H), 6.88-6.85 (m, 2H), 6.69 (s, 1H), 5.59-5.52 (m, 3H), 5.15 (dd, J=5.2 Hz, 13.2 Hz, 1H), 4.53-4.32 (m, 2H), 3.94 (s, 3H), 3.79 (s, 3H), 3.20-3.17 (m, 4H), 2.98-2.89 (m, 5H), 2.75-2.73 (m, 1H), 2.632.59 (m, 3H), 2.41-2.40 (m, 1H), 2.38 (s, 3H), 2.35-2.34 (m, 1H), 2.03-1.99 (m, 2H), 1.83-1.79 (m, 4H), 1.55 (d, J=7.2 Hz, 3H), 1.52-1.49 (m, 4H), 1.31-1.1.27 (m, 12H); MS (ESI) m/z: 918.7 [M+H]$^+$.

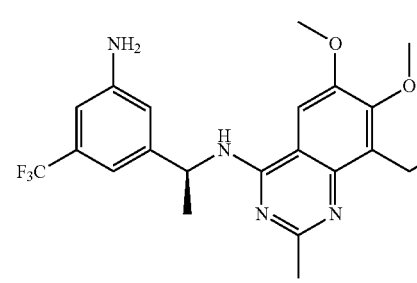
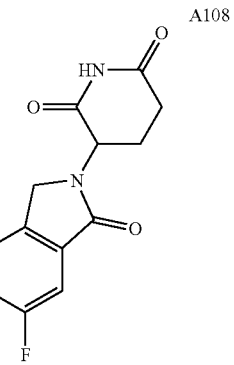

A108

3-(5-(4-(7-(4-(((R)-1-(3-(1,1-Difluoro-2-hydroxyethyl)phenyl)ethyl)amino)-6,7-dimethoxy-2-methylquinazolin-8-yl)heptyl)piperazin-1-yl)-6-fluoro-1-oxoisoindolin-2-yl)-piperidine-2,6-dione A109. MS (ESI) m/z: 846.2 [M+H]$^+$.

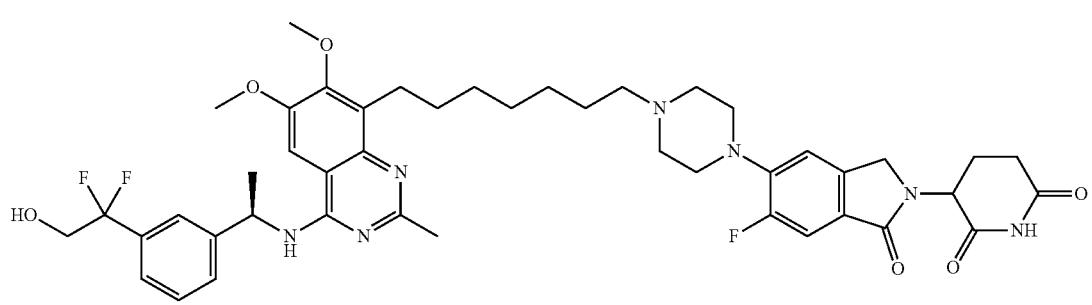

A109

3-(4-(1-(10-(4-(((S)-1-(3-Amino-5-(trifluoromethyl)phenyl)ethyl)amino)-6,7-dimethoxy-2-methylquinazolin-8-yl)decyl)piperidin-4-yl)-6-fluoro-1-oxoisoindolin-2-yl)-piperidine-2,6-dione A110. $^1$H NMR (400 MHz, DMSO-d$_6$) δ 11.00 (s, 1H), 8.18 (s, 1H), 7.99 (d, J=8.0 Hz, 1H), 7.65 (s, 1H), 7.41-7.33 (m, 2H), 6.88 (s, 1H), 6.85 (s, 1H), 6.69 (s, 1H), 5.60-5.50 (m, 3H), 5.14 (dd, J=4.8 Hz, 13.2 Hz, 1H), 4.50-4.30 (m, 2H), 3.94 (s, 3H), 3.80 (s, 3H), 3.05-2.85 (m, 5H), 2.63-2.58 (m, 2H), 2.50-2.39 (m, 1H), 2.38 (s, 3H), 2.38-2.30 (m, 2H), 2.05-1.95 (m, 3H), 1.80-1.70 (m, 4H), 1.55 (d, J=7.2 Hz, 3H), 1.54-1.43 (m, 4H), 1.32-1.20 (m, 12H); MS (ESI) m/z: 890.6 [M+H]$^+$.

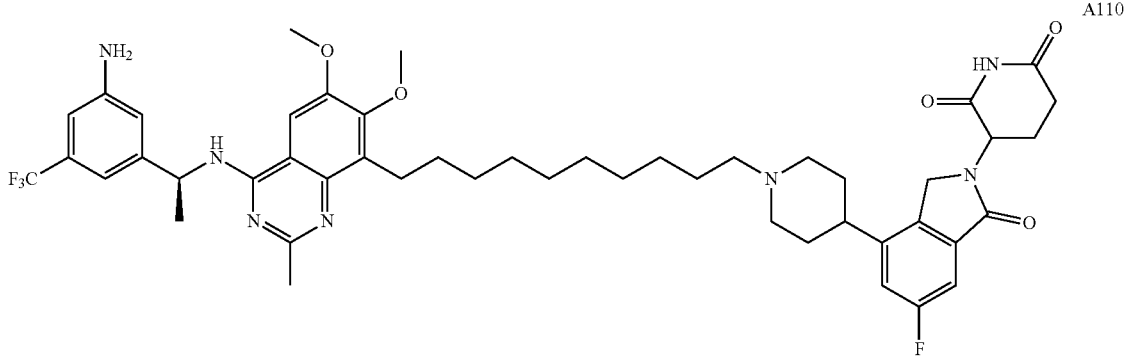 [SMILES: COc1cc2c(N[C@@H](C)c3cc(N)cc(C(F)(F)F)c3)nc(C)nc2c(CCCCCCCCCCN2CCC(c3cc(F)cc4c3CN(C3CCC(=O)NC3=O)C4=O)CC2)c1OC]

A110

3-(4-(1-(8-(4-(((S)-1-(3-Amino-5-(trifluoromethyl)phenyl)ethyl)amino)-6,7-dimethoxy-2-methylquinazolin-8-yl)octyl)piperidin-4-yl)-6-fluoro-1-oxoisoindolin-2-yl)-piperidine-2,6-dione A111. $^1$H NMR (400 MHz, DMSO-d$_6$) δ 11.00 (s, 1H), 8.44 (s, 2H), 8.00 (d, J=8.4 Hz, 1H), 7.65 (s, 1H), 7.48-7.33 (m, 2H), 6.88 (s, 1H), 6.85 (s, 1H), 6.69 (s, 1H), 5.60-5.50 (m, 3H), 5.13 (dd, J=4.4 Hz, 14.4 Hz, 1H), 4.54-4.28 (m, 2H), 3.94 (s, 3H), 3.80 (s, 3H), 3.00-2.90 (m, 5H), 2.70-2.55 (m, 2H), 2.45-2.40 (m, 1H), 2.38 (s, 3H), 2.30-2.24 (m, 2H), 2.05-1.90 (m, 5H), 1.75-1.65 (m, 4H), 1.55 (d, J=7.2 Hz, 3H), 1.52-1.35 (m, 4H), 1.35-1.20 (m, 6H); MS (ESI) m/z: 862.6 [M+H]$^+$.

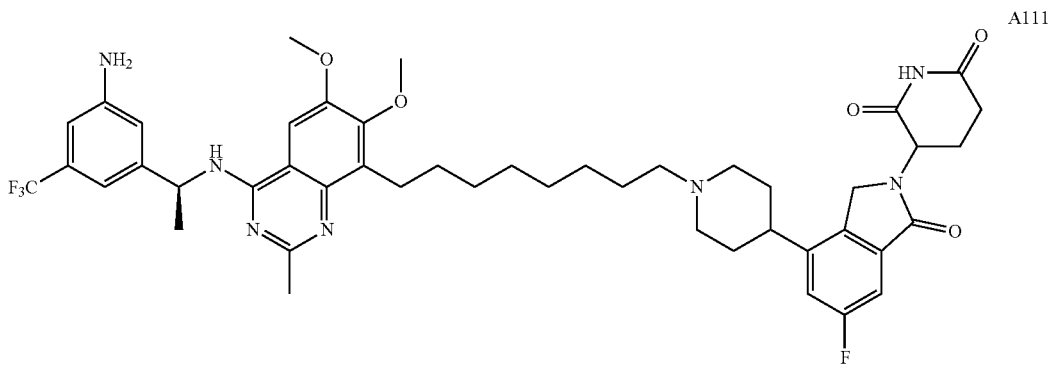 [SMILES: COc1cc2c(N[C@@H](C)c3cc(N)cc(C(F)(F)F)c3)nc(C)nc2c(CCCCCCCCN2CCC(c3cc(F)cc4c3CN(C3CCC(=O)NC3=O)C4=O)CC2)c1OC]

A111

3-(4-((4-(((7-(6,7-Dimethoxy-2-methyl-4-(((S)-1-(4-(2-((methylamino)methyl)-phenyl)thiophen-2-yl)ethyl)amino)quinazolin-8-yl)heptyl)amino)methyl)benzyl)oxy)-1-oxoisoindolin-2-yl)piperidine-2,6-dione A112. $^1$H NMR (400 MHz, DMSO-d$_6$) δ 13.00 (s, 1H), 10.96 (s, 1H), 10.52 (s, 1H), 9.49-9.18 (m, 3H), 8.22 (s, 1H), 7.77-7.72 (m, 1H), 7.60-7.53 (m, 5H), 7.49-7.42 (m, 3H), 7.40-7.29 (m, 4H), 6.13 (s, 1H), 5.29 (s, 2H), 5.11 (dd, J=4.8, 13.2 Hz, 1H), 4.45-4.26 (m, 2H), 4.18-4.08 (m, 4H), 4.00 (s, 3H), 3.89 (s, 3H), 3.11-3.01 (m, 2H), 2.96-2.76 (m, 6H), 2.62-2.55 (m, 3H), 2.47-2.43 (m, 1H), 2.03-1.97 (m, 1H), 1.84 (d, J=5.6 Hz, 3H), 1.71-1.60 (m, 2H), 1.51-1.35 (m, 4H), 1.32-1.23 (m, 6H); MS (ESI) m/z: 924.6 [M+H]$^+$.

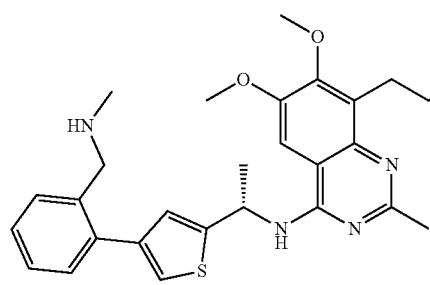

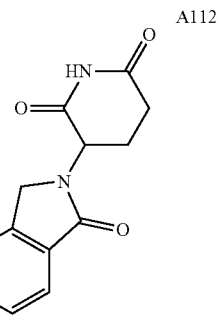

A112

3-(4-((4-(((7-(6,7-Dimethoxy-2-methyl-4-((((R)-1-(4-(2-((methylamino)methyl)-phenyl)thiophen-2-yl)ethyl)amino)quinazolin-8-yl)heptyl)amino)methyl)benzyl)oxy)-1-oxoisoindolin-2-yl)piperidine-2,6-dione A113. $^1$H NMR (400 MHz, DMSO-d$_6$) δ 13.05 (s, 1H), 10.96 (s, 1H), 10.57 (s, 1H), 9.49-9.18 (m, 3H), 8.25 (s, 1H), 7.77-7.72 (m, 1H), 7.62-7.57 (m, 2H), 7.55-7.52 (m, 3H), 7.49-7.43 (m, 3H), 7.38-7.35 (m, 2H), 7.34-7.30 (m, 2H), 6.13 (s, 1H), 5.29 (s, 2H), 5.11 (dd, J=5.2, 13.2 Hz, 1H), 4.45-4.26 (m, 2H), 4.17-4.06 (m, 4H), 4.00 (s, 3H), 3.90 (s, 3H), 3.11-3.05 (m, 2H), 2.96-2.76 (m, 6H), 2.64-2.55 (m, 3H), 2.47-2.43 (m, 1H), 2.02-1.97 (m, 1H), 1.84 (d, J=6.4 Hz, 3H), 1.71-1.61 (m, 2H), 1.49-1.37 (m, 4H), 1.32-1.23 (m, 6H); MS (ESI) m/z: 924.6 [M+H]$^+$.

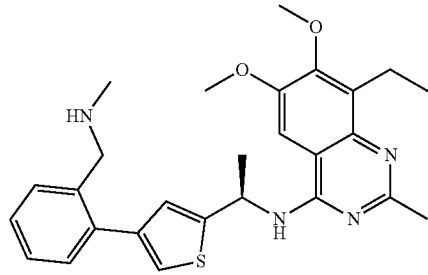

A113

3-(5-(1-(7-(4-(((S)-1-(3-(1,1-Difluoro-2-hydroxyethyl)phenyl)ethyl)amino)-6,7-dimethoxy-2-methylquinazolin-8-yl)heptyl)piperidin-4-yl)-6-fluoro-1-oxoisoindolin-2-yl)-piperidine-2,6-dione A114. $^1$H NMR (400 MHz, DMSO-d$_6$) δ 11.00 (s, 1H), 8.18 (s, 1H), 8.06 (d, J=8.0 Hz, 1H), 7.65-7.56 (m, 4H), 7.48-7.35 (m, 3H), 5.70-5.65 (m, 1H), 5.10 (dd, J=5.2 Hz, 13.6 Hz, 1H), 4.43-4.25 (m, 2H), 3.94 (s, 3H), 3.86-3.80 (m, 5H), 3.03-2.86 (m, 6H), 2.62-2.51 (m, 1H), 2.50-2.33 (m, 6H), 2.15-1.97 (m, 3H), 1.78-1.70 (m, 4H), 1.60 (d, J=7.2 Hz, 3H), 1.52-1.42 (m, 4H), 1.33-1.25 (m, 6H); MS (ESI) m/z: 845.6 [M+H]$^+$.

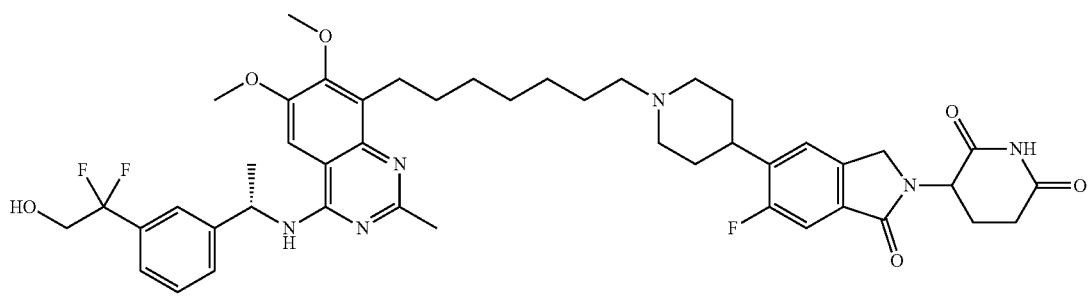

A114

3-(6-(1-(7-(6,7-Dimethoxy-2-methyl-4-(((R)-1-(4-(2-((methylamino)methyl)-phenyl)thiophen-2-yl)ethyl)amino)quinazolin-8-yl)heptyl)piperidin-4-yl)-1-oxoisoindolin-2-yl)piperidine-2,6-dione A115. $^1$H NMR (400 MHz, DMSO-$d_6$) δ 11.00 (s, 1H), 8.23-8.18 (m, 3H), 7.62 (s, 1H), 7.57-7.52 (m, 3H), 7.43 (d, J=1.6 Hz, 1H), 7.36-7.32 (m, 2H), 7.26-7.23 (m, 1H), 6.04-5.93 (m, 1H), 5.10 (dd, J=4.8, 13.2 Hz, 1H), 4.43-4.26 (m, 2H), 3.91 (s, 3H), 3.81-3.78 (m, 6H), 3.10-2.98 (m, 4H), 2.94-2.86 (m, 1H), 2.67-2.56 (m, 3H), 2.47 (s, 3H), 2.32 (s, 3H), 2.14 (t, J=10.1 Hz, 2H), 2.01-1.96 (m, 1H), 1.83-1.70 (m, 6H), 1.56-1.44 (m, 4H), 1.32-1.23 (m, 6H); MS (ESI) m/z: 872.6 [M+H]$^+$.

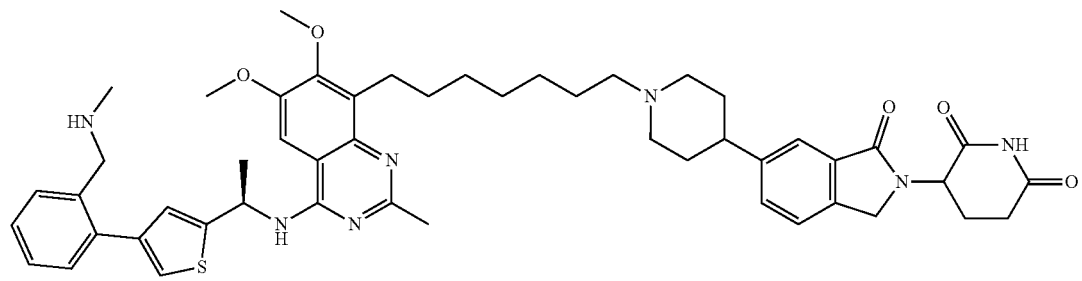

A115

3-(6-(1-(7-(6,7-Dimethoxy-2-methyl-4-(((S)-1-(4-(2-((methylamino)methyl)-phenyl)thiophen-2-yl)ethyl)amino)quinazolin-8-yl)heptyl)piperidin-4-yl)-1-oxoisoindolin-2-yl)piperidine-2,6-dione A116. $^1$H NMR (400 MHz, DMSO-$d_6$) δ 11.00 (s, 1H), 8.23-8.18 (m, 3H), 7.62 (s, 1H), 7.57-7.52 (m, 3H), 7.43 (d, J=1.6 Hz, 1H), 7.36-7.32 (m, 2H), 7.26-7.23 (m, 1H), 6.04-5.93 (m, 1H), 5.09 (dd, J=5.2, 13.2 Hz, 1H), 4.44-4.26 (m, 2H), 3.91 (s, 3H), 3.84-3.76 (m, 6H), 3.12-2.98 (m, 4H), 2.94-2.86 (m, 1H), 2.67-2.56 (m, 3H), 2.47 (s, 3H), 2.33 (s, 3H), 2.16 (t, J=11.2 Hz, 2H), 2.02-1.94 (m, 1H), 1.83-1.70 (m, 6H), 1.56-1.44 (m, 4H), 1.32-1.23 (m, 6H); MS (ESI) m/z: 872.6 [M+H]$^+$.

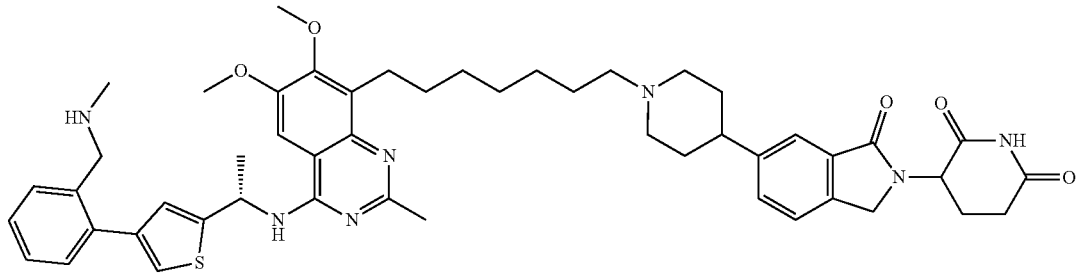

A116

3-(4-(1-(7-(4-(((S)-1-(3-(1,1-Difluoro-2-hydroxyethyl)phenyl)ethyl)amino)-6,7-dimethoxy-2-methylquinazolin-8-yl)heptyl)piperidin-4-yl)-6-fluoro-1-oxoisoindolin-2-yl)-piperidine-2,6-dione A117. $^1$H NMR (400 MHz, DMSO-$d_6$) δ 11.00 (s, 1H), 8.14 (s, 1H), 8.07 (d, J=7.6 Hz, 1H), 7.66-7.63 (m, 2H), 7.57 (d, J=8.0 Hz, 1H), 7.43-7.36 (m, 4H), 5.69-5.59 (m, 2H), 5.14 (dd, J=5.2 Hz, 12.8 Hz, 1H), 4.54-4.32 (m, 2H), 3.95 (s, 3H), 3.87-3.80 (m, 5H), 3.16-3.12 (m, 2H), 3.00-2.88 (m, 3H), 2.71-2.51 (m, 4H), 2.50-2.27 (m, 6H), 2.04-2.00 (m, 1H), 1.90-1.75 (m, 4H), 1.60 (d, J=8.0 Hz, 3H), 1.55-1.50 (m, 4H), 1.35-1.26 (m, 6H); MS (ESI) m/z: 845.6 [M+H]$^+$.

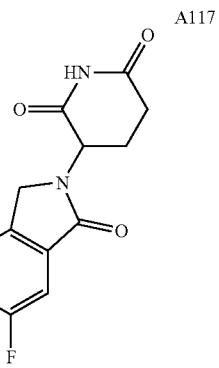

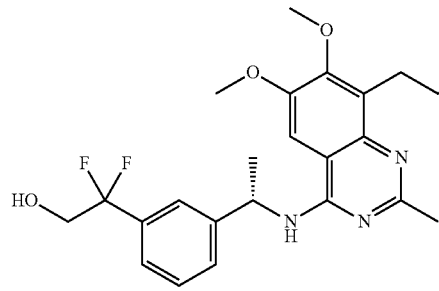

3-(4-((4-(((7-(4-(((R)-1-(3-Bromophenyl)ethyl)amino)-6,7-dimethoxy-2-methyl-quinazolin-8-yl)heptyl)amino)methyl)benzyl)oxy)-1-oxoisoindolin-2-yl)piperidine-2,6-dione A118. $^1$H NMR (400 MHz, DMSO-d$_6$) δ 12.83 (s, 1H), 10.96 (s, 1H), 10.26 (s, 1H), 9.16 (s, 2H), 8.20 (s, 1H), 7.73 (s, 1H), 7.57-7.52 (m, 5H), 7.47 (t, J=8.0 Hz, 2H), 7.35-7.29 (m, 4H), 5.80 (t, J=5.6 Hz, 1H), 5.28 (s, 2H), 5.11 (dd, J=5.2, 13.2 Hz, 1H), 4.45-4.25 (m, 2H), 4.11 (s, 2H), 4.03 (s, 3H), 3.90 (s, 3H), 3.03-2.98 (m, 2H), 2.94-2.85 (m, 3H), 2.70-2.66 (m, 3H), 2.60-2.53 (m, 1H), 2.43-2.32 (m, 1H), 2.02-1.97 (m, 2H), 1.70-1.63 (m, 5H), 1.45-1.20 (m, 8H); MS (ESI) m/z: 877.4 [M+H]$^+$.

(2S,4R)-1-((S)-2-(9-(6,7-Dimethoxy-2-methyl-4-(((R)-1-(4-(2-((methylamino)-methyl)phenyl)thiophen-2-yl)ethyl)amino)quinazolin-8-yl)nonanamido)-3,3-dimethylbutanoyl)-4-hydroxy-N-(4-(4-methylthiazol-5-yl)benzyl)pyrrolidine-2-carboxamide A402. $^1$H NMR (400 MHz, DMSO-d$_6$) δ 12.87 (s, 1H), 10.56 (s, 1H), 9.42 (s, 2H), 9.01 (s, 1H), 8.56 (t, J=6.0 Hz, 1H), 8.26 (s, 1H), 7.83-7.74 (m, 2H), 7.54 (d, J=1.6 Hz, 1H), 7.45-7.37 (m, 9H), 6.14 (t, J=7.2 Hz, 1H), 4.53 (d, J=9.2 Hz, 1H), 4.44-4.34 (m, 8H), 4.24-4.18 (m, 3H), 4.04 (s, 3H), 3.90 (s, 3H), 3.68-3.59 (m, 2H), 3.09-2.98 (m, 2H), 2.79 (s, 3H), 2.44 (s, 3H), 2.33-2.22 (m, 1H), 2.14-2.02 (m, 1H), 1.96-1.88 (m, 1H), 1.85-1.84 (m, 3H), 1.51-1.23 (m, 14H), 0.92 (s, 9H); MS (ESI) m/z: 1017.5 [M+H]$^+$.

3-(4-(2-(4-(6-(4-(((R)-1-(3-(1,1-Difluoro-2-hydroxyethyl)phenyl)ethyl)amino)-6,7-dimethoxy-2-methylquinazolin-8-yl)hexyl)piperazin-1-yl)-2-oxoethoxy)phenyl)piperidine-2,6-dione A304. MS (ESI) m/z: 817.2 [M+H]$^+$.

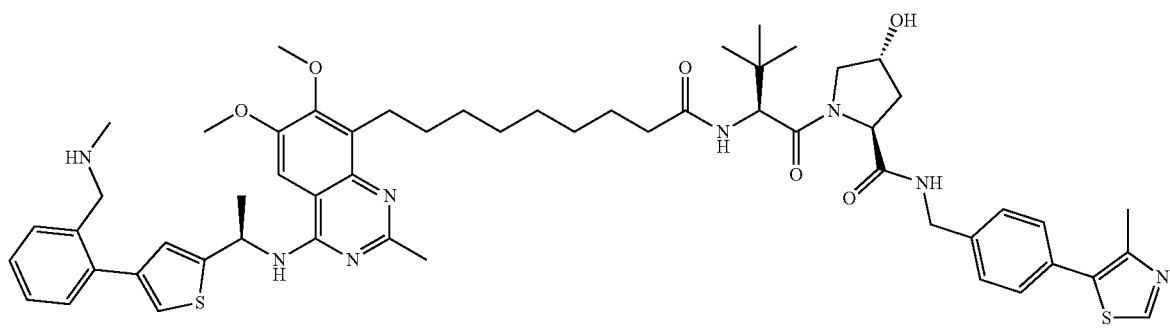
A402
3-(4-(1-(7-((4-(((R)-1-(3-Amino-5-(trifluoromethyl)phenyl)ethyl)amino)-2-methyl-6-(((S)-tetrahydrofuran-3-yl)oxy)quinazolin-7-yl)oxy)heptyl)piperidin-4-yl)-6-fluoro-1-oxoisoindolin-2-yl)piperidine-2,6-dione B101. MS (ESI) m/z: 877.6 [M+H]+.
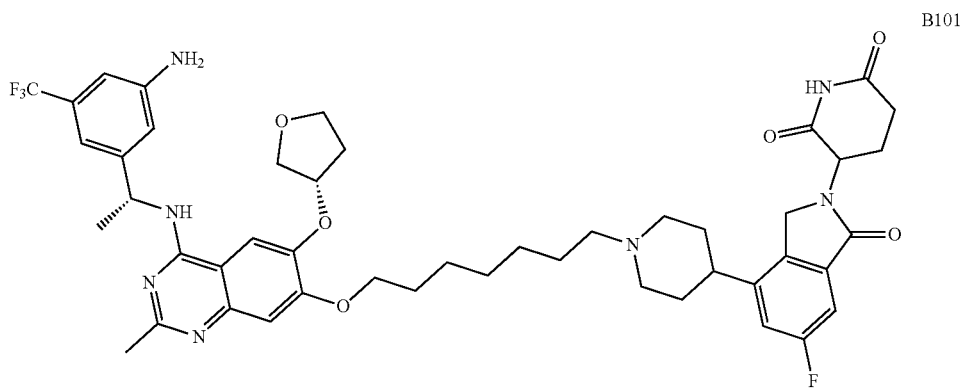 [SMILES: Cc1nc(N[C@H](C)c2cc(N)cc(C(F)(F)F)c2)c2cc(O[C@H]3CCOC3)c(OCCCCCCCN3CCC(c4cc(F)cc5c4CN(C4CCC(=O)NC4=O)C5=O)CC3)cc2n1]
B101
3-(5-(1-(11-((4-(((R)-1-(3-Bromophenyl)ethyl)amino)-6-methoxy-2-methyl-quinazolin-7-yl)oxy)undecanoyl)piperidin-4-yl)-6-fluoro-1-oxoisoindolin-2-yl)piperidine-2,6-dione B102. MS (ESI) m/z: 901.0 [M+H]+.
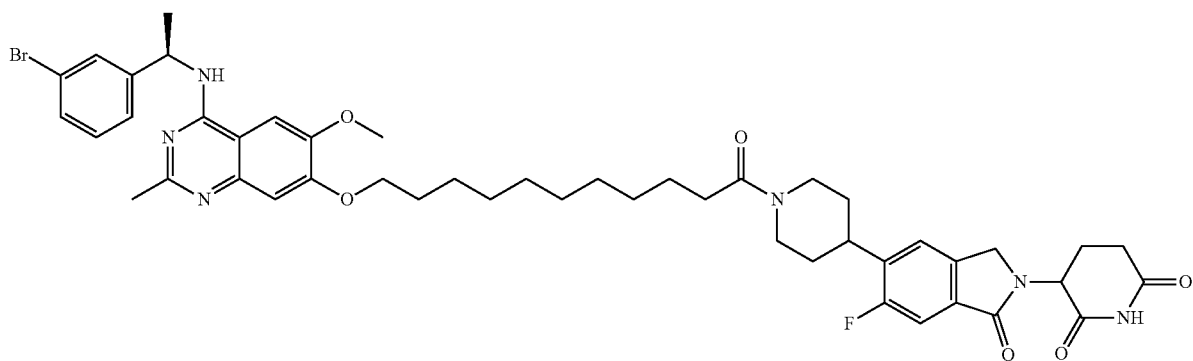
B102

3-(6-((7-((4-(((R)-1-(3-Bromophenyl)ethyl)amino)-6-methoxy-2-methyl-quinazolin-7-yl)oxy)heptyl)amino)-1-oxo-3,4-dihydroisoquinolin-2(1H)-yl)piperidine-2,6-dione B103. MS (ESI) m/z: 752.2 [M+H]⁺.

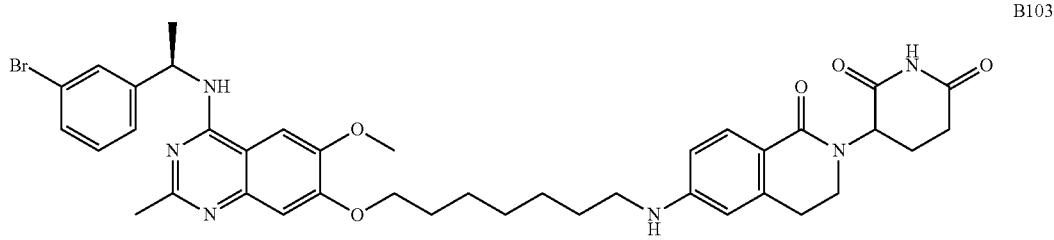 [SMILES: COc1cc2c(N[C@H](C)c3cccc(Br)c3)nc(C)nc2cc1OCCCCCCCNc1ccc2c(c1)CCN(C1CCC(=O)NC1=O)C2=O]

3-(5-((9-((4-(((R)-1-(3-Bromophenyl)ethyl)amino)-6-methoxy-2-methyl-quinazolin-7-yl)oxy)nonyl)amino)-1-oxo-3,4-dihydroisoquinolin-2(1H)-yl)piperidine-2,6-dione B104. MS (ESI) m/z: 785.2 [M+H]⁺.

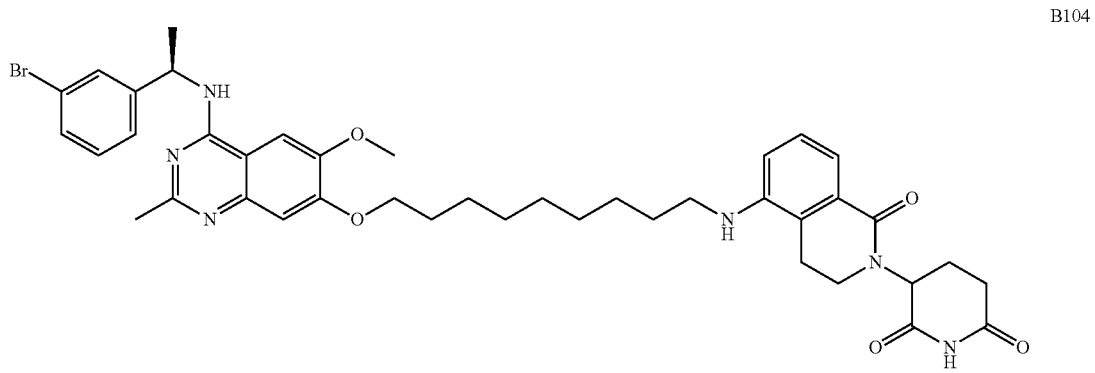 [SMILES: COc1cc2c(N[C@H](C)c3cccc(Br)c3)nc(C)nc2cc1OCCCCCCCCCNc1cccc2c1CCN(C1CCC(=O)NC1=O)C2=O]

3-(5-((7-((4-(((R)-1-(3-Bromophenyl)ethyl)amino)-6-methoxy-2-methyl-quinazolin-7-yl)oxy)heptyl)amino)-1-oxo-3,4-dihydroisoquinolin-2(1H)-yl)piperidine-2,6-dione B105. MS (ESI) m/z: 757.2 [M+H]⁺.

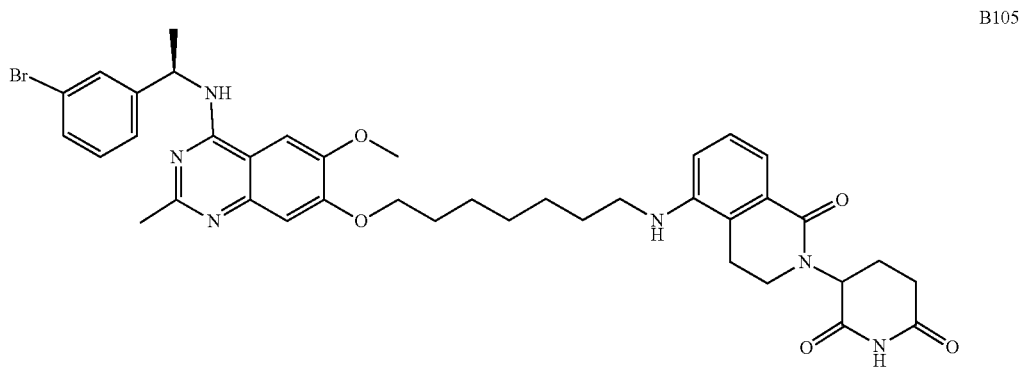 [SMILES: COc1cc2c(N[C@H](C)c3cccc(Br)c3)nc(C)nc2cc1OCCCCCCCNc1cccc2c1CCN(C1CCC(=O)NC1=O)C2=O]

3-(5-(((11-((4-(((R)-1-(3-Bromophenyl)ethyl)amino)-6-methoxy-2-methyl-quinazolin-7-yl)oxy)undecyl)amino)-1-oxo-3,4-dihydroisoquinolin-2(1H)-yl)piperidine-2,6-dione B106. MS (ESI) m/z: 813.5 [M+H]+.

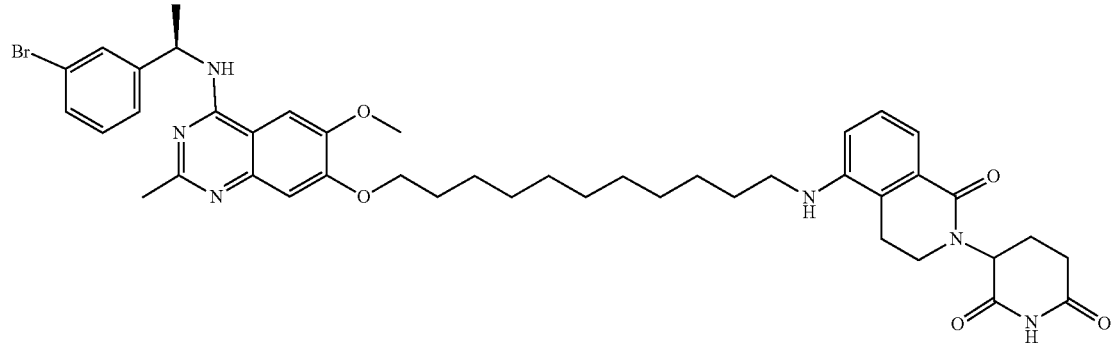

3-(6-((9-((4-(((R)-1-(3-Bromophenyl)ethyl)amino)-6-methoxy-2-methyl-quinazolin-7-yl)oxy)nonyl)amino)-1-oxo-3,4-dihydroisoquinolin-2(1H)-yl)piperidine-2,6-dione B107. MS (ESI) m/z: 785.3 [M+H]+.

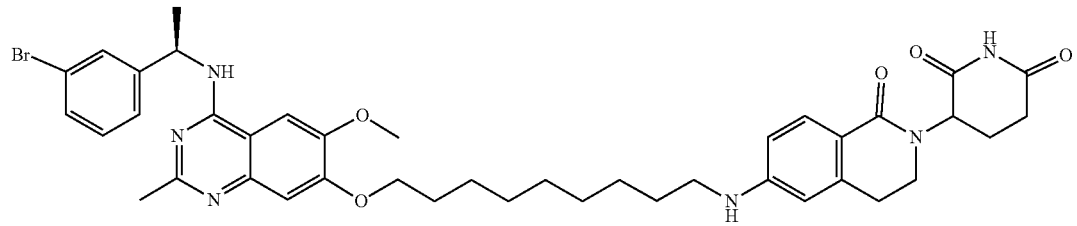

3-(6-((11-((4-(((R)-1-(3-Bromophenyl)ethyl)amino)-6-methoxy-2-methyl-quinazolin-7-yl)oxy)undecyl)amino)-1-oxo-3,4-dihydroisoquinolin-2(1H)-yl)piperidine-2,6-dione B108. MS (ESI) m/z: 813.5 [M+H]+.

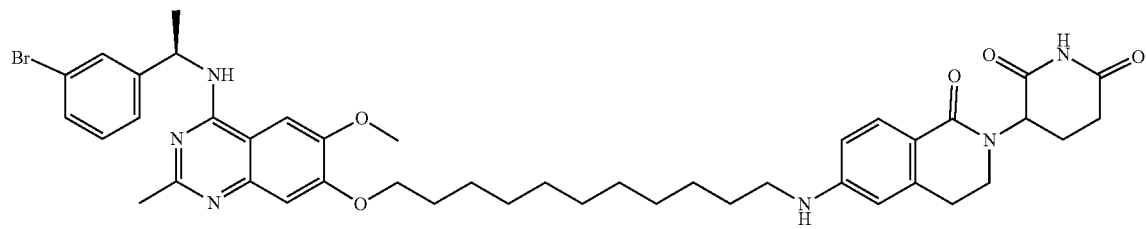

The following compounds are prepared similarly according to the synthetic procedures or methodologies exemplified herein.

3-(5-(1-(5-(4-(((R)-1-(3-(1,1-Difluoro-2-hydroxyethyl)phenyl)ethyl)amino)-6,7-dimethoxy-2-methylquinazolin-8-yl)pentyl)piperidin-4-yl)-6-fluoro-1-oxoisoindolin-2-yl)-piperidine-2,6-dione A119.

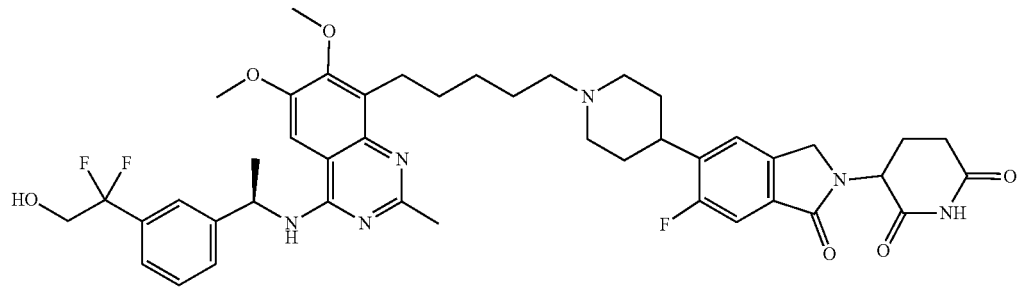

3-(5-(1-(6-(4-(((R)-1-(3-(1,1-Difluoro-2-hydroxyethyl)phenyl)ethyl)amino)-6,7-dimethoxy-2-methylquinazolin-8-yl)hexyl)piperidin-4-yl)-6-fluoro-1-oxoisoindolin-2-yl)-piperidine-2,6-dione A120.

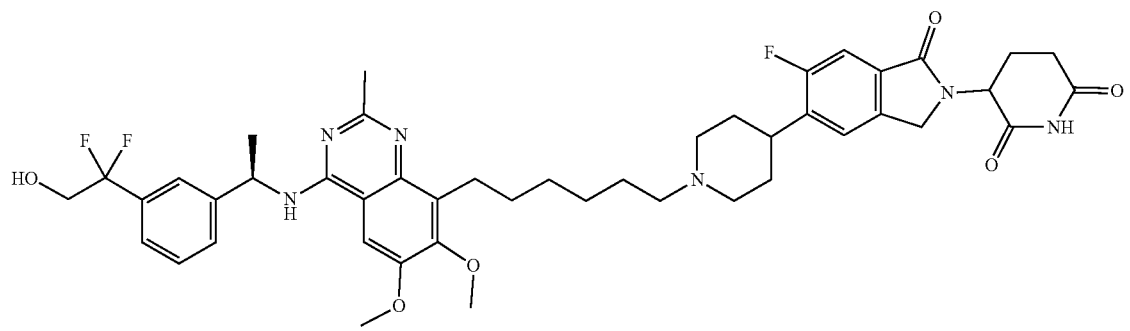

3-(5-(1-((1-(3-(4-(((R)-1-(3-(1,1-Difluoro-2-hydroxyethyl)phenyl)ethyl)amino)-6,7-dimethoxy-2-methylquinazolin-8-yl)propyl)piperidin-4-yl)methyl)piperidin-4-yl)-6-fluoro-1-oxoisoindolin-2-yl)piperidine-2,6-dione A121.

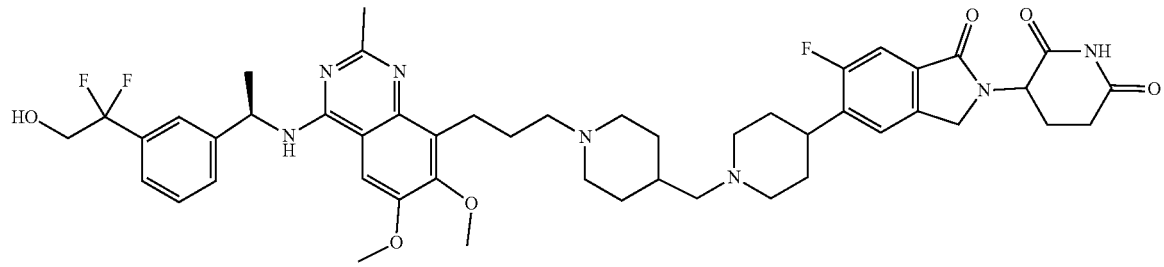

3-(5-(1'-(4-(4-(((R)-1-(3-(1,1-Difluoro-2-hydroxyethyl)phenyl)ethyl)amino)-6,7-dimethoxy-2-methylquinazolin-8-yl)butyl)-[1,4'-bipiperidin]-4-yl)-6-fluoro-1-oxoisoindolin-2-yl)piperidine-2,6-dione A122.

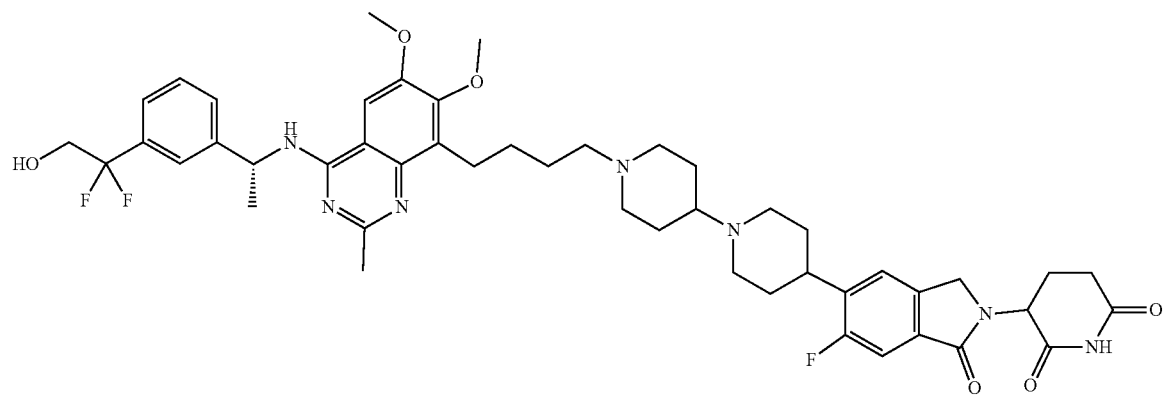

A122

3-(5-(1-(2-(4-(2-(4-(((R)-1-(3-(1,1-Difluoro-2-hydroxyethyl)phenyl)ethyl)amino)-6,7-dimethoxy-2-methylquinazolin-8-yl)ethyl)piperazin-1-yl)ethyl)piperidin-4-yl)-6-fluoro-1-oxoisoindolin-2-yl)piperidine-2,6-dione A123.

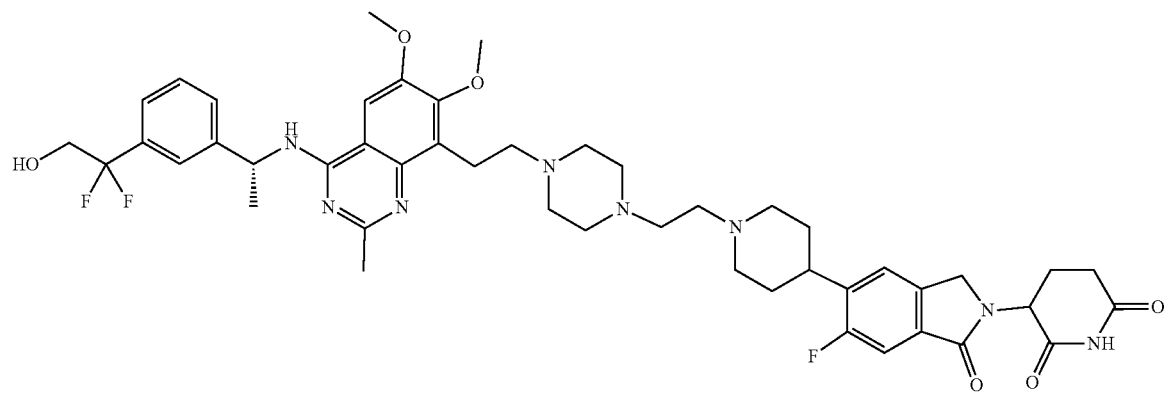

A123

3-(7-(2-(4-(4-(4-(((R)-1-(3-(1,1-Difluoro-2-hydroxyethyl)phenyl)ethyl)amino)-6,7-dimethoxy-2-methylquinazolin-8-yl)butyl)piperazin-1-yl)-2-oxoethoxy)-1-methyl-1H-indazol-3-yl)piperidine-2,6-dione A201.

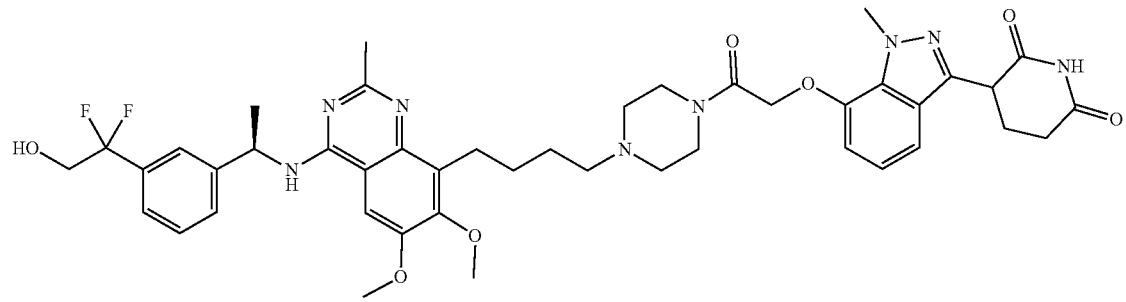

A201

3-(6-(2-(4-(4-(4-(((R)-1-(3-(1,1-Difluoro-2-hydroxy-ethyl)phenyl)ethyl)amino)-6,7-dimethoxy-2-methylquinazolin-8-yl)butyl)piperazin-1-yl)-2-oxoethoxy)-1-methyl-1H-indazol-3-yl)piperidine-2,6-dione A202.

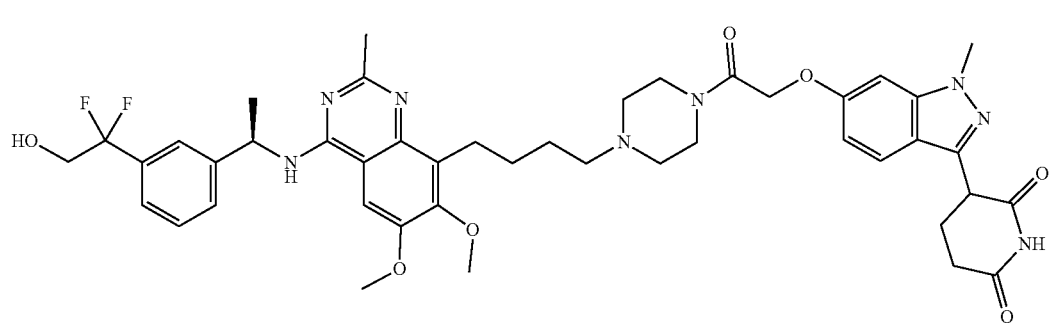

3-(7-(2-(4-(6-(4-(((R)-1-(3-(1,1-Difluoro-2-hydroxy-ethyl)phenyl)ethyl)amino)-6,7-dimethoxy-2-methylquinazolin-8-yl)hexyl)piperazin-1-yl)-2-oxoethoxy)-1-methyl-1H-indazol-3-yl)piperidine-2,6-dione A203.

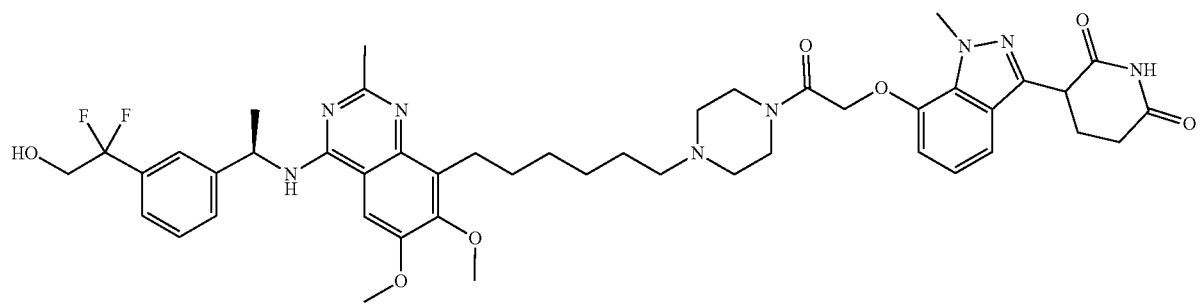

3-(7-(2-(4-(8-(4-(((R)-1-(3-(1,1-Difluoro-2-hydroxy-ethyl)phenyl)ethyl)amino)-6,7-dimethoxy-2-methylquinazolin-8-yl)octyl)piperazin-1-yl)-2-oxoethoxy)-1-methyl-1H-indazol-3-yl)piperidine-2,6-dione A205.

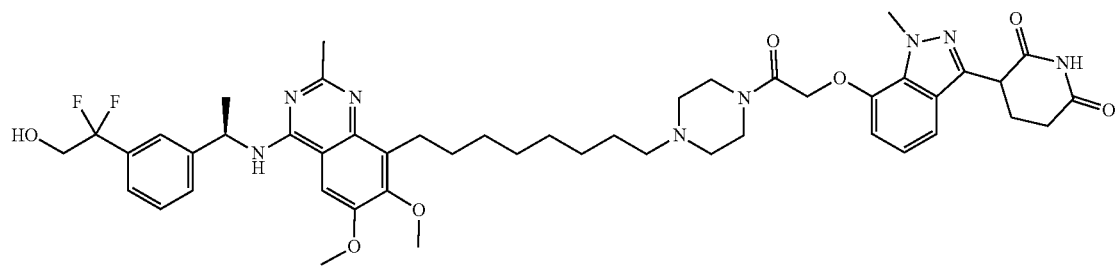

3-(6-(2-(4-(8-(4-(((R)-1-(3-(1,1-Difluoro-2-hydroxy-ethyl)phenyl)ethyl)amino)-6,7-dimethoxy-2-methylquinazolin-8-yl)octyl)piperazin-1-yl)-2-oxoethoxy)-1-methyl-1H-indazol-3-yl)piperidine-2,6-dione A206.

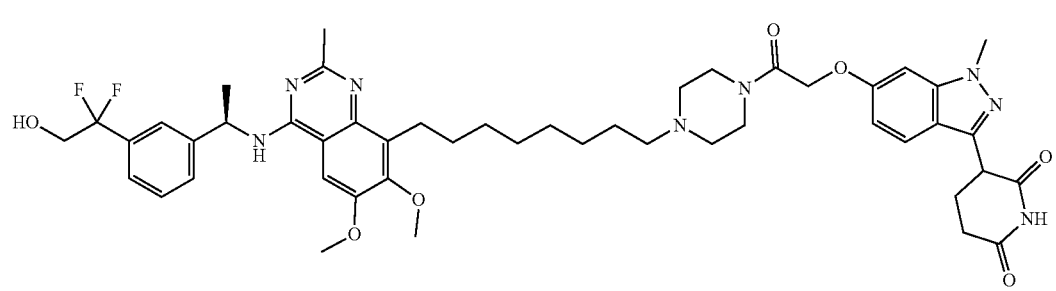

3-(3-(2-(4-(4-(4-(((R)-1-(3-(1,1-Difluoro-2-hydroxy-ethyl)phenyl)ethyl)amino)-6,7-dimethoxy-2-methylquinazolin-8-yl)butyl)piperazin-1-yl)-2-oxoethoxy)phenyl)piperidine-2,6-dione A301.

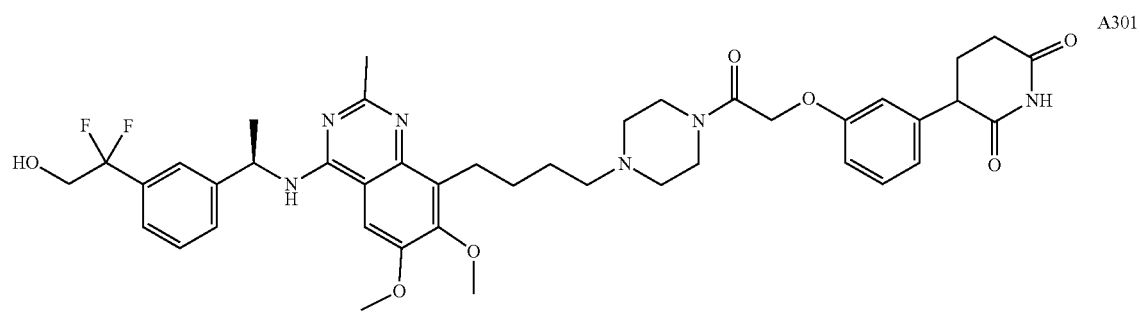 [SMILES: COc1cc2c(N[C@H](C)c3cccc(C(F)(F)CO)c3)nc(C)nc2c(CCCCN2CCN(C(=O)COc3cccc(C4CCC(=O)NC4=O)c3)CC2)c1OC]

3-(4-(2-(4-(4-(4-(((R)-1-(3-(1,1-Difluoro-2-hydroxy-ethyl)phenyl)ethyl)amino)-6,7-dimethoxy-2-methylquinazolin-8-yl)butyl)piperazin-1-yl)-2-oxoethoxy)phenyl)piperidine-2,6-dione A302.

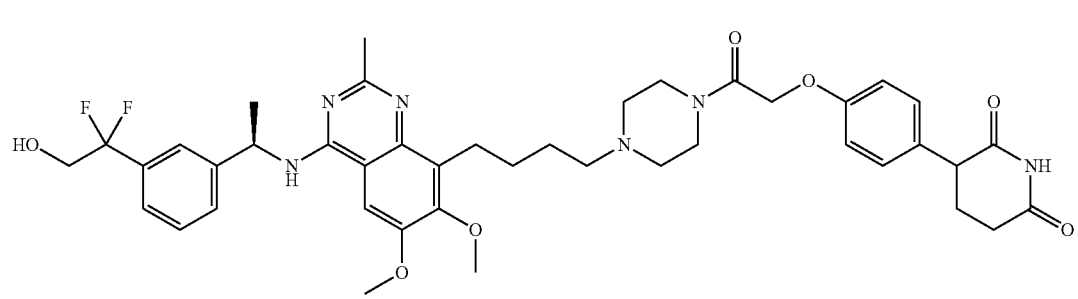

3-(3-(2-(4-(8-(4-(((R)-1-(3-(1,1-Difluoro-2-hydroxyethyl)phenyl)ethyl)amino)-6,7-dimethoxy-2-methylquinazolin-8-yl)octyl)piperazin-1-yl)-2-oxoethoxy)phenyl)piperidine-2,6-dione A305.

streptomycin, and penicillin. The cells were seeded in a white walled 384-well plate at 12,500 cells/well in 50 μL culture media. The cells were incubated at 37° C. under 5% $CO_2$ overnight. The cells were then treated with DMSO

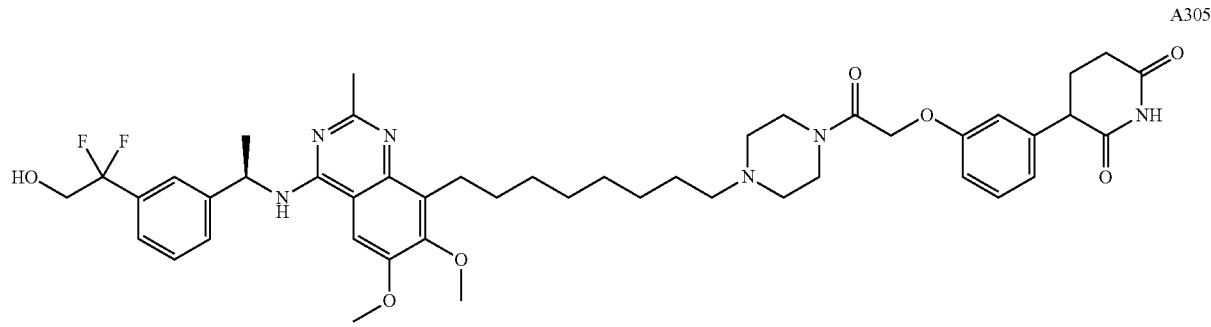 [SMILES: COc1cc2c(N[C@H](C)c3cccc(C(F)(F)CO)c3)nc(C)nc2c(CCCCCCCCN2CCN(C(=O)COc3cccc(C4CCC(=O)NC4=O)c3)CC2)c1OC]

A305

3-(4-(2-(4-(8-(4-(((R)-1-(3-(1,1-Difluoro-2-hydroxyethyl)phenyl)ethyl)amino)-6,7-dimethoxy-2-methylquinazolin-8-yl)octyl)piperazin-1-yl)-2-oxoethoxy)phenyl)piperidine-2,6-dione A306.

(control) or a compound for 6 h at 37° C. under 5% $CO_2$. After incubation, 25 μL media was removed from each cell and 25 μL NANO-GLO® lytic detection reagent was added to each well. After a 10 min incubation with shaking,

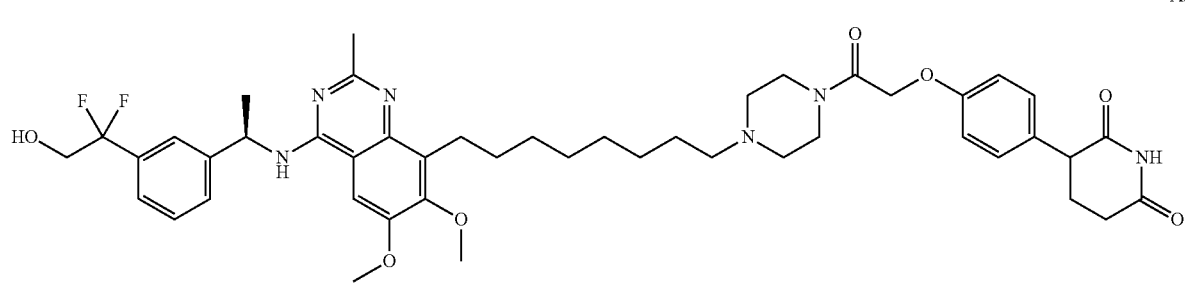

A306

Example B1

Cell Viability Assay

H358, SW48, and AsPC-1 cells were cultured in RPMI 1640 media supplemented with 10% fetal bovine serum, streptomycin, and penicillin. Lovo and SW480 cells were cultured in DMEM media supplemented with 10% fetal bovine serum, streptomycin, and penicillin. The cell lines were plated in their respective medium supplemented with 2.5% fetal bovine serum, streptomycin, and penicillin. All cell lines were plated in white walled 96-well plates at 2,000 cells/well or 384-well plates at 500 cells/well, except Lovo, which were plated at 4,000 or 1,000 cells/well, respectively. The cells were incubated in DMSO (control) or a compound for 3 days at 37° C. under 5% $CO_2$. A CELLTITER-GLO® reagent (100 μL) was then added to each well. After a 10 min incubation with shaking, luminescence was measured using a PERKINELMER ENVISION® multimode plate reader.

Example B2

SOS1-HiBiT Degradation Assay

HEK293 cells were engineered to express a HiBiT-tagged endogenous SOS1 protein. The cells were cultured in DMEM media supplemented with 10% fetal bovine serum, luminescence was measured using a PERKINELMER ENVISION® multimode plate reader.

The results are summarized in Table 1, where "A" represents a $DC_{50}$ of no greater than 100 nM, "B" represents a $DC_{50}$ of greater than 100 nM and no greater than 500 nM; "C" represents a $DC_{50}$ of greater than 500 nM and no greater than 2 μM; and "D" represents a $DC_{50}$ of greater than 2 μM; and where "A'" represents a $D_{max}$ of no less than 70%, "B'" represents a $D_{max}$ of less than 70% and no less than 50%; "C'" represents a $D_{max}$ of less than 50% and no less than 30%; and "D'" represents a $D_{max}$ of less than 30%. Compounds C1 and C2 are (R)-2-(3-(1-(((6,7-dimethoxy-2-methylquinazolin-4-yl)amino)ethyl)phenyl)-2,2-difluoroethan-1-ol and (R)—N-(1-(3-amino-5-(trifluoromethyl)phenyl)ethyl)-6,7-dimethoxy-2-methylquinazolin-4-amine, respectively.

TABLE 1

| Effect on SOS1 Protein Degradation | | |
|---|---|---|
| | Degradation | |
| Compd. No. | $DC_{50}$ | $D_{max}$ |
| C1 | >10,000 nM | 0% |
| C2 | >10,000 nM | 0% |
| A102 | D | D |

Example B3

Protein Degradation Assay

SW48 cells were cultured in RPMI 1640 media supplemented with 10% fetal bovine serum, streptomycin, and penicillin. The cells were plated in a 6 well plate at 2 million cells/well in a culturing media. After overnight incubation, the cells were treated with DMSO (control) or a compound for 24 h at 37° C. under 5% $CO_2$. The media was then removed, and cells were washed with 1×PBS and lysed in the well with an IP Lysis buffer solution. The cells were scraped, and collected into an Eppendorf tube and vortexed. The lysates were stored at −80° C. until protein quantification.

A protein assay was conducted to determine lysate protein concentration, and loading samples were prepared to run on SDS-PAGE for western blot analysis. Samples were run by SDS-PAGE and blots were blocked with INTERCEPT® (PBS) blocking buffer for 1 h at room temperature. Primary antibodies (SOS1 rabbit mAb, 3-actin mouse mAb, p44/42 MAPK (Erk1/2) rabbit mAb, and phospho-p44/42 MAPK (Erk1/2) mouse mAb) were prepared in INTERCEPT® (PBS) blocking buffer and added to blots after the blocking step. After overnight incubation at 4° C. with the primary antibodies, the blots were washed with 0.1% TWEEN-PBS and treated with secondary antibody solutions (IRDYE® 680RD goat anti-rabbit and IRDYE® 800CW goat anti-mouse secondary antibody in the INTERCEPT® (PBS) blocking buffer) for 2 h at room temperature. The blots were washed with 0.1% Tween PBS and then imaged with ODYSSET® CLx.

The examples set forth above are provided to give those of ordinary skill in the art with a complete disclosure and description of how to make and use the claimed embodiments and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula (I):

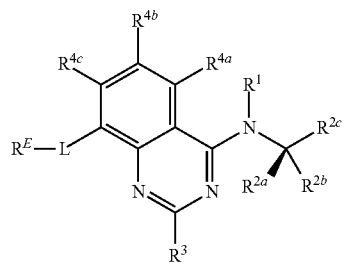

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof; wherein:

$R^1$ is hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^3$, $R^{4a}$, $R^{4b}$, and $R^{4c}$ are each independently (i) hydrogen, deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{14}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$, $R^{2a}$ and $R^{2b}$ are each independently hydrogen, deuterium, halo, $C_{1-6}$ alkyl, $C_{2-6}$ alkenyl, $C_{2-6}$ alkynyl, $C_{3-10}$ cycloalkyl, $C_{6-14}$ aryl, heteroaryl, or heterocyclyl;

$R^{2c}$ is $C_{3-10}$ cycloalkyl, $C_{6-14}$ aryl, heteroaryl, or heterocyclyl;

$R^E$ is a moiety having the structure of Formula (EC-I), (EC-XV), (EC-XXVIII), or (EC-XXXV):

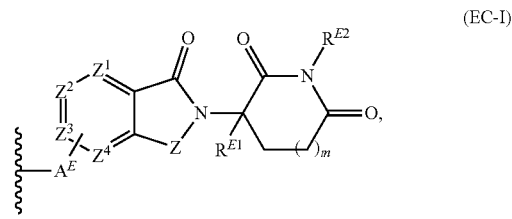

(EC-I)

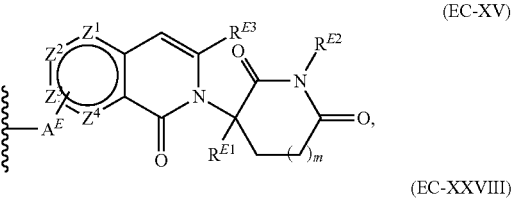

(EC-XV)

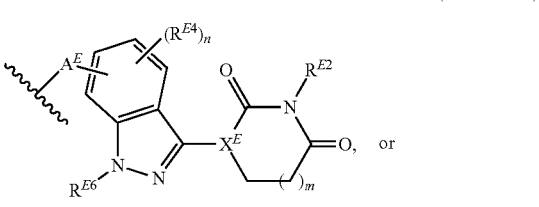

(EC-XXVIII)

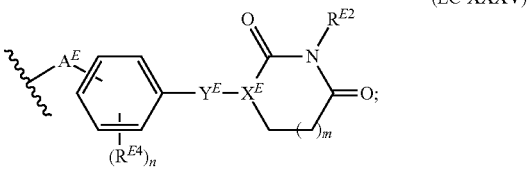

(EC-XXXV)

wherein:
  each $A^E$ is independently a bond, —O—, —N($R^{1b}$)—, —S—, $C_{1-6}$ alkylene, $C_{1-6}$ heteroalkylene, $C_{2-6}$ alkenylene, $C_{2-6}$ heteroalkenylene, $C_{2-6}$ alkynylene, $C_{2-6}$ heteroalkynylene, $C_{3-10}$ cycloalkylene, $C_{6-14}$ arylene, $C_{7-15}$ aralkylene, heteroarylene, heterocyclylene, $C_{1-6}$ heteroalkylene-$C_{6-14}$ arylene, $C_{1-6}$ heteroalkylene-heterocyclylene, or $C_{2-6}$ alkynylene-heterocyclylene;
  each $X^E$ is independently C($R^{E1}$) or N;
  $Y^E$ is a bond, $C_{1-6}$ alkylene, —O—, —S—, —S(O)—, —S(O)$_2$—, or —N($R^{E7}$)—;
  Z is —CH$_2$— or —C(O)—;
  one of $Z^1$, $Z^2$, $Z^3$, and $Z^4$ is —C= and the remaining three of $Z^1$, $Z^2$, $Z^3$, and $Z^4$ are each independently —C($R^{E5}$)=; or $Z^1$ is a bond; one of $Z^2$, $Z^3$, and $Z^4$ is —C=, and the remaining two of $Z^2$, $Z^3$, and $Z^4$ are each independently —C($R^{E5}$)= or —S—;
  each $R^{E1}$ is independently hydrogen, deuterium, halo, or $C_{1-6}$ alkyl;
  each $R^{E2}$ is independently hydrogen or $C_{1-6}$ alkyl;
  $R^{E3}$ is hydrogen, deuterium, halo, or $C_{1-6}$ alkyl;
  each $R^{E4}$ is independently (i) deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, —C(O)O$R^{1a}$, —C(O)N$R^{1b}R^{1c}$, —C(O)S$R^{1a}$, —C(N$R^{1a}$) N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$) N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^{1d}$) N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;
  each $R^{E5}$ is independently hydrogen or $R^{E4}$;
  $R^{E6}$ is (i) hydrogen; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, —C(O)O$R^{1a}$, —C(O)N$R^{1b}R^{1c}$, —C(O)S$R^{1a}$, —C(N$R^{1a}$) N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$) N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{14}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^{1d}$) N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;
  $R^{E7}$ is hydrogen or $C_{1-6}$ alkyl;
  each m is independently an integer of 0, 1, or 2; and
  each n is independently an integer of 0, 1, 2, or 3;
  L is a linker having the structure of —$Z^L$—($R^L$—$Z^L$)$_z$—, wherein:
    each $R^L$ is independently $C_{1-10}$ alkylene, $C_{2-10}$ alkenylene, $C_{2-10}$ alkynylene, $C_{3-10}$ cycloalkylene, $C_{6-14}$ arylene, heteroarylene, or heterocyclylene;
    each $Z^L$ is independently a bond, —C(O)—, —C(O)O—, —C(O)N$R^{1b}$—, —C(O)S—, —C(N$R^{1a}$) N$R^{1b}$—, —C(S)—, —C(S)O—, —C(S)N$R^{1b}$—, —O—, —OC(O)O—, —OC(O)N$R^{1b}$—, —OC(O)S—, —OC(N$R^{1a}$) N$R^{1b}$—, —OC(S)—, —OC(S)O—, —OC(S)N$R^{1b}$—, —OS(O)—, —OS(O)$_2$—, —OS(O)N$R^{1b}$—, —OS(O)$_2$N$R^{1b}$—, —N$R^{1b}$—, —N$R^{1a}$C(O)N$R^{1b}$—, —N$R^{1a}$C(O)S—, —N$R^{1a}$C(N$R^{1d}$) N$R^{1b}$—, —N$R^{1a}$C(S)N$R^{1b}$—, —N$R^{1a}$S(O) N$R^{1b}$—, —N$R^{1a}$S(O)$_2$N$R^{1b}$—, —S—, —S(O)—, —S(O)$_2$—, —S(O)N$R^{1b}$—, or —S(O)$_2$N$R^{1b}$—; and
  z is an integer of 1, 2, 3, 4, 5, 6, 7, 8, 9, or 10; and
  each $R^{1a}$, $R^{1b}$, $R^{1c}$, and $R^{1d}$ is independently hydrogen, deuterium, $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;
  with the proviso that the compound is not any one of 3-(4-(1-(7-(4-(((R)-1-(3-bromo-phenyl)ethyl)amino)-6,7-dimethoxy-2-methyl-quinazolin-8-yl) heptyl)-piperidin-4-yl)-6-fluoro-1-oxoisoindolin-2-yl) piperidine-2,6-dione; 3-(4-(1-(7-(6,7-dimethoxy-2-methyl-4-(((R)-1-(4-(2-((methylamino)methyl)-phenyl) thiophen-2-yl)ethyl)amino) quinazolin-8-yl) heptyl)-piperidin-4-yl)-6-fluoro-1-oxoisoindolin-2-yl) piperidine-2,6-dione; and 3-(4-(1-(7-(6,7-dimethoxy-2-methyl-4-(((S)-1-(4-(2-((methylamino)methyl)-phenyl)thiophen-2-yl)ethyl)amino)-quinazolin-8-yl) heptyl) piperidin-4-yl)-6-fluoro-1-oxoisoindolin-2-yl) piperidine-2,6-dione;
  wherein each alkyl, alkylene, heteroalkyl, heteroalkylene, alkenyl, alkenylene, heteroalkenylene, alkynyl, alkynylene, cycloalkyl, cycloalkylene, aryl, arylene, aralkyl, aralkylene, heteroaryl, heteroarylene, heterocyclyl, and heterocyclylene is optionally substituted with one or more substituents Q, wherein each Q is independently selected from: (a) deuterium, cyano, halo, imino, nitro, and oxo; (b) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more substituents $Q^a$, and (c) —C(O)$R^a$, —C(O)O$R^a$, —C(O)N$R^bR^c$, —C(O)S$R^a$, —C(N$R^a$) N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(N$R^a$) N$R^bR^c$, —OC(S)$R^a$, —OC(S)O$R^a$, —OC(S)N$R^bR^c$, —OP(O)(O$R^b$) O$R^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(N$R^d$) N$R^bR^c$, —N$R^a$C(S)$R^4$, —N$R^a$C(S)O$R^d$, —N$R^a$C(S)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents $Q^a$; or (iii) Rb and Re together with the N atom to which they are attached form heterocyclyl, optionally substituted with one or more substituents $Q^a$;

wherein each $Q^a$ is independently selected from: (a) deuterium, cyano, halo, nitro, imino, and oxo; (b) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(O)S$R^e$, —C(N$R^e$) N$R^f R^g$, —C(S)$R^e$, —C(S)O$R^e$, —C(S)N$R^f R^g$, —O$R^e$, —OC(O)$R^e$, —OC(O)O$R^e$, —OC(O)N$R^f R^g$, —OC(O)S$R^e$, —OC(N$R^e$) N$R^f R^g$, —OC(S)$R^e$, —OC(S)O$R^e$, —OC(S)N$R^f R^g$, —OP(O)(O$R^f$)O$R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^f$, —N$R^e$C(O)N$R^f R^g$, —N$R^e$C(O)S$R^f$, —N$R^e$C(N$R^h$) N$R^f R^g$, —N$R^e$C(S)$R^h$, —N$R^e$C(S)O$R^f$, —N$R^e$C(S)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$, and —S(O)$_2$N$R^f R^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) Rf and $R^g$ together with the N atom to which they are attached form heterocyclyl.

2. The compound of claim 1, wherein $R^{2c}$ is $C_{6-14}$ aryl or heteroaryl, each of which is optionally substituted with one, two, or three substituents Q.

3. The compound of claim 2, wherein $R^{2c}$ is 3-cyano-phenyl, 3-bromo-phenyl, 3-methylphenyl, 3-difluoromethylphenyl, 3-trifluoromethylphenyl, 3-(1,1-difluoroethyl)phenyl, 3-(1-cyano-1-fluoromethyl)phenyl, 3-(1-cyano-1,1-difluoromethyl)-phenyl, 3-(1,1-difluoro-2-hydroxyethyl)phenyl, 3-(2-aminomethylphenyl)phenyl, 3-cyano-5-fluorophenyl, 3-cyano-2-methylphenyl, 3-cyano-5-methylphenyl, 3-cyano-2-trifluoromethyl-phenyl, 3-cyano-5-hydroxyphenyl, 3-cyano-2-methoxyphenyl, 2,3-difluorophenyl, 2,4-difluoro-phenyl, 2-chloro-3-fluorophenyl, 2-chloro-4-fluorophenyl, 2-chloro-3-difluoromethylphenyl, 2-chloro-3-methylphenyl, 3-chloro-2-methylphenyl, 3-difluoromethyl-2-fluorophenyl, 3-difluoro-methyl-2-methylphenyl, 2-fluoro-3-(1,1-difluoro-2-hydroxy-2-methylpropyl)phenyl, 2-fluoro-3-methylphenyl, 3-fluoro-2-methylphenyl, 3-fluoro-4-methylphenyl, 4-fluoro-2-methylphenyl, 2-fluoro-3-difluoromethylphenyl, 2-fluoro-3-trifluoromethylphenyl, 3-fluoro-5-trifluoromethyl-phenyl, 2-fluoro-methyl-3-difluoromethylphenyl, 2,3-di (difluoromethyl)phenyl, 2-methyl-3-trifluoromethylphenyl, 2-ethyl-3-difluoromethylphenyl, 2-methyl-3-methylaminomethylphenyl, 2-methyl-3-methylsulfonylphenyl, 3-methyl-5-trifluoromethylphenyl, 3-hydroxy-5-trifluoro-methylphenyl, 3-amino-5-trifluoromethylphenyl, 3-amino-4-fluoro-5-trifluoromethylphenyl, 5-amino-2-fluoro-3-trifluoromethylphenyl, 5-amino-2-methyl-3-trifluoromethylphenyl, 3-cyano-2,5-difluorophenyl, 3-cyano-5-fluoro-2-methylphenyl, 5-fluoro-2-methyl-3-trifluoromethyl-phenyl, 1,1-difluoro-2,3-dihydroinden-4-yl, naphth-1-yl, 5-(2-aminomethylphenyl) thien-2-yl, 5-(2-(2-aminoethyl)-phenyl) thien-2-yl, 4-(2-methylaminomethylphenyl) thien-2-yl, 4-(2-dimethyl-aminomethyl-phenyl) thien-2-yl, 5-(2-methylaminomethylphenyl) thien-2-yl, 5-(3-fluoro-2-methylaminomethylphenyl) thien-2-yl, 5-(2-dimethylaminomethylphenyl) thien-2-yl, 2-methyl-pyridin-3-yl, 4-amino-6-difluoromethylpyridin-2-yl, 4-amino-6-trifluoromethylpyridin-2-yl, or 3,3-difluoro-2,3-dihydrobenzofuran-7-yl.

4. The compound of claim 1, having the structure of Formula (II):

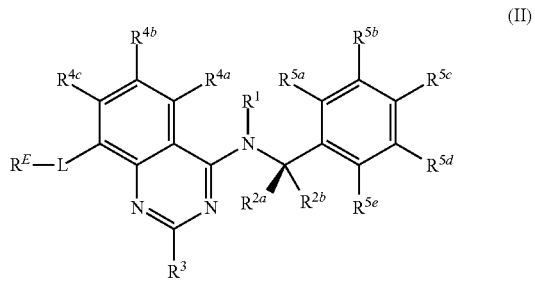

(II)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof; wherein:

$R^{5a}$, $R^{5b}$, $R^{5c}$, $R^{5d}$, and $R^{5e}$ are each independently (i) hydrogen, deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (iii) —C(O)$R^{1a}$, —C(O)O$R^{1a}$, —C(O)N$R^{1b}R^{1c}$, —C(O)S$R^{1a}$, —C(N$R^{1a}$) N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$) N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2 R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{14}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^{1d}$) N$R^{1b}R^{1c}$, —N$R^{1a}$C(S)$R^{14}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2 R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2 R^{1a}$, —S(O)N$R^{1b}R^{1c}$, or —S(O)$_2$N$R^{1b}R^{1c}$, or $R^{5a}$ and $R^{5b}$ or $R^{5b}$ and $R^{5c}$ together with the carbon atoms to which they are attached form $C_{5-10}$ cycloalkyl, $C_{6-14}$ aryl, $C_{7-15}$ aralkyl, heteroaryl, or heterocyclyl, each of which is optionally substituted with one or more substituents Q.

5. The compound of claim 4, having the structure of Formula (XI):

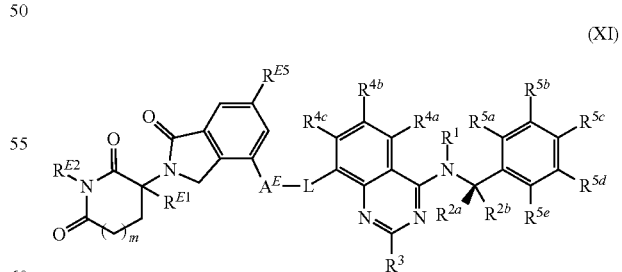

(XI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

6. The compound of claim 4, having the structure of Formula (XII):

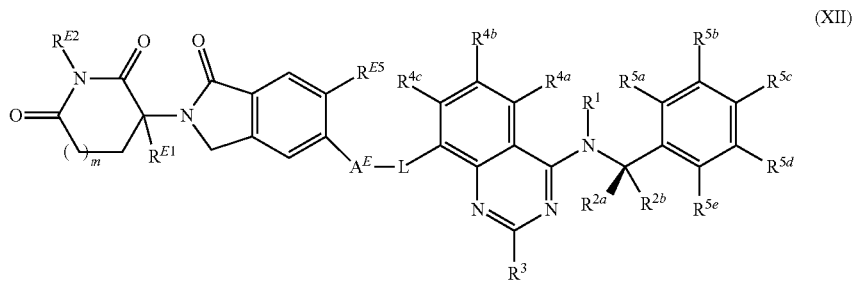

(XII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

7. The compound of claim 4, wherein the compound is a compound of Formula (XIII):

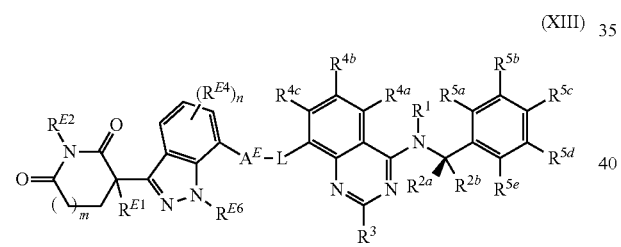

(XIII)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

8. The compound of claim 4, wherein the compound is a compound of Formula (XIV):

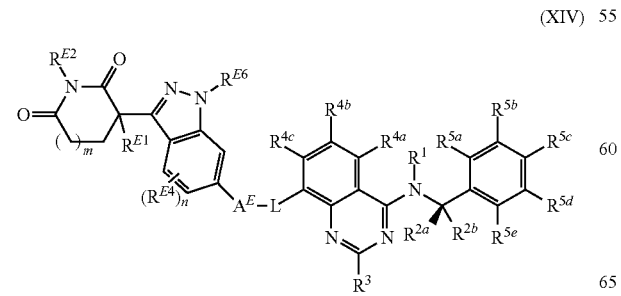

(XIV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

9. The compound of claim 4, having the structure of Formula (XV):

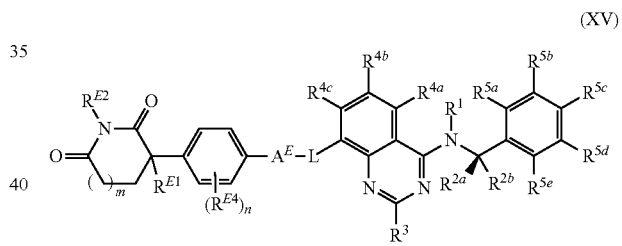

(XV)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

10. The compound of claim 4, having the structure of Formula (XVI):

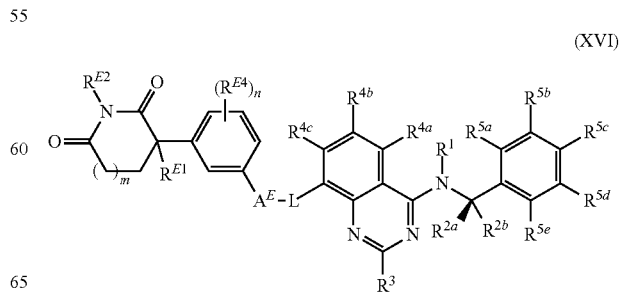

(XVI)

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

11. The compound of claim 1, wherein $R^E$ is a moiety having the structure of Formula (EC-I):

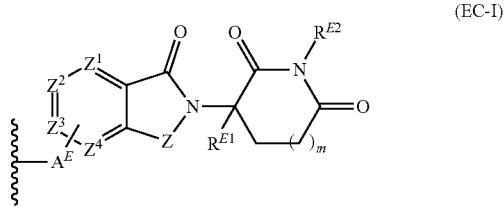

(EC-I)

or an enantiomer, a mixture of enantiomers, a diastereomer, a mixture of two or more diastereomers, a tautomer, a mixture of two or more tautomers, or an isotopic variant thereof;
wherein:
$A_E$ is a bond, —O—, —N($R^{1b}$)—, —S—, $C_{1-6}$ alkylene, $C_{1-6}$ heteroalkylene, $C_{2-6}$ alkenylene, $C_{2-6}$ heteroalkenylene, $C_{2-6}$ alkynylene, $C_{2-6}$ heteroalkynylene, $C_{3-10}$ cycloalkylene, $C_{6-14}$ arylene, $C_{7-15}$ aralkylene, heteroarylene, heterocyclylene, $C_{1-6}$ heteroalkylene-$C_{6-14}$ arylene, $C_{1-6}$ heteroalkylene-heterocyclylene, or $C_{2-6}$ alkynylene-heterocyclylene;
Z is —CH$_2$— or —C(O)—;
one of $Z^1$, $Z^2$, $Z^3$, and $Z^4$ is —C= and the remaining three of $Z^1$, $Z^2$, $Z^3$, and $Z^4$ are each independently —C($R^{E5}$)=; or $Z^1$ is a bond; one of $Z^2$, $Z^3$, and $Z^4$ is —C—, and the remaining two of $Z^2$, $Z^3$, and $Z^4$ are each independently —C($R^{E5}$)= or —S—;
m is an integer of 0, 1, or 2;
$R^{E1}$ is hydrogen, deuterium, halo, or $C_{1-6}$ alkyl;
$R^{E2}$ is hydrogen or $C_{1-6}$ alkyl;
each $R^{E4}$ is independently (i) deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; and
each $R^{E5}$ is independently hydrogen or $R^{E4}$,
wherein each alkyl, heteroalkyl, alkylene, heteroalkylene, alkenyl, alkenylene, heteroalkenylene, alkynyl, alkynylene, heteroalkynylene, cycloalkyl, cycloalkylene, aryl, arylene, aralkyl, aralkylene, heteroaryl, heteroarylene, heterocyclyl, and heterocyclylene is optionally substituted with one or more substituents Q.

12. The compound of claim 1, wherein $R^E$ is a moiety having the structure of Formula (EC-XV):

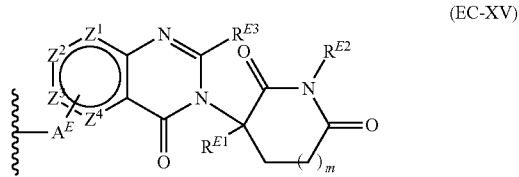

(EC-XV)

or an enantiomer, a mixture of enantiomers, a diastereomer, a mixture of two or more diastereomers, a tautomer, a mixture of two or more tautomers, or an isotopic variant thereof;
wherein:
$A^E$ is a bond, —O—, —N($R^{1b}$)—, —S—, $C_{1-6}$ alkylene, $C_{1-6}$ heteroalkylene, $C_{2-6}$ alkenylene, $C_{2-6}$ heteroalkenylene, $C_{2-6}$ alkynylene, $C_{2-6}$ heteroalkynylene, $C_{3-10}$ cycloalkylene, $C_{6-14}$ arylene, $C_{7-15}$ aralkylene, heteroarylene, heterocyclylene, $C_{1-6}$ heteroalkylene-$C_{6-14}$ arylene, $C_{1-6}$ heteroalkylene-heterocyclylene, or $C_{2-6}$ alkynylene-heterocyclylene;
one of $Z^1$, $Z^2$, $Z^3$, and $Z^4$ is —C= and the remaining three of $Z^1$, $Z^2$, $Z^3$, and $Z^4$ are each independently —C($R^{E5}$)—; or $Z^1$ is a bond; one of $Z^2$, $Z^3$, and $Z^4$ is —C—, and the remaining two of $Z^2$, $Z^3$, and $Z^4$ are each independently —C($R^{E5}$)= or —S—;
m is an integer of 0, 1, or 2;
$R^{E1}$ is hydrogen, deuterium, halo, or $C_{1-6}$ alkyl;
$R^{E2}$ is hydrogen or $C_{1-6}$ alkyl;
$R^{E3}$ is hydrogen, deuterium, halo, or $C_{1-6}$ alkyl;
each $R^{E4}$ is independently (i) deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$) N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^{1d}$) N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O) $R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; and
each $R^{E5}$ is independently hydrogen or $R^{E4}$,
wherein each alkyl, heteroalkyl, alkylene, heteroalkylene, alkenyl, alkenylene, heteroalkenylene, alkynyl, alkynylene, heteroalkynylene, cycloalkyl, cycloalkylene, aryl, arylene, aralkyl, aralkylene, heteroaryl, heteroarylene, heterocyclyl, and heterocyclylene is optionally substituted with one or more substituents Q.

13. The compound of claim 1, wherein $R^E$ is a moiety having the structure of:

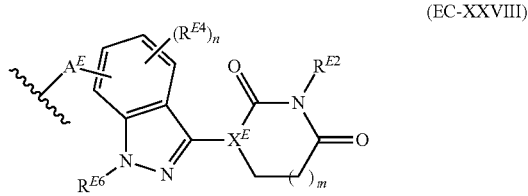

(EC-XXVIII)

or an enantiomer, a mixture of enantiomers, a diastereomer, a mixture of two or more diastereomers, a tautomer, a mixture of two or more tautomers, or an isotopic variant thereof;

wherein:

$A^E$ is a bond, —O—, —N($R^{1b}$)—, —S—, $C_{1-6}$ alkylene, $C_{1-6}$ heteroalkylene, $C_{2-6}$ alkenylene, $C_{2-6}$ heteroalkenylene, $C_{2-6}$ alkynylene, $C_{2-6}$ heteroalkynylene, $C_{3-10}$ cycloalkylene, $C_{6-14}$ arylene, $C_{7-15}$ aralkylene, heteroarylene, heterocyclylene, $C_{1-6}$ heteroalkylene-$C_{6-14}$ arylene, $C_{1-6}$ heteroalkylene-heterocyclylene, or $C_{2-6}$ alkynylene-heterocyclylene;

$X^E$ is C($R^{E1}$) or N;

$R^{E1}$ is hydrogen, deuterium, halo, or $C_{1-6}$ alkyl;

$R^{E2}$ is hydrogen or $C_{1-6}$ alkyl;

each $R^{E4}$ is independently (i) deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{E6}$ is (i) hydrogen; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (iii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

m is an integer of 0, 1, or 2; and n is an integer of 0, 1, 2, or 3;

wherein each alkyl, heteroalkyl, alkylene, heteroalkylene, alkenyl, alkenylene, heteroalkenylene, alkynyl, alkynylene, heteroalkynylene, cycloalkyl, cycloalkylene, aryl, arylene, aralkyl, aralkylene, heteroaryl, heteroarylene, heterocyclyl, and heterocyclylene is optionally substituted with one or more substituents Q.

14. The compound of claim 1, wherein $R^E$ is a moiety having the structure of:

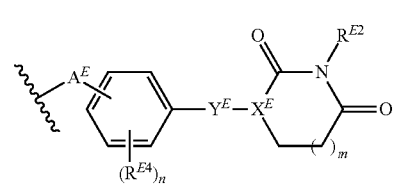

(EC-XXXV)

or an enantiomer, a mixture of enantiomers, a diastereomer, a mixture of two or more diastereomers, a tautomer, a mixture of two or more tautomers, or an isotopic variant thereof;

wherein:

$A^E$ is a bond, —O—, —N($R^{1b}$)—, —S—, $C_{1-6}$ alkylene, $C_{1-6}$ heteroalkylene, $C_{2-6}$ alkenylene, $C_{2-6}$ heteroalkenylene, $C_{2-6}$ alkynylene, $C_{2-6}$ heteroalkynylene, $C_{3-10}$ cycloalkylene, $C_{6-14}$ arylene, $C_{7-15}$ aralkylene, heteroarylene, heterocyclylene, $C_{1-6}$ heteroalkylene-$C_{6-14}$ arylene, $C_{1-6}$ heteroalkylene-heterocyclylene, or $C_{2-6}$ alkynylene-heterocyclylene;

$X^E$ is C($R^{E1}$) or N;

$Y^E$ is a bond, $C_{1-6}$ alkylene, —O—, —S—, —S(O)—, —S(O$_2$)—, or —N($R^{E7}$)—;

$R^{E1}$ is hydrogen, deuterium, halo, or $C_{1-6}$ alkyl;

$R^{E2}$ is hydrogen or $C_{1-6}$ alkyl;

each $R^{E4}$ is independently (i) deuterium, cyano, halo, or nitro; (ii) $C_{1-6}$ alkyl, $C_{1-6}$ heteroalkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) —C(O)$R^{1a}$, C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{E7}$ is hydrogen or $C_{1-6}$ alkyl;

m is an integer of 0, 1, or 2; and n is an integer of 0, 1, 2, 3, or 4;

wherein each alkyl, heteroalkyl, alkylene, heteroalkylene, alkenyl, alkenylene, heteroalkenylene, alkynyl, alkynylene, heteroalkynylene, cycloalkyl, cycloalkylene, aryl, arylene, aralkyl, aralkylene, heteroaryl, heteroarylene, heterocyclyl, and heterocyclylene is optionally substituted with one or more substituents Q.

15. A pharmaceutical composition comprising the compound of claim 1, or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof, and a pharmaceutically acceptable excipient.

16. The compound of claim 1, wherein $R^E$ is a moiety having the structure of:
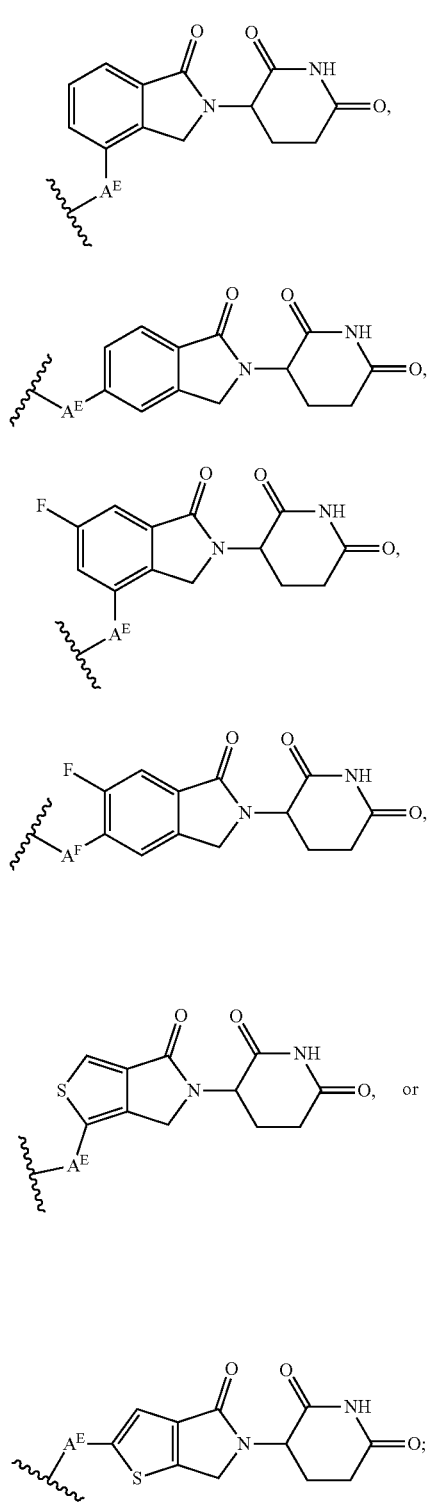
or an enantiomer, a mixture of enantiomers, a diastereomer, a mixture of two or more diastereomers, a tautomer, a mixture of two or more tautomers, or an isotopic variant thereof.
17. The compound of claim 1, wherein $R^E$ is a moiety having the structure of:
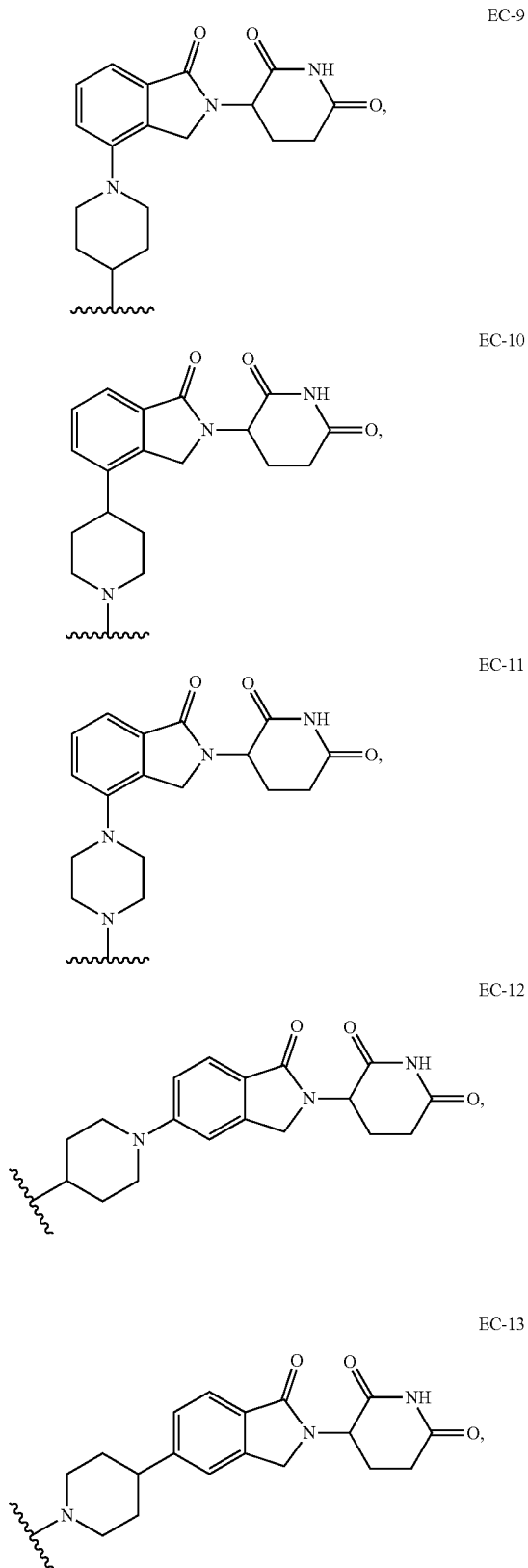

EC-14
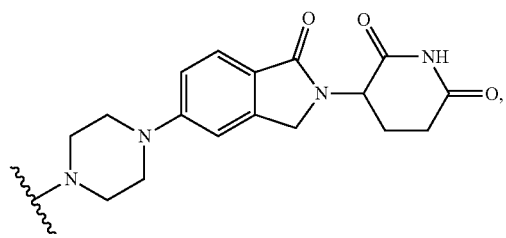
EC-15
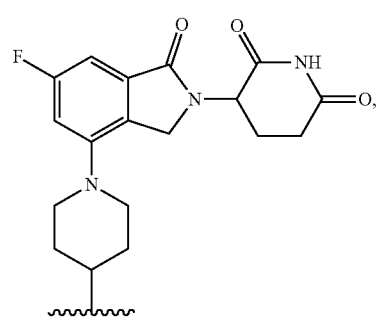
EC-16
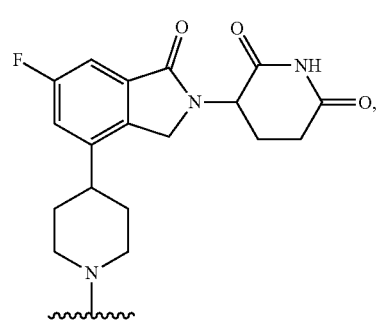
EC-17
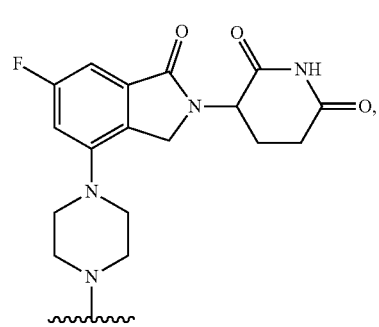
EC-18
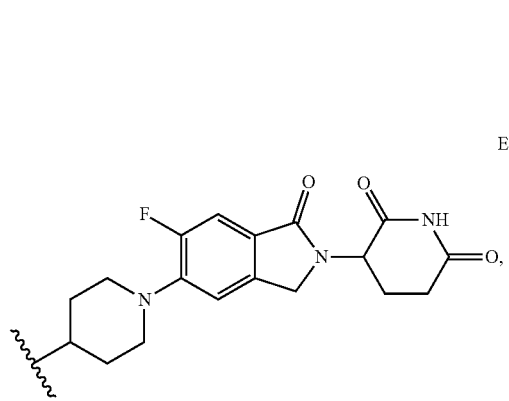
EC-19
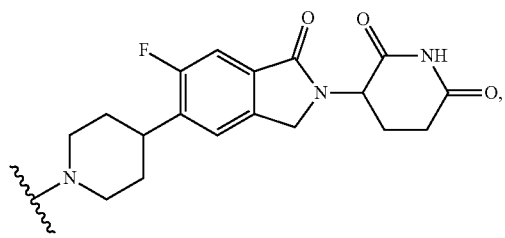
EC-20
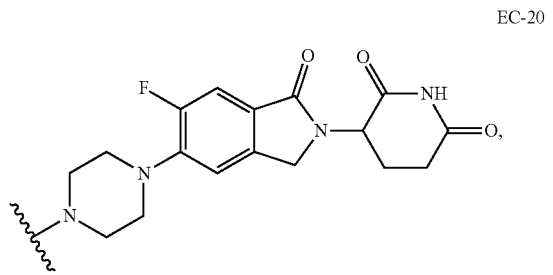
EC-21
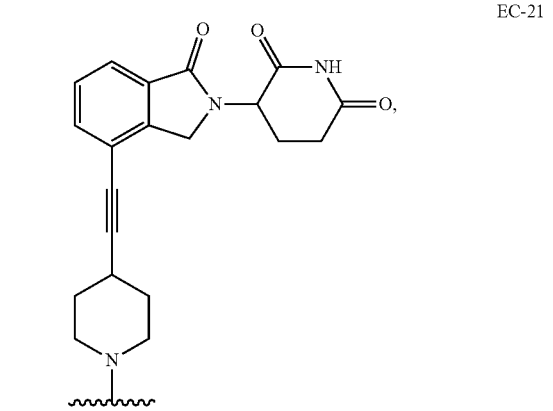
EC-22
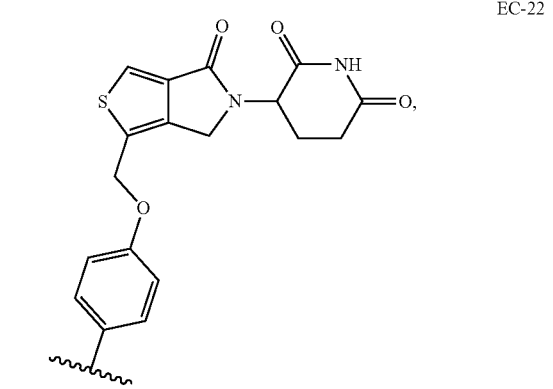
EC-23
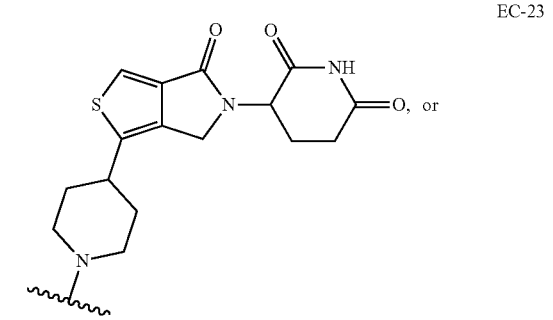
or -continued

EC-24

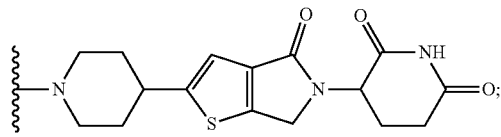

or an enantiomer, a mixture of enantiomers, a tautomer, a mixture of two or more tautomers, or an isotopic variant thereof.

18. The compound of claim 1, wherein $R^E$ is a moiety having the structure of:

EC-31

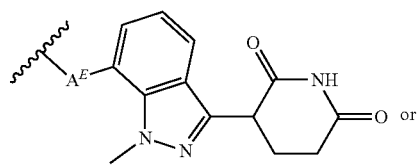

or

EC-32

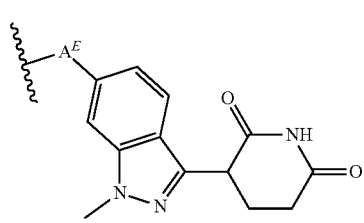

or an enantiomer, a mixture of enantiomers, a diastereomer, a mixture of two or more diastereomers, a tautomer, a mixture of two or more tautomers, or an isotopic variant thereof.

19. The compound of claim 1, wherein $R^E$ is a moiety having the structure of:

EC-33

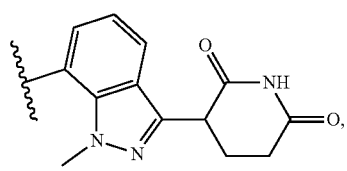

EC-34

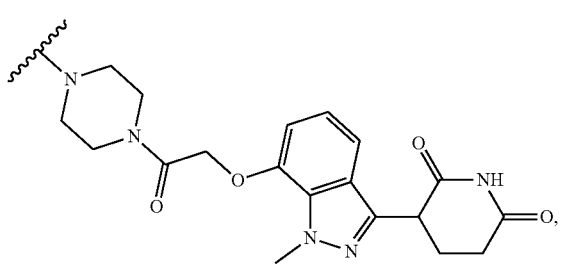

-continued

EC-35

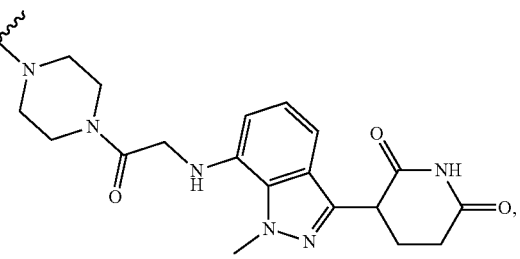

EC-36

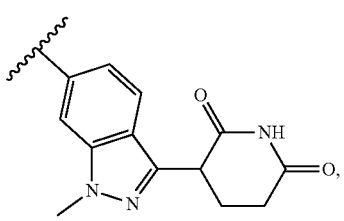

EC-37

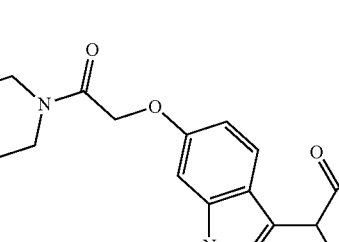

or

EC-38

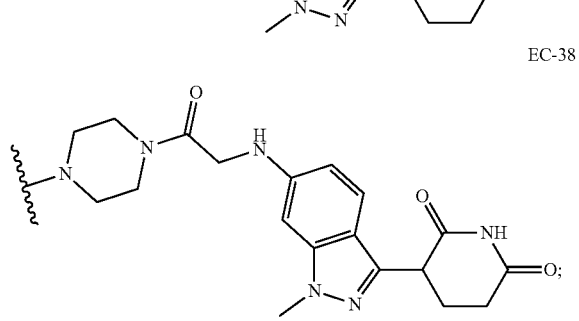

or an enantiomer, a mixture of enantiomers, a tautomer, a mixture of two or more tautomers, or an isotopic variant thereof.

20. The compound of claim 1, wherein $R^E$ is a moiety having the structure of:

EC-39

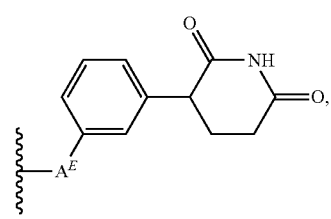

EC-40

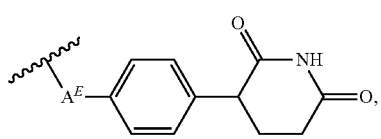

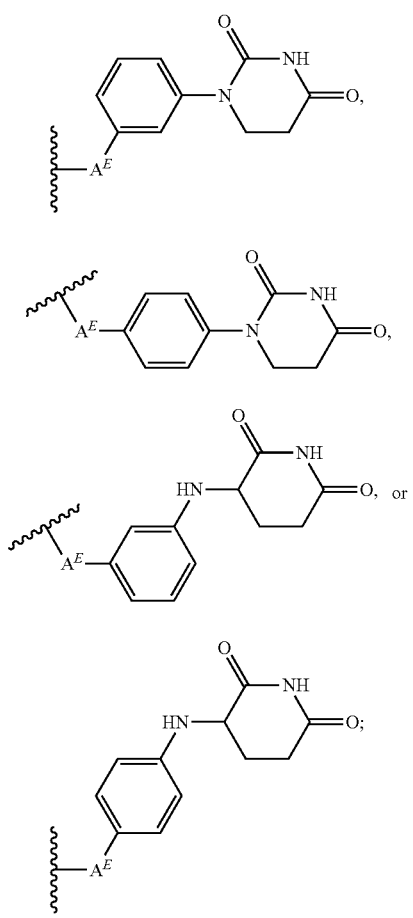
EC-41
EC-42
EC-43
EC-44
or an enantiomer, a mixture of enantiomers, a diastereomer, a mixture of two or more diastereomers, a tautomer, a mixture of two or more tautomers, or an isotopic variant thereof.
21. The compound of claim 1, wherein $R^E$ is a moiety having the structure of:
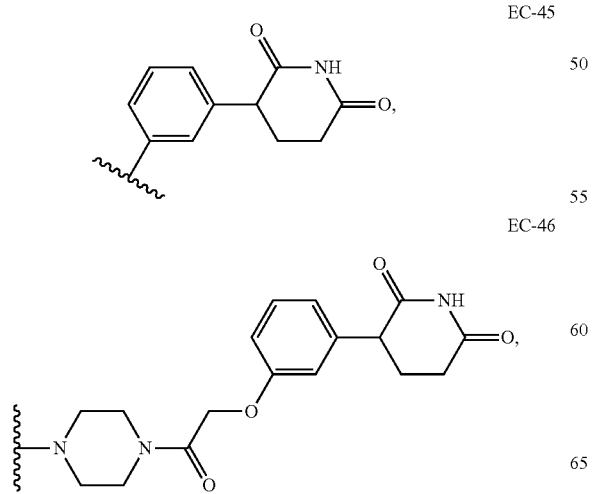
EC-45
EC-46
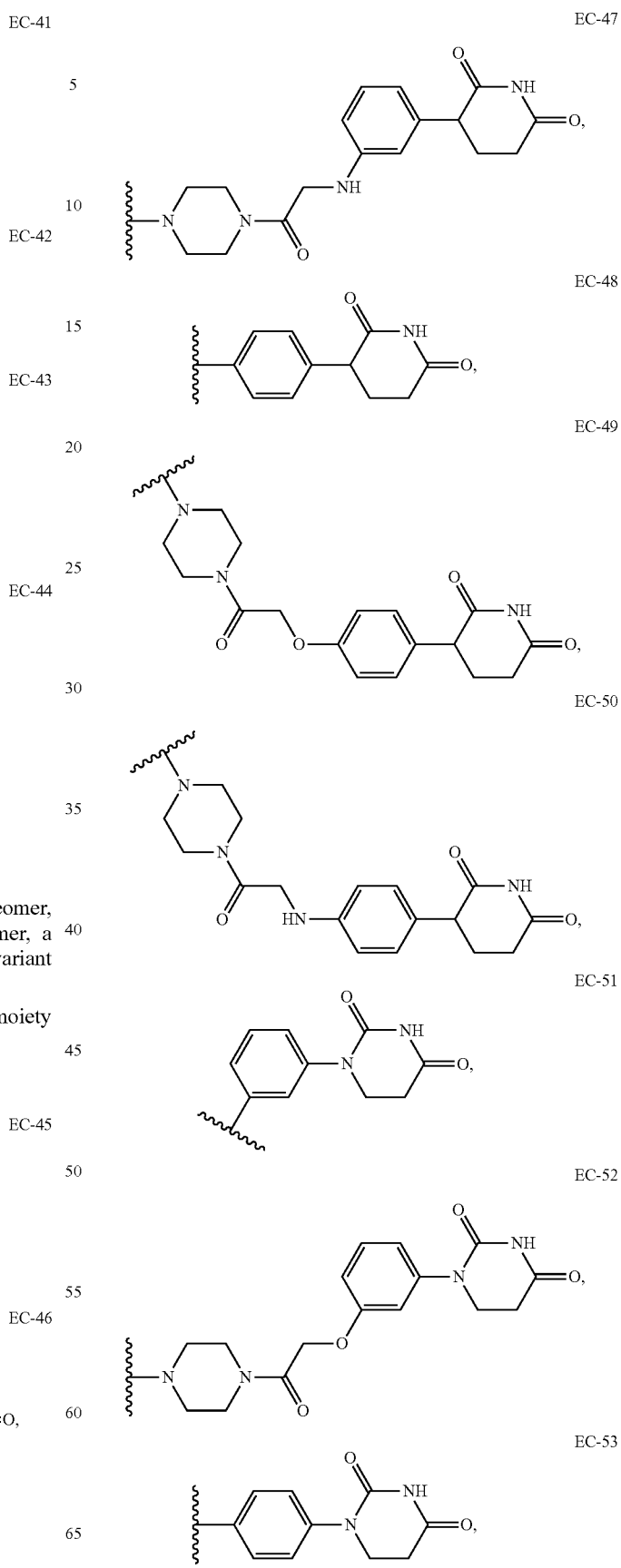
EC-47
EC-48
EC-49
EC-50
EC-51
EC-52
EC-53

-continued
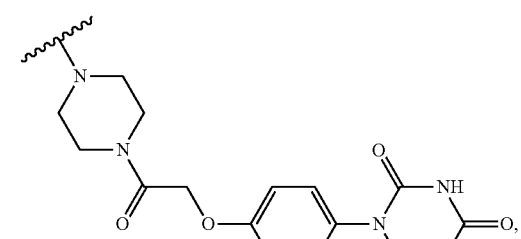
EC-54
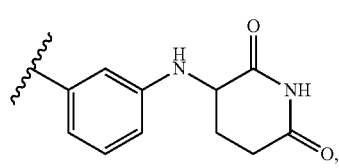
EC-55
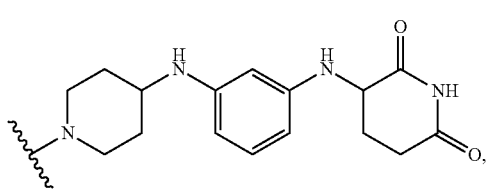
EC-56
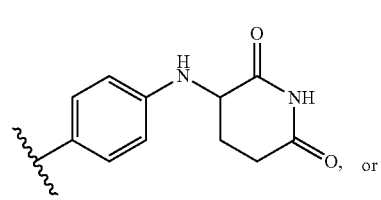
EC-57, or
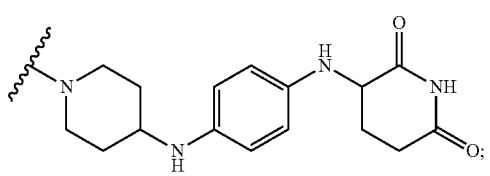
EC-58
or an enantiomer, a mixture of enantiomers, a tautomer, a mixture of two or more tautomers, or an isotopic variant thereof.
22. The compound of claim 1, wherein L is:
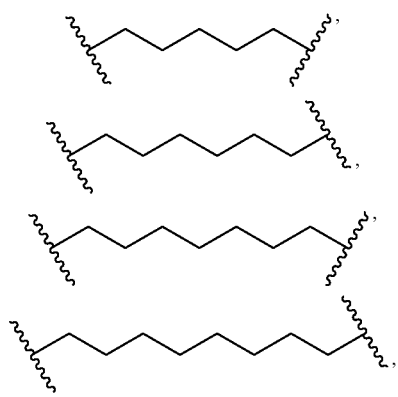
-continued
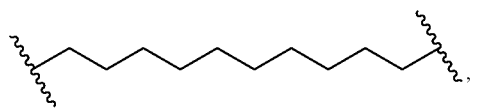
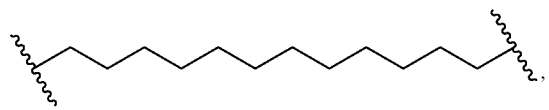
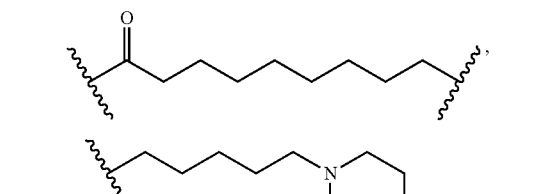
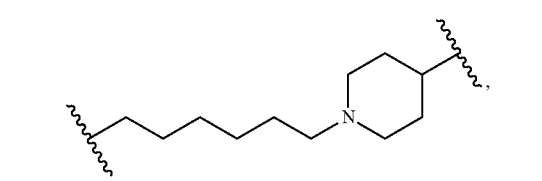
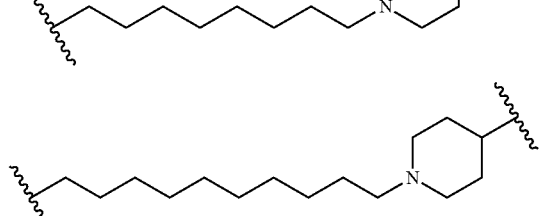
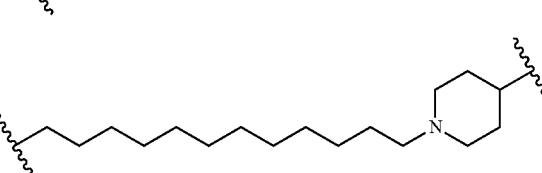
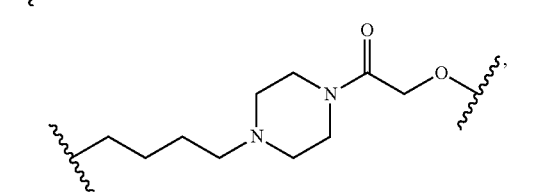
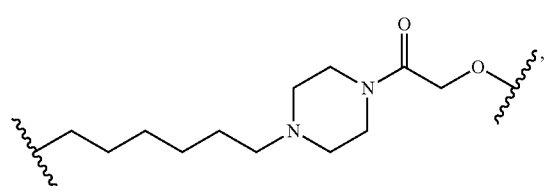

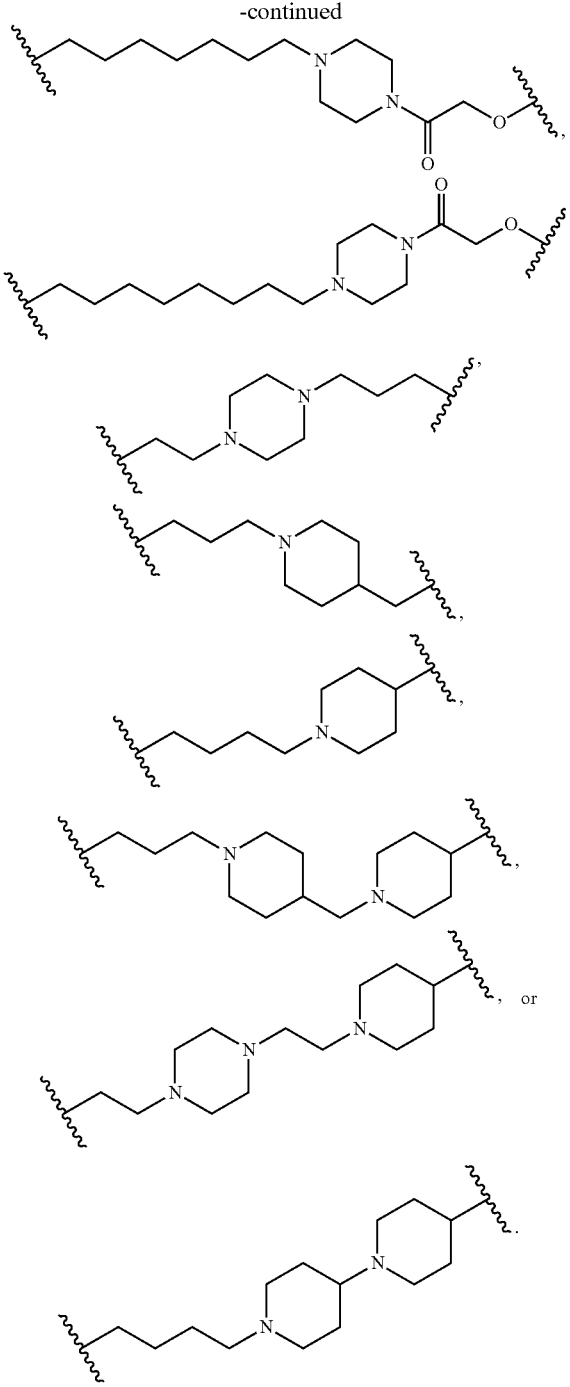

23. A compound of:
3-(4-(1-(6-(4-(((R)-1-(3-amino-5-(trifluoromethyl)phenyl)ethyl) amino)-6,7-dimethoxy-2-methylquinazolin-8-yl) hexyl) piperidin-4-yl)-6-fluoro-1-oxoisoindolin-2-yl)-piperidine-2,6-dione A101;
3-(5-(4-(7-(4-(((R)-1-(3-(1,1-difluoro-2-hydroxyethyl) phenyl)ethyl) amino)-6,7-dimethoxy-2-methylquinazolin-8-yl) heptyl) piperazin-1-yl)-6-fluoro-1-oxoisoindolin-2-yl)-piperidine-2,6-dione A102;
3-(4-(1-(6-(4-(((S)-1-(3-amino-5-(trifluoromethyl)phenyl)ethyl) amino)-6,7-dimethoxy-2-methylquinazolin-8-yl) hexyl) piperidin-4-yl)-6-fluoro-1-oxoisoindolin-2-yl)-piperidine-2,6-dione A103;
3-(4-(1-(7-(4-(((R)-1-(3-(1,1-difluoro-2-hydroxyethyl) phenyl)ethyl) amino)-6,7-dimethoxy-2-methylquinazolin-8-yl) heptyl) piperidin-4-yl)-6-fluoro-1-oxoisoindolin-2-yl)-piperidine-2,6-dione A104;
3-(4-(1-(8-(4-(((R)-1-(3-amino-5-(trifluoromethyl)phenyl)ethyl) amino)-6,7-dimethoxy-2-methylquinazolin-8-yl) octyl) piperidin-4-yl)-6-fluoro-1-oxoisoindolin-2-yl)-piperidine-2,6-dione A105;
3-(4-(1-(10-(4-(((R)-1-(3-amino-5-(trifluoromethyl)phenyl)ethyl) amino)-6,7-dimethoxy-2-methylquinazolin-8-yl) decyl) piperidin-4-yl)-6-fluoro-1-oxoisoindolin-2-yl)-piperidine-2,6-dione A106;
3-(4-(1-(12-(4-(((R)-1-(3-amino-5-(trifluoromethyl)phenyl)ethyl) amino)-6,7-dimethoxy-2-methylquinazolin-8-yl) dodecyl) piperidin-4-yl)-6-fluoro-1-oxoisoindolin-2-yl)-piperidine-2,6-dione A107;
3-(4-(1-(12-(4-(((S)-1-(3-amino-5-(trifluoromethyl)phenyl)ethyl) amino)-6,7-dimethoxy-2-methylquinazolin-8-yl) dodecyl) piperidin-4-yl)-6-fluoro-1-oxoisoindolin-2-yl)-piperidine-2,6-dione A108;
3-(5-(4-(7-(4-(((R)-1-(3-(1,1-difluoro-2-hydroxyethyl) phenyl)ethyl) amino)-6,7-dimethoxy-2-methylquinazolin-8-yl) heptyl) piperazin-1-yl)-6-fluoro-1-oxoisoindolin-2-yl)-piperidine-2,6-dione A109;
3-(4-(1-(10-(4-(((S)-1-(3-amino-5-(trifluoromethyl)phenyl)ethyl) amino)-6,7-dimethoxy-2-methylquinazolin-8-yl) decyl) piperidin-4-yl)-6-fluoro-1-oxoisoindolin-2-yl)-piperidine-2,6-dione A110;
3-(4-(1-(8-(4-(((S)-1-(3-amino-5-(trifluoromethyl)phenyl)ethyl) amino)-6,7-dimethoxy-2-methylquinazolin-8-yl) octyl) piperidin-4-yl)-6-fluoro-1-oxoisoindolin-2-yl)-piperidine-2,6-dione A111;
3-(4-((4-(((7-(6,7-dimethoxy-2-methyl-4-(((S)-1-(4-(2-((methylamino)methyl)-phenyl)thiophen-2-yl)ethyl) amino) quinazolin-8-yl) heptyl)amino) methyl)benzyl) oxy)-1-oxoisoindolin-2-yl) piperidine-2,6-dione A112;
3-(4-((4-(((7-(6,7-dimethoxy-2-methyl-4-(((R)-1-(4-(2-((methylamino)methyl)-phenyl)thiophen-2-yl)ethyl) amino) quinazolin-8-yl) heptyl)amino) methyl)benzyl) oxy)-1-oxoisoindolin-2-yl) piperidine-2,6-dione A113;
3-(5-(1-(7-(4-(((S)-1-(3-(1,1-difluoro-2-hydroxyethyl) phenyl)ethyl) amino)-6,7-dimethoxy-2-methylquinazolin-8-yl) heptyl) piperidin-4-yl)-6-fluoro-1-oxoisoindolin-2-yl)-piperidine-2,6-dione A114;
3-(6-(1-(7-(6,7-dimethoxy-2-methyl-4-(((R)-1-(4-(2-((methylamino)methyl)-phenyl)thiophen-2-yl)ethyl) amino) quinazolin-8-yl) heptyl) piperidin-4-yl)-1-oxoisoindolin-2-yl)-piperidine-2,6-dione A115;
3-(6-(1-(7-(6,7-dimethoxy-2-methyl-4-(((S)-1-(4-(2-((methylamino)methyl)-phenyl)thiophen-2-yl)ethyl) amino) quinazolin-8-yl) heptyl) piperidin-4-yl)-1-oxoisoindolin-2-yl)-piperidine-2,6-dione A116;
3-(4-(1-(7-(4-(((S)-1-(3-(1,1-difluoro-2-hydroxyethyl) phenyl)ethyl) amino)-6,7-dimethoxy-2-methylquinazolin-8-yl) heptyl) piperidin-4-yl)-6-fluoro-1-oxoisoindolin-2-yl)-piperidine-2,6-dione A117;
3-(4-((4-(((7-(4-(((R)-1-(3-bromophenyl)ethyl)amino)-6,7-dimethoxy-2-methyl-quinazolin-8-yl) heptyl)amino) methyl)benzyl)oxy)-1-oxoisoindolin-2-yl) piperidine-2,6-dione A118;
3-(5-(1-(5-(4-(((R)-1-(3-(1,1-difluoro-2-hydroxyethyl) phenyl)ethyl) amino)-6,7-dimethoxy-2-methylquinazolin-8-yl) pentyl) piperidin-4-yl)-6-fluoro-1-oxoisoindolin-2-yl)-piperidine-2,6-dione A119;
3-(5-(1-(6-(4-(((R)-1-(3-(1,1-difluoro-2-hydroxyethyl) phenyl)ethyl) amino)-6,7-dimethoxy-2-methylquinazolin-8-yl) hexyl) piperidin-4-yl)-6-fluoro-1-oxoisoindolin-2-yl)-piperidine-2,6-dione A120;

3-(5-(1-((1-(3-(4-(((R)-1-(3-(1,1-difluoro-2-hydroxyethyl)phenyl)ethyl) amino)-6,7-dimethoxy-2-methylquinazolin-8-yl) propyl) piperidin-4-yl)methyl) piperidin-4-yl)-6-fluoro-1-oxoisoindolin-2-yl) piperidine-2,6-dione A121;

3-(5-(1'-(4-(4-(((R)-1-(3-(1,1-difluoro-2-hydroxyethyl)phenyl) amino)-6,7-dimethoxy-2-methylquinazolin-8-yl)butyl)-[1,4'-bipiperidin]-4-yl)-6-fluoro-1-oxoisoindolin-2-yl) piperidine-2,6-dione A122;

3-(5-(1-(2-(4-(2-(4-(((R)-1-(3-(1,1-difluoro-2-hydroxyethyl)phenyl)ethyl) amino)-6,7-dimethoxy-2-methylquinazolin-8-yl)ethyl) piperazin-1-yl)ethyl) piperidin-4-yl)-6-fluoro-1-oxoisoindolin-2-yl) piperidine-2,6-dione A123;

3-(7-(2-(4-(4-(4-(((R)-1-(3-(1,1-difluoro-2-hydroxyethyl)phenyl)ethyl) amino)-6,7-dimethoxy-2-methylquinazolin-8-yl)butyl) piperazin-1-yl)-2-oxoethoxy)-1-methyl-1H-indazol-3-yl) piperidine-2,6-dione A201;

3-(6-(2-(4-(4-(4-(((R)-1-(3-(1,1-difluoro-2-hydroxyethyl)phenyl)ethyl) amino)-6,7-dimethoxy-2-methylquinazolin-8-yl)butyl) piperazin-1-yl)-2-oxoethoxy)-1-methyl-1H-indazol-3-yl) piperidine-2,6-dione A202;

3-(7-(2-(4-(6-(4-(((R)-1-(3-(1,1-difluoro-2-hydroxyethyl)phenyl)ethyl) amino)-6,7-dimethoxy-2-methylquinazolin-8-yl) hexyl) piperazin-1-yl)-2-oxoethoxy)-1-methyl-1/-indazol-3-yl) piperidine-2,6-dione A203;

3-(6-(2-(4-(6-(4-(((R)-1-(3-(1,1-difluoro-2-hydroxyethyl)phenyl)ethyl) amino)-6,7-dimethoxy-2-methylquinazolin-8-yl) hexyl) piperazin-1-yl)-2-oxoethoxy)-1-methyl-1/-indazol-3-yl) piperidine-2,6-dione A204;

3-(7-(2-(4-(8-(4-(((R)-1-(3-(1,1-difluoro-2-hydroxyethyl)phenyl)ethyl) amino)-6,7-dimethoxy-2-methylquinazolin-8-yl) octyl) piperazin-1-yl)-2-oxoethoxy)-1-methyl-1H-indazol-3-yl) piperidine-2,6-dione A205;

3-(6-(2-(4-(8-(4-(((R)-1-(3-(1,1-difluoro-2-hydroxyethyl)phenyl)ethyl) amino)-6,7-dimethoxy-2-methylquinazolin-8-yl) octyl) piperazin-1-yl)-2-oxoethoxy)-1-methyl-1H-indazol-3-yl) piperidine-2,6-dione A206;

3-(4-(1-(7-((4-(((R)-1-(3-amino-5-(trifluoromethyl)phenyl)ethyl) amino)-2-methyl-6-(((S)-tetrahydrofuran-3-yl)oxy) quinazolin-7-yl)oxy) heptyl) piperidin-4-yl)-6-fluoro-1-oxoisoindolin-2-yl) piperidine-2,6-dione B101; or 3-(5-(1-(11-((4-(((R)-1-(3-bromophenyl)ethyl)amino)-6-methoxy-2-methyl-quinazolin-7-yl)oxy) undecanoyl) piperidin-4-yl)-6-fluoro-1-oxoisoindolin-2-yl) piperidine-2,6-dione B102;

or an enantiomer, a mixture of enantiomers, a diastereomer, a mixture of two or more diastereomers, a tautomer, a mixture of two or more tautomers, or an isotopic variant thereof; or a pharmaceutically acceptable salt, solvate, or hydrate thereof.

\* \* \* \* \*